United States Patent
Shelton, IV et al.

(10) Patent No.: US 7,448,525 B2
(45) Date of Patent: Nov. 11, 2008

(54) PNEUMATICALLY POWERED SURGICAL CUTTING AND FASTENING INSTRUMENT WITH MANUALLY OPERATED RETRACTION APPARATUS

(75) Inventors: Frederick E. Shelton, IV, New Vienna, OH (US); Jerome R. Morgan, Cincinnati, OH (US); Eugene L. Timperman, Cincinnati, OH (US); Leslie M. Fugikawa, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 15 days.

(21) Appl. No.: 11/497,936

(22) Filed: Aug. 2, 2006

(65) Prior Publication Data

US 2008/0029577 A1 Feb. 7, 2008

(51) Int. Cl.
*A61B 17/068* (2006.01)
(52) U.S. Cl. .................. 227/176.1; 227/19; 227/180.1; 606/139; 606/219
(58) Field of Classification Search .................. 227/19, 227/175.1, 176.1, 180.1, 178.1; 606/139, 606/219
See application file for complete search history.

(56) References Cited

U.S. PATENT DOCUMENTS

| | | | |
|---|---|---|---|
| 2,037,727 A | 4/1936 | Chapelle | |
| 3,643,851 A | 2/1972 | Green et al. | |
| 3,662,939 A | 5/1972 | Bryan | |
| 3,717,294 A | 2/1973 | Green | |
| 3,815,476 A | 6/1974 | Green et al. | |
| 3,819,100 A | 6/1974 | Noiles et al. | |
| 3,894,174 A | 7/1975 | Cartun | |
| 3,940,844 A | 3/1976 | Colby et al. | |
| 4,331,277 A | 5/1982 | Green | |
| 4,357,940 A | 11/1982 | Muller | |
| 4,383,634 A | 5/1983 | Green | |
| 4,402,445 A | 9/1983 | Green | |
| 4,415,112 A | 11/1983 | Green | |
| 4,461,305 A | 7/1984 | Cibley | |

(Continued)

FOREIGN PATENT DOCUMENTS

CA     2512960 A1     1/2006

(Continued)

OTHER PUBLICATIONS

International Search Report, Application No. PCT/US2007/014879, Jan. 22, 2008 (5 pages).

(Continued)

*Primary Examiner*—Scott A. Smith

(57) ABSTRACT

A surgical instrument for use in connection with a pneumatically powered tool having a firing mechanism operably supported therein that is movable between an unactuated position and an actuated position. In various embodiments, a drive system operably communicates with the pneumatically powered tool and is configured to selectively apply at least a drive system generated firing motion to the firing mechanism of the pneumatically powered tool to cause the firing mechanism to move from the unactuated position to the actuated position in response to a flow of gas from a source of gas fluidically coupled to said drive system. A retraction member communicates with the drive system to enable a manually generated retraction motion to be applied thereto to manually move the firing mechanism in a distal direction from the actuated position to the unactuated position.

19 Claims, 72 Drawing Sheets

U.S. PATENT DOCUMENTS

| | | | |
|---|---|---|---|
| 4,475,679 A | 10/1984 | Fleury, Jr. | |
| 4,500,024 A | 2/1985 | DiGiovanni et al. | |
| 4,520,817 A | 6/1985 | Green | |
| 4,522,327 A | 6/1985 | Korthoff et al. | |
| 4,526,174 A | 7/1985 | Froehlich | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,606,343 A | 8/1986 | Conta et al. | |
| 4,610,383 A | 9/1986 | Rothfuss et al. | |
| 4,629,107 A | 12/1986 | Fedotov et al. | |
| 4,671,445 A | 6/1987 | Barker et al. | |
| 4,709,120 A | 11/1987 | Pearson | |
| 4,715,520 A | 12/1987 | Roehr, Jr. et al. | |
| 4,728,020 A | 3/1988 | Green et al. | |
| 4,754,909 A | 7/1988 | Barker et al. | |
| 4,767,044 A | 8/1988 | Green | |
| 4,869,414 A | 9/1989 | Green et al. | |
| 4,869,415 A | 9/1989 | Fox | |
| 4,892,244 A | 1/1990 | Fox et al. | |
| 4,941,623 A | 7/1990 | Pruitt | |
| 4,944,443 A | 7/1990 | Oddsen et al. | |
| 4,955,959 A | 9/1990 | Tompkins et al. | |
| 5,005,754 A | 4/1991 | Van Overloop | |
| 5,027,834 A | 7/1991 | Pruitt | |
| 5,031,814 A | 7/1991 | Tompkins et al. | |
| 5,040,715 A | 8/1991 | Green et al. | |
| 5,061,269 A | 10/1991 | Muller | |
| 5,065,929 A | 11/1991 | Schulze et al. | |
| 5,080,556 A | 1/1992 | Carreno | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,137,198 A | 8/1992 | Nobis et al. | |
| 5,156,315 A | 10/1992 | Green et al. | |
| 5,211,649 A | 5/1993 | Kohler et al. | |
| 5,246,156 A | 9/1993 | Rothfuss et al. | |
| 5,253,793 A | 10/1993 | Green et al. | |
| RE34,519 E | 1/1994 | Fox et al. | |
| 5,275,323 A | 1/1994 | Schulze et al. | |
| 5,307,976 A | 5/1994 | Olson et al. | |
| 5,318,221 A | 6/1994 | Green et al. | |
| 5,350,400 A | 9/1994 | Esposito et al. | |
| 5,379,933 A | 1/1995 | Green et al. | |
| 5,383,880 A | 1/1995 | Hooven | |
| 5,395,033 A | 3/1995 | Byrne et al. | |
| 5,397,046 A | 3/1995 | Savage et al. | |
| 5,403,312 A | 4/1995 | Yates et al. | |
| 5,413,267 A | 5/1995 | Solyntjes et al. | |
| 5,413,268 A | 5/1995 | Green et al. | |
| 5,415,335 A | 5/1995 | Knodell, Jr. | |
| 5,425,745 A | 6/1995 | Green et al. | |
| 5,431,322 A | 7/1995 | Green et al. | |
| 5,433,721 A | 7/1995 | Hooven et al. | |
| 5,445,304 A | 8/1995 | Plyley et al. | |
| 5,456,401 A | 10/1995 | Green et al. | |
| 5,462,215 A | 10/1995 | Viola et al. | |
| 5,465,895 A | 11/1995 | Knodel et al. | |
| 5,465,896 A | 11/1995 | Allen et al. | |
| 5,470,006 A | 11/1995 | Rodak | |
| 5,472,132 A | 12/1995 | Savage et al. | |
| 5,474,566 A | 12/1995 | Alesi et al. | |
| 5,478,003 A | 12/1995 | Green et al. | |
| 5,480,089 A | 1/1996 | Blewett | |
| 5,480,409 A | 1/1996 | Riza | |
| 5,482,197 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,529,235 A | 6/1996 | Boiarski et al. | |
| 5,535,934 A | 7/1996 | Boiarski et al. | |
| 5,535,935 A | 7/1996 | Vidal et al. | |
| 5,547,117 A | 8/1996 | Hamblin et al. | |
| 5,554,169 A | 9/1996 | Green et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,564,615 A | 10/1996 | Bishop et al. | |
| 5,575,799 A | 11/1996 | Bolanos et al. | |
| 5,577,654 A | 11/1996 | Bishop | |
| 5,580,067 A | 12/1996 | Hamblin et al. | |
| 5,584,425 A | 12/1996 | Savage et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,609,285 A | 3/1997 | Grant et al. | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,634,584 A | 6/1997 | Okorocha et al. | |
| 5,636,779 A | 6/1997 | Palmer | |
| 5,636,780 A | 6/1997 | Green et al. | |
| 5,639,008 A | 6/1997 | Gallagher et al. | |
| 5,645,209 A | 7/1997 | Green et al. | |
| 5,647,526 A | 7/1997 | Green et al. | |
| 5,651,491 A | 7/1997 | Heaton et al. | |
| 5,653,374 A | 8/1997 | Young et al. | |
| 5,657,921 A | 8/1997 | Young et al. | |
| 5,662,258 A | 9/1997 | Knodel et al. | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,685,474 A | 11/1997 | Seeber | |
| 5,688,270 A | 11/1997 | Yates et al. | |
| 5,690,269 A | 11/1997 | Bolanos et al. | |
| 5,692,668 A | 12/1997 | Schulze et al. | |
| 5,697,543 A | 12/1997 | Burdorff | |
| 5,702,408 A | 12/1997 | Wales et al. | |
| 5,704,534 A | 1/1998 | Huitema et al. | |
| 5,706,997 A | 1/1998 | Green et al. | |
| 5,709,680 A | 1/1998 | Yates et al. | |
| 5,711,472 A | 1/1998 | Bryan | |
| 5,713,505 A | 2/1998 | Huitema | |
| 5,715,988 A | 2/1998 | Palmer | |
| 5,718,359 A | 2/1998 | Palmer et al. | |
| 5,732,871 A | 3/1998 | Clark et al. | |
| 5,735,445 A | 4/1998 | Vidal et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,255 A | 6/1998 | Chrisman et al. | |
| 5,762,256 A | 6/1998 | Mastri et al. | |

| Patent | Date | Inventor |
|---|---|---|
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,823,066 A | 10/1998 | Huitema et al. |
| 5,826,776 A | 10/1998 | Schulze et al. |
| 5,833,690 A | 11/1998 | Yates et al. |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,911,353 A | 6/1999 | Bolanos et al. |
| 5,915,616 A | 6/1999 | Viola et al. |
| 5,918,791 A | 7/1999 | Sorrentino et al. |
| 5,941,442 A | 8/1999 | Geiste et al. |
| 5,954,259 A | 9/1999 | Viola et al. |
| 5,988,479 A | 11/1999 | Palmer |
| 6,010,054 A | 1/2000 | Johnson et al. |
| 6,017,356 A | 1/2000 | Frederick et al. |
| 6,022,352 A | 2/2000 | Vandewalle |
| 6,032,849 A | 3/2000 | Mastri et al. |
| 6,079,606 A | 6/2000 | Milliman et al. |
| 6,083,234 A | 7/2000 | Nicholas et al. |
| 6,102,271 A | 8/2000 | Longo et al. |
| 6,109,500 A | 8/2000 | Alli et al. |
| H1904 H | 10/2000 | Yates et al. |
| 6,131,789 A | 10/2000 | Schulze et al. |
| 6,155,473 A | 12/2000 | Tompkins et al. |
| 6,171,330 B1 | 1/2001 | Benchetrit |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,315,184 B1 | 11/2001 | Whitman |
| 6,320,123 B1 | 11/2001 | Reimers |
| 6,330,965 B1 | 12/2001 | Milliman et al. |
| 6,358,224 B1 | 3/2002 | Tims et al. |
| 6,412,639 B1 | 7/2002 | Hickey |
| 6,416,486 B1 | 7/2002 | Wampler |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,522,101 B2 | 2/2003 | Malackowski |
| 6,619,529 B2 | 9/2003 | Green et al. |
| 6,629,988 B2 | 10/2003 | Weadock |
| 6,644,532 B2 | 11/2003 | Green et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,773,438 B1 | 8/2004 | Knodel et al. |
| 6,786,382 B1 | 9/2004 | Hoffman |
| 6,793,652 B1 | 9/2004 | Whitman et al. |
| 6,805,273 B2 | 10/2004 | Bilotti et al. |
| 6,817,509 B2 | 11/2004 | Geiste et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,066,944 B2 | 6/2006 | Laufer et al. |
| 7,083,075 B2 | 8/2006 | Swayze et al. |
| 7,097,089 B2 | 8/2006 | Marczyk |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,159,750 B2 | 1/2007 | Racenet et al. |
| 7,168,604 B2 | 1/2007 | Milliman et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,225,964 B2 | 6/2007 | Mastri et al. |
| 7,246,734 B2 | 7/2007 | Shelton, IV |
| 2002/0117534 A1 | 8/2002 | Green et al. |
| 2003/0216778 A1 | 11/2003 | Weadock |
| 2004/0028502 A1 | 2/2004 | Cummins |
| 2004/0094597 A1 | 5/2004 | Whitman et al. |
| 2004/0097987 A1 | 5/2004 | Pugsley et al. |
| 2004/0108357 A1 | 6/2004 | Milliman et al. |
| 2004/0111081 A1 | 6/2004 | Whitman et al. |
| 2004/0122471 A1 | 6/2004 | Toby et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232199 A1 | 11/2004 | Shelton, IV et al. |
| 2004/0232201 A1 | 11/2004 | Wenchell et al. |
| 2004/0243176 A1 | 12/2004 | Hahnen et al. |
| 2005/0006434 A1 | 1/2005 | Wales et al. |
| 2005/0021026 A1 | 1/2005 | Baily |
| 2005/0023324 A1 | 2/2005 | Doll et al. |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0103819 A1 | 5/2005 | Racenet et al. |
| 2005/0107824 A1 | 5/2005 | Hillstead et al. |
| 2005/0131390 A1 | 6/2005 | Heinrich et al. |
| 2005/0145671 A1 | 7/2005 | Viola |
| 2005/0165415 A1 | 7/2005 | Wales |
| 2005/0173490 A1 | 8/2005 | Shelton, IV |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0203550 A1 | 9/2005 | Laufer et al. |
| 2005/0230453 A1 | 10/2005 | Viola |
| 2005/0263562 A1 | 12/2005 | Shelton, IV et al. |

| Publication | Date | Inventor |
|---|---|---|
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0025813 A1 | 2/2006 | Shelton et al. |
| 2006/0025816 A1 | 2/2006 | Shelton |
| 2006/0049229 A1 | 3/2006 | Milliman et al. |
| 2006/0060630 A1 | 3/2006 | Shelton, IV et al. |
| 2006/0097026 A1 | 5/2006 | Shelton, IV |
| 2006/0100643 A1 | 5/2006 | Laufer et al. |
| 2006/0108393 A1 | 5/2006 | Heinrich et al. |
| 2006/0122636 A1 | 6/2006 | Bailley et al. |
| 2006/0142772 A1 | 6/2006 | Ralph et al. |
| 2006/0149163 A1 | 7/2006 | Hibner et al. |
| 2006/0151567 A1 | 7/2006 | Roy |
| 2006/0226196 A1 | 10/2006 | Hueil et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0034666 A1 | 2/2007 | Holsten et al. |
| 2007/0034668 A1 | 2/2007 | Holsten et al. |
| 2007/0045379 A1 | 3/2007 | Shelton, IV |
| 2007/0073340 A1 | 3/2007 | Shelton, IV et al. |
| 2007/0075114 A1 | 4/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0102476 A1 | 5/2007 | Shelton, IV et al. |
| 2007/0106317 A1 | 5/2007 | Shelton, IV et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |

FOREIGN PATENT DOCUMENTS

| | | |
|---|---|---|
| CA | 2514274 A1 | 1/2006 |
| DE | 273689 C | 5/1914 |
| DE | 9412228 U | 9/1994 |
| DE | 69328576 T2 | 1/2001 |
| DE | 20112837 U1 | 10/2001 |
| DE | 20121753 U1 | 4/2003 |
| DE | 10314072 B1 | 10/2004 |
| EP | 0122046 A1 | 10/1984 |
| EP | 0033548 B1 | 5/1986 |
| EP | 0639349 A2 | 2/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0669104 A1 | 8/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0603472 B1 | 11/1998 |
| EP | 0878169 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520523 A1 | 4/2005 |
| EP | 1520525 A1 | 4/2005 |
| EP | 1522264 A1 | 4/2005 |
| EP | 1550408 A1 | 7/2005 |
| EP | 1557129 A1 | 7/2005 |
| EP | 1064883 B1 | 8/2005 |
| EP | 1621141 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1300117 B1 | 8/2007 |
| FR | 1112936 A | 3/1956 |
| GB | 939929 A | 10/1963 |
| GB | 2336214 A | 10/1999 |
| JP | 6007357 A | 1/1994 |
| JP | 7051273 A | 2/1995 |

| | | | |
|---|---|---|---|
| JP | 8033641 A | 2/1996 |
| JP | 8229050 A1 | 9/1996 |
| JP | 2001286477 A | 10/2001 |
| JP | 2002369820 A | 12/2002 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/29639 A1 | 11/1995 |
| WO | WO 96/35464 A1 | 11/1996 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 00/57796 A1 | 10/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/17799 A1 | 3/2002 |
| WO | WO 02/30297 A2 | 4/2002 |
| WO | WO 02/043571 A2 | 6/2002 |
| WO | WO 02/067785 A2 | 9/2002 |
| WO | WO 03/000138 A2 | 1/2003 |
| WO | WO 03/001329 A2 | 1/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105702 A2 | 12/2003 |
| WO | WO 2004/006980 A2 | 1/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2005/027983 A2 | 3/2005 |
| WO | WO 2005/096954 A2 | 10/2005 |
| WO | WO 2006/044490 A2 | 4/2006 |
| WO | WO 2006/044581 A2 | 4/2006 |
| WO | WO 2003/083748 A1 | 8/2006 |
| WO | WO 2006/132992 A1 | 12/2006 |
| WO | WO 2007/016290 A2 | 2/2007 |

OTHER PUBLICATIONS

U.S. Appl. No. 11/475,412, filed Jun. 27, 2006.
U.S. Appl. No. 11/497,898, filed Aug. 2, 2006.
U.S. Appl. No. 11/497,831, filed Aug. 2, 2006.
U.S. Appl. No. 11/497,770, filed Aug. 2, 2006.
U.S. Appl. No. 11/497,760, filed Aug. 2, 2006.
U.S. Appl. No. 11/497,832, filed Aug. 2, 2006.
U.S. Appl. No. 11/497,937, filed Aug. 2, 2006.
U.S. Appl. No. 11/498,282, filed Aug. 2, 2006.
Disclosed Anonymously, "Motor-Driven Surgical Stapler Improvements," Research Disclosure Database No. 526041, Published: Feb. 2008.

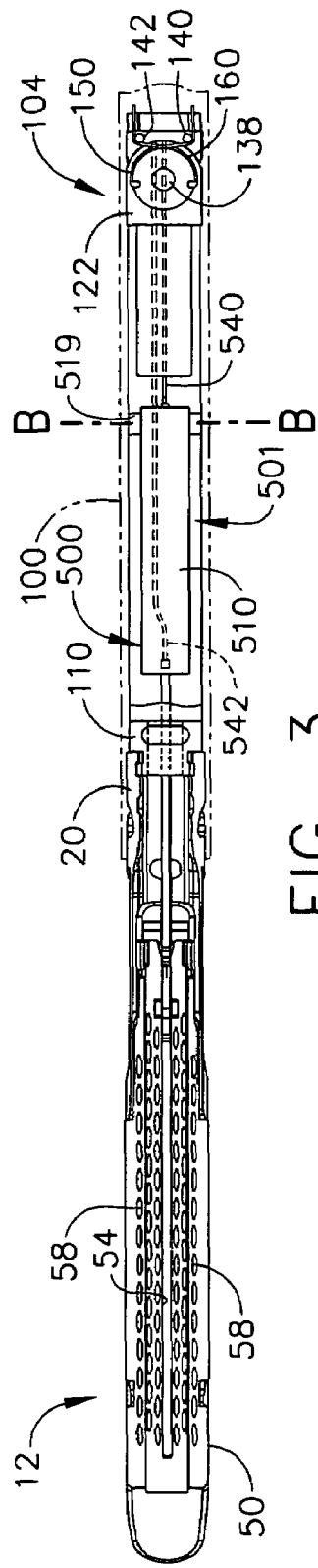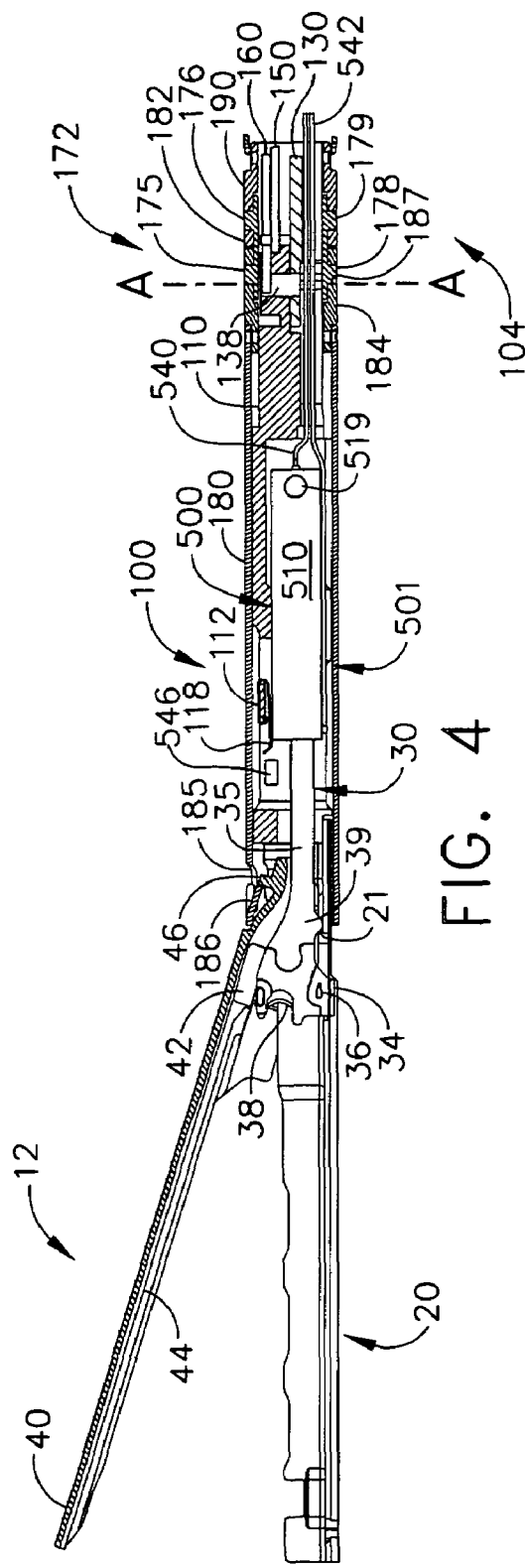

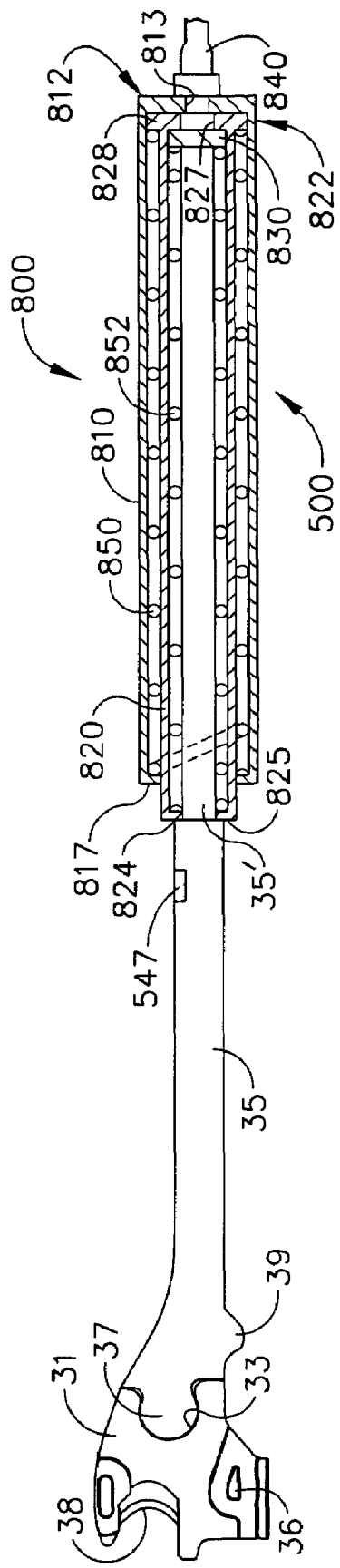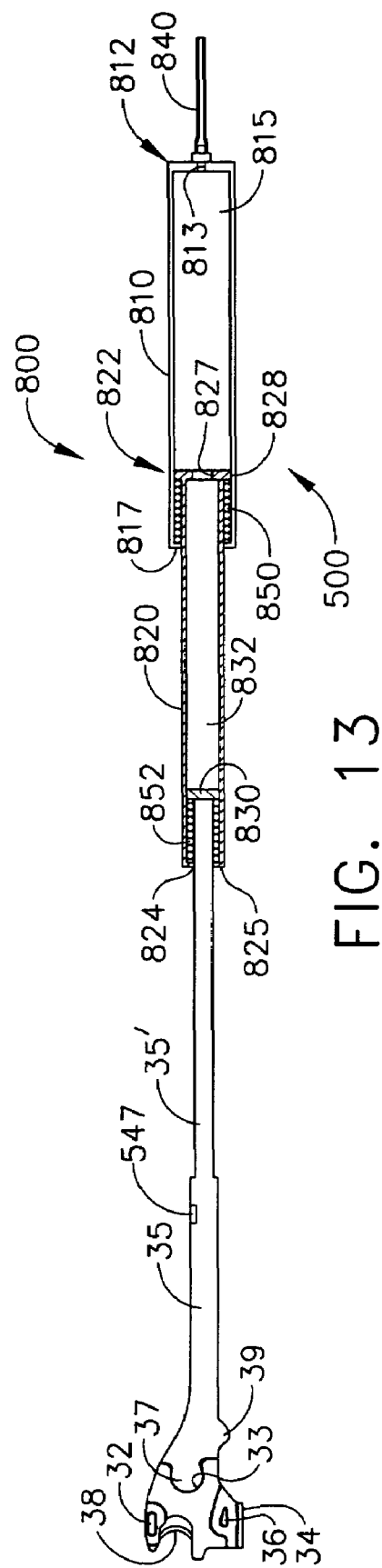

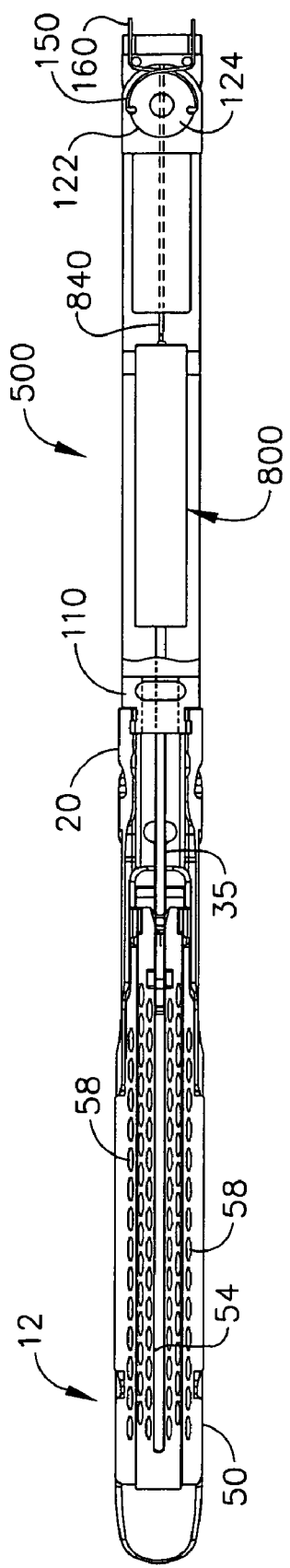
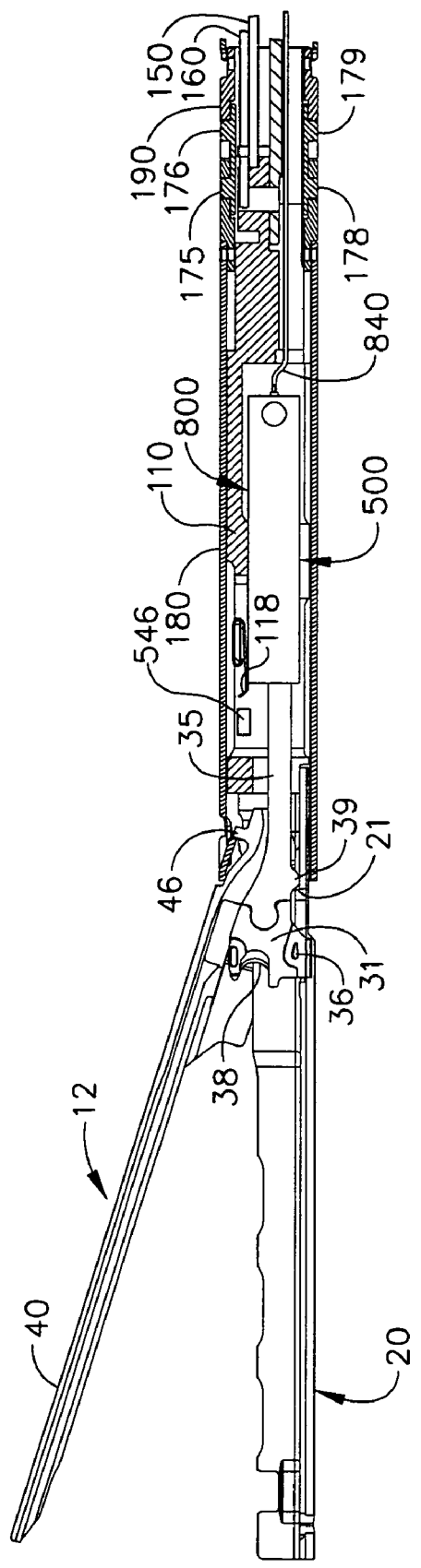
FIG. 14
FIG. 15

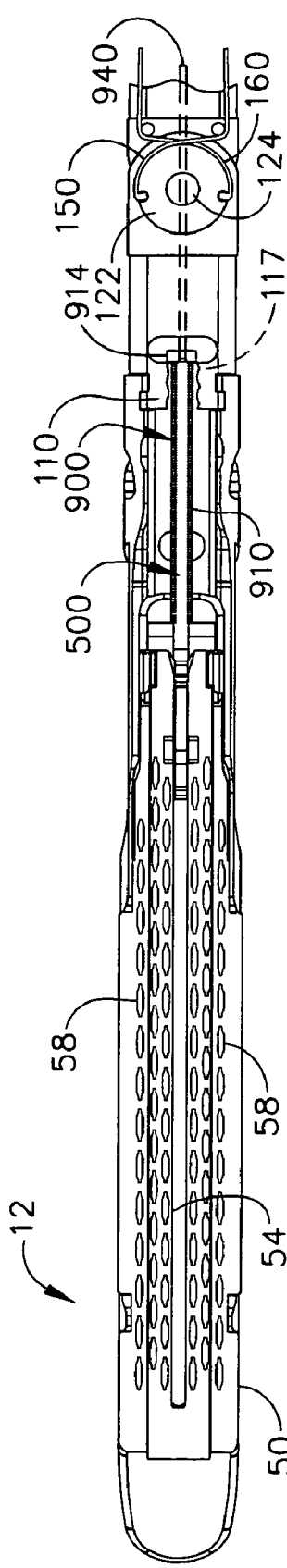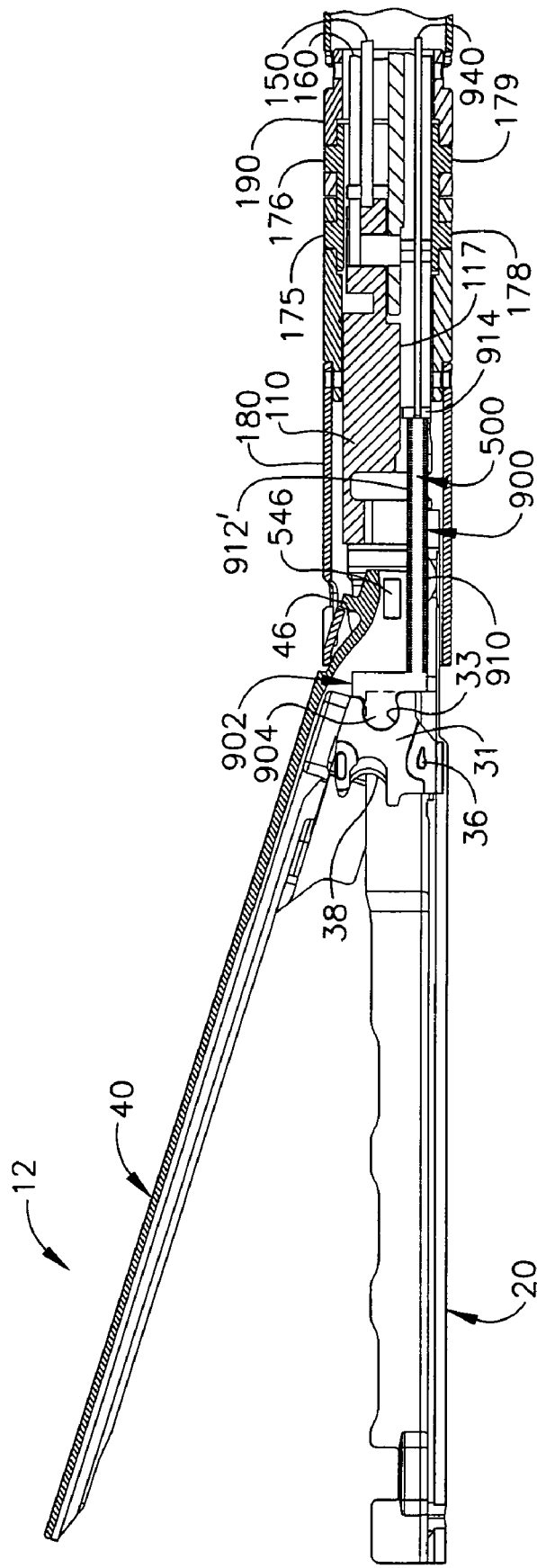

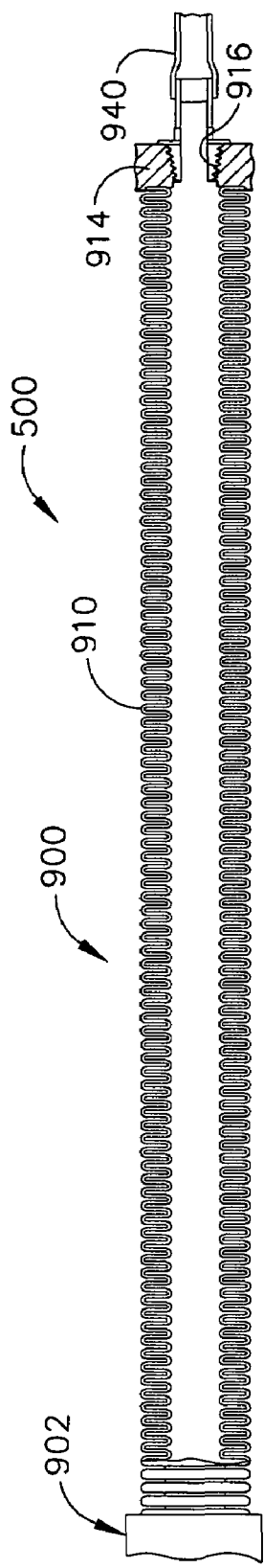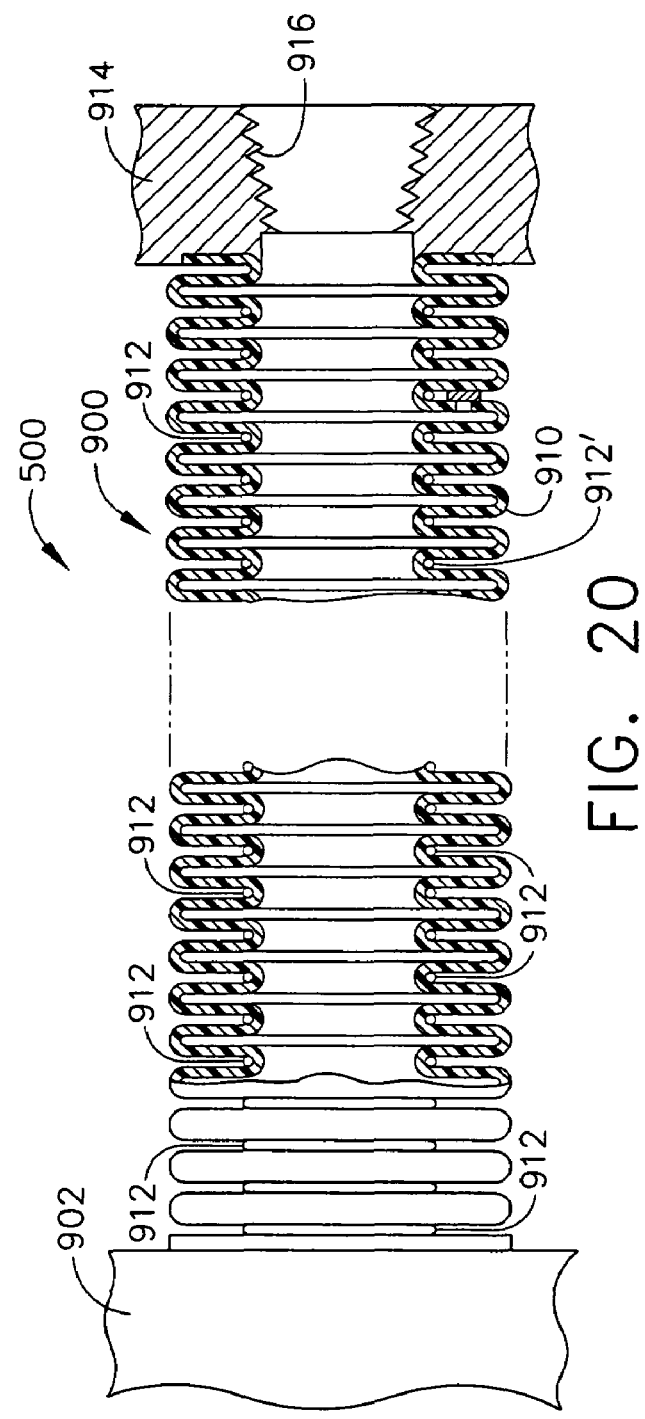

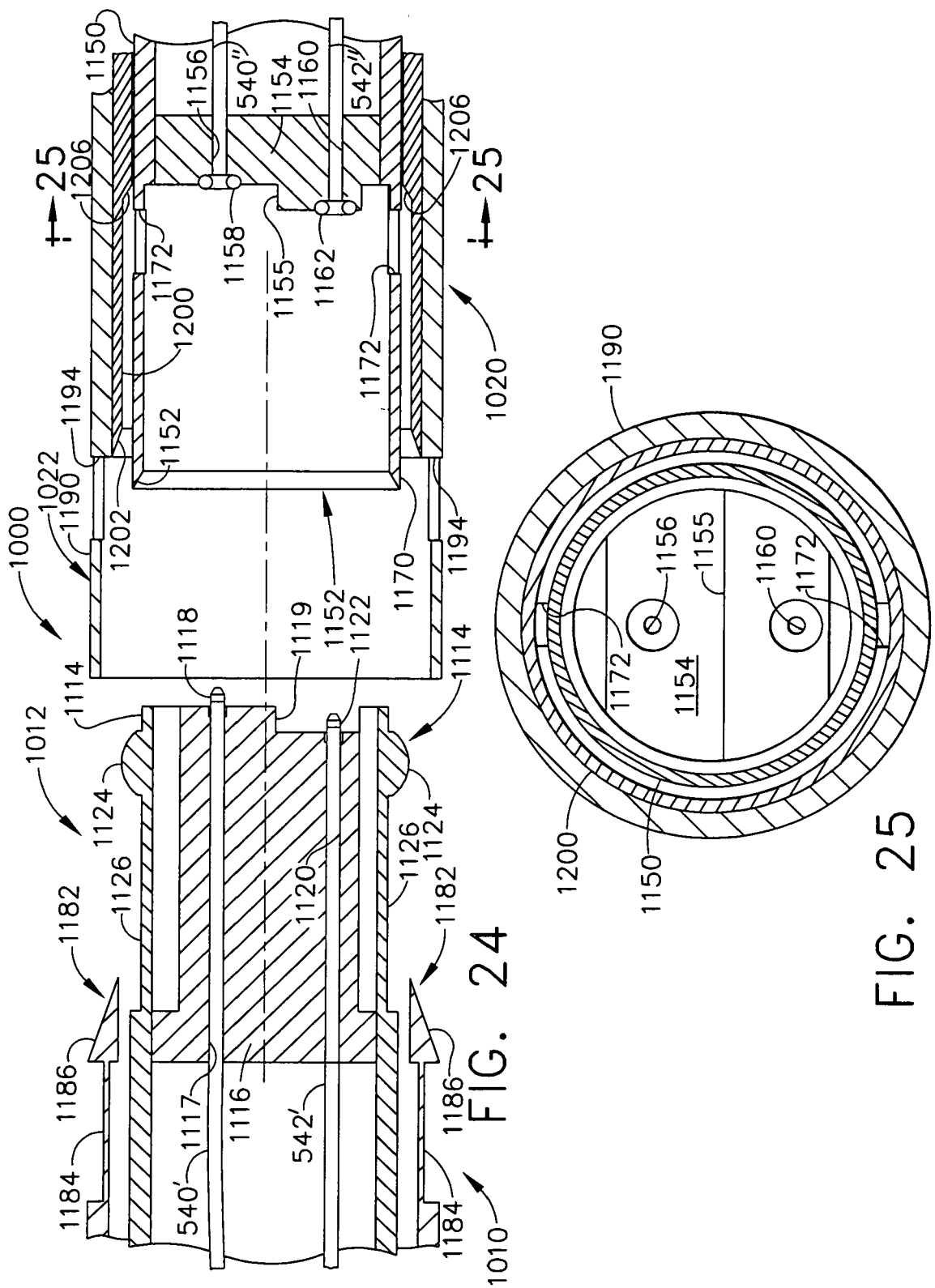

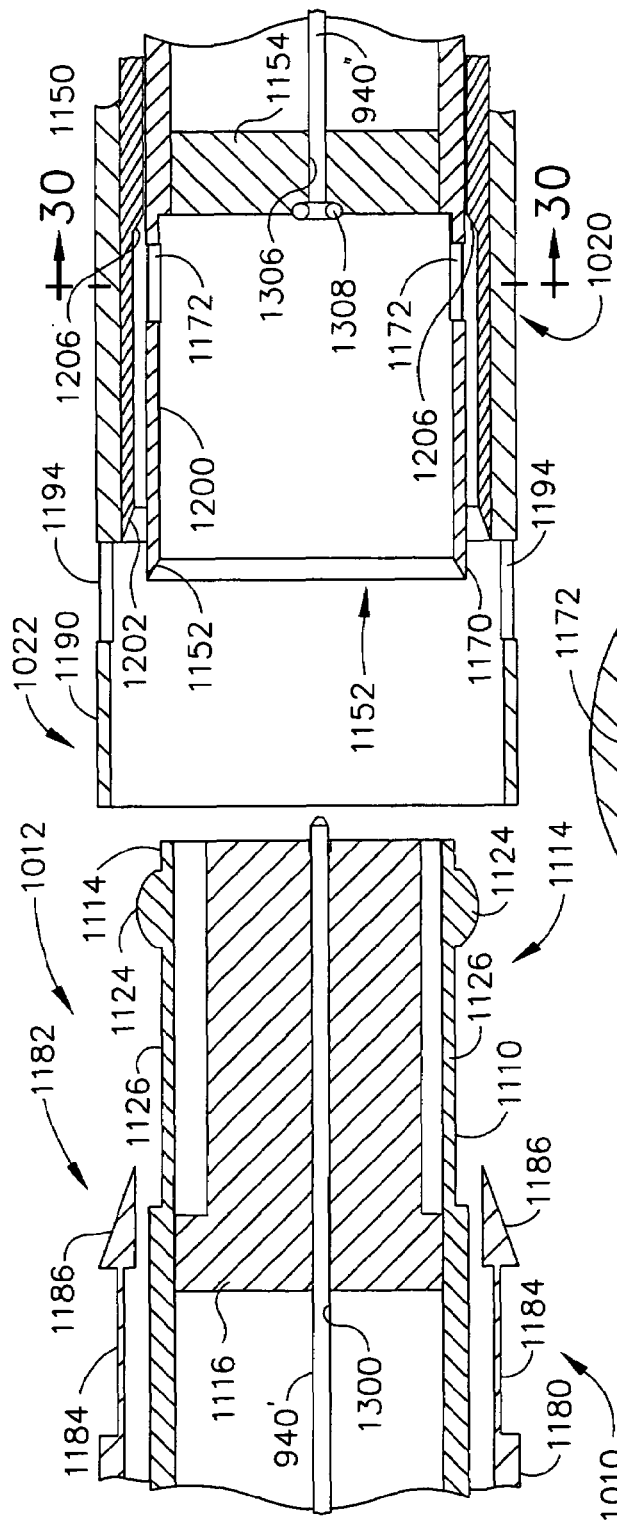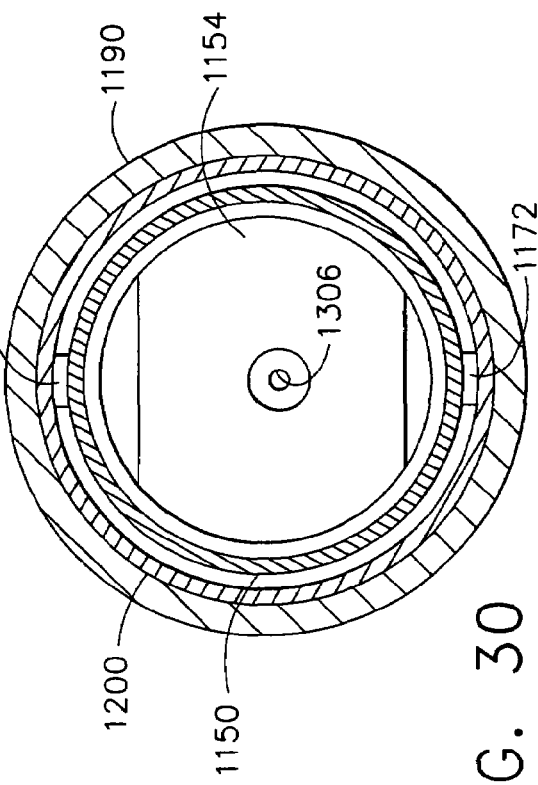
FIG. 29
FIG. 30

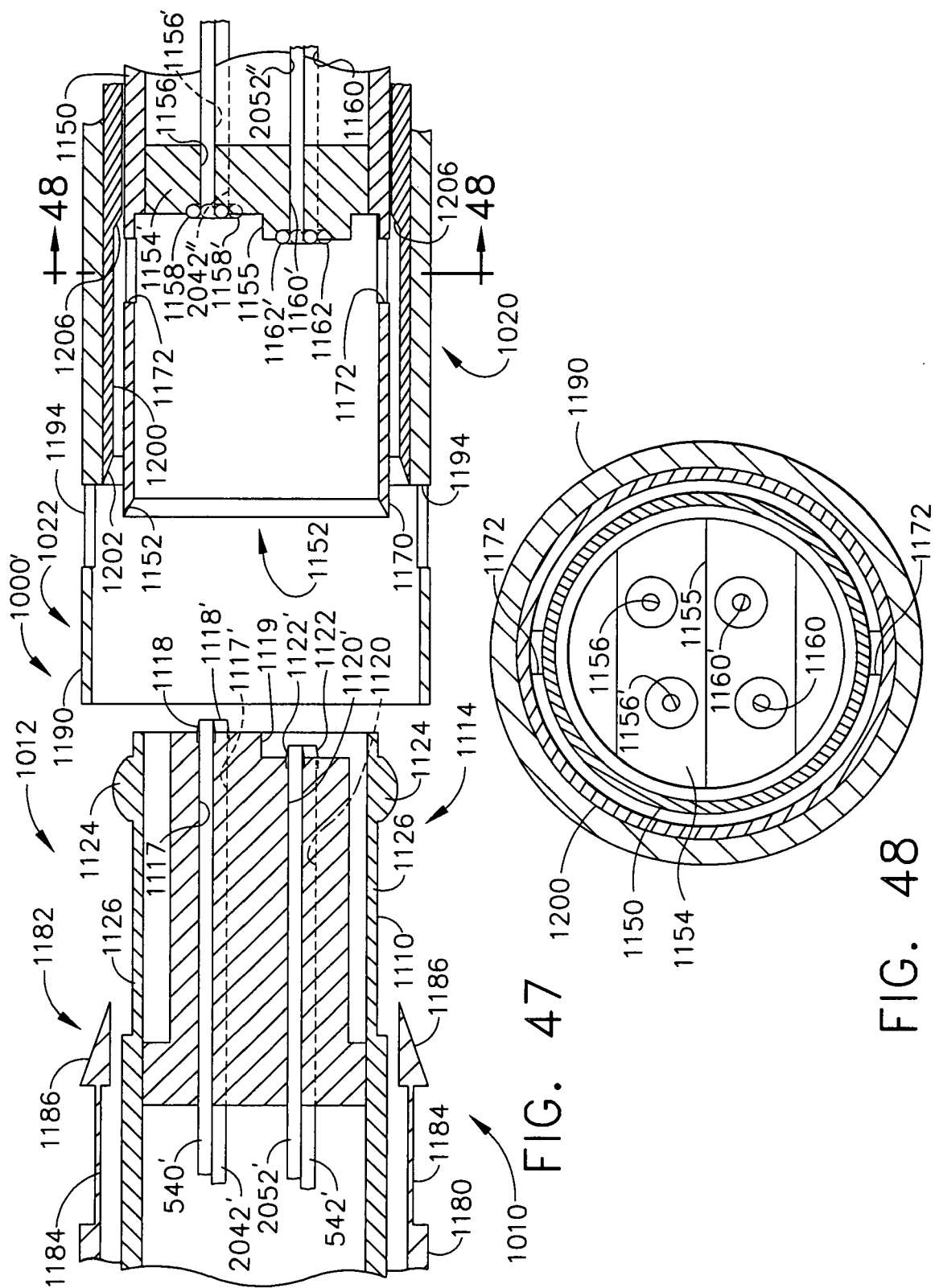

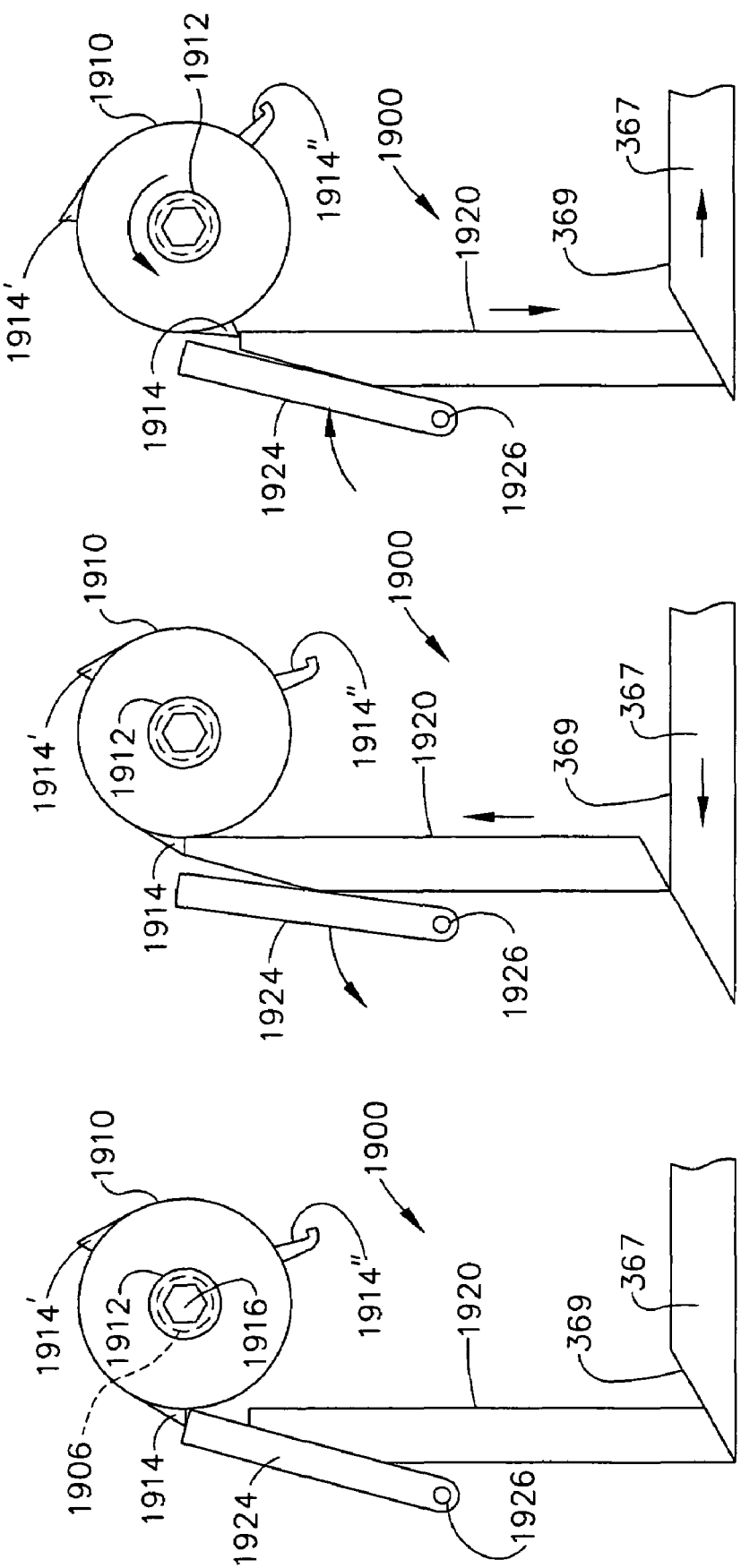

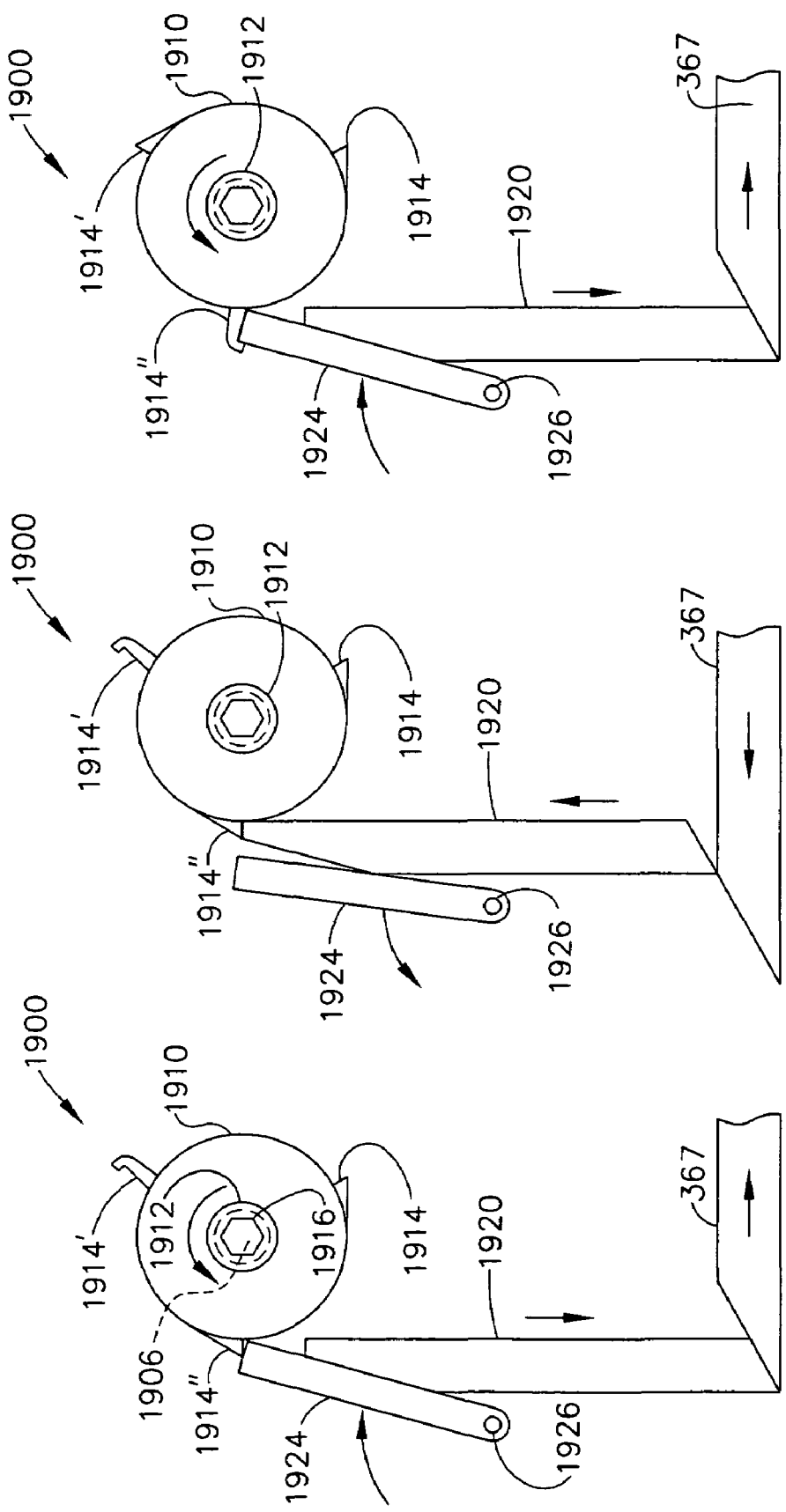

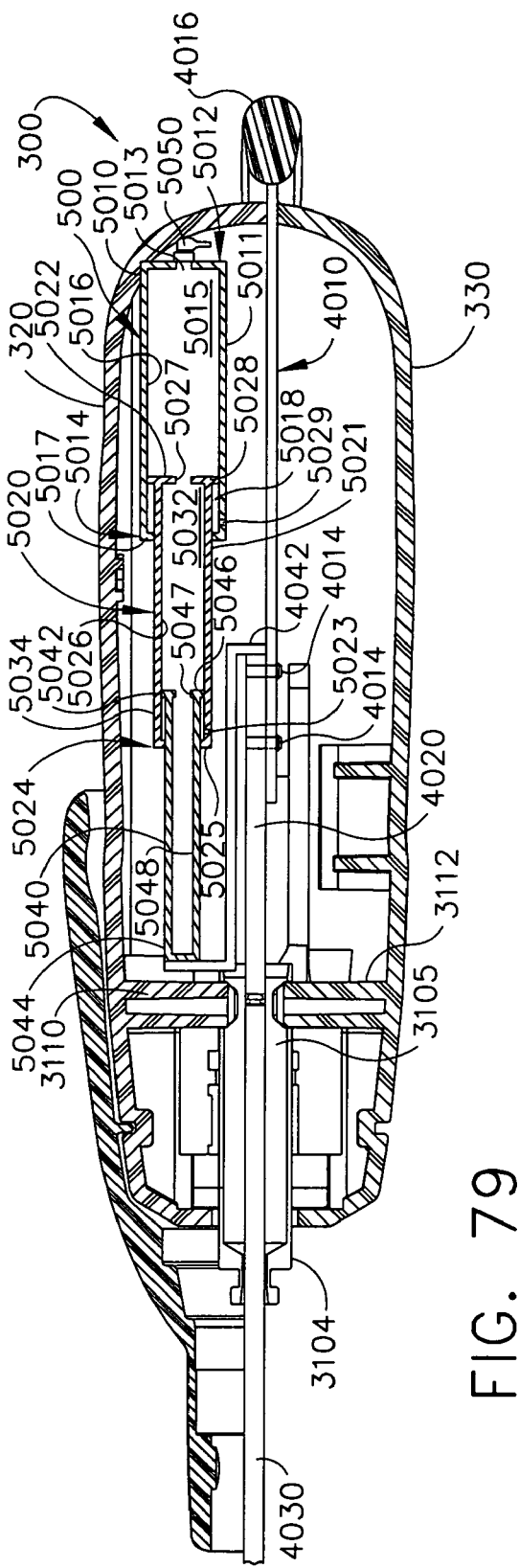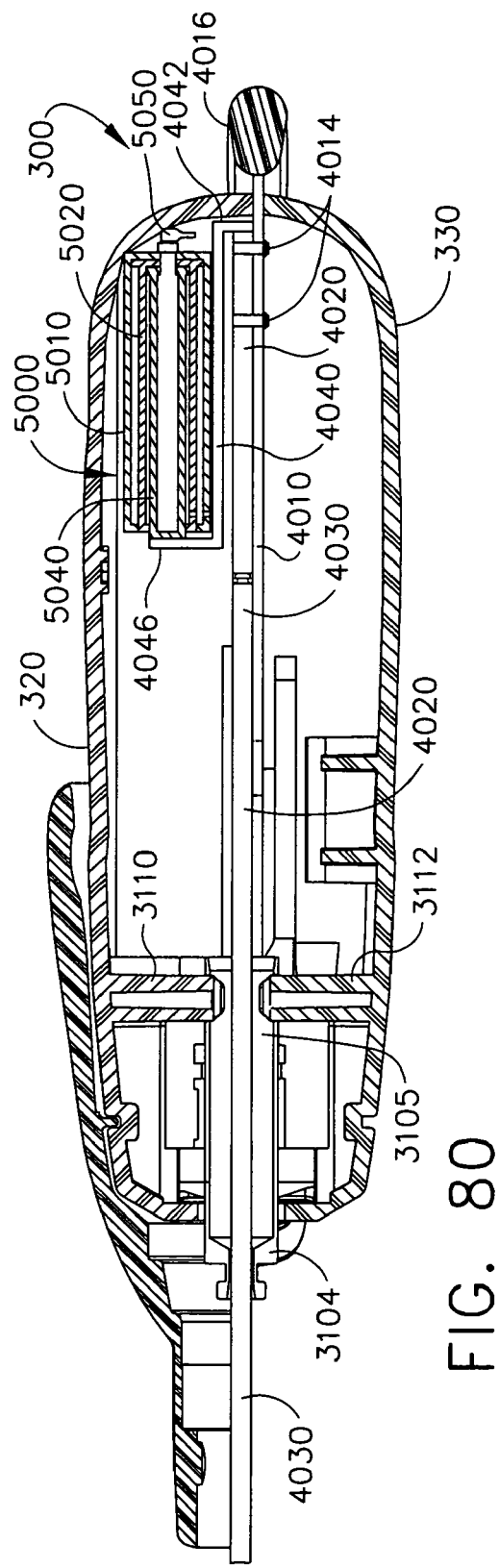
FIG. 79
FIG. 80

PNEUMATICALLY POWERED SURGICAL CUTTING AND FASTENING INSTRUMENT WITH MANUALLY OPERATED RETRACTION APPARATUS

CROSS REFERENCE TO RELATED APPLICATIONS

This application is related to the following concurrently-filed U.S. patent applications, which are incorporated herein by reference:

(1) PNEUMATICALLY POWERED SURGICAL CUTTING AND FASTENING INSTRUMENT WITH ACTUATOR AT DISTAL END; Inventors: Frederick E. Shelton, IV, Jerome R. Morgan, Eugene L. Timperman, and Leslie M. Fugikawa, application Ser. No. 11/497,832;

(2) PNEUMATICALLY POWERED SURGICAL CUTTING AND FASTENING INSTRUMENT WITH A VARIABLE CONTROL OF THE ACTUATING RATE OF FIRING WITH MECHANICAL POWER ASSIST; Inventors: Frederick E. Shelton, IV, Jerome R. Morgan, Eugene L. Timperman, and Leslie M. Fugikawa, application Ser. No. 11/497,898;

(3) PNEUMATICALLY POWERED SURGICAL CUTTING AND FASTENING INSTRUMENT WITH AUDIBLE AND VISUAL FEEDBACK FEATURES; Inventors: Frederick E. Shelton, IV, Jerome R. Morgan, Eugene L. Timperman, and Leslie M. Fugikawa, application Ser. No. 11/497,937;

(4) PNEUMATICALLY POWERED SURGICAL CUTTING AND FASTENING INSTRUMENT WITH REPLACEABLE POWER SOURCES; Inventors: Frederick E. Shelton, IV, Jerome R. Morgan, Eugene L. Timperman, and Leslie M. Fugikawa, application Ser. No. 11/497,831;

(5) PNEUMATICALLY POWERED SURGICAL CUTTING AND FASTENING INSTRUMENT WITH IMPROVED VOLUME STORAGE; Inventors: Frederick E. Shelton, IV and Jerome R. Morgan, application Ser. No. 11/497,770;

(6) PNEUMATICALLY POWERED SURGICAL CUTTING AND FASTENING INSTRUMENT WITH MECHANICAL LINKAGE COUPLING END EFFECTOR AND TRIGGER MOTION; Inventors: Frederick E. Shelton, IV, Jerome R. Morgan, Eugene L. Timperman, and Leslie M. Fugikawa, application Ser. No. 11/498,282; and (7) SURGICAL CUTTING AND FASTENING INSTRUMENT WITH DISTALLY MOUNTED PNEUMATICALLY POWERED ROTARY DRIVE MEMBER; Inventors: Frederick E. Shelton, IV, Jerome R. Morgan, Eugene L. Timperman, and Leslie M. Fugikawa, application Ser. No. 11/497,760.

BACKGROUND

The present invention generally concerns surgical instruments and, more particularly, pneumatically powered surgical cutting and fastening instruments. The present invention may have application in conventional endoscopic and open surgical instrumentation as well as application in robotic-assisted surgery.

Surgical cutting and fastening instruments (staplers) have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Over the years, a variety of different methods for actuating the cutting and staple deployment components have been developed. For example, U.S. Pat. No. 6,978,921 to Shelton, IV et al. discloses a surgical stapling instrument that employs tissue severing and staple deployment components that are driven through manual actuation of various trigger mechanisms on the handle. Other surgical stapling apparatuses have been developed that employ battery powered motors. Such a device is disclosed in U.S. Pat. No. 5,954,259 to Viola et al. Still other surgical staplers are actuated by a source of pressurized gas. For example, U.S. Pat. No. 6,619,529 to Green et al. discloses a surgical stapler that employs a source of pressurized gas in the handle that is used to power a cylinder that is also located within the handle. The cylinder houses a piston assembly that is actuated by admission of the pressurized gas into the cylinder. The piston is configured to coact with components located in the elongated tube portion and handle member to cause the deployment of the staples and the surgical knife in the distally mounted end effector. Such design, however, employs a complex collection of components for transmitting the motion of the handle-mounted piston to the components located in the end effector portion of the device. In addition, when using such a device, there is a risk that the power source becomes depleted during the surgical procedure because there is no way of monitoring the amount of gas remaining in the gas cartridge. If this occurs during the firing or retraction cycles, such devices lack means for easily exchanging the spent container with a new container or auxiliary power source.

Another pneumatically powered surgical stapling device is disclosed in US Patent Publication No. US 2006/0151567 to Roy. This device employs a pneumatically powered motor or piston system supported in the handle of the device for creating a motion that is employed to actuate the end effector. This device may be powered by removable cartridges or from an external power source, such as the hospital's existing pneumatic air or gas supply.

Such pneumatically powered devices that employ cartridges or containers in the handle portion of the device are also hampered by the size of the gas cylinder required to store the pressurized gas at sufficient volumes to facilitate actuation of the device a desired number of times at a minimum usable pressure. In the past, devices designed for large numbers of applications/procedures would either require a large cylinder to be used or, if smaller cylinders were used, such cylinders would have undesirably high pressures. In addition, devices that employ removable cartridges that can be used an unlimited number of times must be reprocessed and resterilized. Such arrangements can dramatically change performance capabilities and may therefore be less desirable.

Other problems exist with prior pneumatically actuated endocutters. For example, once the surgeon activates the instrument through a single switch or activation trigger, the instrument progresses through or at least attempts to complete the firing cycle. Thereafter, the firing components may be retracted by the drive system. While the surgeon employing the device disclosed in US Patent Publication US 2006/0151567 can interrupt the firing cycle and/or adjust the flow of gas to the device through a trigger assembly, there is no means to monitor the device's progress. In addition, such prior devices lack a means for manually retracting the knife and firing bar mechanism, should operating pressure be lost or interrupted during the procedure. Further, that device lacks a means for enabling the clinician to manually apply additional force to the drive system to assist with the advancement of the firing mechanism or to slow its advancement.

Consequently there is a need for a pneumatically powered surgical stapling device that does not require the use of an extensive collection of components to transfer the pneumatically generated stapling and firing motions to the end effector components.

There is another need for a pneumatically powered surgical stapling device that provides a means for the surgeon to control and monitor the progress of the device as it moves through the firing and retraction cycles.

There is another need for a pneumatically powered surgical stapling device that provides tactile and other feedback to the surgeon concerning the forces encountered during firing and also notification of when the device has reached its actuated position and is ready to be retracted.

There is a need for a pneumatically powered surgical stapling device that is economical and has the ability to easily interchange power sources, while limiting the number of times that such sources may be interchanged.

There is another need for methods and apparatuses for more efficiently storing gas in cylinders used to power surgical stapling devices such that more uses can be powered from a single cylinder.

There is still another need for a pneumatically powered stapling device that has means for manually retracting the knife and firing bar assembly should pneumatic power be lost or interrupted.

There is yet other need for devices with one or more of the above mentioned features and that also has an end effector that can be selectively articulated relative to the handle assembly and/or portion of the elongate shaft assembly to which it is attached.

There is still another need for devices with one or more of the above-identified features that is also capable of accommodating removably attachable end effectors to facilitate use of the device in connection with disposable end effector arrangements.

SUMMARY

In one general aspect, the present invention is directed to a surgical instrument for use in connection with a pneumatically powered tool having a firing mechanism operably supported therein that is movable between an unactuated position and an actuated position. In various embodiments, the surgical instrument comprises a drive system operably communicating with the pneumatically powered tool and being configured to selectively apply at least a drive system generated firing motion to the firing mechanism of the pneumatically powered tool to cause the firing mechanism to move from the unactuated position to the actuated position in response to a flow of gas from a source of gas fluidically coupled to the drive system. The surgical instrument further comprises a retraction member that communicates with the drive system to enable a manually generated retraction motion to be applied to the driev system to manually move the firing mechanism in a distal direction from the actuated position to the unactuated position.

In another general aspect, the present invention is directed to a surgical instrument that comprises a handle assembly and a closure drive that is supported by the handle assembly. The closure drive may be configured to generate a closing motion and an opening motion. A pneumatically powered drive system may be supported by the handle assembly and is configured to selectively generate a firing motion and a retraction motion. An elongate shaft assembly may be coupled to the handle assembly. The elongate shaft may communicate with the closure drive to transfer the opening and closing motions and may also communicate with the pneumatically powered drive system to transfer the firing and retraction motions. The instrument may further comprise an end effector that is coupled to the elongate shaft assembly. In various embodiments the end effector may comprise an elongate channel that is sized to receive a staple cartridge therein and further have an anvil that is pivotally coupled to the elongate channel and which is pivotally responsive to the open and closing motions from the elongate shaft assembly. The end effector may further include a firing mechanism that is operably supported within one of the elongate channel and the staple cartridge and is movable from an unactuated position to an actuated position in response to an application of the firing motion from the pneumatically powered drive system. The firing mechanism may be further movable from the actuated position to the unactuated position in response to another application of the retraction motion from the pneumatically powered drive system. Various embodiments further include a retraction member that communicates with the pneumatically powered drive system to enable a manually generated retraction motion to be applied thereto to manually move the firing mechanism in a distal direction from the actuated position to the unactuated position.

DRAWINGS

Various embodiments of the present invention are described herein by way of example in conjunction with the following Figures, wherein like numerals may be used to describe like parts and wherein:

FIG. 3 is a top view of the end effector of FIGS. 1 and 2 with the anvil portion removed therefrom and the closure tube assembly illustrated in phantom lines;

FIG. 4 is a cross-sectional side elevational view of the end effector arrangement of FIG. 3 with the anvil portion attached thereto and shown in an open position;

FIG. 12 is a side view of another knife bar and firing drive member arrangement of the present invention with the knife bar being retracted into a cylinder assembly shown in cross-section;

FIG. 13 is another side view of the knife bar and cylinder arrangements depicted in FIG. 12 with the knife bar in the extended position;

FIG. 14 is a top view of an end effector and spine assembly arrangement housing the cylinder and knife bar arrangements depicted in FIGS. 12 and 13;

FIG. 15 is a cross-sectional side elevational view of the end effector and spine assembly arrangement depicted in FIG. 14 with the anvil portion attached thereto and in the open position;

FIG. 17 is a top view of another knife bar and spine assembly arrangement that supports another firing drive member in the form of a bellows assembly of another embodiment of the present invention;

FIG. 18 is a cross-sectional side elevational view of the end effector and spine assembly arrangements of the embodiment depicted in FIG. 17;

FIG. 19 is a partial cross-sectional assembly view of a bellows assembly of the embodiments depicted in FIGS. 17 and 18;

FIG. 20 is an enlarged view of a portion of the bellows assembly of FIG. 19;

FIG. 24 is a cross-sectional view of the quick disconnect joint arrangement of the embodiment of FIGS. 22 and 23 prior to coupling the distal shaft assembly to the proximal shaft assembly;

FIG. 25 is a cross-sectional view of the proximal shaft assembly taken along line 25-25 in FIG. 24;

FIG. 29 is a partial cross-sectional view of another quick disconnect joint arrangement that may be employed with the embodiment depicted in FIGS. 12-16A;

FIG. 30 is a cross-sectional view of the proximal shaft assembly taken along line 30-30 in FIG. 29;

FIG. 47 is a cross-sectional view of the quick disconnect joint arrangement of the embodiment of FIG. 46 prior to coupling the distal shaft assembly to the proximal shaft assembly;

FIG. 48 is a cross-sectional view of the joint assembly of the embodiments of FIG. 47 taken along line 48-48 in FIG. 47;

FIG. 64 is a diagrammatic view of a lockout system embodiment of the present invention in an initial position;

FIG. 65 is another diagrammatic view of the lockout system of FIG. 64 illustrating the action thereof when the grip portion is initially attached to the primary attachment portion of the handle assembly;

FIG. 66 is another diagrammatic view of the lock out system of FIGS. 64 and 65 prior to the second detachment of the grip portion from the primary attachment portion of the handle assembly;

FIG. 67 is another diagrammatic view of the lock out system of FIGS. 64-66 that illustrates the positions of the system components when the grip portion has been attached to the primary attachment portion;

FIG. 68 is another diagrammatic view of the lock out system of FIGS. 64-67 that illustrates the position of the system components during the second attachment of the grip portion to the primary attachment portion;

FIG. 69 is another diagrammatic view illustrating the lock out system after the grip portion has been attached to the primary attachment portion for the second and final time;

FIG. 79 is a top cross-sectional view of a handle assembly arrangement of the embodiments depicted in FIGS. 70-78 with the cylinder assembly in an extended position;

FIG. 80 is another top cross-sectional view of a handle assembly arrangement of the embodiments depicted in FIGS. 70-79 with the cylinder assembly in a retracted position;

DETAILED DESCRIPTION

Figure 1:
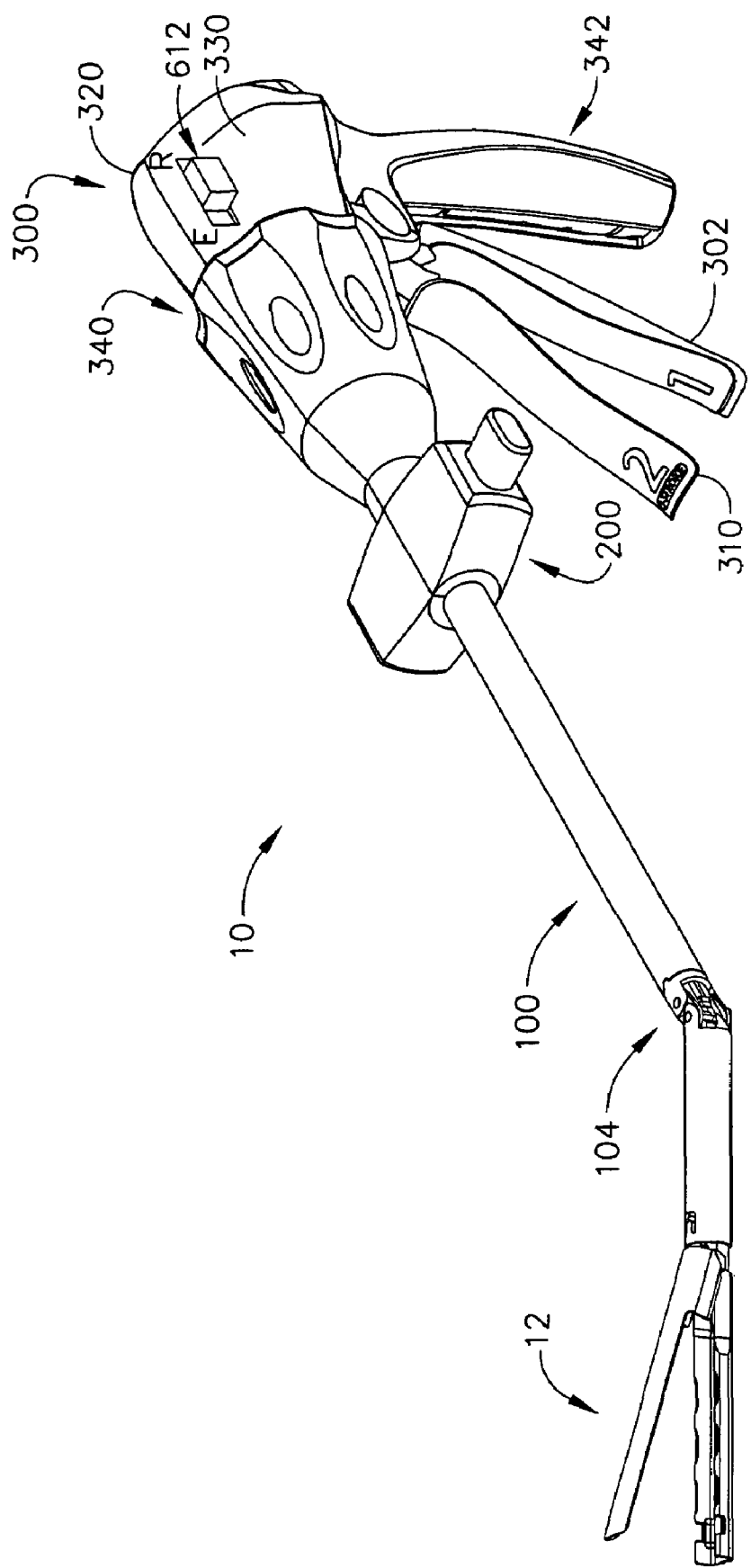
FIG. 1 is a perspective view of an embodiment of a surgical cutting and fastening instrument of the present invention.

Turning to the Drawings wherein like numerals denote like components throughout the several views, FIG. 1 depicts a surgical stapling and severing instrument 10 that is capable of practicing several unique benefits of the present invention. The embodiment illustrated in FIG. 1 includes a handle assembly 300, an elongate shaft assembly 100, and an end effector 12 that is connected to the elongate shaft assembly 100. Various embodiments of the present invention may include an end effector that is pivotally attached to the elongate shaft assembly 100 and pivotally driven by bending cables or bands such as those disclosed in U.S. patent application Ser. No. 11/329,020, filed Jan. 10, 2006, U.S. Patent Publication No. US-2007-0158385 A1 entitled "SURGICAL INSTRUMENT HAVING AN ARTICULATING END EFFECTOR", the disclosure of which is herein incorporated by reference. However, as the present Detailed Description proceeds, those of ordinary skill in the art will appreciate that various embodiments of the present invention may be successfully practiced in connection with end effector arrangements that employ different pivoting mechanisms and controls and, as will be explained in further detail below, may even be successfully employed with non-articulating end effector arrangements.

As can be seen in FIG. 1, the handle assembly 300 of the instrument 10 may include a closure trigger 302 and a firing trigger 310. It will be appreciated that instruments having end effectors directed to different surgical tasks may have different numbers or types of triggers or other suitable controls for operating an end effector. The end effector 12 is shown separated from the handle assembly 300 by the preferably elongate shaft assembly 100. A clinician may articulate the end effector 12 relative to the shaft assembly 100 by utilizing an articulation control 200.

It should be appreciated that spatial terms such as vertical, horizontal, right, left etc., are given herein with reference to the figures assuming that the longitudinal axis of the surgical instrument 10 is co-axial to the central axis of the elongate shaft assembly 100, with the triggers 302, 310 extending downwardly at an acute angle from the bottom of the handle assembly 300. In actual practice, however, the surgical instrument 10 may be oriented at various angles and, as such, these spatial terms are used relative to the surgical instrument 10 itself. Further, "proximal" is used to denote a perspective of a clinician who is behind the handle assembly 300 who places the end effector 12 distal, or away from him or herself.

As used herein, the term, "pressurized gas" refers to any gas suitable for use in pneumatically powered systems employed in a sterile environment. Non-limiting examples of such mediums include compressed air, carbon dioxide ($CO_2$), Nitrogen, Oxygen, Argon, Helium, Sodium Hydride, Propane, Isobutane, Butane Chlorofluorocarbons, Dimethyl ether. Methyl ethyl ether, Nitrous Oxide, Hyrdofluoroalkanes (HFA)—either, for example, HFA 134a (1,1,1,2,-tetrafluoroethane) or HFA 227 (1,1,1,2,3,3,3-heptafluoropropane).

As used herein, the term "fluidically coupled" means that the elements are coupled together with an appropriate line or other means to permit the passage of pressurized gas therebetween. As used herein, the term "line" as used in "supply line" or "return line" refers to an appropriate passage formed from rigid or flexible conduit, pipe, tubing, etc. for transporting pressurized gas from one component to another.

As used herein the terms "pneumatic signal" or "pneumatic drive signal" refer to the flow of gas from a source of pressurized gas to one or more components that are fluidically coupled to the source of pressurized gas or the flow of gas between components that are fluidically coupled together.

As used herein, the phrase, "substantially transverse to the longitudinal axis" where the "longitudinal axis" is the axis of the shaft, refers to a direction that is nearly perpendicular to the longitudinal axis. It will be appreciated, however, that directions that deviate some from perpendicular to the longitudinal axis are also substantially transverse to the longitudinal axis.

Figure 2:
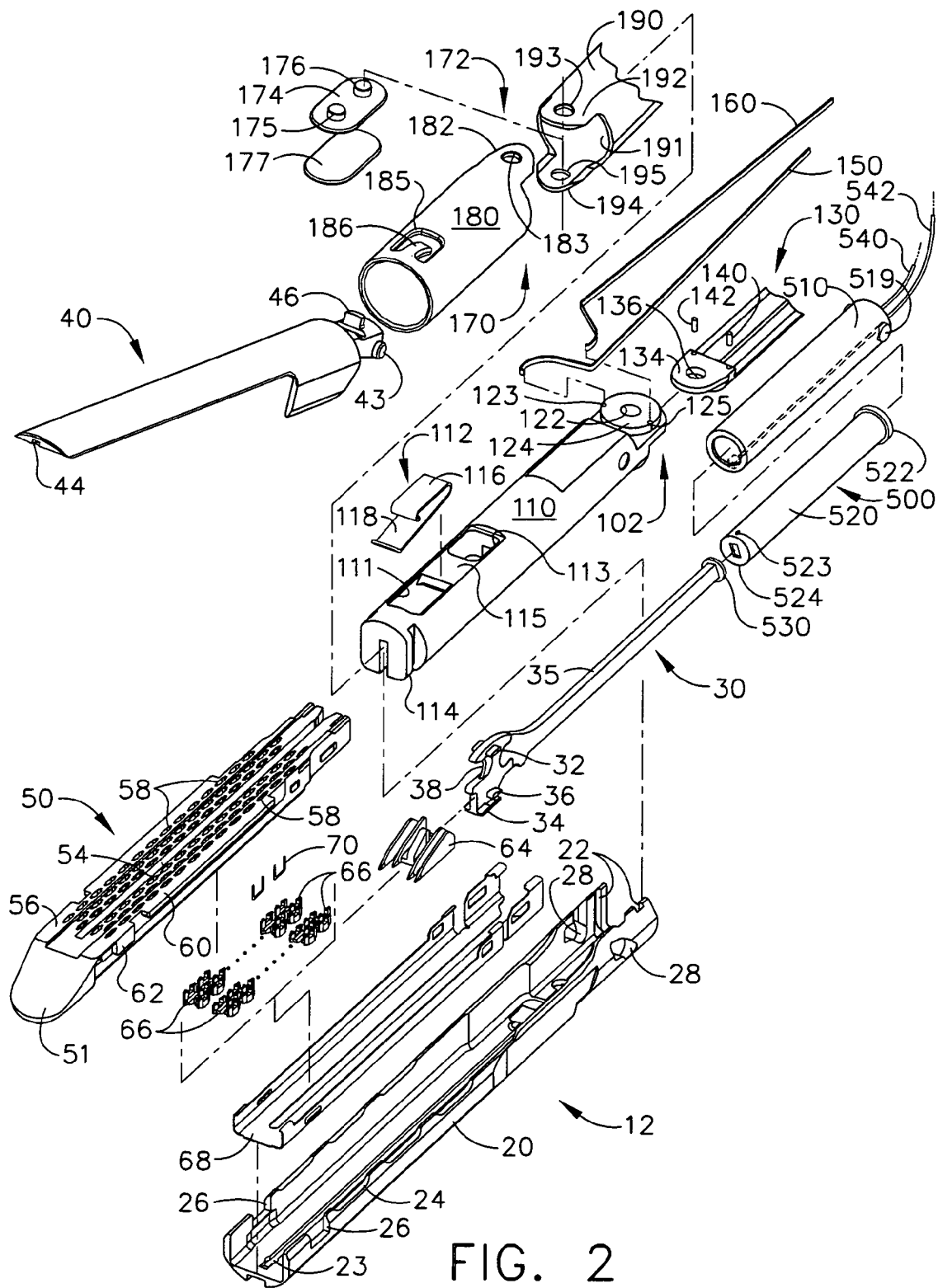
FIG. 2 is an exploded assembly view of an end effector arrangement that may be employed in connection with various embodiments of the present invention.

FIG. 2 illustrates an exploded assembly view of one type of pneumatically operated tool assembly or end effector that may be employed in various embodiments of the present invention. The pneumatically operated tool assembly 12 shown in FIGS. 1-4 is configured to act as an endocutter. As the present Detailed Description proceeds, however, it will be appreciated that various unique and novel drive arrangements of embodiments of the present invention could also be conceivably employed to drive other end effectors configured to perform other surgical tasks and thus requiring the removal, modification, or addition of components from what is shown in the Figures. Also, it will be appreciated that the end effectors 12 shown in FIGS. 1-4 may be customized for specific surgical applications.

One type of end effector that may be employed with various embodiments of the present invention is depicted in FIG. 2. As can be seen in that Figure, the end effector 12 employs an E-beam firing mechanism ("knife assembly") 30 that, in addition to cutting tissue and firing staples located in a staple cylinder seated therein, advantageously controls the spacing of an anvil portion of the end effector 12 relative to the staple cylinder. Various aspects of E-beam firing mechanisms are described in U.S. Pat. No. 6,978,921, entitled Surgical Stapling Instrument Incorporating An E-Beam Firing Mechanism to Shelton, I V. et al., the relevant portions of which are herein incorporated by reference. As the present Detailed Description proceeds, however, those of ordinary skill in the art will appreciate that other knife and firing mechanism configurations may be advantageously employed without departing from the spirit and scope of the present invention.

As used herein, the term "firing mechanism" refers to the portion or portions of the pneumatically powered tool and/or end effector that move from an unactuated position wherein the firing mechanism may be essentially at rest to an actuated or end position wherein that portion or portions have been moved or repositioned to a final position wherein such movement thereof resulted in the tool completing one or more actions in response to the application of at least one firing motion thereto. The firing mechanism may comprise, for example: (i) components that are completely supported by the pneumatically powered tool and interface with components in the surgical device; (ii) a combination of components that are located in the pneumatically powered tool and in the surgical device; or (ii) components that are supported by the surgical device and are movable into and out of the pneumatically powered tool. As used herein, the term "firing stroke" refers to the actual movement of the firing mechanism from the unactuated position to the actuated position. The term "retraction stroke" refers to the return movement of the firing mechanism from the actuated position to the unactuated position.

As can be seen in FIG. 2, the end effector 12 includes a distal member that, in various non-limiting embodiments, comprise an elongate channel 20 that has a pivotally translatable anvil 40 attached thereto. The elongate channel 20 is configured to receive and support a staple cartridge 50 that is responsive to the knife assembly 30 to drive staples 70 into forming contact with the anvil 40. It will be appreciated that, although a readily replaceable staple cartridge is advantageously described herein, a staple cartridge consistent with aspects of the present invention may be permanently affixed or integral to the elongate channel 20.

In various embodiments, the firing mechanism or knife assembly 30 includes vertically spaced pins that control the spacing of the end effector 12 during firing. In particular, upper pins 32 are staged to enter an anvil pocket 42 near the pivot between the anvil 40 and elongate channel 20. See FIG. 4. When fired with the anvil 40 closed, the upper pins 32 advance distally within a longitudinal anvil slot 44 extending distally through anvil 40. Any minor upward deflection in the anvil 40 is overcome by a downward force imparted by the upper pins 32.

Knife assembly 30 also includes a knife bar cap 34 that upwardly engages a channel slot 23 (FIG. 2) formed in the elongate channel 20, thereby cooperating with the upper pins 32 to draw the anvil 40 and the elongate channel 20 slightly closer together in the event of excess tissue clamped therebetween. In various embodiments, the knife assembly 30 may advantageously include middle pins 36 that pass through a firing drive slot (not shown) formed in a lower surface of the cartridge 50 and an upward surface of the elongate channel 20, thereby driving the staples 70 therein as described below. The middle pins 36, by sliding against the elongate channel 20, advantageously resist any tendency for the end effector 12 to be pinched shut at its distal end. However, the unique and novel aspects of various embodiments of the present invention may be attained through use of other knife assembly arrangements.

Returning to FIG. 2, a distally presented cutting edge 38 between the upper and middle pins 32, 36 on the knife assembly 30 traverses through a proximally presented, vertical slot 54 in the cartridge 50 to sever clamped tissue. The affirmative positioning of the knife assembly 30 with regard to the elongate channel 20 and anvil 40 assure that an effective cut is performed. In various embodiments, the lower surface of the anvil 40 may be provided with a plurality of staple forming pockets therein (not shown) that are arrayed to correspond to a plurality of staple apertures 58 in an upper surface 56 of the staple cartridge 50 when the staple cartridge 50 is received within the elongate channel. In various embodiments, the staple cartridge 50 may be snap fit into the elongate channel 20. Specifically, extension features 60, 62 of the staple cartridge 50 functionally and releasably engage recesses 24, 26, respectively of the elongate channel 20.

As can also be seen in FIG. 2, the staple cartridge 50 comprises a cartridge body 51, a wedge sled 64, staple drivers 66, staples 70, and a cartridge tray 68. When assembled, the cartridge tray 68 holds the wedge sled 64, staple drivers 66, and staples 70 inside the cartridge body 51. The elongate channel 20 is coupled to the handle assembly 300 by the elongate shaft assembly 100 which includes a distal spine or frame section 110 and a proximal spine or frame section 130. The elongate channel 20 has proximally placed attachment cavities 22 that each receive a corresponding channel anchoring member 114 formed on the distal end of the distal spine section 110. The elongate channel 20 also has anvil cam slots 28 that pivotally receive a corresponding anvil pivot 43 on the anvil 40. A closure sleeve assembly 170 is received over the spine assembly 102 and includes distal closure tube segment 180 and a proximal closure tube segment 190. As will be discussed below, axial movement of the closure sleeve assembly 170 relative to the spine assembly 102 causes the anvil 40 to pivot relative to the elongate channel 20.

As can be seen in FIG. 2, a locking spring 112 is mounted in the distal spine segment 110 as a lockout for the knife assembly 30. Distal and proximal square apertures 111, 113 are formed on top of the distal spine segment 110 to define a clip bar 115 therebetween that receives a top arm 116 of the locking spring 112 whose lower, distally extended arm 118 asserts a downward force on a distal end of a cylinder assembly 501 supporting the piston bar portion 35 protruding from the knife assembly 30 as will be discussed in further detail below. It will be appreciated that various embodiments may include other types of lockouts or no lockouts at all.

In the embodiment depicted in FIGS. 1-6, the end effector 12 may be articulated relative to the proximal closure tube segment 190 (and handle assembly 300) by a collection of cables or bands that are bent to pull the end effector 12 about a pivot 104. Those of ordinary skill in the art will understand that such arrangement represents just one of many articulation arrangements that may be employed in connection with these types of devices. In this embodiment, the proximal end of the distal spine segment 110 has a boss 122 thereon. The distal end of the proximal spine segment 130 is provided with a tang 134 that has an aperture 136 therethrough. The proximal spine segment 130 is positioned relative to the distal spine segment 110 such that the aperture 136 is coaxially aligned with an aperture 124 in boss 122 to enable a pivot pin 138 to extend therethrough. See FIG. 4. Such arrangement, when assembled, permits the end effector 12 to pivot relative to the proximal spine segment 130 about pivot axis A-A.

As indicated above, this embodiment employs bands to articulate the end effector 12. In particular, the bands 150, 160 may extend distally toward the articulation pivot 104 as shown in FIGS. 2 and 3. Band 150 may extend through the proximal closure tube segment 190 along its left side where it is routed around band member 160 and across to the right side of the proximal closure tube segment 190. There, the band 150 may be mechanically coupled to boss 122, for example, at connection point 123. Likewise, band 160 may extend through the proximal closure tube segment 190 along its right side where it is routed around band member 150 and across to the left side of the proximal closure tube segment 190. There, band 160 may be mechanically coupled to the boss 122 at connection point 125.

FIG. 3 is a top view of the end effector and spine assembly 102 with the closure tube assembly 100 depicted in phantom lines. FIG. 4 is a partial cross-sectional side view of the same portion of the instrument 10. As can be seen in FIG. 4, bands 150 and 160 are shown offset from one another to prevent interference in movement according to one non-limiting embodiment. For example, band 150 is shown at a lower position than band 160. In another non-limiting embodiment, the vertical positioning of bands 150 and 160 may be reversed. As can also be seen in FIGS. 2 and 3, the band member 150 extends around a pin 140 in the tang portion 134 of the proximal frame segment 130. Likewise, band 160 extends around pin 142 in the tang portion 134 of the proximal frame segment 130. See also, FIG. 2.

Figure 5:
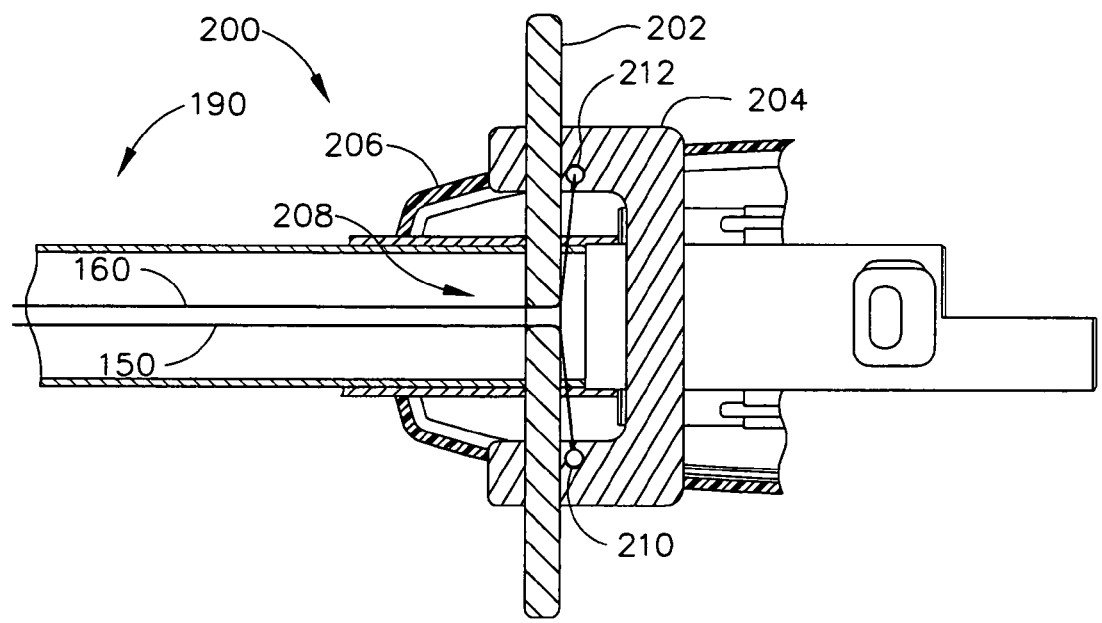
FIG. 5 is a cross-sectional top view of a portion of an articulation control that may be employed with various embodiments of the present invention.

Band portions 150 and 160 may extend from the boss 122 and along the proximal closure tube segment 190 to the articulation control 200, shown in FIG. 5. The articulation control 200 may include an articulation slide 202, a frame 204 and an enclosure 206. Band portions 150, 160 may pass through the articulation slide 202 by way of slot 208 or other aperture, although it will be appreciated that the band portions 150, 160 may be coupled to the slide 202 by any suitable means. The articulation slide 202 may be one piece, as shown in FIG. 5, or may in one non-limiting embodiment, include two pieces with an interface between the two pieces defining the slot 208. In one non-limiting embodiment, the articulation slide 202 may include multiple slots, for example, with each slot corresponding to one of band portions 150, 160. Enclosure 206 may cover the various components of the control 200 to prevent debris from entering.

In various embodiments, band portions 150, 160 may be anchored to the frame 204 at connection points 210, 212 proximally located from the slot 208. The non-limiting embodiment of FIG. 5 shows that the band portions 150, 160 are pre-bent from connection points 210, 212 to the slot 208 located near the longitudinal axis of the proximal closure tube segment 190. It will be appreciated that band portions 150, 160 may be anchored anywhere in the instrument 10 located proximally from the slot 208, including the handle assembly 300.

Figure 6:
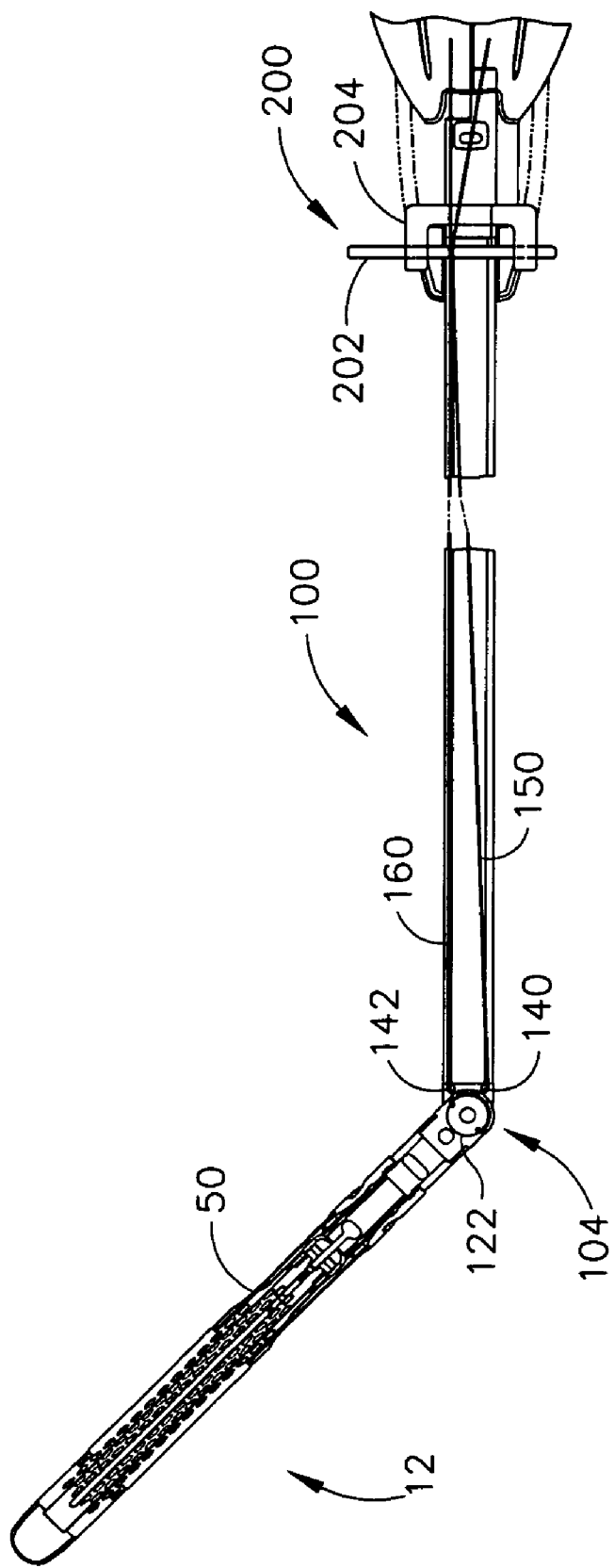
FIG. 6 is a top cross-sectional view illustrating the articulation of the end effector depicted in FIG. 1.

In use, the embodiment of FIG. 2 may have an unarticulated position as shown in FIG. 3. The articulation control 200 and bands 150, 160 are shown in a centered position roughly at the longitudinal axis of the shaft assembly 100. Accordingly, the end effector 12 is in a neutral or unarticulated position. In FIG. 6, the articulation control 200 is shown with the articulation slide 202 pushed through the articulation frame to the right side of the shaft assembly 100. Accordingly, bands 150, 160 are bent toward the right side of the shaft assembly 100. It can be seen that the bending of band 150 to the right exerts a laterally directed force on the boss 122 that is offset from the boss's 122 pivot point. This offset force causes the boss 122 to rotate about articulation pivot 104, in turn causing the end effector 12 to pivot to the right as shown. It will be appreciated that pushing the articulation slide 202 to the left side of the shaft assembly 100 may exert a laterally directed force on bands 150, 160, bending both bands 150, 160 toward the left side of the shaft assembly 100. The bending of band 160 then exerts a laterally directed force on boss 122, which as above, is offset from the boss's 122 pivot point. This, in turn, causes the boss 122 to rotate about the articulation pivot causing the end effector 12 to pivot to the left.

In various embodiments, the shaft assembly 100 is comprised of a closure tube assembly 170 that is received on the spine assembly 102. See FIG. 2. The closure tube assembly 170 comprises a distal closure tube segment 180 and a proximal closure tube segment 190. The distal closure tube segment 180 and the proximal closure tube segment 190 may be fabricated from a polymer or other suitable material. The proximal closure tube segment 190 is hollow and has an axial passage 191 extending therethrough that is sized to receive a portion of the spine assembly 102 therein.

In the embodiment depicted in FIGS. 2 and 4, a double pivot closure joint 172 is employed. It will be appreciated that the invention is not limited to a double pivot closure joint design and may include any suitable closure tube or sleeve, or no closure tube or sleeve at all. With particular reference to FIG. 4, the distal closure tube segment 180 has upper and lower proximally projecting tangs 182, 184. The distal closure tube segment 180 further includes a horseshoe aperture 185 and tab 186 for engaging the anvil open/closing tab 46 on the anvil 40 to cause the anvil 40 to pivot between open and closed positions as will be discussed in further detail below. See FIG. 2.

The proximal closure tube segment 190 is similarly provided with a distally extending upper tang 192 and a distally extending lower tang 194. An upper double pivot link 174 includes upwardly projecting distal and proximal pivot pins 175, 176 that engage respectively an upper distal pin hole 183 in the upper proximally projecting tang 182 and an upper proximal pin hole 193 in the upper distally projecting tang 192. The joint arrangement further includes a lower double pivot link 177 that has downwardly projecting distal and proximal pivot pins 178, 179 (not shown in FIG. 2, but see FIG. 4) that engage respectively a lower distal pin hole 187 in the lower proximally projecting tang 184 and a lower proximal pin hole 195 in the lower distally projecting tang 194.

In use, the closure tube assembly 170 is translated distally to close the anvil 40, for example, in response to the actuation of the closure trigger 302. The anvil 40 is closed by distally translating the closure tube assembly 170 on the spine assembly 102, causing the back of the horseshoe aperture 185 to strike the open/closing tab 46 on the anvil 40 and cause it to pivot to the closed position. To open the anvil 40, the closure tube assembly 170 is axially moved in the proximal direction on the spine assembly 102 causing the tab 186 to contact and push against the open/closing tab 46 to pivot the anvil 40 to the opened position.

Figure 7:
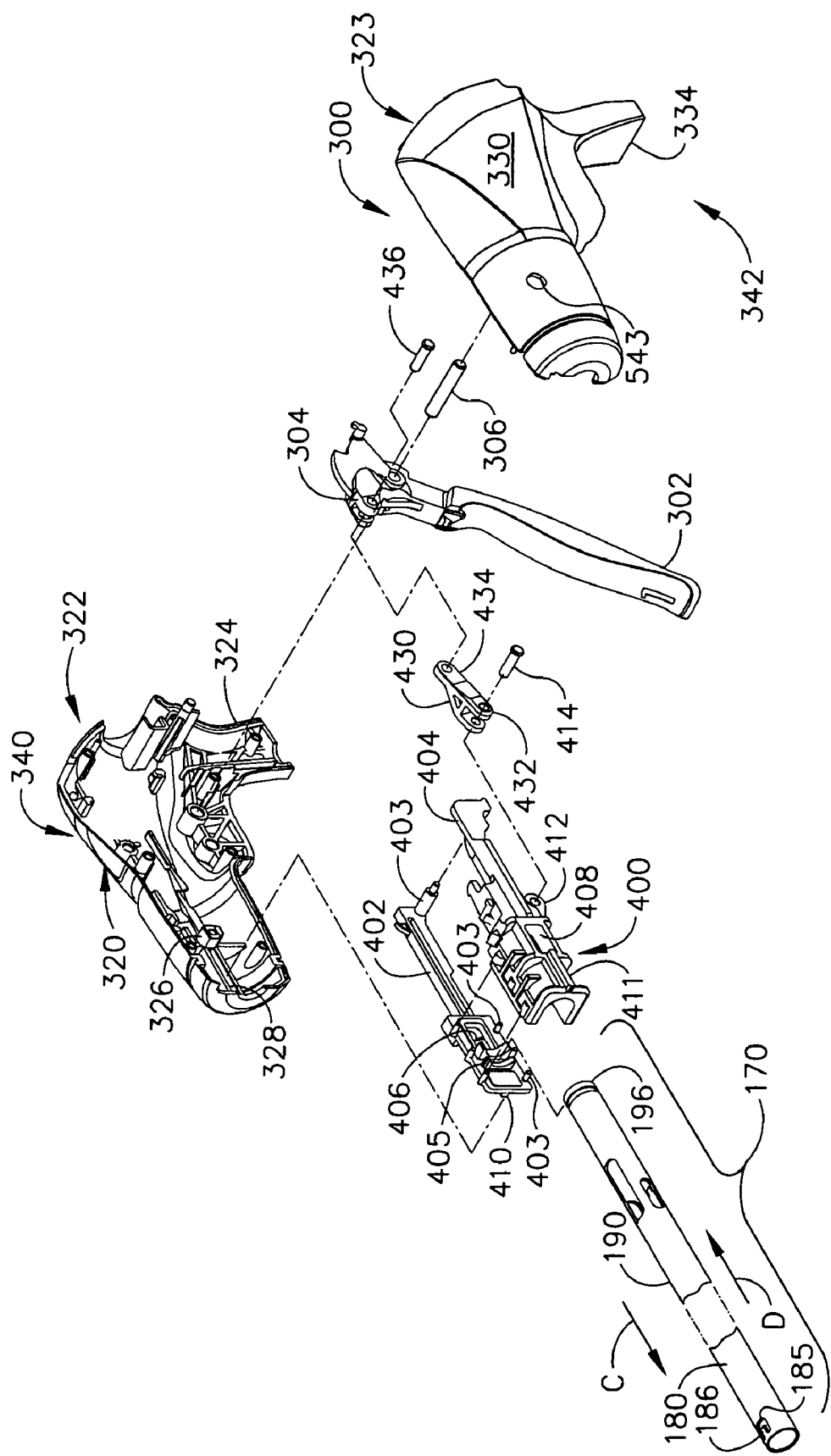
FIG. 7 is an exploded assembly view illustrating an embodiment of a closure tube assembly and shuttle arrangement supported within the handle assembly with other components housed within the housing assembly being omitted for clarity.

FIG. 7 illustrates an exploded assembly view of a non-limiting handle assembly 300 of various embodiments of the present invention. In the embodiment depicted in FIG. 7, the handle assembly has a "pistol grip" configuration and is formed from a right hand case member 320 and a left handed case member 330 that are molded or otherwise fabricated from a polymer or other suitable material and are designed to mate together. Such case members 320 and 330 may be attached together by snap features, pegs and sockets molded or otherwise formed therein and/or by adhesive, screws, bolts, clips, etc. The upper portion 322 of the right hand case member 320 mates with a corresponding upper portion 323 of the left hand case member 330 to form a primary housing portion designated as 340. Similarly, the lower grip portion 324 of the right hand case member 320 mates with the lower grip portion 334 of the left hand case member to form a grip portion generally designated as 342. In the embodiment depicted in FIG. 7, the entire grip portion 342 is integral with the primary housing portion 340. Such arrangement may be particularly well-suited for applications wherein a source of pressurized gas is permanently installed within the grip portion 342. Such arrangement is also suited for use with sources of pressurized gas that are external to the handle assembly 300 and plugged into the control components housed therein through a port or ports in the housing assembly. In other embodiments, as will be described in further detail below, the grip portion 342 is detachable from the primary housing portion 340. As will be appreciated as the present Detailed Description proceeds, such arrangement provides a myriad of benefits and advantages. Those of ordinary skill in the art will readily appreciate, however, that the handle assembly 300 may be provided in a variety of different shapes and sizes.

For the purposes of clarity, FIG. 7 only illustrates the components employed to control the axial movement of the closure tube assembly 170 which ultimately controls the opening and closing of the anvil 40. As can be seen in that Figure, a closure shuttle 400 that is coupled to the closure trigger 302 by a linkage assembly 430 is supported within the primary housing portion 340. Closure shuttle 400 may also be fabricated in two pieces 402, 404 that are molded or otherwise fabricated from a polymer or other suitable material and are designed to mate together. For example, in the embodiment illustrated in FIG. 7, the right hand portion 402 may be provided with fastener posts 403 that are designed to be received within corresponding sockets (not shown) in the left hand portion 404. The right and left hand portions 402, 404 may be otherwise retained together by snap members and/or adhesive and/or bolts, screws, clips, etc. As can be seen in that Figure, a retention groove 196 is provided in the proximal end of the proximal closure tube segment 190. The right hand portion 402 of the closure shuttle 400 has a right retention flange segment 405 that is adapted to cooperate with a left retention flange segment (not shown) on the left hand portion 404 of the closure shuttle 400 to form a retention flange assembly that extends into the retention groove 196 in the proximal closure tube segment 190.

As can also be seen in FIG. 7, a right spine assembly retention peg 326 protrudes inward from the right hand case member 320. Such peg 326 protrudes into an elongated slot or window 406 in the right hand portion 402 of the closure shuttle 400. A similar closure shuttle retention peg (not shown) protrudes inward from the left hand case member 330 to be received in another window or slot 408 provided in the left hand side portion 404 of the closure shuttle 400. The retention pegs serve to non-movably affix the proximal end of the proximal spine segment 130 (not shown in FIG. 7) to the handle assembly 300 while permitting the closure shuttle 400 to move axially relative thereto. The retention pegs may be mechanically attached to the proximal end of the proximal spine segment 130 by, for example, bolts, screws, adhesive, snap features, etc. In addition, the closure shuttle 400 is provided with laterally extending guide rails 410, 411. Rail 410 is configured to be slidably received within rail guide 328 the right hand case member 320 and rail 411 is configured to be slidably received within a rail guide (not shown) in left hand case member 330.

Axial movement of the closure shuttle 400 and closure tube assembly 170 in the distal direction (arrow "C") is created by moving the closure trigger 302 toward the grip portion 342 of the handle assembly 300 and axial movement of the closure shuttle 400 in the proximal direction (arrow "D") is created by moving the closure trigger 302 away from the grip portion 342. In various embodiments, the closure shuttle 400 is provided with a connector tab 412 that facilitates the attachment of the closure linkage assembly 430 thereto. See FIGS. 8 and 9. The closure linkage assembly 430 includes a yoke portion 432 that is pivotally pinned to the connector tab 412 by a pin 414. The closure linkage assembly 430 further has a closure arm 434 that is pivotally pinned to a yoke assembly 304 formed on the closure trigger 302 by a closure pin 436 as illustrated in FIG. 7. The closure trigger 302 is pivotally mounted within the handle assembly 300 by a pivot pin 306 that extends between the right hand case member 320 and the left hand case member 330.

When the clinician desires to close the anvil 40 to clamp tissue within the end effector 12, the clinician draws the closure trigger 302 toward the grip portion 342. As the clinician draws the closure trigger 302 toward the grip portion 342, the closure linkage assembly 430 moves the closure shuttle 400 in the distal "C" direction until the closure linkage assembly 430 moves into the locked position illustrated in FIG. 8. When in that position, the linkage assembly 430 will tend to retain the closure shuttle 400 in that locked position. As the closure shuttle 400 is moved to the locked position, the closure tube assembly 170 is moved distally on the spine assembly 102 causing the closure/opening tab 46 on the anvil 40 to be contacted by the proximal end of the horseshoe aperture 185 in the distal closure tube segment 180 to thereby pivot the anvil 40 to the closed (clamped) position.

In various embodiments, to further retain the closure shuttle 400 in the closed position, the closure trigger 302 may be provided with a releasable locking mechanism 301 that is adapted to engage the grip portion 342 and releasably retain the closure trigger 302 in the locked position. Other locking devices may also be used to releasably retain the closure shuttle 400 in the locked position. In the embodiment depicted in FIGS. 8, 8A, 8B, and 9, the closure trigger 302 includes a flexible longitudinal arm 303 that includes a lateral pin 305 extending therefrom. The arm 303 and pin 305 may be made from molded plastic, for example. The pistol grip portion 342 of the handle assembly 300 includes an opening 350 with a laterally extending wedge 352 disposed therein. When the closure trigger 302 is retracted, the pin 305 engages the wedge 352, and the pin 305 is forced downward (i.e., the arm 303 is rotated CW) by the lower surface 354 of the wedge 352. When the pin 305 fully passes the lower surface 354, the CW force on the arm 303 is removed, and the pin 305 is rotated CCW such that the pin 305 comes to rest in a notch 356 behind the wedge 352 thereby locking the closure trigger 302. The pin 305 is further held in place in the locked position by a flexible stop 358 extending from the wedge 352.

To unlock the closure trigger 302, the operator may further squeeze the closure trigger 302, causing the pin 305 to engage a sloped back wall 359 of the opening 350, forcing the pin 305 upward past the flexible stop 358. The pin 305 is then free to travel out an upper channel in the opening 360 such that the closure trigger 302 is no longer locked to the pistol grip portion 342. Further details of such arrangement may be found in U.S. patent application Ser. No. 11/344,020, filed Jan. 31, 2006, U.S. Patent Publication No. US-2007-0175960 A1 and entitled Surgical Instrument Having A Removable Battery to Shelton, IV et al., the relevant portions of which are herein incorporated by reference. Other releasable locking arrangements could also be employed.

Figure 10:
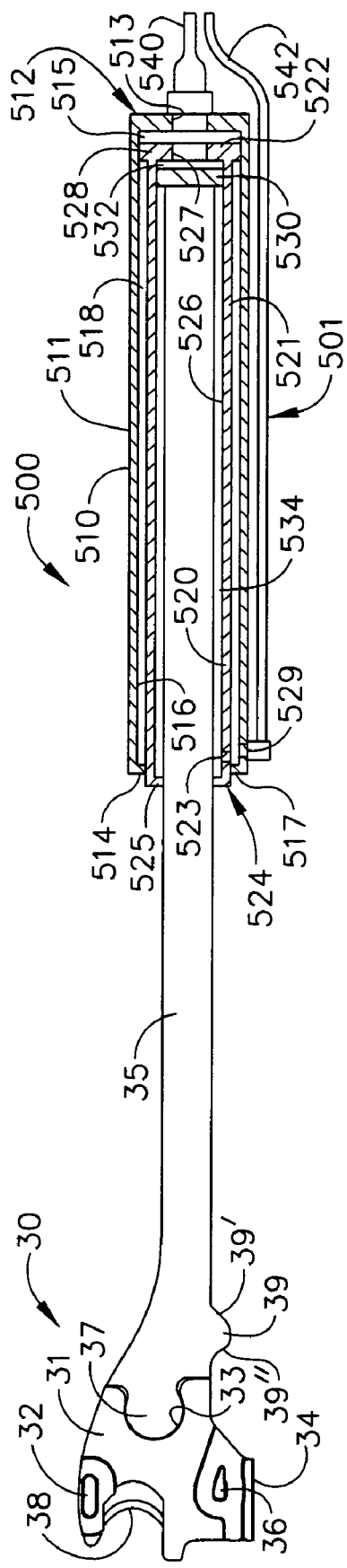
FIG. 10 is a side view of a knife bar arrangement and a firing drive member that comprises a two stage cylinder assembly of various embodiments of the present invention with the cylinder assembly shown in cross-section.
Figure 11:
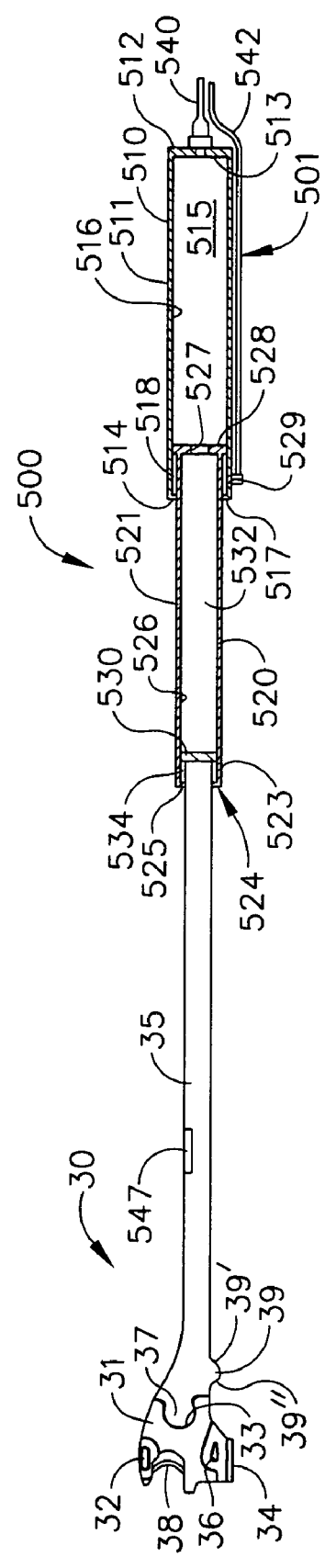
FIG. 11 is another side view of the knife bar and two stage cylinder arrangements depicted in FIG. 10 with the knife bar in the extended position.

In various embodiments of the present invention, the knife assembly 30 may have a substantially rigid piston bar portion 35 protruding therefrom or otherwise attached thereto that is part of a drive member 500 that is operably supported by the distal spine segment 110 and configured to apply at least two actuation motions (e.g., firing motion and retraction motion) to the knife assembly 30. In the embodiments depicted in FIGS. 3, 4, 10, and 11, the drive member 500 comprises a two stage pneumatically-actuated cylinder assembly 501. The knife assembly 30 may comprise a unitary component or it may be provided in multiple pieces to facilitate easier assembly of the instrument 10. For example, as shown in FIGS. 10 and 11, the knife bar assembly 30 comprise a distal portion 31 that contains the upper pins 32, the cap 34, the middle pins 36 and the knife 38. Distal portion 31 may be provided with an aperture 33 therein sized to receive a protrusion 37 provided on the distal end of the piston bar portion 35. The protrusion 37 may be frictionally received within the aperture 33 and/or retained therein by adhesive, welding, etc.

The cylinder assembly 501 comprises a first cylinder housing 510 that has a first closed proximal end 512 and a first open distal end 514 that opens into a first axial passage 516 within the first cylinder housing 510. The cylinder assembly 501 also comprises a second cylinder housing 520 that has a second proximal end 522 and a second open distal end 524 that opens into a second axial passage 526. The second closed proximal end 522 has a first piston head 528 formed thereon that is sized relative to the first axial passage 516 to create a substantially airtight sliding seal with the first wall 511 of the first cylinder housing 510 to define a first cylinder area 515 between the distal side of the first proximal end 512 and the proximal side of the first piston head 528. The first distal end 514 of the first cylinder housing 510 further has an inwardly extending first flange 517 formed thereon for establishing a substantially airtight sliding seal with the outer wall surface of the second cylinder housing 520 to define a second cylinder area 518 between the proximal side of the first flange 517 and the distal side of the first piston head 528.

A first passage 527 is provided through the first piston head 528. As can also be seen in FIGS. 10 and 11, the proximal end of the piston bar 35 extends through the second open distal end 524 of the second cylinder housing 520 and into second axial passage 526. A second piston head 530 is formed on or otherwise attached to the proximal end of the piston bar 35. The second piston head 530 is sized relative to the second axial passage 526 to create a substantially airtight sliding seal with a second wall 521 of the second cylinder housing 520 to define a third cylinder area 532. The second distal end 524 of the second cylinder housing 520 further has an inwardly extending second flange 525 formed thereon for establishing a substantially airtight sliding seal with the piston bar 35 to define a fourth cylinder area 534 between the proximal side of the second flange 525 and the distal side of the second piston head 530.

As can be seen in FIGS. 3 and 4, the cylinder assembly 501 is mounted within the distal spine segment 110. In various embodiments, a pair of trunions 519 are provided on the proximal end of the first cylinder housing 510. The trunions 519 are received within trunion bores 119 in the distal spine segment 110 to enable the cylinder assembly 501 to pivot within the distal spine segment 110 about a pivot axis B-B. See FIG. 3. A first supply line or supply conduit 540 extends from a directional control valve 610 in the handle assembly 300 (FIGS. 8 and 9) through the proximal closure tube segment 190 to be coupled to the first proximal end 512 of the first cylinder housing 510 to supply pressurized gas through a first supply port 513 or opening in the first proximal end 512 of the first cylinder housing 510. See FIGS. 10 and 11. In addition, a second supply line 542 extends from the directional control valve 610 through the proximal closure tube segment 190 and is connected to the first cylinder housing 510 adjacent the distal end 514 thereof to supply pressurized gas into the second cylinder area 518 through a second port 529.

Figure 8A:
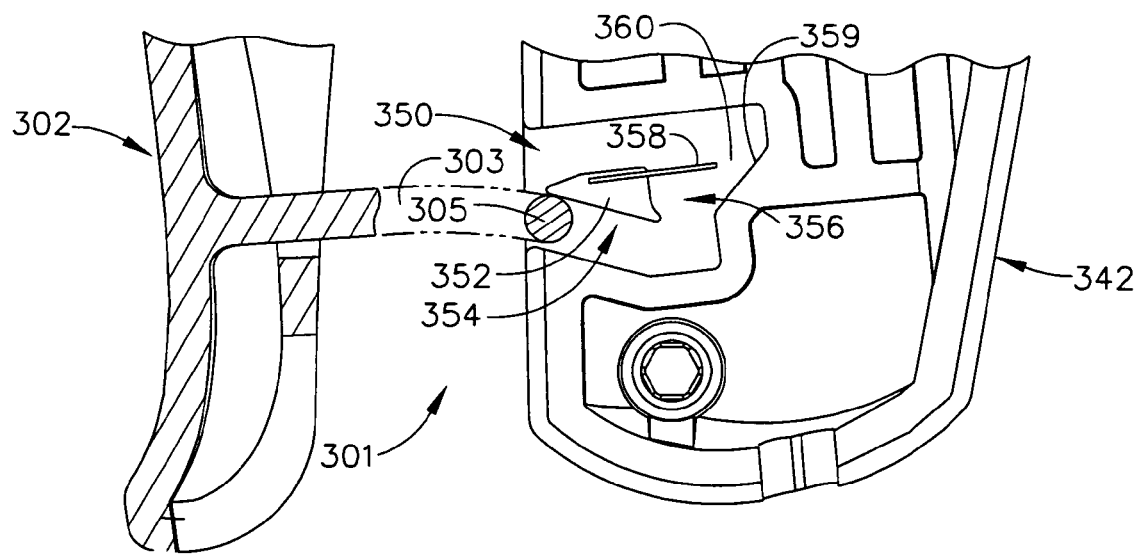
FIG. 8A is a partial cross-sectional view of a portion of a closure trigger locking system that may be employed in connection with various embodiments of the present invention.
Figure 8:
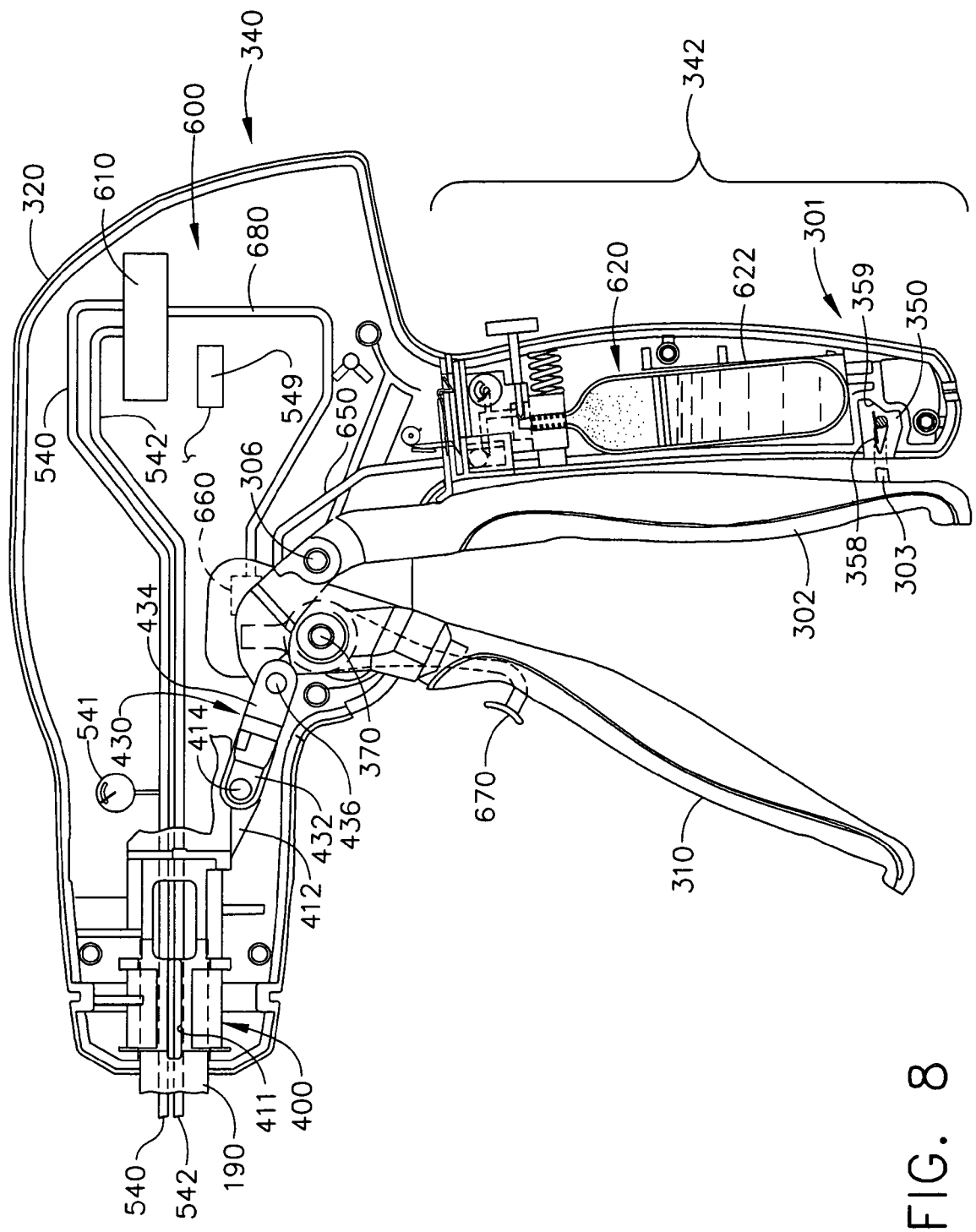
FIG. 8 is a cross-sectional view of a housing assembly arrangement of various embodiments of the present invention.
Figure 8B:
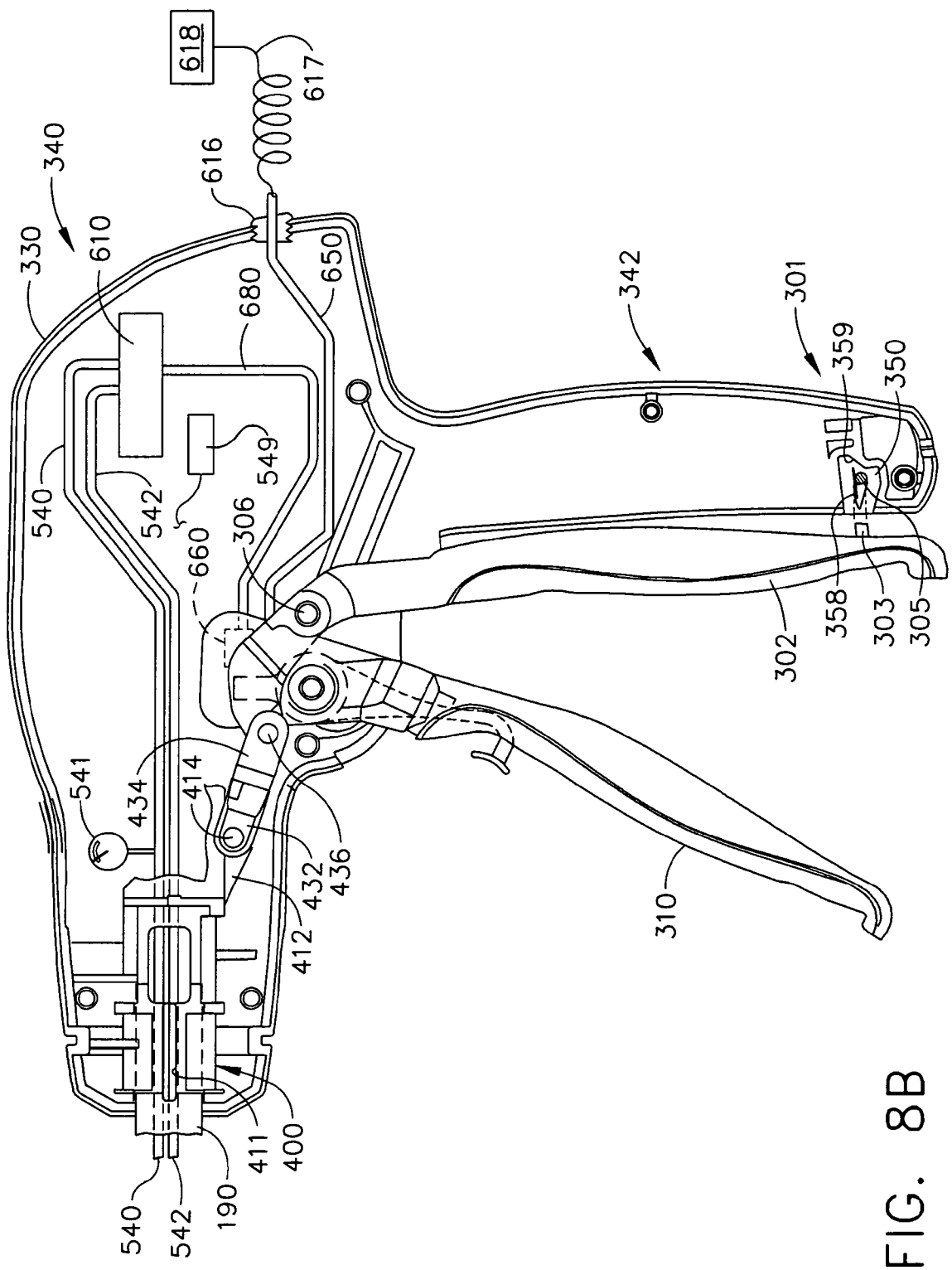
FIG. 8B is a cross-sectional view of another handle assembly embodiment of the present invention wherein the source of pressurized gas is external to the handle assembly.
Figure 9:
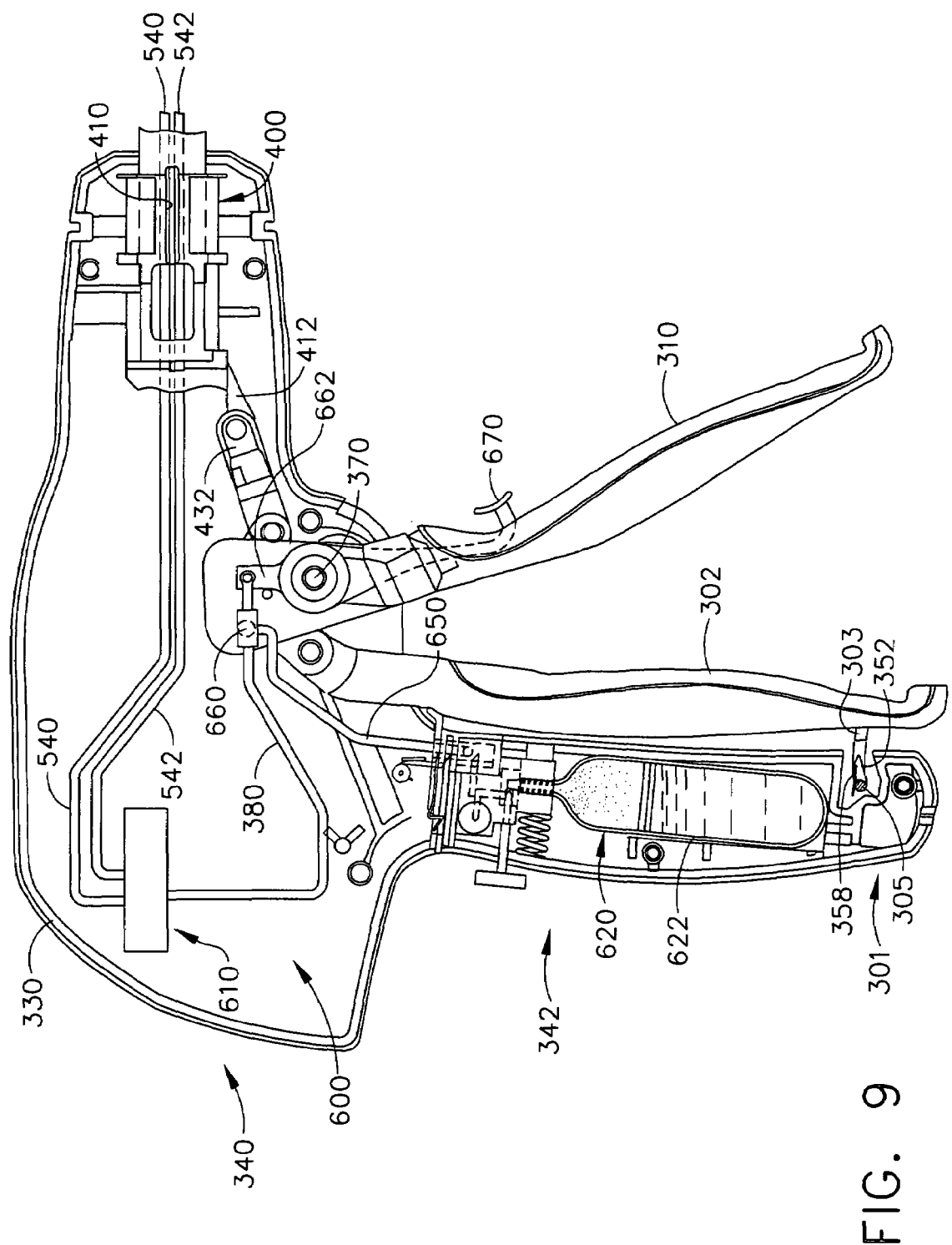
FIG. 9 is another cross-sectional view of the handle assembly of FIG. 8.

With reference to FIGS. 8-11, the extension and retraction of the firing mechanism or knife assembly 30 will now be explained. As can be seen in FIGS. 8 and 9, the supply lines 540 and 542 are coupled to a conventional directional valve 610 which is part of an actuator system 600 housed within the handle housing 350. In various embodiments, the directional valve 610 may be shifted manually between forward (extend) and reverse (retract) positions by a selector switch 612 or push buttons that are accessible through the handle housing 350. See FIG. 1. In the embodiment depicted in FIGS. 8 and 9, a removable source 620 of pressurized gas is employed. As will be further discussed in detail below, such source of pressurized gas comprises a cylinder 622 that may be rechargeable with a preferred pressurized gas. Those of ordinary skill in the art will appreciate, however, that nonreplaceable/rechargeable sources (cylinders) of pressurized gas could also be effectively employed. Still in other embodiments, the handle assembly 300 may be provided with a port 616 for supplying pressurized gas from an external source 618 of pressurized gas. For example, the instrument 10 could be coupled to the facility's compressed air supply 618 through a flexible supply line 617. See FIG. 8B.

Figure 55:
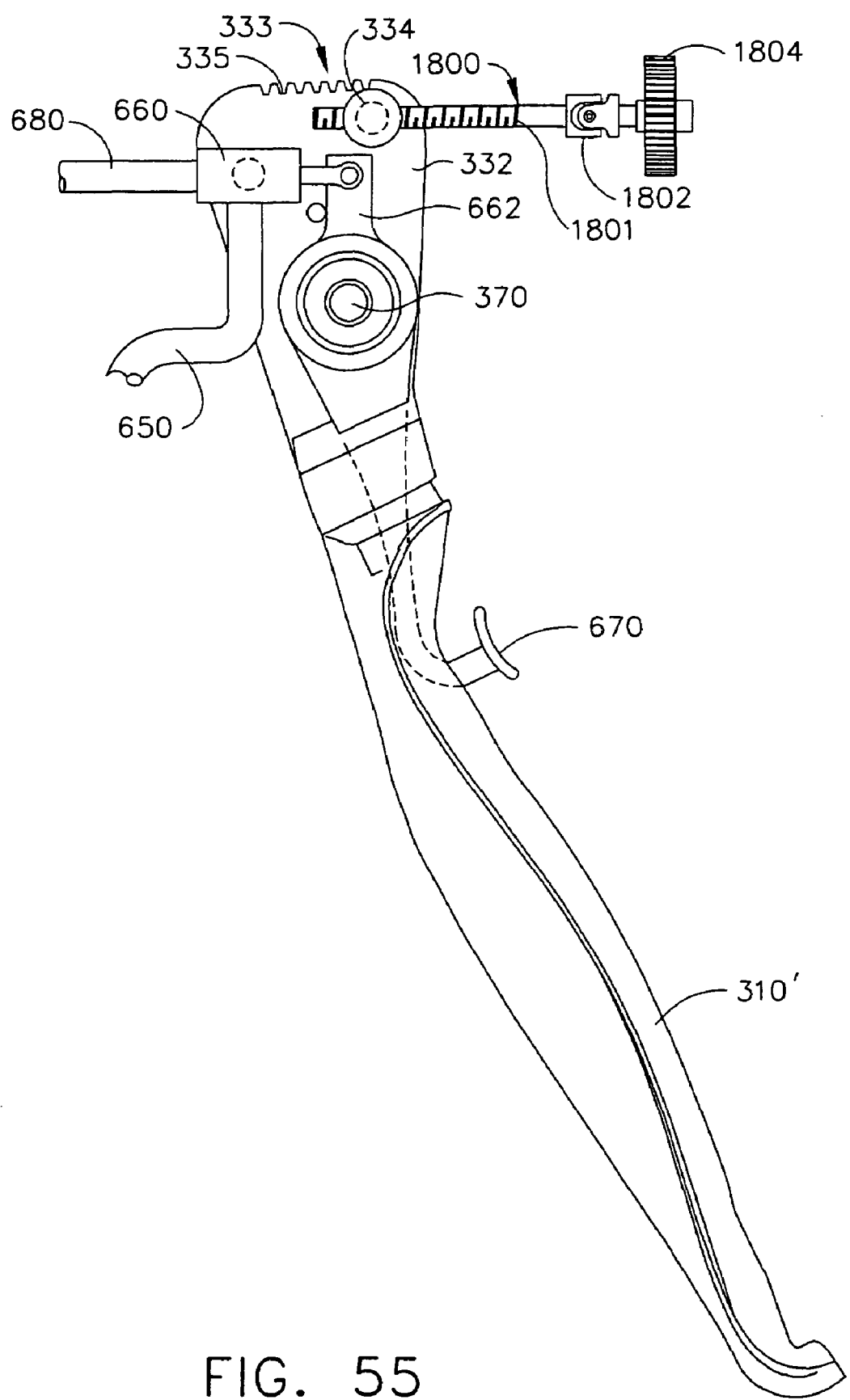
FIG. 55 is a side view of a relative position firing trigger arrangement of various embodiments of the present invention.

The unique and novel aspects of the removable/rechargeable cylinder 622 will be discussed in further detail below. However, for the purpose of explaining the extension and retraction of the piston bar 35 and knife assembly 30, it can be seen that pressurized gas flows from the cylinder 622 (or external pressure source 618) through a supply line 650 into a variable force actuator that may comprise a conventional rate valve 660. As can most particularly be seen in FIGS. 9 and 55, the rate valve 660 is coupled to a supply linkage 662 that is attached to an activation trigger 670. As used herein, the term "variable force actuation assembly" at least comprises the rate valve 660 and the activation trigger 670 and their respective equivalent structures. In various embodiments, activation trigger 670 is supported adjacent the firing trigger 310 that is pivotally coupled to the handle assembly 300 by a pivot pin 370 that extends between the right hand case member 320 and left hand case member 330. Squeezing the activation trigger 670 inward towards the firing trigger 310 causes the rate valve 660 to increase the flow rate of the pressurized gas flowing from the cylinder 622 into a supply line 680 coupled to the directional valve 610. Depending upon the position of the directional valve 610, the pressurized gas will either flow into supply line 540 or 542. For example, when the directional valve 610 is actuated by the clinician to fire the knife assembly 30, pressurized gas is permitted to flow through the supply line 540 into the first cylinder area 515 through the first opening 527 in the first piston head 528 and into the third cylinder area 532 upon actuation of activation trigger 670. As the pressurized gas enters the third cylinder area 532, the second piston head 530 forces the piston bar 35 distally. Gas located in the fourth cylinder area vents therefrom through exhaust opening 523 in the second cylinder housing 520. Similarly, the gas contained in the second cylinder area 518 is permitted to vent therefrom through second opening 529 into the second supply line 542. The second supply line 542 carries the vented gas to the directional valve 610 wherein it is ultimately vented therefrom. Continued application of pressurized gas to the first cylinder area 515 and the third cylinder area 532 causes the knife assembly 30 to be fully extended through the end effector 12. As the knife assembly 30 passes through the end effector 12, it severs the tissue clamped therein and fires the staples 70 in the staple cartridge 50 (drives the staples into forming contact with the lower surface of the anvil 40). Once the knife assembly 30 has been advanced to its distal-most position in the end effector 12, the clinician discontinues the application of pressurized gas by releasing the activation trigger 670.

To retract the firing mechanism or knife assembly 30, the clinician manually moves the selector switch 612 or appropriate button for adjusting the directional valve 610 to the retract position and begins to squeeze the activation trigger 670 which causes the pressurized gas to flow into the second supply line 542. Gas flowing through the second supply line 542 enters the second cylinder area 518 which causes the second cylinder housing 520 to retract proximally into the first cylinder housing 510. Gas in the first cylinder area 515 is permitted to vent through the first supply opening 513 into the first supply line 540. Gas passing through the first supply line 540 enters the directional valve 610 wherein it is vented therefrom. Once the pressurized gas entering the second cylinder area 518 has caused the second cylinder housing 520 to retract into the first cylinder housing 510 as shown in FIG. 10, gas passing through the second opening 529 is now able to pass through the exhaust opening 523 in the first cylinder housing 510 and into the fourth cylinder area 534. As pressurized gas enters the fourth cylinder area 534, the second piston head 530 draws the piston bar 35 proximally into the second cylinder housing 520. Gas in the third cylinder area 532 passes through the first opening 527 into the first cylinder area 515 from which it is vented in the manner described above.

The variable force actuator in the form of rate valve 660 of various embodiments of the present invention may employ springs or other biasing means (not shown) to bias the rate valve 660 to an unactuated position. When in the unactuated position, the rate valve 660 may be configured to prevent any flow of gas from the sources of gas 620 or 618 through an orifice (not shown) within the valve 660. Thus, when the actuator trigger 670 is in the unactuated position, the device is essentially off.

In the embodiments described above, the rate valve 660 may be mechanically coupled to the activation trigger 670 by the supply linkage arm 662 such that, as the clinician squeezes the activation trigger 670 inward toward the firing trigger 310, the linkage arm 662 causes the rate valve 660 to permit the flow rate of the gas to increase through the valve 660. Thus, quickly squeezing the activation trigger 670 may cause the firing rate of the device to increase and slowing the rate that the activation trigger 670 is squeezed slows the firing rate. Thus, the amount of gas flow permitted through the rate valve 660 can be substantially proportionate to the amount of manual force applied to the activation trigger 670.

In other embodiments, the rate valve 660 may be electronically controlled such that upon actuation of the activation trigger, the rate valve 660 digitally spurts gas therefrom. The rate valve 660 discharges a small amount of gas in a pulse manner and the harder that the activation trigger 670 is squeezed, the closer the pulses will be. Such arrangement serves to selectively regulate the volume of gas employed to actuate the device.

Also, in still other embodiments, the actuation mechanism may comprises a different type of mechanism that is not pivotally supported relative to the handle assembly as is the activation trigger 670. For example, the activation trigger could comprises a spring actuated slide switch, etc. Accordingly, the protection afforded to those embodiments of the present invention should not be solely limited to embodiments employing a pivoting actuated trigger.

Also in various embodiments, a pressure gage 541 may be fluidically coupled to supply line 540 as shown in FIGS. 8 and 8A. A window 543 may be provided through a corresponding portion of the handle assembly 300 to enable the clinician to view the gage 541 or other arrangements may be employed to enable the clinician to view the gage 541 during use. See FIG. 7. In various embodiments, the pressure gage 541 may comprise an electronically powered gage or a dial gage. In these non-limiting embodiments, the gage 541 provides a means for providing feedback on the forces encountered during the firing stroke. Those of ordinary skill in the art will understand that, in certain non-limiting embodiments, the force necessary to actuate the firing mechanism is directly proportionate to the pressure in the cylinder assembly 501. If those forces are small, then the cylinder assembly 501 does not require large pressures to be actuated. On the other hand, if the forces needed to actuate the cylinder assembly 501 are high, more gas will have to be released into the cylinder assembly 501 increasing the pressure therein to fully actuate the firing mechanism. The pressure gage 541 serves to provide the clinician with a proportionate reading to the forces being experienced by the end effector.

Figure 8C:
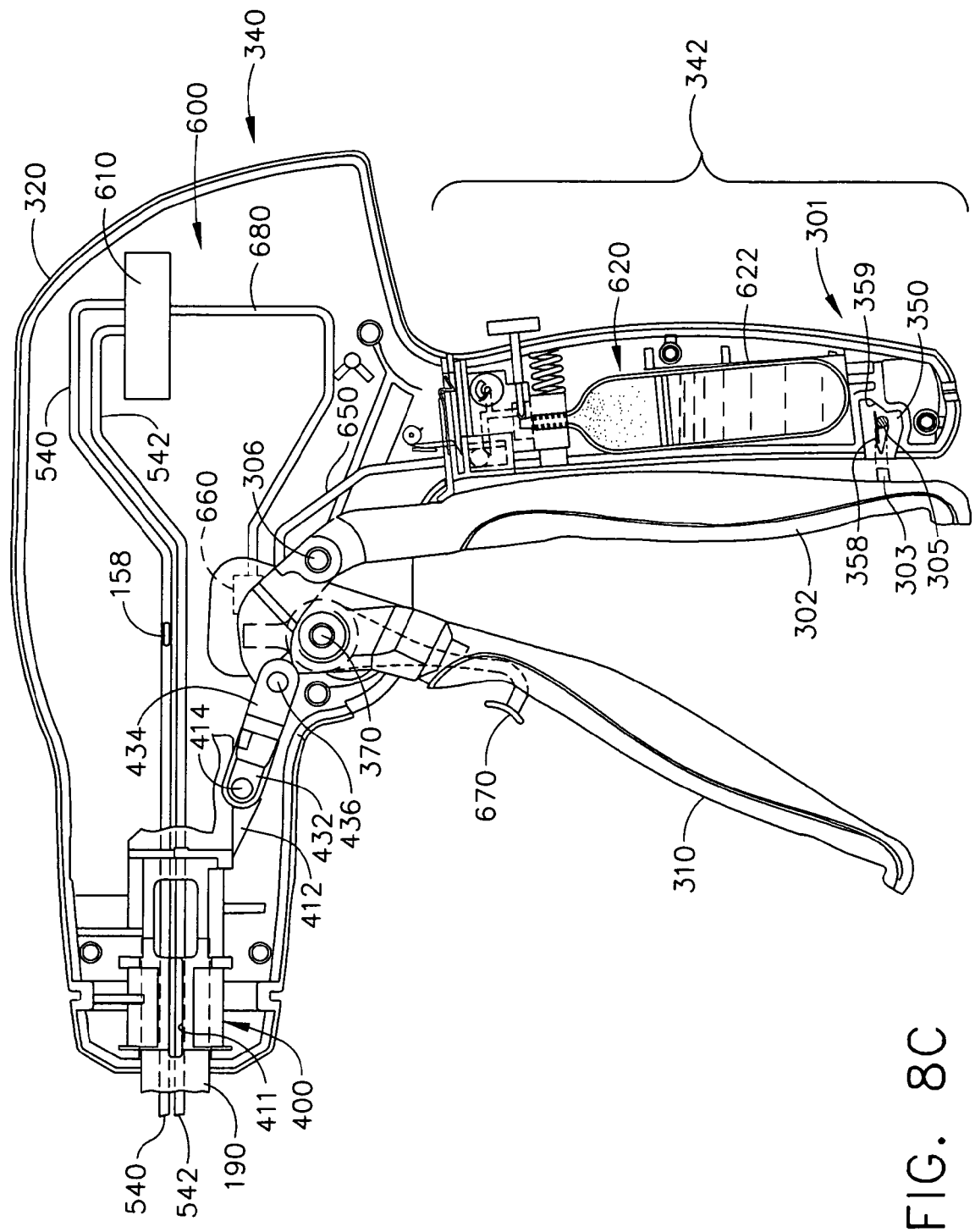
FIG. 8C is a cross-sectional view of another handle assembly embodiment of the present invention.

In other various embodiments, an audible outlet 545 may be provided in the supply line 540 as shown in FIG. 8C. Such audible outlet permits a small amount of gas to be released from the supply line 540. The ensuing whistle pitch caused from the discharge of that gas would increase as the pressure forces increased. The clinician can then relate the pitch of the whistle to the forces experienced by the firing mechanism. Thus, such arrangement provides the clinician with an audible feedback mechanism for monitoring the firing forces being experienced by the drive system 500 and ultimately the firing mechanism.

Various non-limiting embodiments may also be provided with means for automatically notifying the clinician when the firing mechanism has reached the end of the firing stroke. For example, as shown in FIG. 4, a limit switch 546 may be provided within the distal spine segment 110 for detecting an activation member 547 embedded into or otherwise attached to the firing rod 35 as shown in FIG. 11. The activation member 547 is so located such that when the firing bar 35 and firing mechanism reaches the end of the firing stroke, the activation member 547 is detected by the limit switch 546 which may be electrically coupled to the directional control valve 610 for transmitting an appropriate signal thereto. Upon receipt of such signal, the directional control valve 610 may be configured to automatically shift to the retract position and to permit the firing mechanism to be retracted. In addition, the limit switch 546 may be coupled to an indication member generally designated as 549 in FIG. 8. In various embodiments, the indication member may provide the clinician with an audible signal, a visual signal or a combination of audible and visual signals indicating that the firing mechanism has reached the end of the firing stroke. For example, the indication member may comprise a sound generating device, an led, a vibration generating device, etc. or a combination of such devices. The limit switch and related control components may be powered by a battery (not shown) supported in the housing assembly 300 or it may be provided with electrical power from an external source of electrical power. Thus, various non-limiting embodiments of the present invention may be provided with a means for providing the clinician with a visual and/or audible signal indicating that the firing mechanism has reached the end of the firing stroke and/or a means for automatically pneumatically retracting the firing mechanism to the unactuated position.

As can be seen in FIGS. 4, 10, and 11, a locking protrusion 39 may be formed on the bottom of the piston bar 35. When the knife assembly 30 is in the fully retracted position as shown in FIG. 4, the arm 118 of the locking spring 112 applies a biasing force to the distal end of the cylinder assembly 501. Because the cylinder assembly 501 is pivotally mounted within the distal spine segment 110 by trunions 519, the distal end of the cylinder assembly 501 pivots downwardly within the distal spine segment 110 and further causes the locking protrusion 39 on the piston bar 35 to drop into a locking opening 21 in the elongate channel 20. Such arrangement serves to lock the knife assembly 30 in the retracted position by virtue of the frictional engagement of the locking protrusion 39 with the portions of the elongate channel 20 defining the locking opening therein. As can be seen in FIGS. 10 and 11, the locking protrusion 39 has a proximal ramp surface 39' and a distal ramp surface 39" to enable the locking protrusion to easily enter and exit the locking opening in the elongate channel 20. Those of ordinary skill in the art will readily appreciate that other knife bar locking arrangements may be successfully employed without departing from the spirit and scope of the present invention.

FIGS. 12-16A illustrate another embodiment of the present invention wherein the drive member 500 comprises a cylinder assembly 800 that is similar in construction as cylinder assembly 501 described above, except for the differences noted below. For example, in this embodiment, springs 850, 852 are employed to retract the piston bar 35. As can be seen in FIGS. 12 and 13, the cylinder assembly 800 includes a first housing 810 that has a first closed end 812 and a first supply port 813 therethrough. A first supply line 840 is attached to the first closed end 812 to supply pressurized gas through the first supply port 813. In this embodiment, the first cylinder housing 810 lacks the second opening 529 that was described in connection with various embodiments described above. A second cylinder housing 820 is slidably received in the first cylinder housing 810 and has a second closed proximal end 822 that has a first piston head 828 formed thereon. A first cylinder area 815 is defined between the first closed end 812 and the first piston head 828. A first retraction spring 850 is provided between the first piston head 828 and a first flange 817 formed on the distal end of the first cylinder housing 810.

The first retraction spring 850 serves to bias the second cylinder housing 820 into the retracted position in the first cylinder 810 as shown in FIG. 12. The piston bar 35 has a stepped end 35' that is sized to enter the second distal end 824 of the second cylinder housing 820. A second flange 825 is formed on the second distal end 824 to achieve a substantially sliding seal with the stepped portion 35' of the piston bar 35. A second piston head 830 is provided on the proximal end of the stepped piston bar section 35' to define a third cylinder area 832 between the second piston head 830 and the first piston head 828. A first opening 827 is provide through the first piston head 828 to enable air to pass between the first cylinder area 815 and the third cylinder area 832. A second retraction spring 852 is provided between the second flange 825 and the second piston head 830 as shown in FIG. 12 to bias the second piston head 830 and stepped piston bar 35' to the fully retracted position within the second cylinder housing 820 as shown in FIG. 12.

Figure 16:
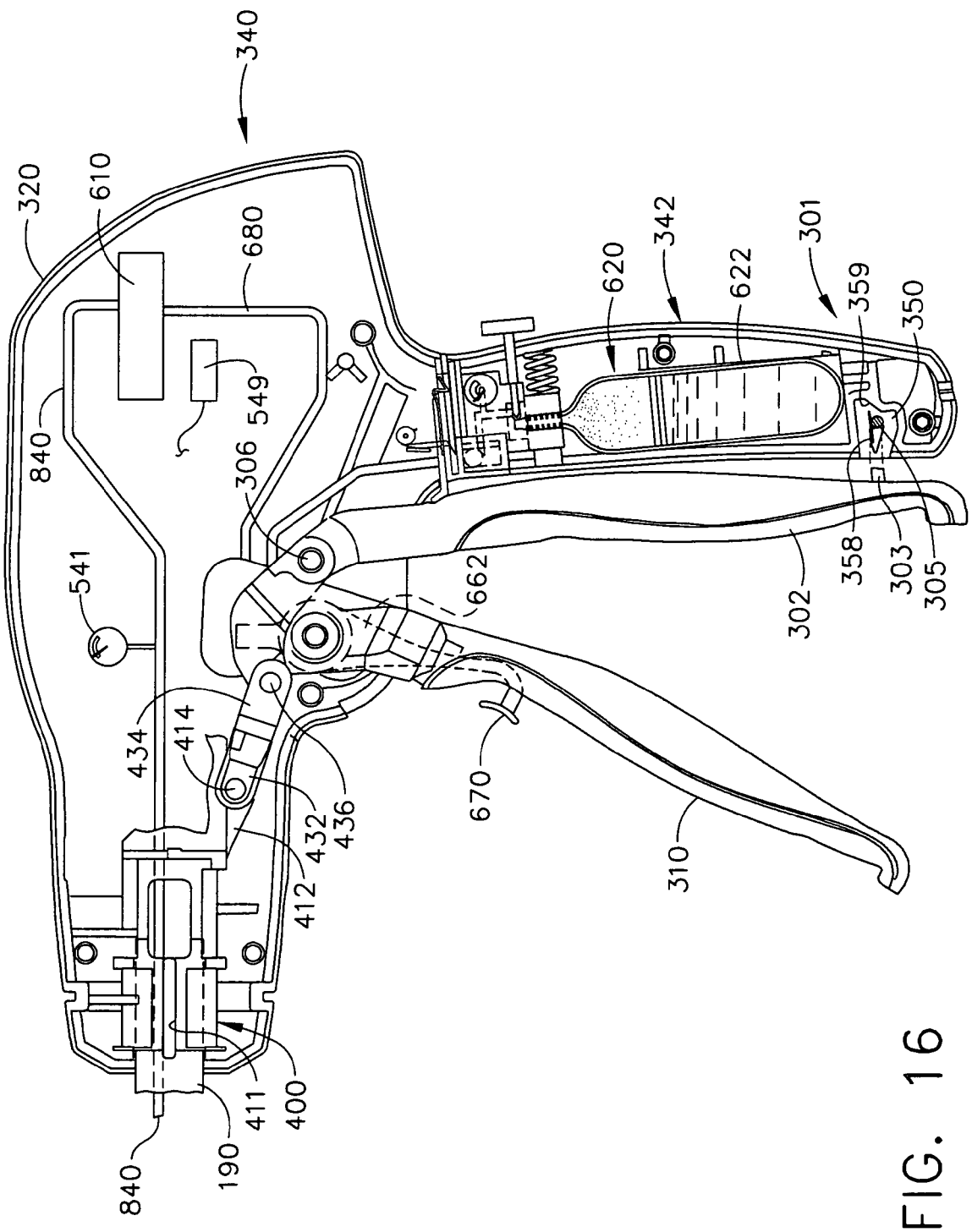
FIG. 16 is a cross-sectional view of a handle assembly that may be used in connection with the embodiment depicted in FIGS. 12-15.

This embodiment of the present invention may be operated as follows. As can be seen in FIG. 16, the handle assembly 300 is provided with a replaceable source 620 of pressurized gas as was discussed above. However, those of ordinary skill in the art will appreciate that nonreplaceable sources (cylinders) of pressurized gas could also be effectively employed. Still in other embodiments, the handle assembly 300 may be provided with a port 616 for facilitating attachment of the directional control valve 610 and related components to an external source of pressurized gas 618. See FIG. 16A. For example, the instrument 10 could be coupled to the facility's compressed air line through a flexible supply line 617.

To operate the instrument, the clinician moves the direction control valve selector switch 612 (FIG. 1) or push buttons to the forward (extend) position and begins to squeeze the activation trigger 670 (FIG. 16) which permits the pressurized gas to flow from the cylinder 622 (or external source 618) through the supply line 680 through the directional control valve 610 and into the supply line 840. The pressurized gas flows from the first supply line 840 through the first supply port 813 into the first cylinder area 815, through the first opening 827 and into the third cylinder area 832. Gas entering the third cylinder area 832 causes the second piston head 830 and the stepped portion 35' of the piston bar 35 to move distally. After the second piston head 830 has moved to a fully extended position (FIG. 13), gas continuing to enter the first cylinder area 815 biases the second housing 820 to its fully extended position. Once the knife assembly 30 has been advanced to its distal-most position in the end effector 12, the clinician discontinues the application of pressurized gas by releasing the activation trigger 670.

To retract the firing mechanism or knife assembly 30, the clinician 30 moves the directional valve selector switch 612 to the reverse (retract) position wherein the first supply line 840 is connected to a vent in the directional valve 610. Gas in the third cylinder area 832 and the first cylinder area 815 is permitted to exit through the first supply port 813 into the supply line 840 and is ultimately vented through the directional valve 610. As the gas exits the third cylinder area 832, the second retract spring 852 retracts the stepped portion 35' of the piston bar 35 into the second cylinder housing 820. Likewise, as the gas exists the first cylinder area 815, the first retraction spring 850 biases the second cylinder housing 520 into the first cylinder housing 810.

Figure 16A:
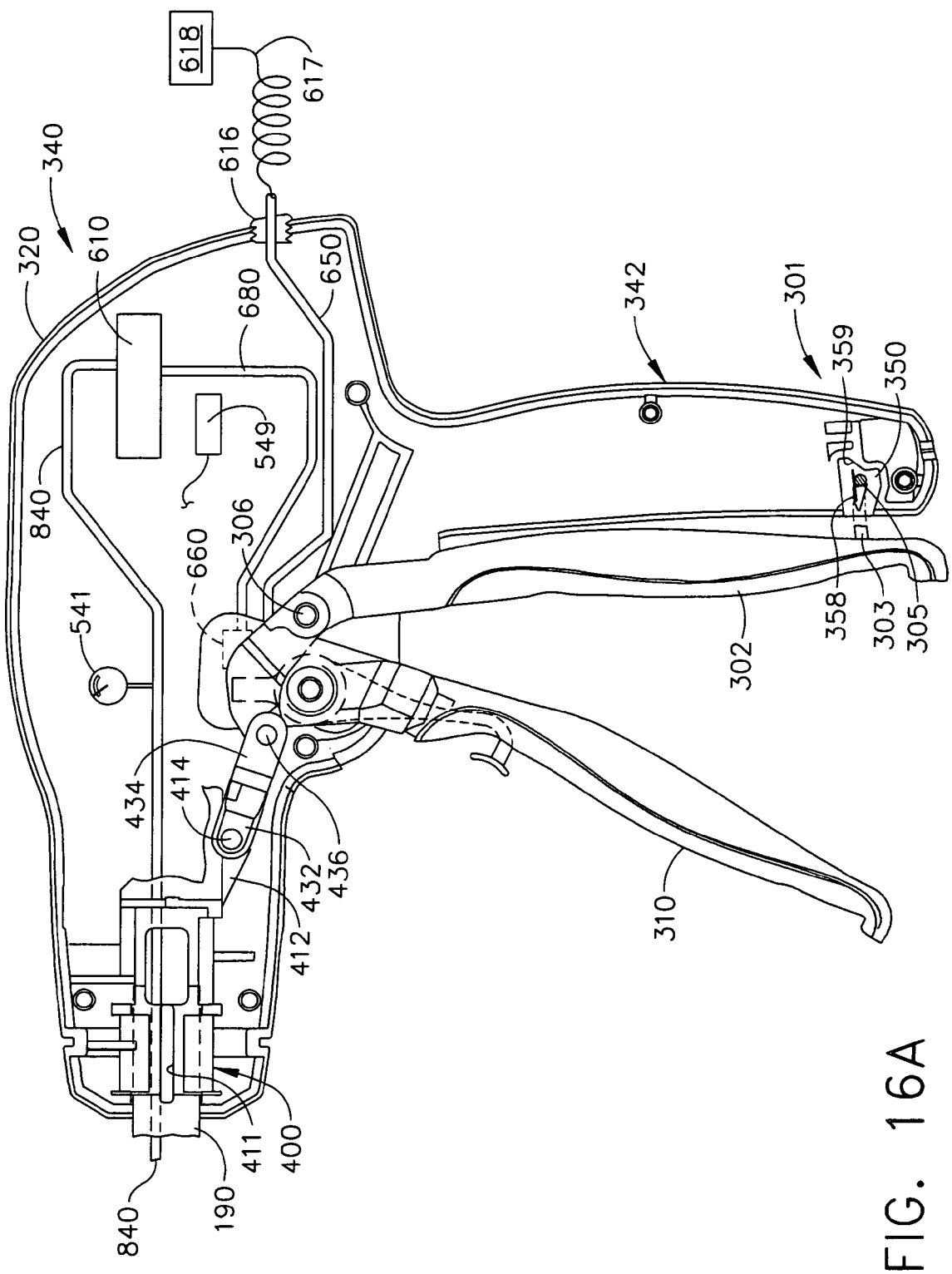
FIG. 16A is a cross-sectional view of another handle assembly that may be used in connection with the embodiment depicted in FIGS. 12-15 wherein the source of pressurized gas is external to the handle assembly.
Figure 16B:
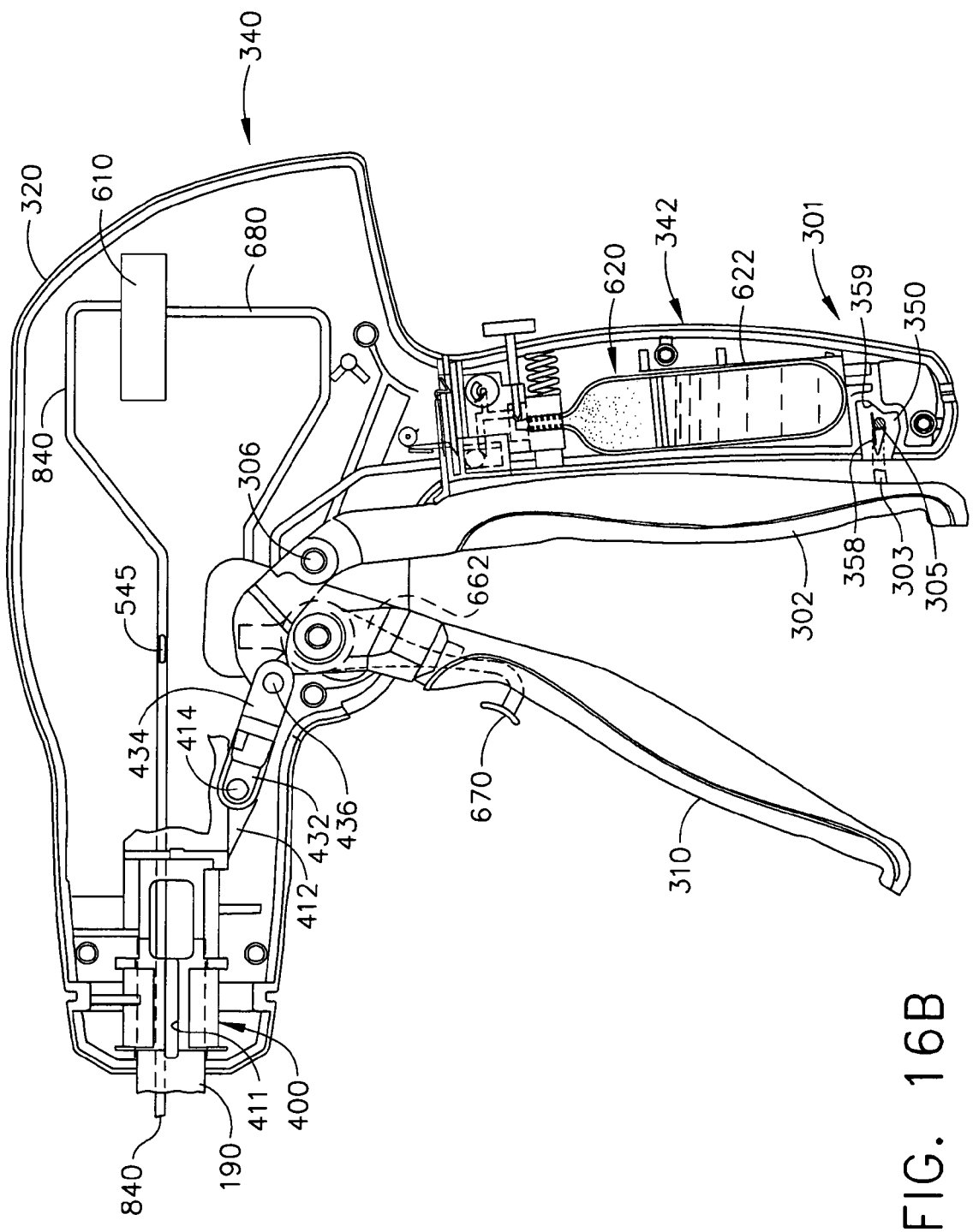
FIG. 16B is a cross-sectional view of another handle assembly embodiment of the present invention.

Also in this embodiment, a pressure gage 541 may be fluidically coupled to supply line 840 as shown in FIGS. 16 and 16A which can function in the manner described above and serves to provide the clinician with a proportionate reading to the forces being experienced by the end effector. In other various embodiments, an audible outlet 545 may be provided in the supply line 840 as shown in FIG. 16B which can function in the manner described above to provide the clinician with an audible feedback mechanism for monitoring the firing forces being experienced by the drive system 500 and ultimately the firing mechanism. In other alternative embodiments, a limit switch 546 (FIG. 15) may be provided within the distal spine segment 110 for detecting an activation member 547 (FIGS. 12 and 13) embedded into the firing rod 35 for automatically controlling the directional switch 610 and/or providing visual and or audible signals indicating that the firing mechanism has reached the end of the firing stroke.

FIGS. 17-21A illustrate yet another embodiment of the present invention wherein the drive member 500 comprises a bellows assembly 900. The bellows assembly 900 may have a distal end 902 (FIG. 20) that is attached to distal portion 31 of the knife bar assembly 30. The distal end 902 has a protrusion 904 formed thereon that sized to be received in an aperture 33 in portion 31. The protrusion 904 may be frictionally received within the aperture 33 and/or retained therein by adhesive, welding, etc. The distal portion 31 may be constructed and configured as was described in detail above.

The bellows assembly 900 further includes an expandable/retractable bellows portion 910 that is sized to extend and retract within a bellows passage 117 in the distal spine segment as shown in FIG. 18. The bellows portion 910 may be formed with wire containment rings 912 as shown in FIG. 20 and be attached to a base portion 914 that is non-movably attached to the distal spine segment 110 or comprises an integral portion of the distal spine segment 110. The base 914 may be attached to the distal spine segment 110 by adhesive, screws, etc. A supply port 916 is provided through the bellows base 914 and a supply line 940 is attached to the supply port 916. The supply line 940 is also coupled to the directional control valve 610 in the handle assembly 300. See FIGS. 21, 21A. The directional control valve 610 also communicates with a vacuum port 620 mounted in the handle assembly 300 through a vacuum line 922. The vacuum port 620 is attachable to a source of vacuum 630 by, for example, a flexible line 632. The source of vacuum may be a permanent vacuum supply line in the facility. A flexible vacuum line 632 may be attached from the port 620 to the vacuum source 630 to enable the clinician to freely manipulate the instrument.

This instrument may be provided with the closure tube assembly 170 and closure trigger 310 arrangements described above. Thus, tissue may be clamped in the end effector 12 in the manner described above. After the tissue has been clamped in the end effector 12, the clinician may fire the instrument as follows. The clinician moves the selector switch 612 (FIG. 1) or buttons for the directional control valve 610 to the forward (extend) position and begins to squeeze the activation trigger 670. As the activation trigger 670 is squeezed, the rate valve 660 permits the pressurized gas to flow from the pressure source 620 (FIG. 21) or 618 (FIG. 21A) to the directional control valve 610. The directional control valve 610 permits the pressurized gas to flow through the supply line 940 into the bellows 910 causing it to extend distally. As the bellows 910 extends distally, it drives the knife assembly 30 through the end effector 12 severing the tissue clamped therein and driving the staples 70 in the staple cartridge 50 into forming contact with the bottom surface of the anvil 40. After the knife assembly 30 has been driven to its distal-most position in the end effector 12, the clinician releases the activation trigger 670. To retract the knife assembly 30, the clinician moves the selector switch 612 for the directional control valve 610 to the retract position to thereby permit the source of vacuum 630 to be coupled to the supply line 940. The application of the vacuum to the supply line 940 causes the bellows 910 to retract to its retracted position illustrated in FIG. 18. After the bellows 910 has been fully retracted, the clinician may move the selector switch 612 or buttons to a position wherein the directional control valve stops the application of vacuum to the supply line 940. However, the remaining vacuum within the supply line 940 may serve to retain the bellows 910 in the retracted position.

Figure 21:
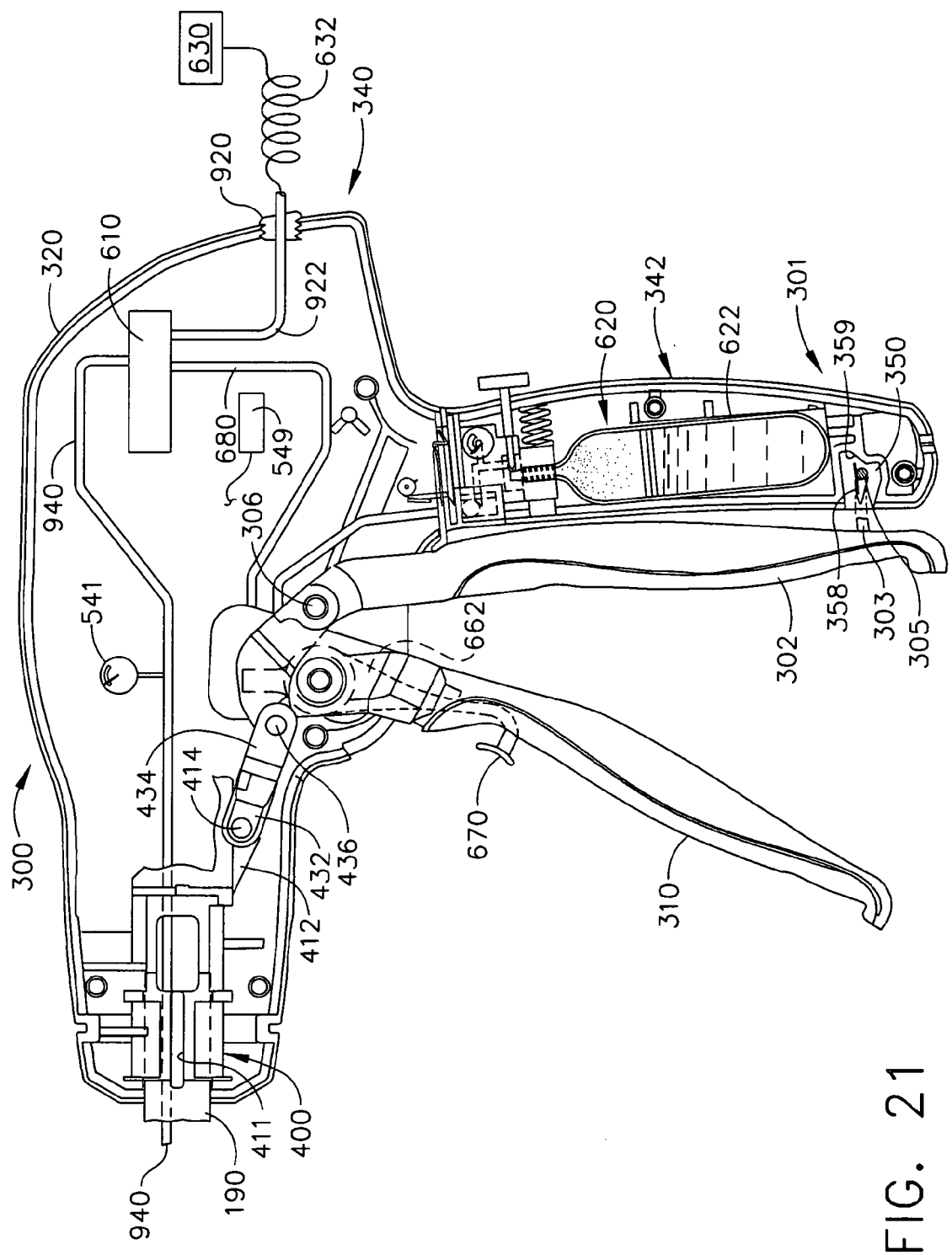
FIG. 21 is a cross-sectional view of a handle assembly embodiment that may be used in connection with the embodiments depicted in FIGS. 17-20.

In the embodiment depicted in FIG. 21, a removable source 620 of pressurized gas is employed. As will be further discussed in detail below, such source of pressurized gas comprises a cylinder 622 that may be rechargeable. Those of ordinary skill in the art will appreciate, however, that nonreplaceable/rechargeable sources (cylinders) of pressurized gas or pressurized fluid could also be effectively employed. Still in other embodiments, the handle assembly 300 may be provided with a port 616 for supplying pressurized gas to an external source of pressurized gas. For example, the instrument 10 could be coupled to the facility's compressed air line through a flexible supply line 617. See FIG. 21A.

Figure 21A:
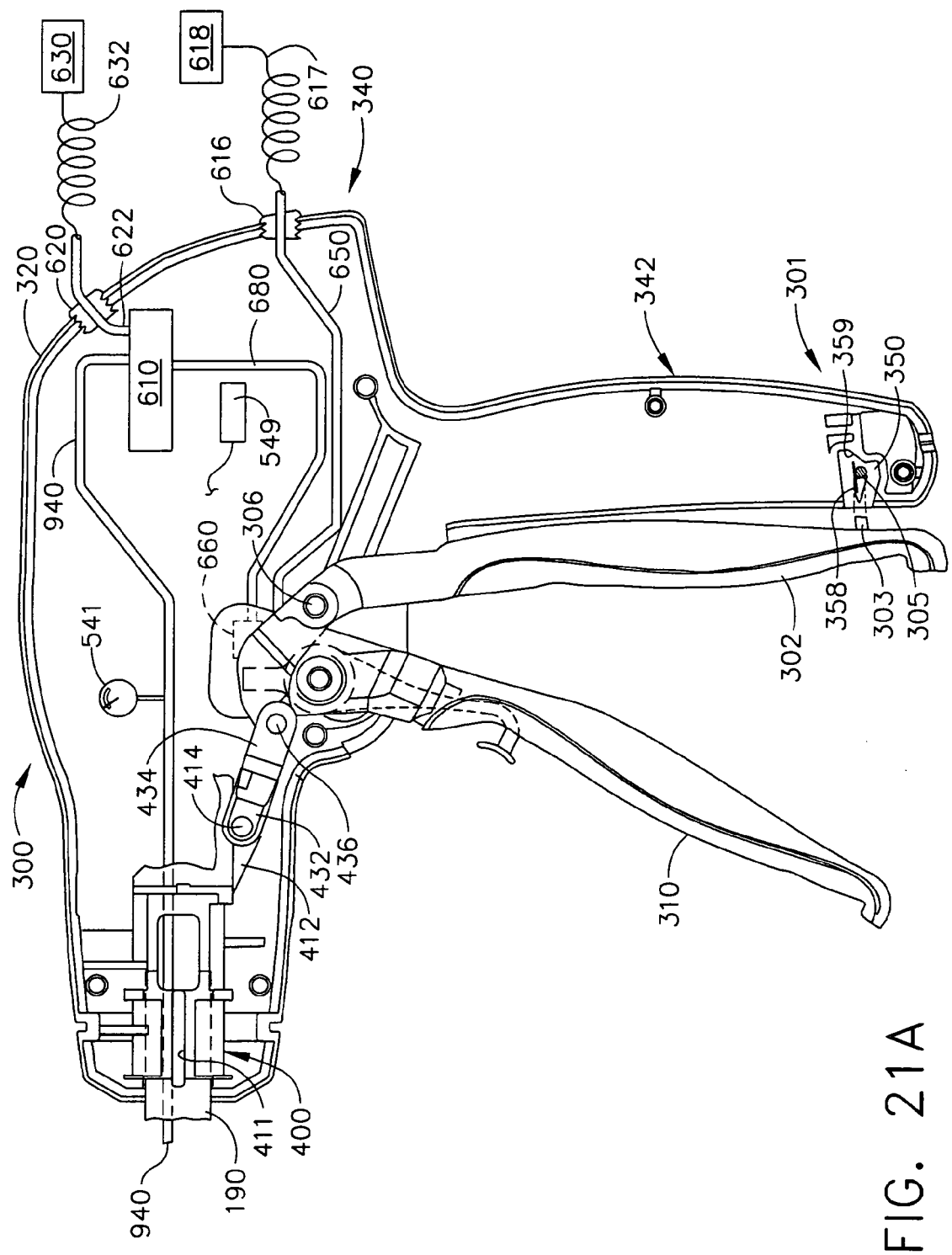
FIG. 21A is a cross-sectional view of another handle assembly embodiment that may be used in connection with the embodiments of FIGS. 17-20 wherein the source of pressurized gas is external to the handle assembly.
Figure 21B:
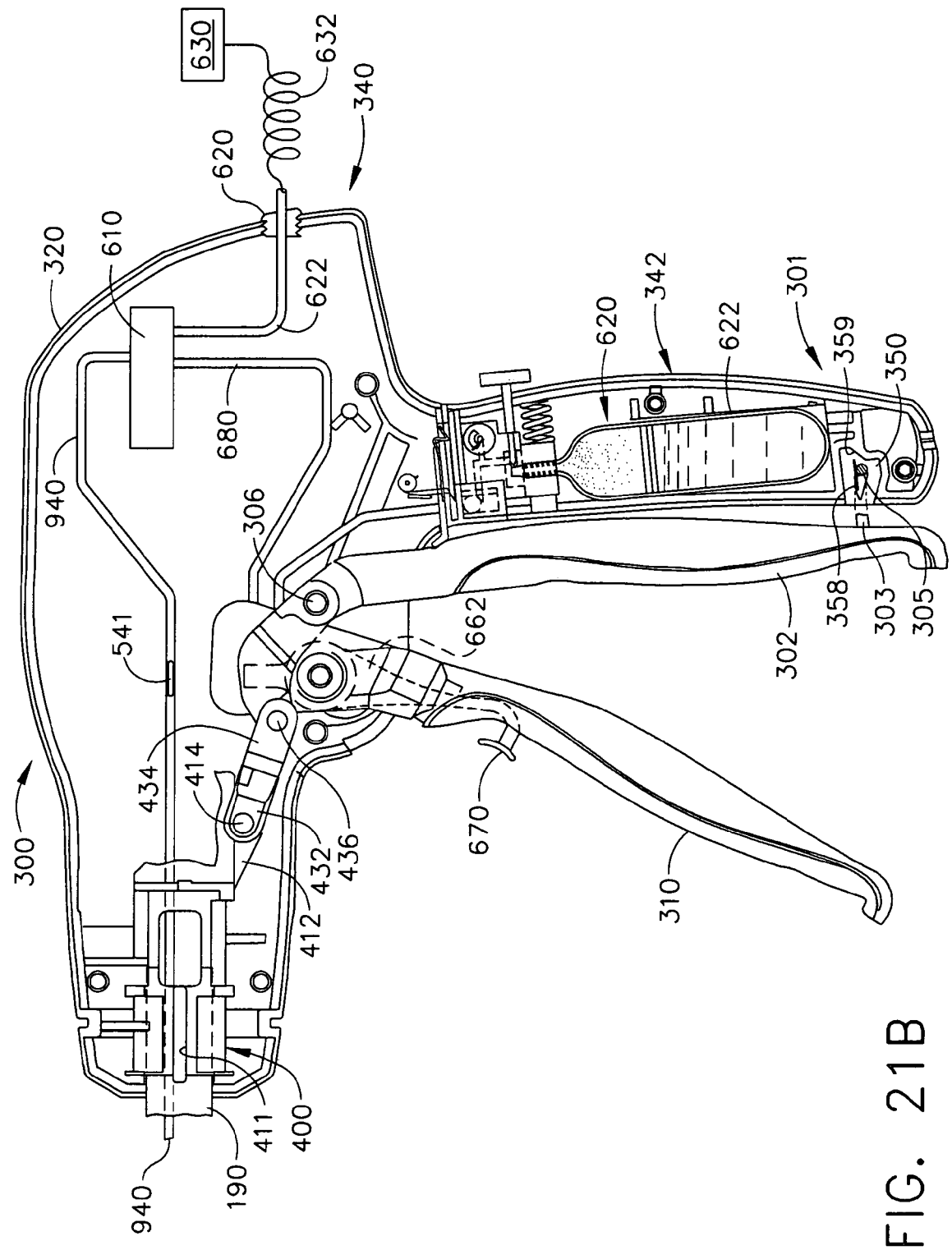
FIG. 21B is a cross-sectional view of another handle assembly embodiment of the present invention.
Figure 22:
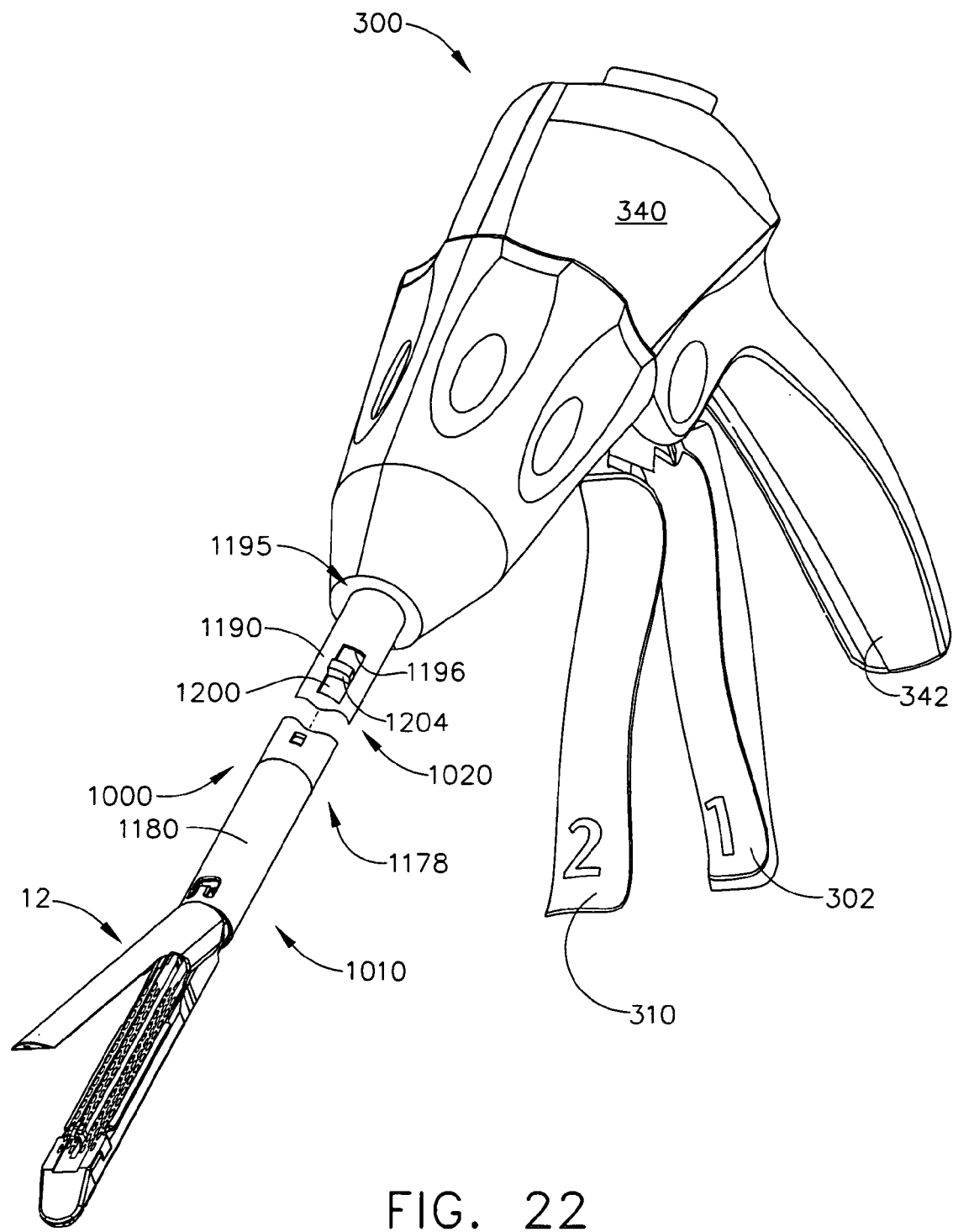
FIG. 22 is a perspective view of another surgical cutting and fastening instrument according to other embodiments of the present invention.

Also in this embodiment, a pressure gage 541 may be fluidically coupled to supply line 940 as shown in FIGS. 21 and 21A which can function in the manner described above and serves to provide the clinician with a proportionate reading to the forces being experienced by the end effector. In other various embodiments, an audible outlet 545 may be provided in the supply line 940 as shown in FIG. 21B which can function in the manner described above to provide the clinician with an audible feedback mechanism for monitoring the firing forces being experienced by the drive system 500 and ultimately the firing mechanism. In other alternative embodiments, a limit switch 546 (FIG. 18) may be provided within the distal spine segment 110 for detecting an activation member 912' (FIG. 20) on the bellows assembly 900 for automatically controlling the directional switch 610 and/or providing visual and or audible signals indicating that the firing mechanism or knife assembly 30 has reached the end of the firing stroke.

Figure 23:
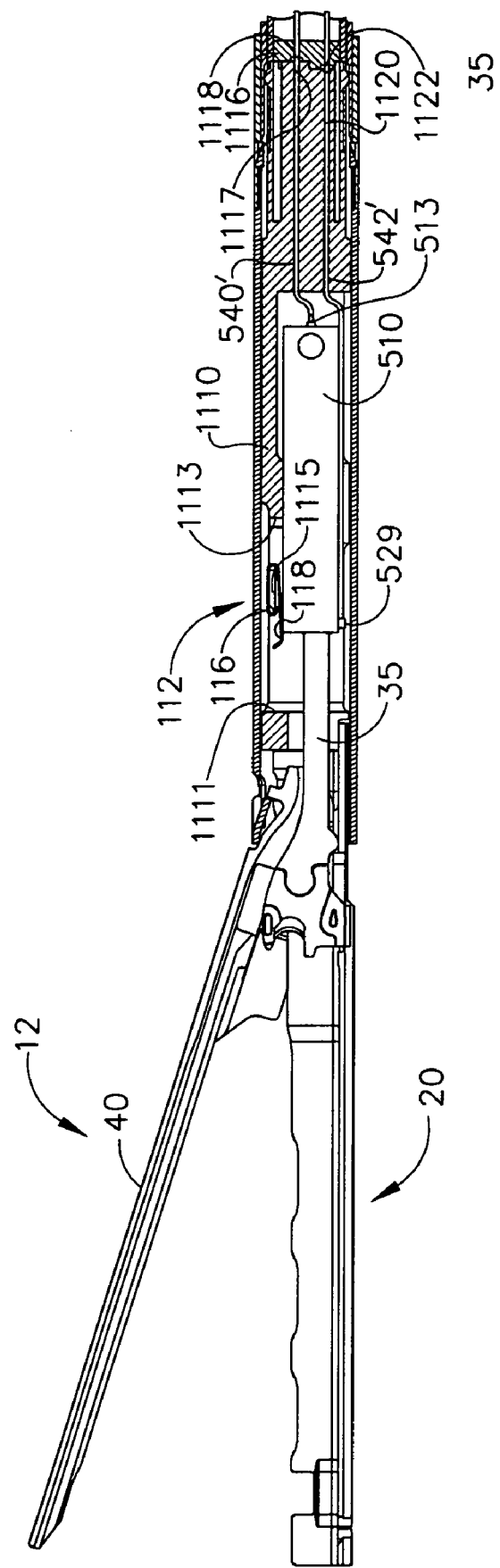
FIG. 23 is a cross-sectional side elevational view of the end effector and spine assembly of the embodiment depicted in FIG. 22.
Figure 26:
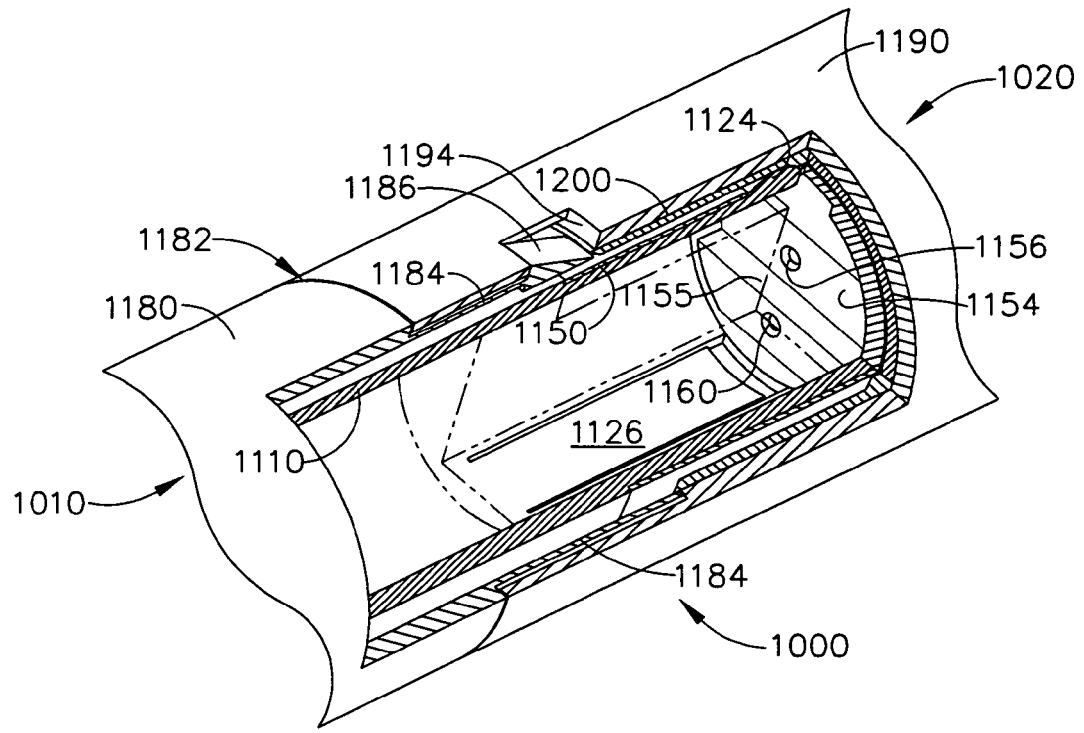
FIG. 26 is a partial perspective view of the distal shaft assembly attached to the proximal shaft assembly with a portion of the distal shaft assembly omitted for clarity.

FIGS. 22-27 illustrate a non-articulating disposable end effector 12 that employs many of the unique and novel attributes of the embodiments describe above. As can be seen in FIG. 23, this embodiment may employ the end effector 12 and any of the drive members 500 that were described in detail above. In this embodiment, however, the end effector 12 may be disposable and attached to a distal shaft assembly 1010 that may be releasably detachable to a proximal shaft assembly 1020 by a unique and novel quick disconnect type joint generally designated as 1000. Once the end effector 12 has been used, the end effector 12 and distal shaft assembly 1010 to which it is attached may be detached from the proximal shaft assembly 1020 and, if desired, discarded. A new sterile end effector 12, complete with its own distal shaft assembly 1010 and cylinder arrangement, may then be attached to the proximal shaft assembly 1020 to complete another surgical procedure. As will be explained in further detail below, the distal shaft assembly 1010 includes a distal spine segment 1110 and a distal closure tube segment 1180. The proximal shaft assembly 1020 includes a proximal spine segment 1150, a proximal closure tube segment 1190 and a release sleeve 1200.

The distal spine segment 1110 and the proximal spine segment 1150 cooperate to form a spine assembly 1030. See FIG. 27. In this embodiment, the distal spine segment 1110 may be substantially identical to the distal spine segment 110 as was described in detail above, except that their respective proximal ends differ. Likewise, the proximal spine segment 1150 may be substantially identical to the proximal spine segment 130 as described above, except that its distal end differs to enable the distal spine segment 1110 and proximal spine segment 1150 to be non-pivotally coupled together. Also in this embodiment, the distal closure tube segment 1180 may be substantially identical to the distal closure tube segment 180 described above except that their proximal ends differ. Likewise, the proximal closure tube segment 1190 may be substantially identical to the proximal closure tube segment 190 except that their distal ends differ to enable the distal closure tube segment 1180 and proximal closure tube segment 1190 to be non-pivotally attached to each other.

As can be seen in FIG. 23, a locking spring 112 is mounted in the distal spine segment 1110 as a lockout for the piston bar 35. Distal and proximal square apertures 1111, 1113 are formed on top of the distal spine section 1110 to define a clip bar 1115 therebetween that receives a top arm 116 of the locking spring 112 whose lower, distally extended arm 118 asserts a downward force on a distal end of the cylinder assembly as was discussed above. It will be appreciated that various embodiments may include other types of lockouts or no lockouts at all.

The proximal end 1114 of the distal spine segment 1110 has a distal connector portion 1116 formed therein. See FIGS. 24 and 27. As can be seen in FIG. 24, the distal connector portion 1116 has a first distal supply port 1117 that is coupled to first supply line segment 540'. A second distal supply port 1120 is provided in the distal connector portion 1116 and is coupled to a second supply line segment 542'. As can be seen in FIG. 23, the first supply line segment 540' is coupled to first supply port 513 in the first cylinder housing 510 and the second supply line segment 542' is coupled to the second supply port 529 in the distal end of the first housing 510. A first supply nozzle portion 1118 protrudes in the proximal direction from the first distal supply port 1117 as shown. A second supply nozzle portion 1122 protrudes outward in the proximal direction from the second supply port 1120.

Figure 27:
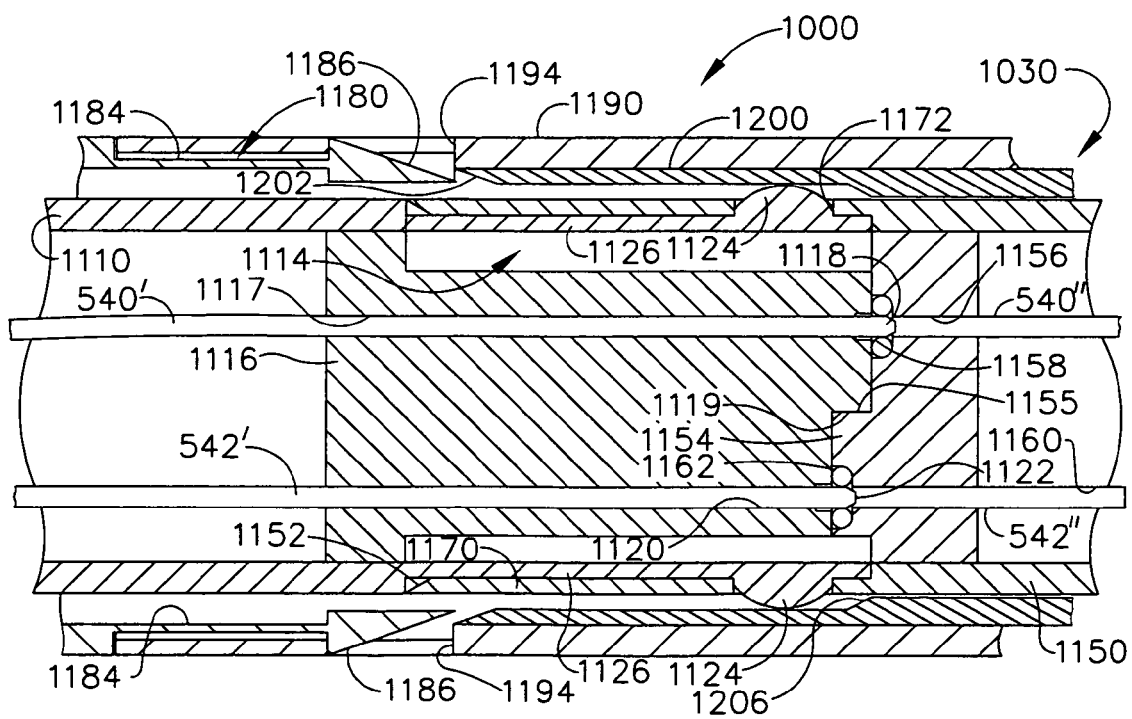
FIG. 27 is a cross-sectional side elevational view of the joint assembly of the embodiments of FIGS. 24-26 with the distal shaft assembly coupled to the proximal shaft assembly.
Figure 28:
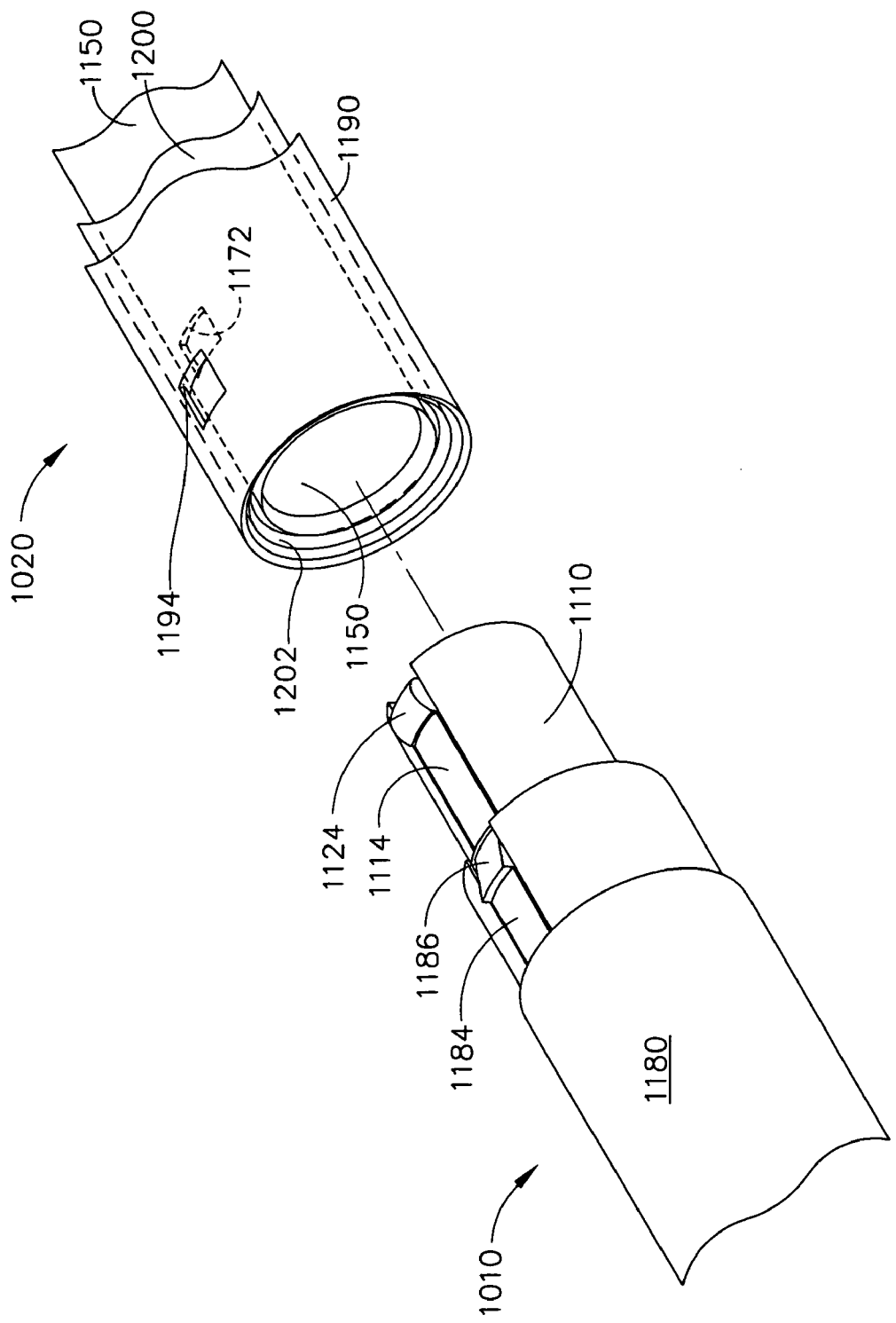
FIG. 28 is a perspective view of a portion of the distal shaft assembly prior to attachment to a portion of the proximal shaft assembly.

Similarly, the distal end 1152 of the proximal spine segment 1150 has a second connector portion 1154 that has a first proximal supply port 1156 that is coupled to another first supply line segment 540". The second connector portion 1154 further has a second proximal supply port 1160 therein that is coupled to another second supply line segment 542". The first proximal supply port 1156 is configured to removably receive the first supply nozzle 1118 therein (FIG. 27) and the second proximal supply port 1160 is sized to removably receive the second supply nozzle 1122 therein. As can be seen in FIGS. 24 and 27, a first O-ring seal 1158 is associated with the first proximal supply port 1156 for forming a substantially airtight seal (or fluid-tight) between the first supply line segment 540' and the another first supply line segment 540" when the first nozzle 1118 is inserted into the first proximal supply port 1156. When coupled together in that manner, the first supply line segments 540' and 540" are joined to form a first supply line 540. Likewise, a second O-ring seal 1162 is associated with the second proximal supply port 1160 for forming another substantially airtight (or fluid-tight) seal between the second supply line segment 542' and the another second supply line segment 542" when the second supply nozzle 1122 is inserted into the second proximal supply port 1160. When coupled together in that manner, the second supply line segments 542' and 542" form a second supply line 542. Those of ordinary skill in the art will understand that other detachable coupling arrangements, quick disconnect arrangements may be employed to removably connect the first supply line segment 540' with the another first supply line segment 540" and the second supply line segment 542' with the other second supply line segment 542" without departing from the spirit and scope of the present invention.

The distal connector portion 1116 and the proximal connector portion 1154 may be configured so that they may be coupled together in only one orientation. For example, as shown in FIG. 24, the distal connector portion 1116 may be provided with a notched portion 1119 that is adapted to mate with another notched portion 1155 in the proximal connector portion 1154 to ensure that the first nozzle 1118 engages first proximal supply port 1156 and the second nozzle 1122 engages the second proximal supply port 1160 during installation. Such unique and novel attachment arrangement prevents the inadvertent attachment of the first nozzle 1118 to the second proximal supply port 1160 and the second nozzle 112 to the first proximal supply port 1156. Other key-like configurations may be employed to ensure that the distal connector portion 1116 and the proximal connector portion 1154 are coupled in the proper orientation.

As can also be seen in FIGS. 24 and 27, the distal end 1152 of the proximal spine segment 1150 has a hollow sleeve portion 1170 that protrudes distally. Such hollow sleeve portion 1170 is sized to receive the proximal end 1114 of the distal spine segment 1110 therein. To releasably lock the distal spine segment 1110 to the proximal spine segment 1150, a pair of opposing detent members 1124 are formed on the proximal end 1114 of the distal spine segment 1110. The detents 1124 are located on flexible tabs 1126 cut or otherwise formed in the distal spine segment 1110 such that when the proximal end 1114 of the distal spine segment 1110 is inserted into the hollow sleeve portion 1170 of the proximal spine segment 1150 and the first nozzle 1118 is sealingly coupled to the first proximal supply port 1156 and the second nozzle 1122 is sealingly coupled to the second proximal supply port 1160, the detent members 1124 are received in corresponding openings 1172 in the hollow sleeve portion 1170. See FIGS. 24 and 27.

Releasable attachment of the distal closure tube segment 1180 to the proximal closure tube segment 1190 will be described with reference to FIGS. 24-27. As can be seen in those Figures, the proximal end 1182 of the distal closure tube segment 1180 has at least two bayonet-type locking tabs 1184 protruding in a proximal direction therefrom. Each locking tab 1184 has a tapered locking wedge 1186 formed thereon that are sized to be received in corresponding lock openings 1194 in the proximal closure tube segment 1190. When in the position illustrated in FIGS. 26 and 27, the distal spine segment 1110 is locked to the proximal spine segment 1150 to form the spine assembly 1030 and the distal closure tube segment 1180 is locked to the proximal closure tube segment 1190 to form the closure tube assembly 1178. Such arrangement permits the closure tube assembly 1178 to move proximally and distally on the spine assembly 1030 to open and close the anvil 40 on the end effector 12 in the various manners described above.

To attach the distal shaft assembly 1010 to the proximal shaft assembly 1020, the user aligns the proximal end 1012 of the distal shaft assembly 1010 with the distal end 1022 of the proximal shaft assembly 1020 as shown in FIG. 24 and then inserts the distal end 1012 into the proximal end 1022. When the detents 1124 are received in the locking openings 1172 and the locking wedges 1186 are received in the openings 1194, the distal shaft assembly 1010 is locked to the proximal shaft assembly 1020. The anvil 40 may be closed by moving the closure tube assembly 1178 distally by grasping the closure trigger 310 and pivoting it to the grip portion 342 of the handle assembly 300 in the manners described above. The knife bar 30 may be driven by actuating the activation trigger 670 in the manners described above.

Figure 31:
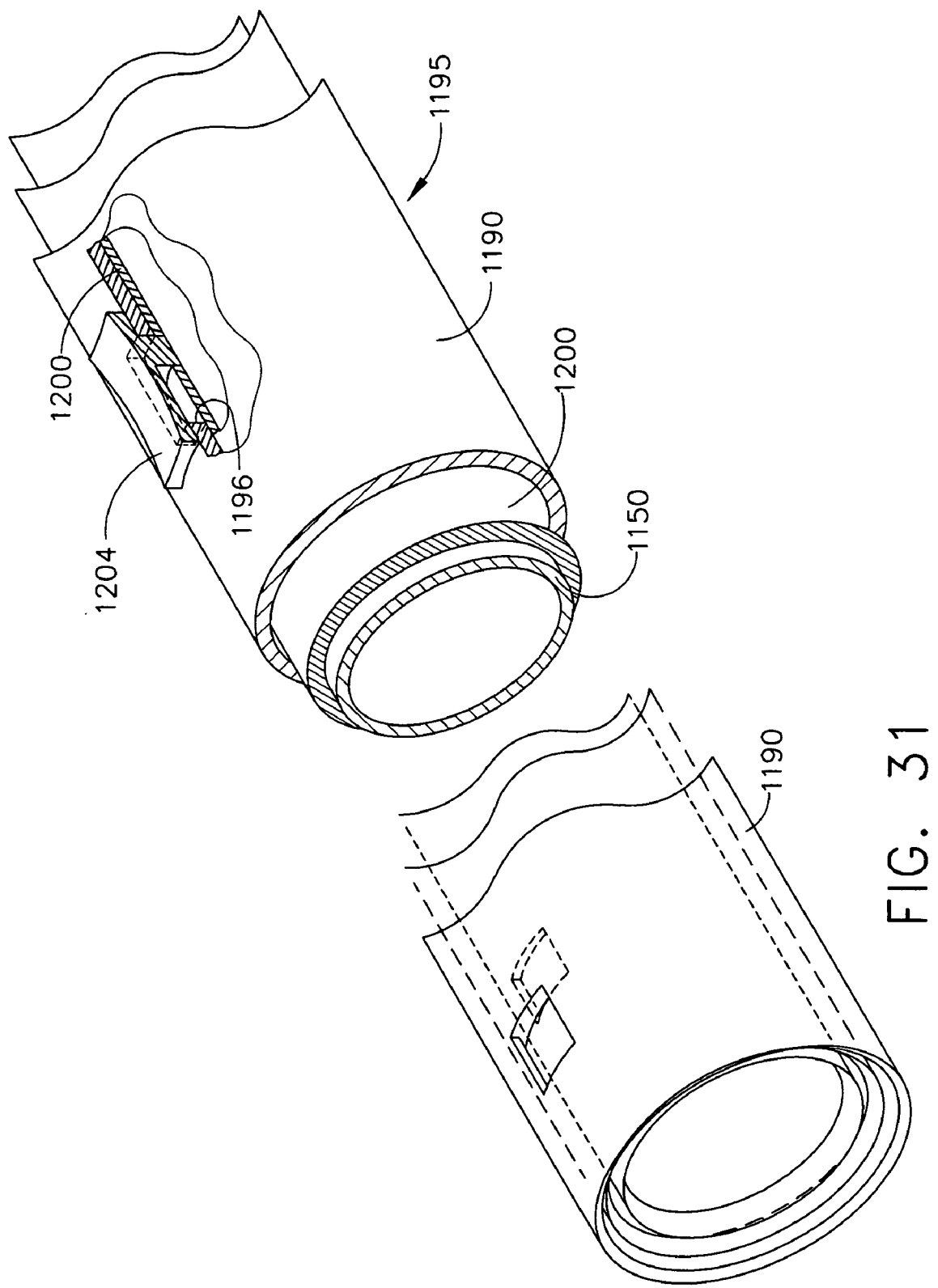
FIG. 31 is a perspective view of a portion of a proximal shaft assembly that may be used in connection with the embodiments depicted in FIGS. 22-30.

To enable the distal shaft assembly 1010 to be easily detached from the proximal shaft assembly 1020, various embodiments employ a release sleeve arrangement. In these embodiments, a release sleeve segment 1200 is slidably journaled over the proximal spine segment 1150 between the proximal spine segment 1150 and the proximal closure tube segment 1190. In various embodiments, the proximal end of the release sleeve 1200 may be provided with a release button 1204 that protrudes through a corresponding slot 1196 in the proximal end 1195 of the proximal closure tube segment 1190. See FIGS. 22 and 31. Such arrangement permits the release sleeve 1200 to be axially moved distally and proximally on the proximal spine segment 1150 without hampering the axial travel of the proximal closure tube segment 1190 on the spine assembly 1030.

As can most particularly be seen in FIG. 27, the distal end 1202 of the release sleeve 1200 is beveled inward and is oriented such that it is adjacent the two closure tube lock openings 1194 in the proximal closure tube segment 1190. To release the distal shaft assembly 1010 from the proximal shaft assembly 1020, the user moves the release button distally in slot 1196 to move the release sleeve 1200 distally. As the beveled distal end 1204 of the release sleeve 1200 contacts the locking wedges 1186, the locking wedges 1186 are moved inwardly out of engagement with the lock openings 1194 in the proximal closure tube segment 1190. Further movement of the release sleeve 1200 in the distal direction causes a second beveled interior edge 1206 in the release sleeve 1200 to contact the locking detents 1124 and bias them inwardly out of engagement with the openings 1172 in the proximal spine segment 1150 thereby enabling the distal shaft assembly 1010 to be detached from the proximal spine assembly 1020.

The embodiment depicted in FIGS. 22-28 may be effectively used with a cylinder assembly 501 of the type described above. The embodiment depicted in FIGS. 29 and 30 may be effectively used with the cylinder assembly 800 or the bellows assembly 900 described above. As can be seen in FIGS. 29 and 30, the distal connector portion 1116 only has one port 1300 formed therein that is coupled to supply line segment 940'. A first supply nozzle 1302 protrudes in the proximal direction from the first distal supply port 1300 as shown. Likewise, the connector portion 1154 only has one proximal supply port 1306 that is coupled to another first supply line segment 940". The proximal supply port 1306 is configured to removably receive the first supply nozzle 1302 therein. As can be seen in FIGS. 29 and 30, an O-ring seal 1308 is associated with the proximal supply port 1306 for forming a substantially airtight seal (or fluid-tight) between the first supply line segment 940' and the another first supply line segment 940" when the supply nozzle 1302 is inserted into the proximal supply port 1306. When coupled together in that manner, the first supply line segments 940' and 940" are joined to form a first supply line 940. The supply line 940 can then supply pressurized gas to the cylinder assembly 800 or the bellows assembly 900 in the manners described above.

Figure 32:
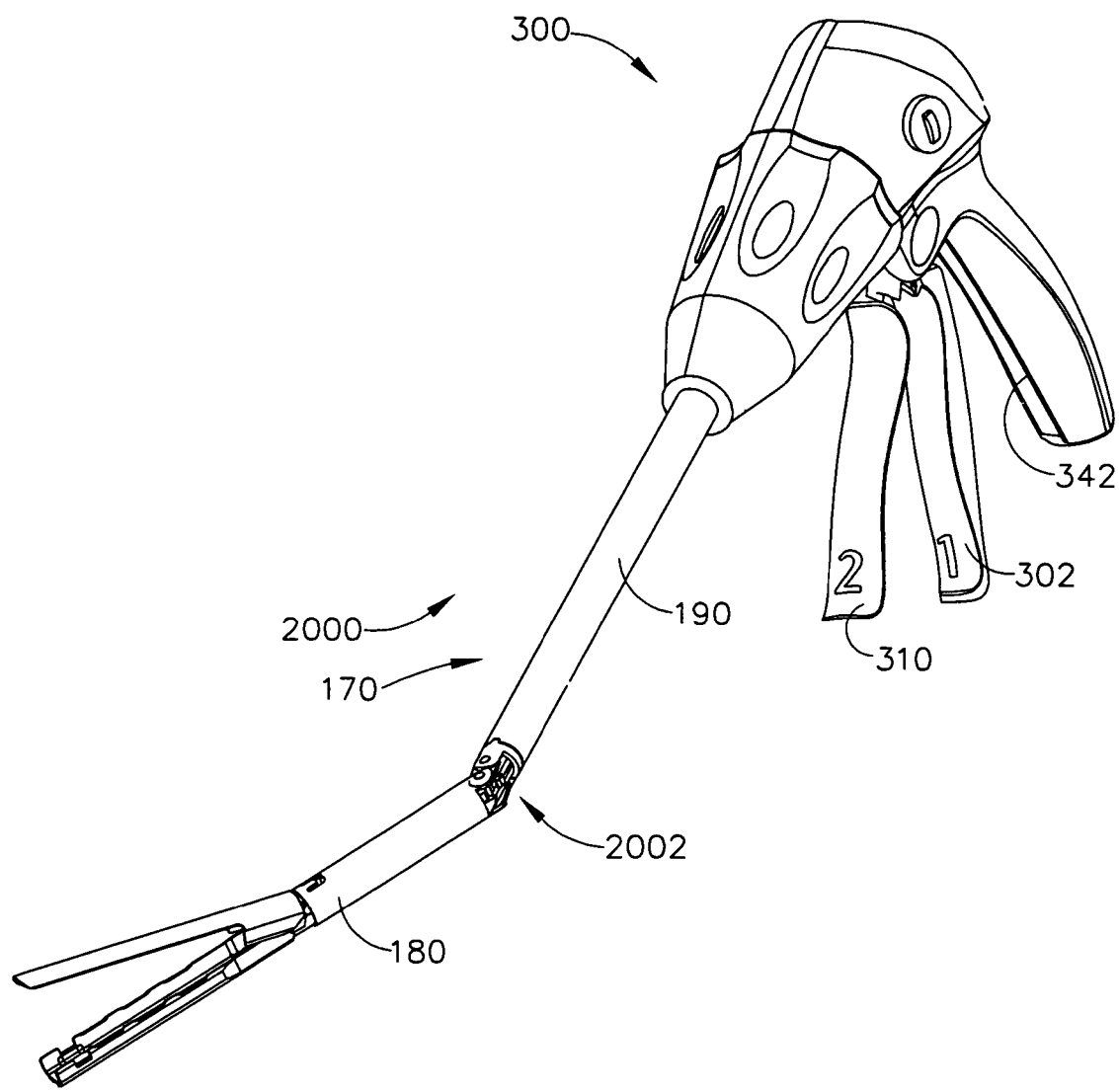
FIG. 32 is a perspective view of another surgical cutting and fastening instrument of the present invention that employs a pneumatically actuated articulation joint of various embodiments of the present invention.
Figure 33:
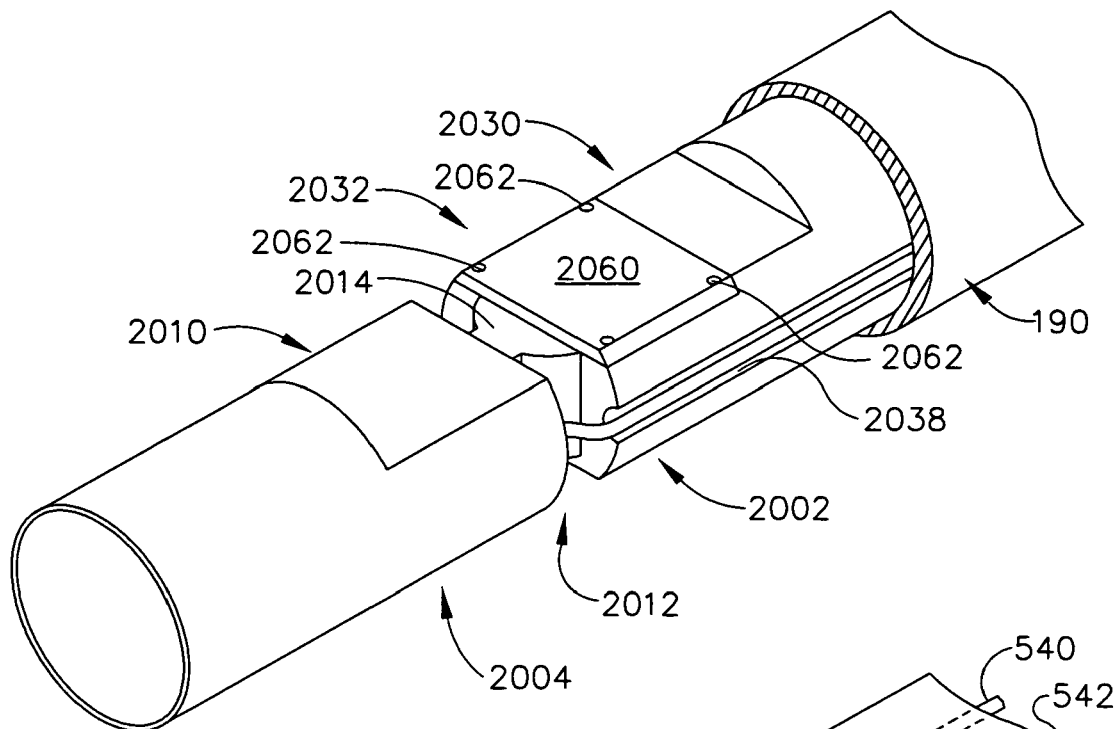
FIG. 33 is a partial perspective view of a portion of the articulation joint attaching a distal spine segment to a proximal spine segment of the embodiment depicted in FIG. 32.
Figure 34:
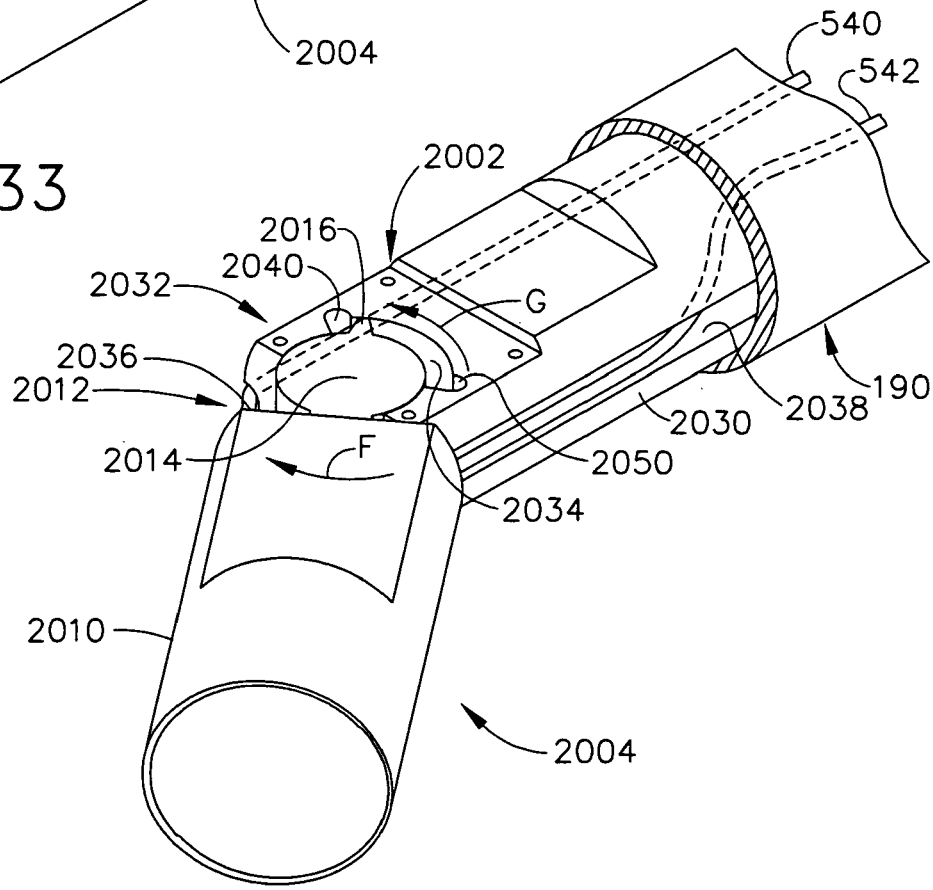
FIG. 34 is another perspective view of the articulation joint arrangement of FIG. 33 with the cover removed therefrom and illustrating the distal spine segment articulated relative to the proximal spine segment.
Figure 35:
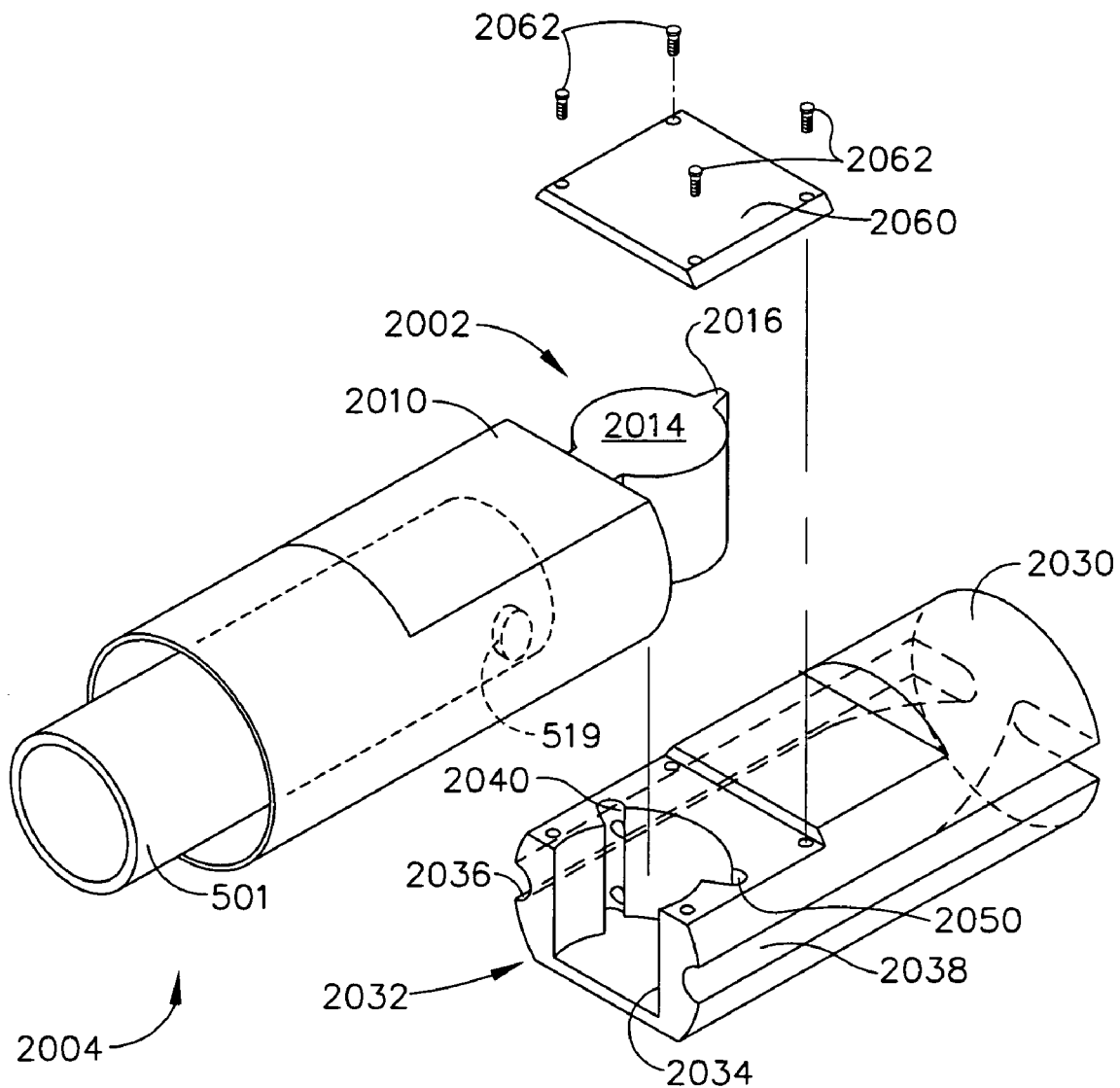
FIG. 35 is an exploded assembly view of the articulation joint arrangement of FIGS. 33 and 34.

FIG. 32 illustrates an alternative articulatable surgical cutting and stapling instrument 2000 that a pneumatically powered articulation joint assembly 2002 that may be employed in connection with the end effector 12 and the closure tube assembly 170 described above. This embodiment may also employ the cylinder assembly 501 (FIG. 10) described above. As can be seen in FIGS. 33-35, the joint assembly 2002 includes a spine assembly 2004 that comprises a distal spine segment 2010 has a pivot member 2014 protruding from its proximal end 2012 thereof. The pivot member 2014 has an actuator fin 2016 protruding therefrom. As shown in FIG. 35, the cylinder assembly 501 is pivotally mounted within the distal spine segment 2010 on trunions 519.

Figure 36:
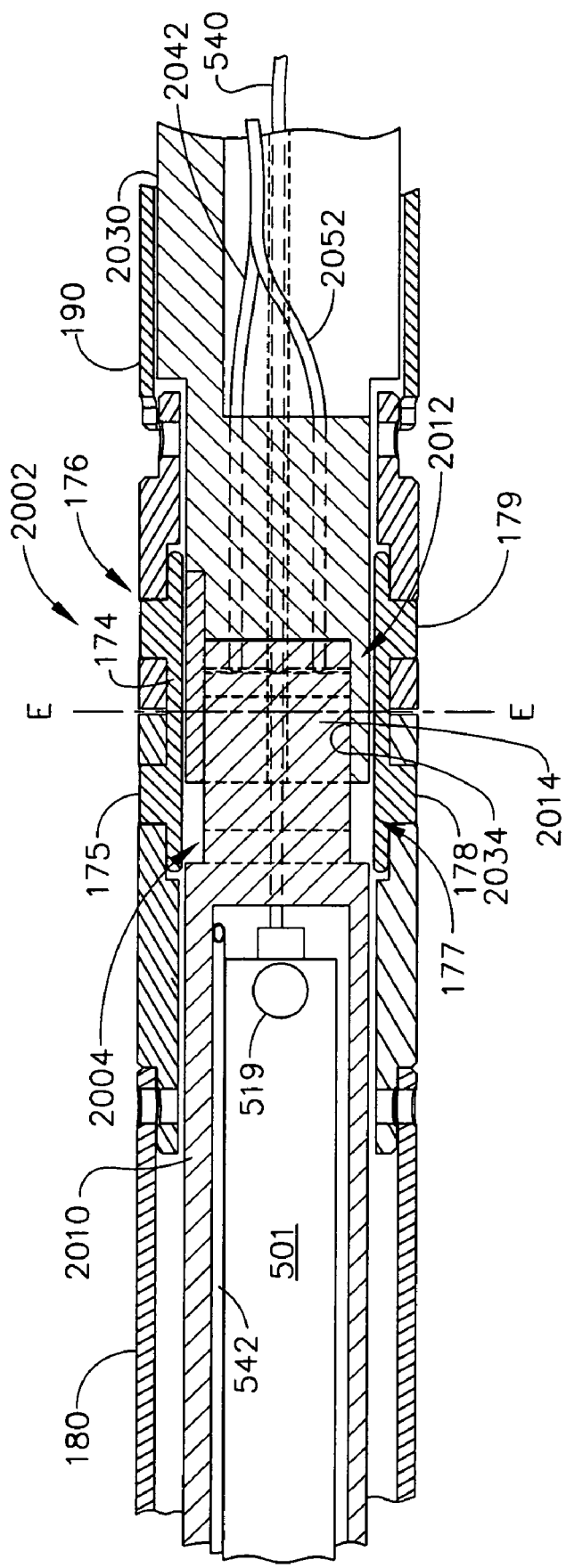
FIG. 36 is a cross-sectional side view of the joint assembly of FIGS. 33-35.
Figure 37:
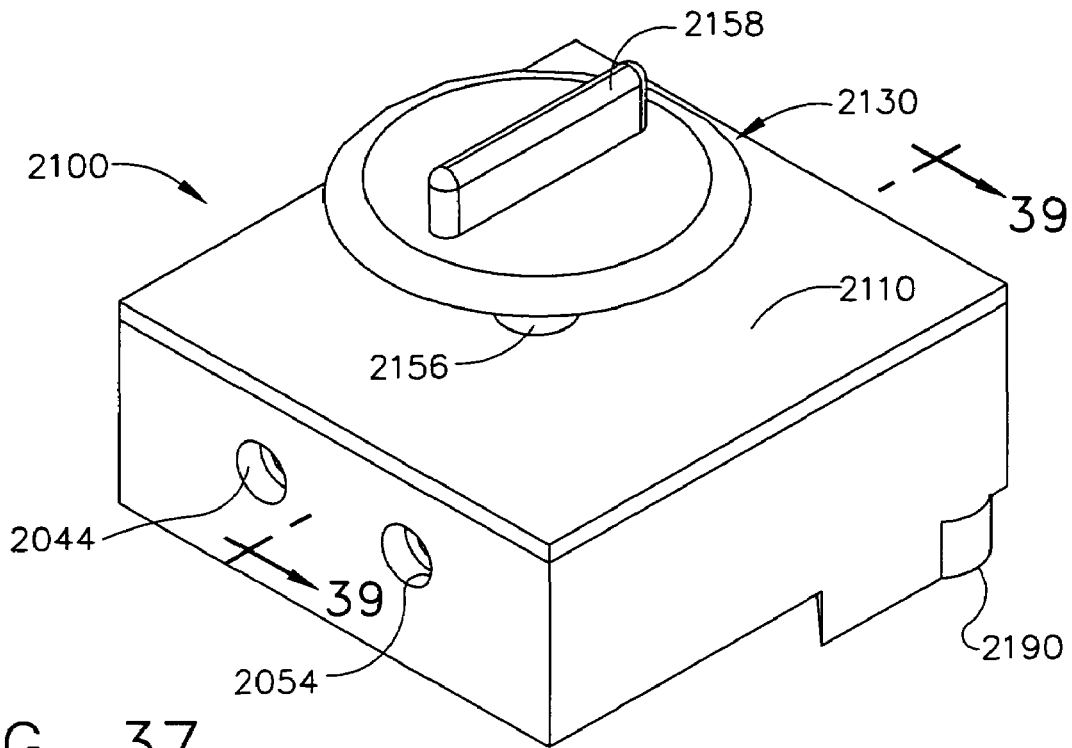
FIG. 37 is a perspective view of a switch assembly embodiment of the present invention.

The pivot member 2014 is pivotally received within a pivot socket 2034 formed on the distal end 2032 of the proximal spine segment 2030. The pivot member 2014 is free to pivot relative to the proximal spine member 2030 about pivot axis E-E. See FIG. 36. As can be seen in FIG. 35, the distal end 2032 of the proximal spine segment 2030 has a groove 2036 formed therein for accommodating a portion of the first supply line 540. Similarly a second groove 2038 is provided in the distal end 2032 of the proximal spine segment 2030 for accommodating the second supply line 542 therein. The supply lines 540, 542 pass around the pivot socket 2034 and into the proximal end 2012 of the distal spine segment 2010 wherein they are attached to the cylinder assembly 501 in the various manners described above. Those of ordinary skill in the art will appreciate that a sufficient amount of slack may be provided in the supply lines 540 and 542 within the hollow proximal spine segment 2030 to enable the distal spine segment 2010 to freely pivot about the pivot axis E-E relative to the proximal spine segment 2030. By supporting the supply lines 540, 542 in the grooves 2036, 2038, respectively, those supply lines will not interfere with the axial travel of the closure tube assembly 170 relative to the spine assembly 2004.

As can also be seen in FIG. 35, a first vertical supply passage 2040 is provided in communication with the pivot socket 2034. Similarly, a second vertical supply passage 2050 is also provided in communication with the pivot socket 2034 as shown in FIG. 35. A third supply line 2042 extending from a switch assembly 2100 mounted in the handle assembly 300 communicates with the first vertical supply passage 2040 and a fourth supply line 2052 extending from the switch assembly 2100 communicates with the second vertical passage 2050. To assemble the joint assembly 2002, the pivot member 2014 is inserted into the pivot socket 2034 and a cover 2060 is attached to the proximal spine segment 2030 as shown with screws 2062 or other suitable fasteners. Thus, pressurized gas entering the first vertical supply passage 2040 from the third supply line 2042 will cause the distal spine segment 2010 to pivot about pivot axis E-E in the "F" direction and pressurized gas entering the second vertical supply port 2050 from the fourth supply line 2052 will cause the distal spine segment 2010 to pivot relative to the proximal spine segment 2030 about the pivot axis E-E in the "G" direction. See FIG. 34.

Figure 38:
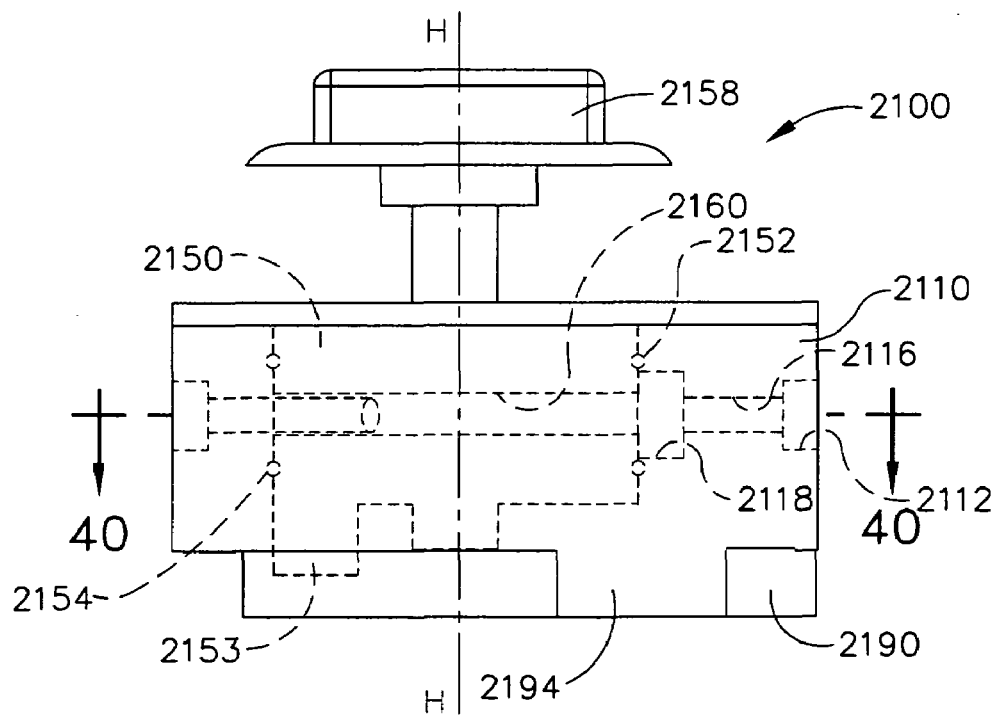
FIG. 38 is a side elevational view of the switch assembly of FIG. 37.
Figure 39:
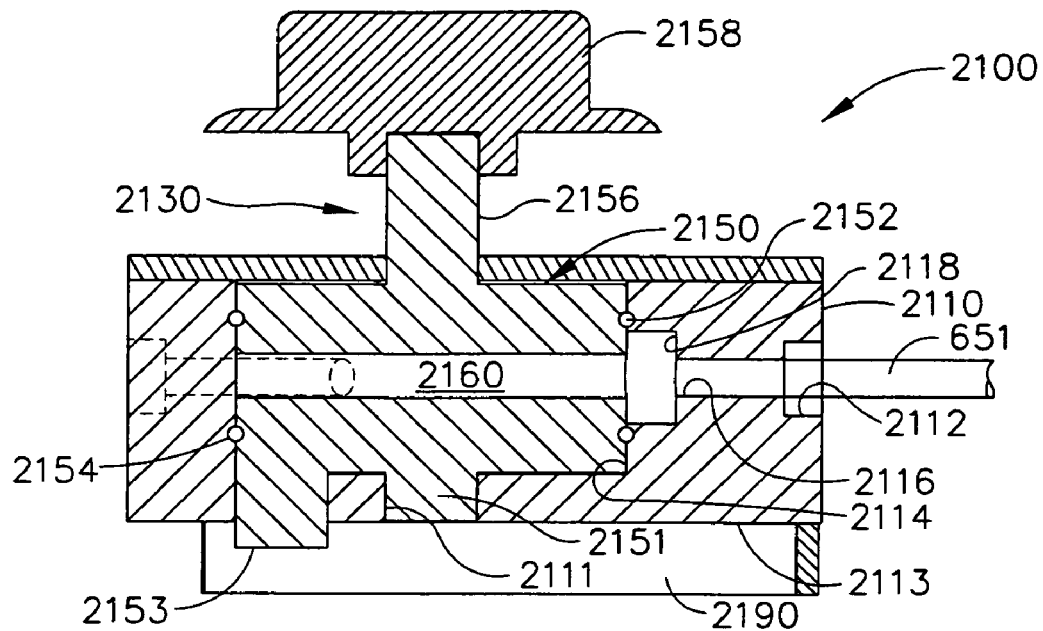
FIG. 39 is a cross-sectional view of the switch assembly of FIGS. 37 and 38 taken along line 39-39 in FIG. 37.
Figure 43:
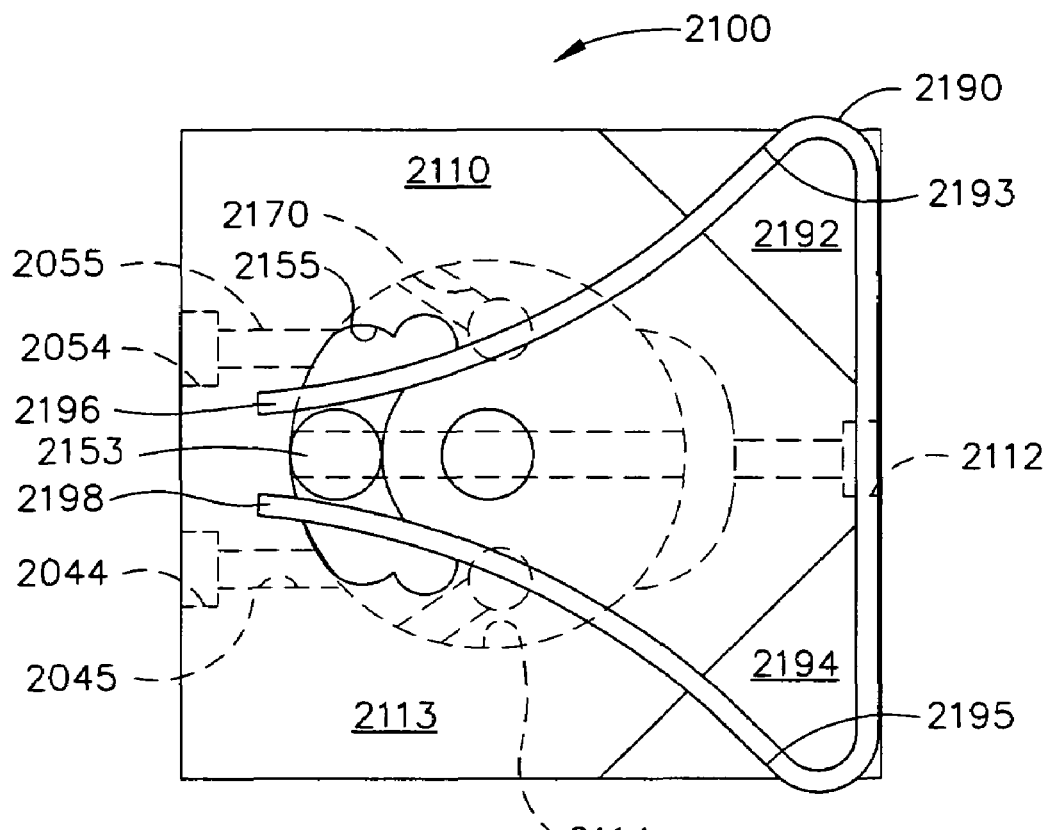
FIG. 43 is a bottom view of the switch assembly of FIGS. 37-42.
Figure 44:
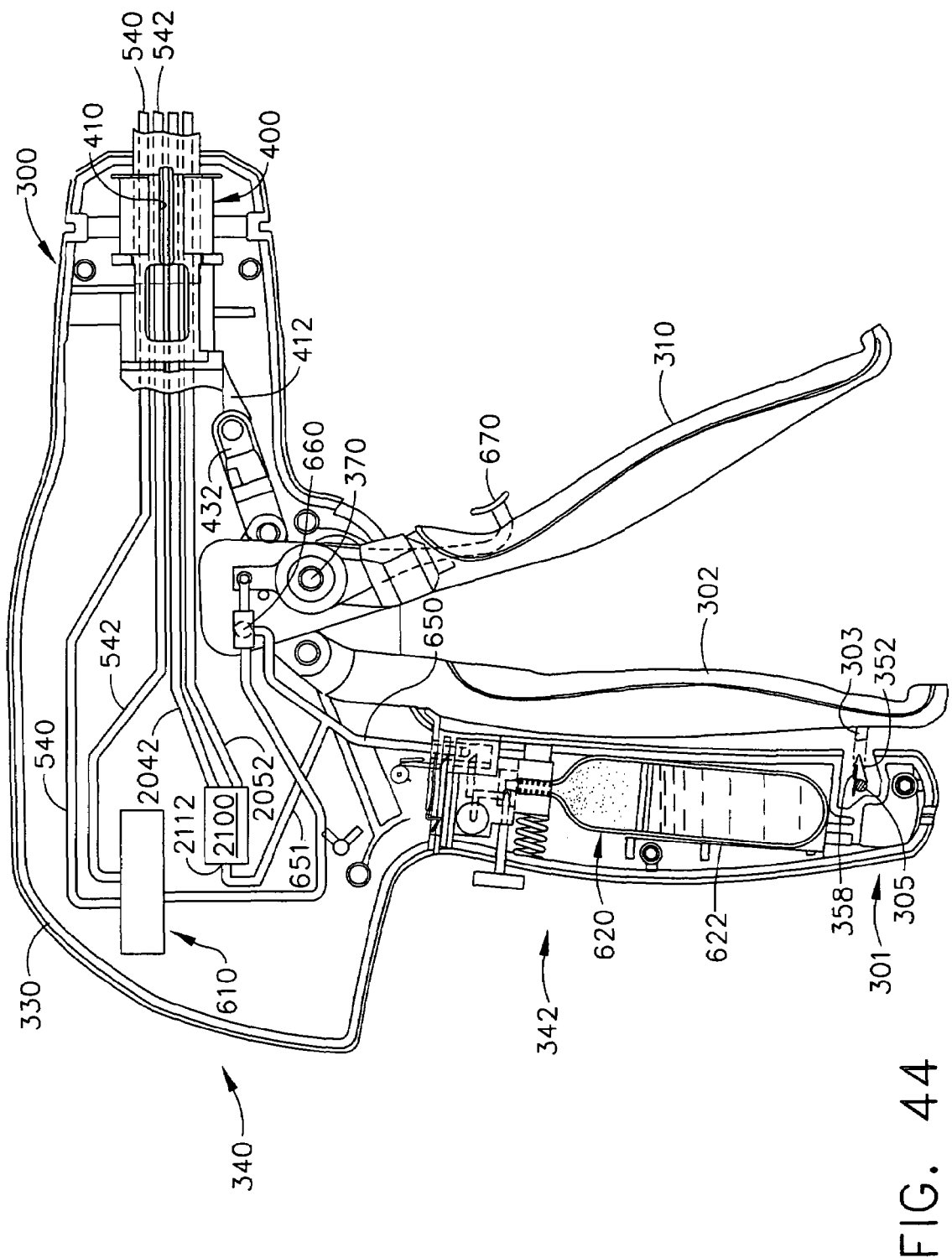
FIG. 44 is a cross-sectional view of a handle assembly that has the switch assembly of FIGS. 37-43 therein and houses a source of pressurized gas.
Figure 45:
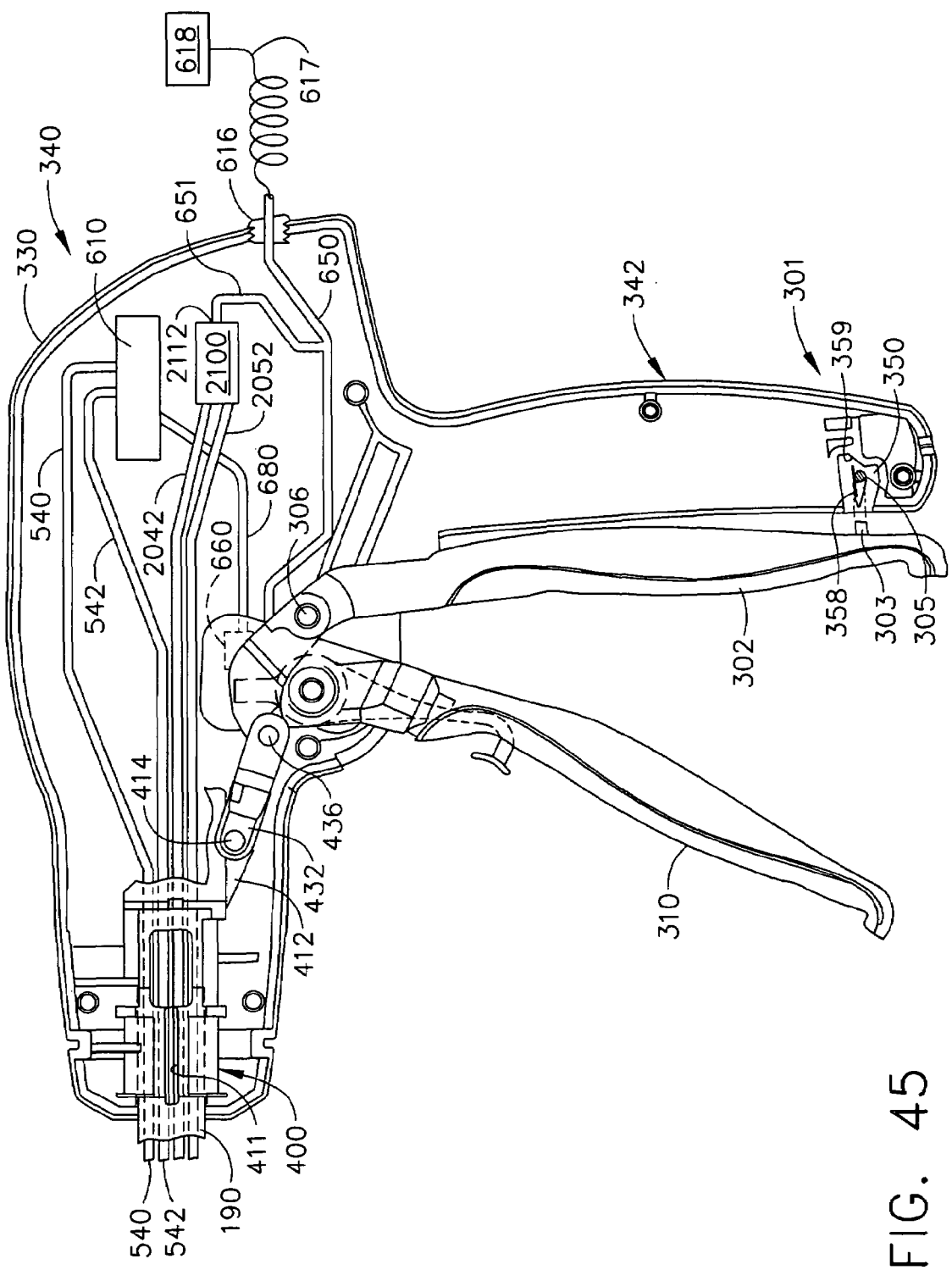
FIG. 45 is a cross-sectional view of a handle assembly that has the switch assembly of FIGS. 37-43 therein and wherein the source of pressurized gas is external to the handle assembly.

Referring to FIGS. 37-45, a construction and operation of the switch assembly 2100 of various embodiments will be explained. In various non-limiting embodiments, the switch assembly 2100 comprises a switch block 2110 that has a supply port 2112 therein. The supply port 2112 is coupled to a supply line 651 for receiving pressurized gas from the source of pressurized gas 620 (FIG. 44) or 618 (FIG. 45). In particular, a supply line 651 may extend from supply line 650 to port 2112. A switch cavity 2114 is provided in the switch block 2110 and is sized to pivotally receive a body portion 2150 of a selector member assembly 2130 therein. A pivot rod 2151 protrudes out of the bottom of the body portion 2150 to be pivotally seated in pivot hole 2111 in the switch block 2110. See FIG. 39. Such arrangement permits the selector member assembly 2130 to be selectively rotated about switch axis H-H. See FIG. 38. A pair of O-rings 2152, 2154 or other suitable seal members may be provided as shown in FIGS. 38 and 39 to establish a substantially airtight seal between the body portion 2150 of the selector member assembly 2130 and the switch block 2110. A stem 2156 protrudes from the body portion 2150 to receive a selector handle 2158. Rotation of the selector handle 2158 causes the body portion 2150 to rotate within the switch cavity 2114. As can be seen in FIG. 39, the supply port 2112 communicates with a supply passage 2116 in the switch block 2110 that communicates with a header area 2118 also formed in the switch block 2110.

Figure 40:
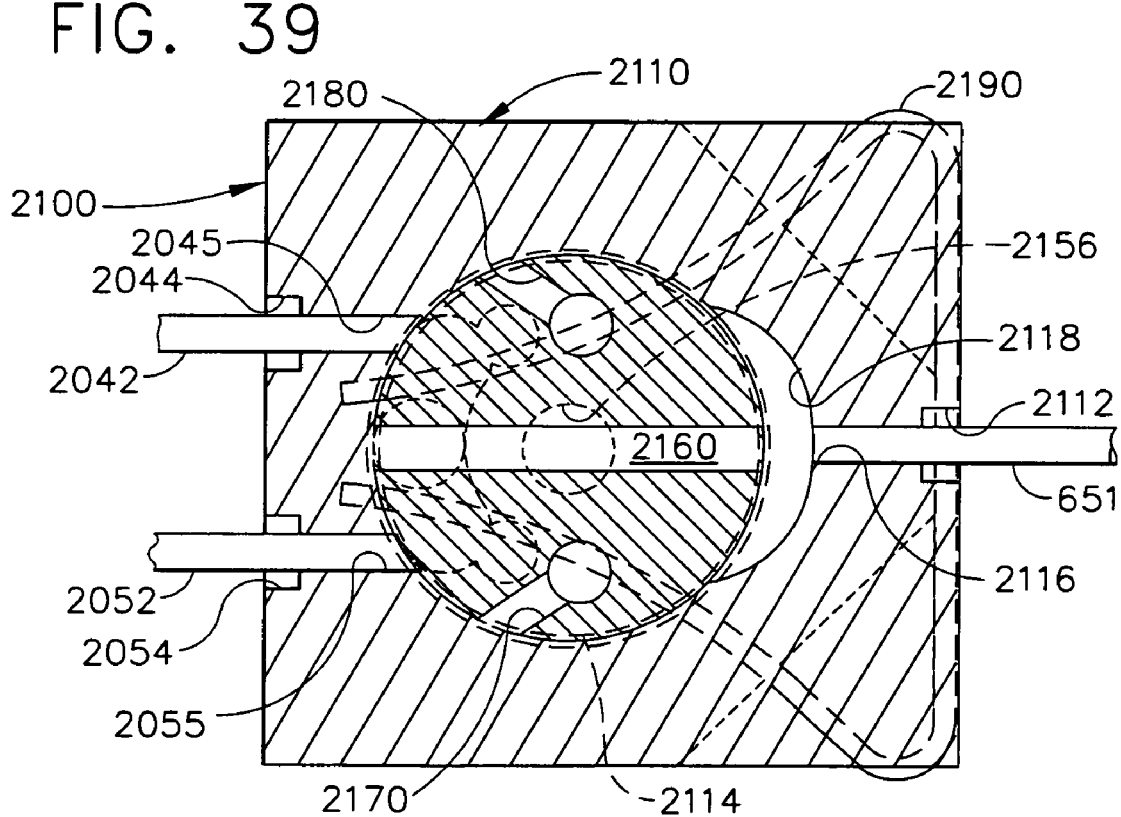
FIG. 40 is a cross-sectional view of the switch assembly in the off position taken along line 40-40 in FIG. 38.

The body portion 2150 of the selector member assembly 2130 has a central supply port 2160 therethrough that communicates with the header area 2118. A third supply passage 2045 is provided in the switch block 2110. See FIG. 40. The third supply passage 2045 extends between the switch cavity 2114 and a third supply port 2044 to which the third supply line 2042 is attached. Likewise, a fourth supply passage 2055 is provided in the switch block 2110 and extends between the switch cavity 2114 and a fourth supply port 2054 to which the fourth supply line 2052 is attached. When the selector member assembly 2130 is positioned as shown in FIG. 40, pressurized gas entering the switch block 2110 through the supply port 2112 into the supply passage 2116 passes into the header area 2118 and may flow into the central supply passage 2160. However, the pressurized gas will be blocked at the end of the central supply passage 2160. Thus, the switch is in the off position in FIG. 40.

Figure 41:
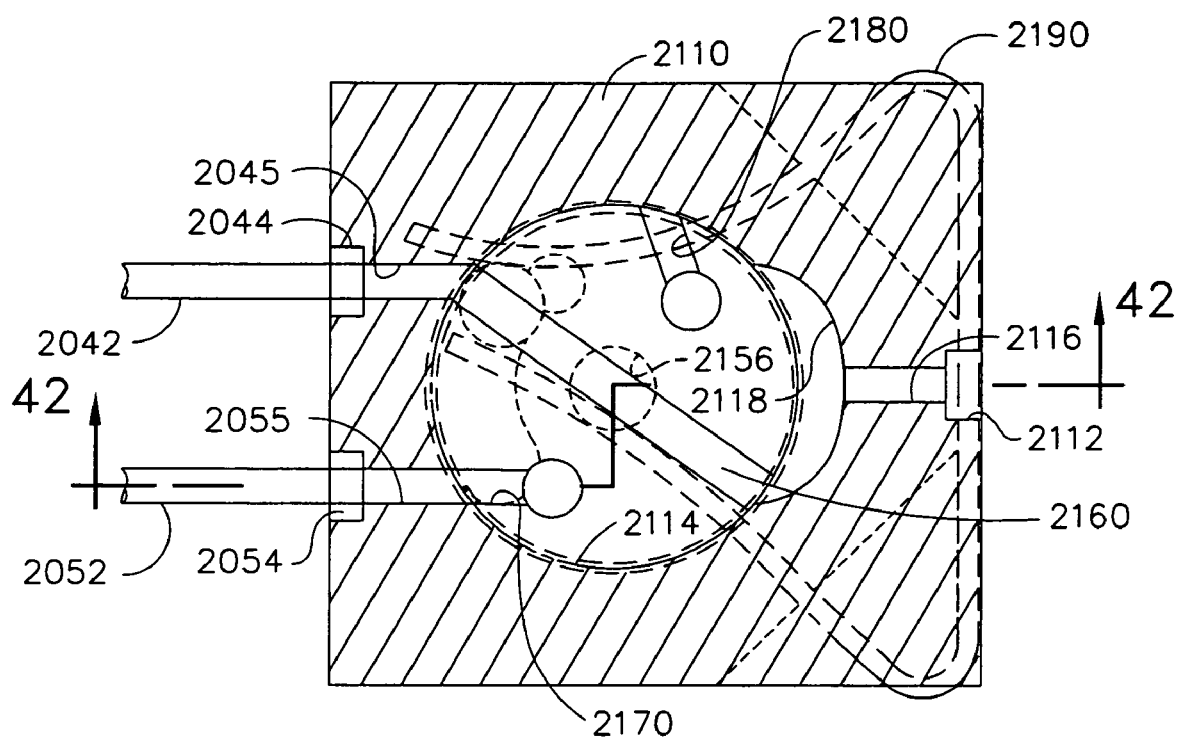
FIG. 41 is another cross-sectional view of the switch assembly of FIGS. 37-40 in an actuated position.
Figure 42:
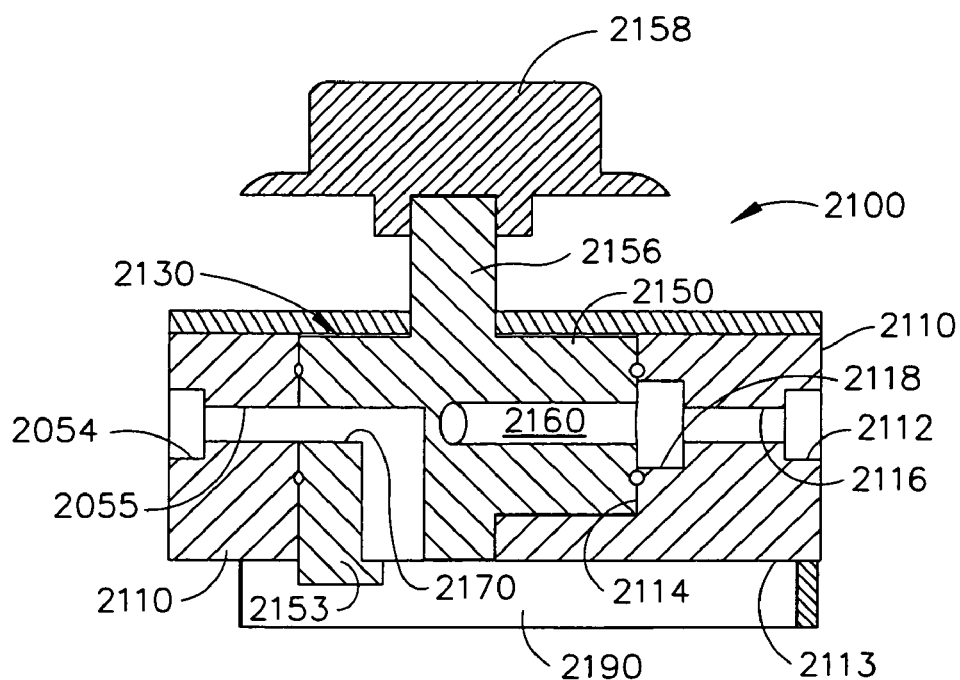
FIG. 42 is a cross-sectional view of the switch assembly of FIG. 41 taken along line 42-42 in FIG. 41.

To pivot the distal spine segment 2010 to the right (opposite of the position shown in FIG. 34), the selector member assembly 2130 is pivoted to the position illustrated in FIG. 41. As can be seen in that Figure, pressurized gas entering the switch block 2110 through the supply port 2112 through supply passage 2116 and into the header area 2118 is transferred through the central supply port 2160 into the third supply passage 2045 and into the third supply line 2042. The pressurized gas then flows into the first vertical supply passage 2040 and contacts the actuator fin 2016 on the pivot member 2014 to force the pivot member 2014 in the "F" direction. Pressurized gas on the opposite side of the actuator fin 2016 enters the second vertical passage 2050 and flows into the fourth supply line 2052. As the pressurized gas enters the fourth port 2054 in the switch block 2110, it flows into the fourth supply passage 2055 and into a fourth vent passage 2170 in the body portion 2150. The fourth vent passage 2170 communicates with a undercut vent area 2155 in the body portion 2150 of the selector member assembly 2130. See FIG. 43. Thus, the pressurized gas in the fourth supply line 2052 is vented through the fourth vent passage 2170 and out of the switch through the undercut vent area 2155.

To pivot the distal spine segment 2010 to the position shown in FIG. 34, the clinician rotates the selector member assembly 2130 such that the central supply passage 2160 now extends between the header area 2118 and the fourth supply passage 2055. Thus, pressurized gas flowing from the supply line 651 into the supply passage 2116 and into the header area 2118 flows through the central supply passage 2160 into the fourth supply passage 2055. The pressurized gas flows out through the fourth supply port 2054 and into the fourth supply line 2052. The fourth supply line 2052 transfers the pressurized gas into the second vertical supply passage 2050. As the pressurized gas enters the second vertical supply passage 2050, the actuator fin 2016 pivots the pivot member 2014 in the "G" direction. See FIG. 34. The gas on the opposite side of the actuator fin 2016 flows through the first vertical supply passage 2040 and into the third supply line 2042. The gas exits the third supply line 2042 into the third supply passage 2045 and flows into a third vent passage 2180 provided in the body portion 2150. The third vent passage 2180 is oriented to vent the gas out through the undercut vent area 2155.

Another unique and novel feature of this embodiment, is an automatic neutral feature arrangement that enables the clinician to lock the distal spine portion 2010 (and end effector 12) in a desired articulated position simply by releasing the selector switch handle 2158. More specifically, a return spring 2190 configured as shown is mounted in the switch block 2110 as shown in FIGS. 40, 41, and 43. To retain the spring 2190 in the switch block 2110, a pair of opposing bosses 2192, 2194 protrude from the bottom surface 2113 of the switch block 2110. The spring 2190 is retained within slots 2193, 2195 in the bosses 2192, 2194, respectively. See FIG. 43. As can be seen in FIG. 43, a return rod 2153 protrudes from the body portion 2150 of the selector member assembly 2130. The return rod 2153 is received between the free ends 2196, 2198 of the return spring 2190. FIG. 43 illustrates the body portion 2150 in the neutral or closed position.

Thus, when the clinician desires to articulate the end effector 12, he or she rotates the selector handle 2158 to move the body portion 2150 of the selector member assembly 2130 in the rotational direction corresponding to the desired articulation travel. As the clinician rotates the body portion 2150, it is rotated against the force generated by one of the free ends 2196, 2198 of the return spring 2190. Once the clinician has articulated the end effector 12 to the desired position, he or she releases the selector handle 2158 and the return spring 2190 moves the body portion 2150 to the closed position, which retains the end effector 12 in that position. If the clinician desires to adjust the articulated position of the end effector 12, he or she merely rotates the selector handle 2158 in the desired direction to attain the desired position and thereafter releases the handle 2158 to retain the end effector 12 in that position.

FIG. 44 illustrates the arrangement of the control system components used in connection with the switch 2100 for various non-limiting embodiments of the present invention. As can be seen in that Figure, a removable source 620 of pressurized gas is employed. The gas flowing from the source 620 flows through supply line 650 to the rate valve 660 and through the supply line 651 to port 2112 in the switch assembly 2100. In the embodiments depicted in FIG. 44, the source 620 comprises a replaceable/rechargeable canister 622 that is supported within the grip portion 342 of the housing assembly 300. The cylinder 622 may be rechargeable. Those of ordinary skill in the art will appreciate, however, that nonreplaceable/rechargeable sources (cylinders) of pressurized gas could also be effectively employed. Still in other embodiments, the handle assembly 300 may be provided with a port 616 for supplying pressurized gas from an external source 618 of pressurized gas. For example, the instrument could be coupled to the facility's compressed air line (not shown) through a flexible supply line 617. See FIG. 45.

Figure 46:
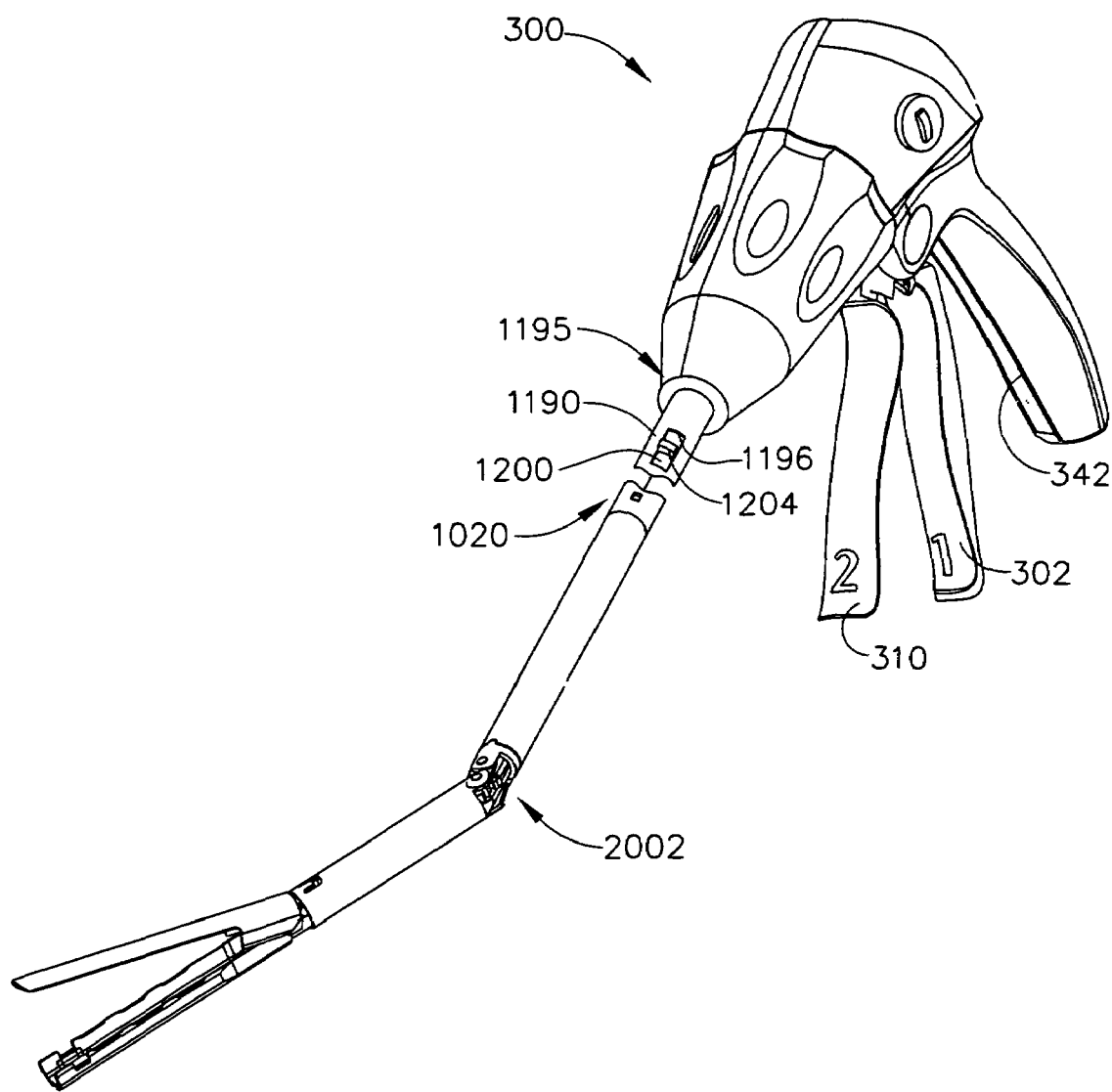
FIG. 46 is a perspective view of another surgical stapling and cutting instrument of the present invention that employs the articulation joint embodiments depicted in FIGS. 33-36 and the quick disconnect joint embodiments depicted in FIGS. 23-31.
Figure 49:
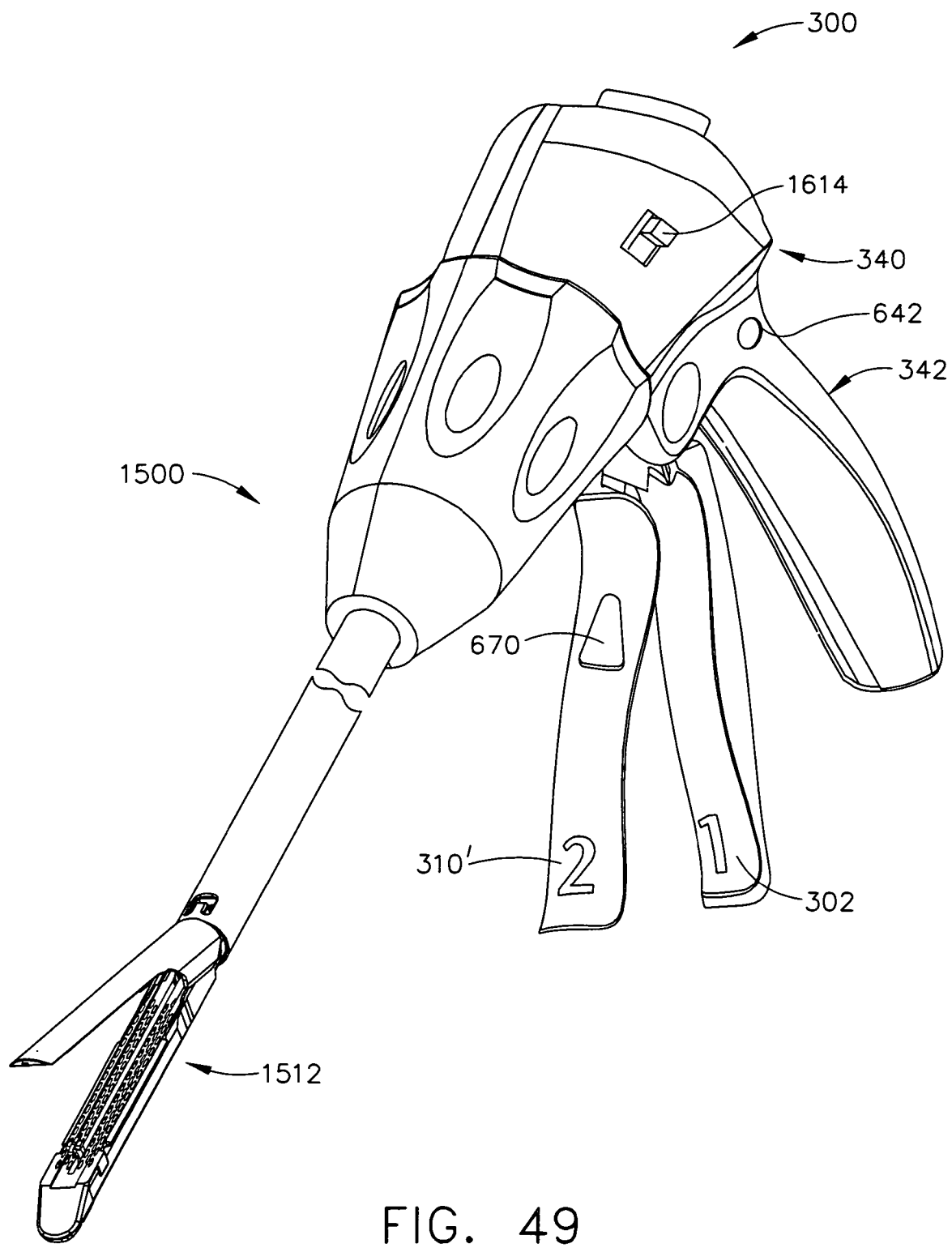
FIG. 49 is a perspective view of another surgical cutting and fastening instrument embodiment of the present invention.

FIGS. 46-48 illustrate the use of the articulation joint assembly 2002 arrangement in connection with a quick disconnect joint 1000' of the type and construction described above. In this arrangement, however, a total of four ports are used. As can be seen in FIG. 47, the distal connector portion 1116 has a first distal supply port 1117 that is coupled to first supply line segment 540'. A second distal supply port 1120 is provided in the distal connector portion 1116 and is coupled to a second supply line segment 542'. A first supply nozzle portion 1118 protrudes in the proximal direction from the first distal supply port 1117 as shown. A second supply nozzle portion 1122 protrudes outward in the proximal direction from the second supply port 1120.

The distal connector portion 1116 further has a third distal supply port 1117' that is coupled to a third supply line segment 2042'. A fourth distal supply port 1120' is provided in the distal connector portion 1116 and is coupled to a fourth supply line segment 2052'. A third supply nozzle portion 1118' protrudes in the proximal direction from the third distal supply port 1117' as shown. A fourth supply nozzle portion 1122' protrudes outward in the proximal direction from the fourth supply port 1120'.

Similarly, the distal end 1152 of the proximal spine segment 1150 has a second connector portion 1154 that has a first proximal supply port 1156 that is coupled to another first supply line segment 540". The second connector portion 1154 further has a second proximal supply port 1160 therein that is coupled to another second supply line segment 542". The first proximal supply port 1156 is configured to removably receive the first supply nozzle 1118 therein and the second proximal supply port 1160 is sized to removably receive the second supply nozzle 1122 therein. As can be seen in FIG. 47, a first O-ring seal 1158 is associated with the first proximal supply port 1156 for forming a substantially airtight seal (or fluid-tight) between the first supply line segment 540' and the another first supply line segment 540" when the first nozzle 1118 is inserted into the first proximal supply port 1156. When coupled together in that manner, the first supply line segments 540' and 540" are joined to form a first supply line 540. Likewise, a second O-ring seal 1162 is associated with the second proximal supply port 1160 for forming another substantially airtight (or fluid-tight) seal between the second supply line segment 542' and the another second supply line segment 542" when the second supply nozzle 1122 is inserted into the second proximal supply port 1160. When coupled together in that manner, the second supply line segments 542' and 542" form a second supply line 542.

In addition, the distal end 1152 of the proximal spine segment 1150 has a second connector portion 1154 that has a third proximal supply port 1156' that is coupled to another third supply line segment 2042". The second connector portion 1154 further has a fourth proximal supply port 1160' therein that is coupled to another fourth supply line segment 2052". The third proximal supply port 1156' is configured to removably receive the third supply nozzle 1118' therein and the fourth proximal supply port 1160' is sized to removably receive the fourth supply nozzle 1122' therein. As can be seen in FIG. 47, a third O-ring seal 1158' is associated with the third proximal supply port 1156' for forming a substantially airtight seal (or fluid-tight) between the third supply line segment 2042' and the another third supply line segment 2042" when the third nozzle 1118' is inserted into the third proximal supply port 1156'. When coupled together in that manner, the third supply line segments 2042' and 2042" are joined to form a third line 2042. Likewise, a fourth O-ring seal 1162' is associated with the fourth proximal supply port 1160' for forming another substantially airtight (or fluid-tight) seal between the fourth supply line segment 2052' and the another fourth supply line segment 2052" when the fourth supply nozzle 1122' is inserted into the fourth proximal supply port 1160'. When coupled together in that manner, the fourth supply line segments 2052' and 2052" form a fourth supply line 2052. Those of ordinary skill in the art will understand that other detachable coupling arrangements, quick disconnect arrangements may be employed without departing from the spirit and scope of the present invention.

As indicated above in the Background section hereof, as endocutter systems became smaller and smaller, the challenges of developing a pneumatically powered system that could generate the necessary drive forces became greater. Such problems were somewhat easier to address by using electric motors to drive rotary drive shafts. Rotary motion can readily be transmitted over long flexible or articulatable drive shafts. Although tremendous strides have been made in electric motor size and torque capabilities, the effectiveness of such systems will be limited by the size of the distal elongated shaft diameter and the size of motor that can be fitted in that area for the motor to be as close to the stapling mechanism as possible. In many current applications, the desired size of the shaft diameter prevents the electric motor from being located at the distal end of the system while being able to provide sufficient energy to drive the system.

The following embodiments address such problems and shortcomings associated with use of electric drive motors. As will be discussed below, these embodiments employ a pneumatically powered motor to transmit rotary power to a rotary driven endocutter. Pneumatically powered motors generally produce torques and rotations per minute that are proportionate to the pressure and volume of the gas transmitted to the motor. In the non-limiting embodiments depicted in FIGS. 49-56, an articulated drive shaft assembly is employed to transmit the rotary motion from the pneumatically powered pneumatically powered motor to the end effector. Those of ordinary skill in the art will understand, however, that the unique and novel aspects of these embodiments of the present invention may also be effectively used in connection with other known rotary driven end effectors and other surgical instruments that employ a flexible drive shaft arrangement for conveying rotary drive motion to the endocutter. In addition, the unique and novel aspects of these embodiments of the present invention may be effectively employed in connection with nonarticulating end effector arrangements.

FIGS. 49-56 illustrate a surgical cutting and stapling instrument 1500 of the present invention that employs a rotary driven endocutter 1512. A variety of rotary driven endocutters and other surgical instruments exist. For example, one such rotary endocutter arrangement is disclosed in U.S. patent application Ser. No. 11/343,447, filed Jan. 31, 2006, U.S. Patent Publication No. US-2007-0175957 A1 and entitled Motor Driven Surgical Cutting and Fastening Instrument With Adaptive User Feedback to Shelton, IV et al., the relevant portions of which are herein incorporated by reference. Other examples are disclosed in U.S. patent application Ser. No. 11/475,412, entitled Manually Driven Surgical Cutting and Fastening Instrument to Shelton, IV et al., filed Jun. 27, 2006, the relevant portions of which are herein incorporated by reference.

Figure 50:
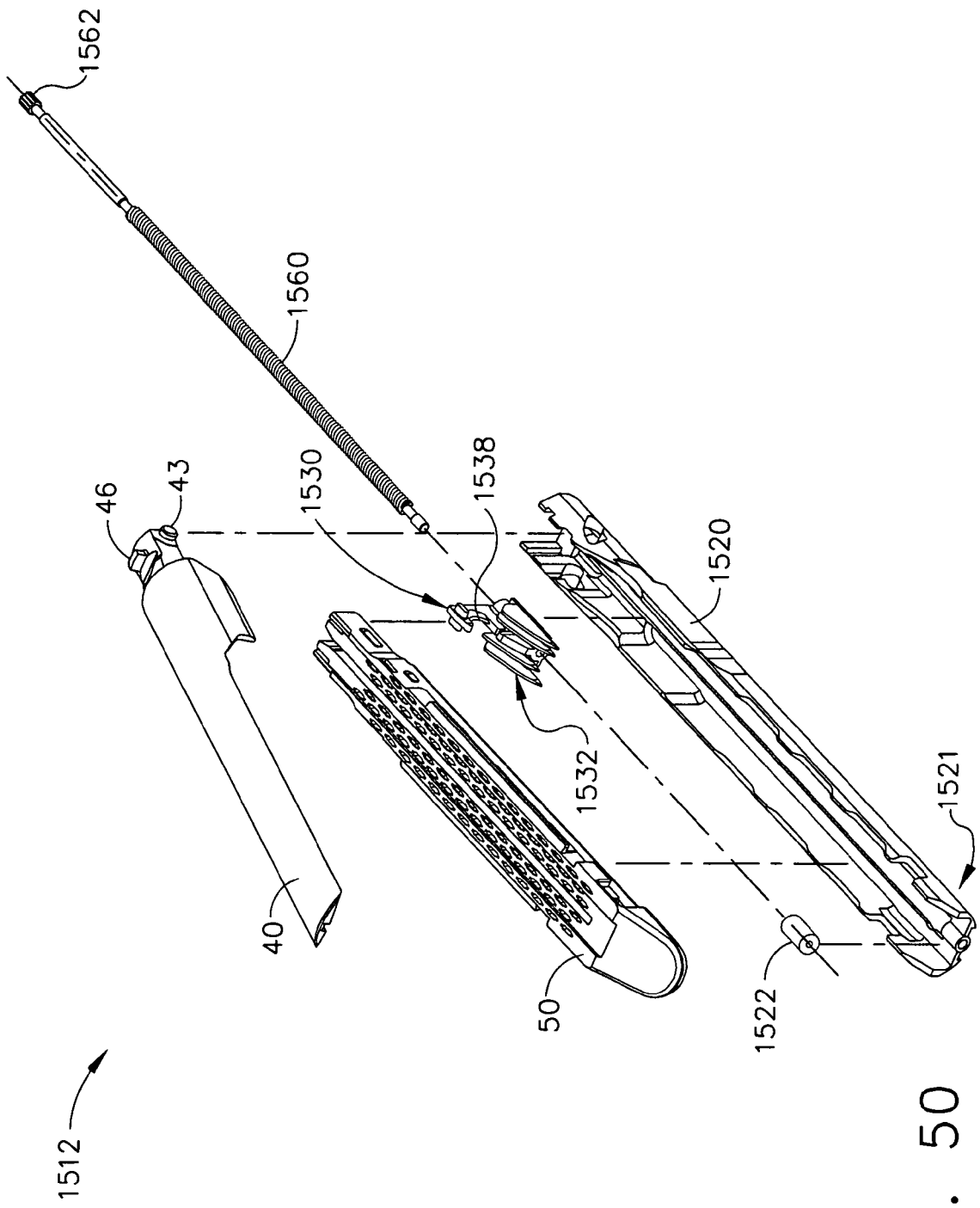
FIG. 50 is an exploded assembly view of an end effector arrangement that may be employed in connection with the embodiment depicted in FIG. 49.

FIG. 50 is an exploded view of the end effector 1512 according to various non-limiting embodiments. As shown in the illustrated embodiment, the end effector 1512 may include an elongate channel 1520 that is sized to receive a pneumatically operated tool. The pneumatically operated tool of various non-limiting embodiments comprises a staple cartridge 50 that operably supports a "firing mechanism" therein. This embodiment includes a wedge sled assembly 1530 that carries a knife portion 1538 thereon. The wedge sled assembly 1530 is threaded onto a helical drive screw 1560. A bearing 1522, positioned at a distal end 1521 of the elongate channel 1520, receives the helical drive screw 1560, allowing the helical drive screw 1560 to freely rotate with respect to the elongate channel 1520. The helical drive screw 1560 may interface with a threaded opening (not shown) of the wedge sled assembly 1530 such that rotation of the drive screw 1560 causes the wedge sled assembly 1530 to translate distally or proximately (depending on the direction of the rotation) through the elongate channel 1520 between a full extended or actuated position wherein the staples supported in the cartridge have all been fired and a fully retracted position or unactuated position. Accordingly, when the helical drive screw 1560 is rotated in one direction, the wedge sled assembly 1530 is driven distally through the cartridge 50 severing tissue clamped within the end effector 1512 and firing the staples within the cartridge 50 into forming contact with the bottom surface of an anvil 40 that is pivotally coupled to the elongate channel 1520. The sled portion 1532 of the wedge sled assembly 1530 may be made of, for example, plastic, and may have a sloped distal surfaces 1534. As the wedge sled assembly 1530 traverses the elongate channel 1520, the sloped forward surfaces 1534 may push up or drive the staples in the staple cartridge 50 through the clamped tissue and against the anvil 40 (not shown in FIG. 52). The anvil 40 turns the staples, thereby stapling the severed tissue. When the wedge sled assembly 1530 is retracted, the knife portion 1538 and sled portion 1532 and sled portion 1532 may become disengaged, thereby leaving the sled portion 1532 at the distal end of the elongate channel 1520. Those of ordinary skill in the art will appreciate that other pneumatically operated tools with other firing mechanisms may be employed.

Figure 51:
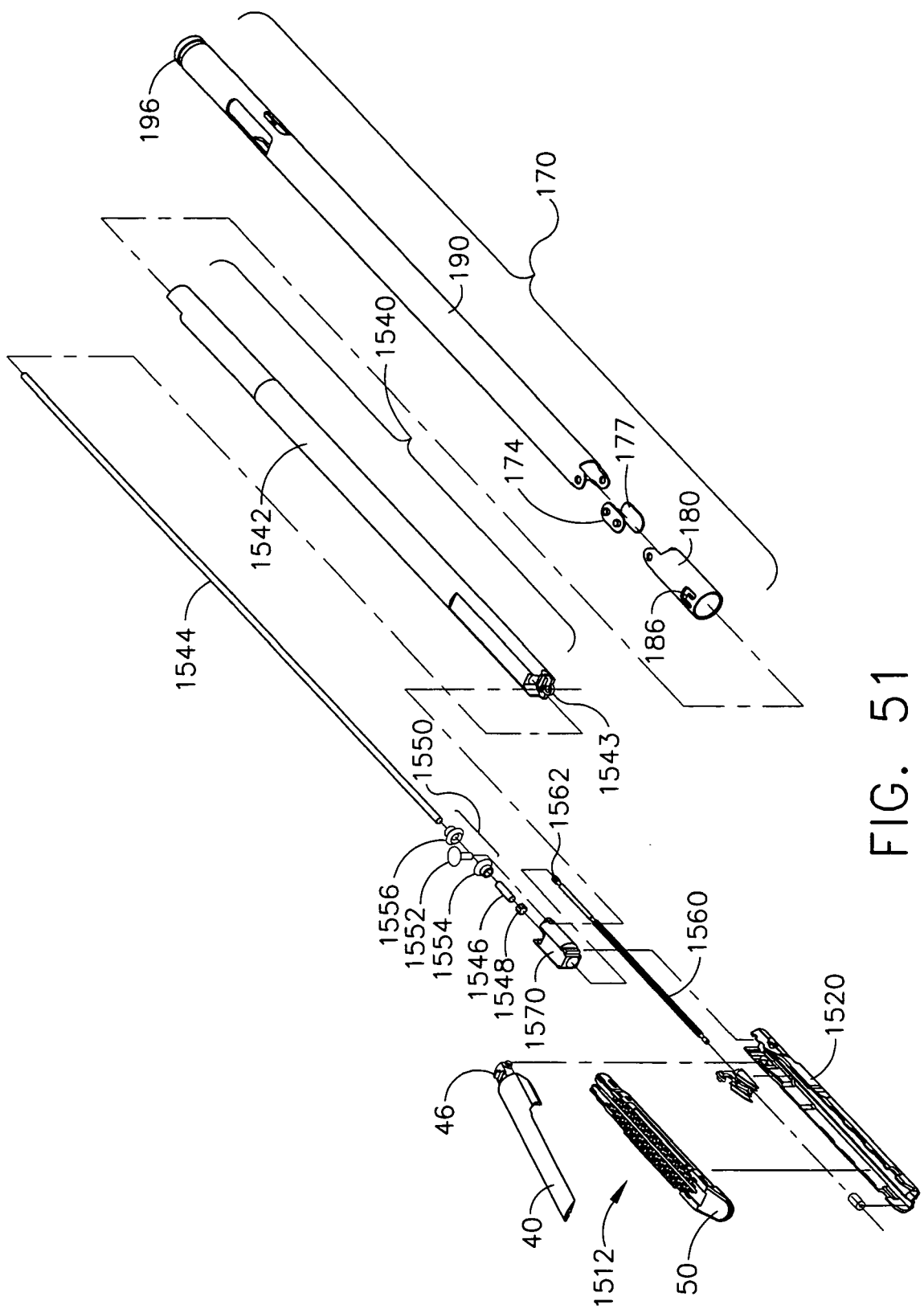
FIG. 51 is an exploded assembly view of an end effector arrangement, spine assembly and closure tube assembly that may be employed in connection with the embodiment depicted in FIG. 49.
Figure 52:
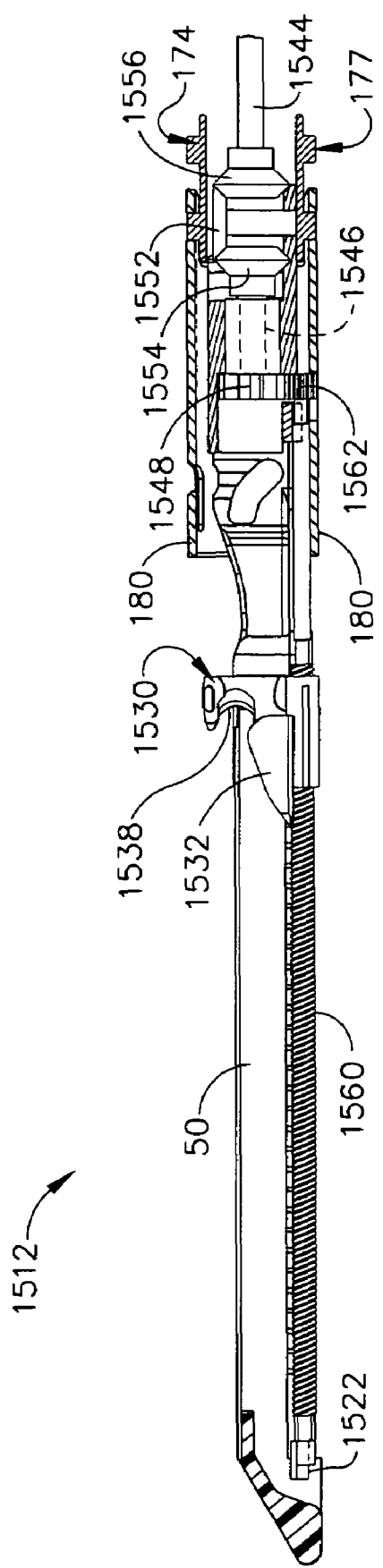
FIG. 52 is a cross-sectional side elevational view of the end effector, spine assembly and closure tube assembly of FIG. 51 with the anvil portion omitted for clarity.

FIGS. 51 and 52 illustrate one drive shaft arrangement for transmitting rotational motion to the helical drive screw 1560 from a pneumatically driven motor in the handle assembly 300. As can be seen from reference to FIG. 51, this embodiment may employ a closure tube assembly 170 that was described in detail above. The closure tube assembly 170 is slidably received on a spine assembly 1540 that comprises a proximal spine segment 1542 that rotatably supports a main rotational (or proximate) drive shaft 1544 that communicates with a secondary (or distal) drive shaft 1546 via a bevel gear assembly 1550 that includes gears 1552, 1554, 1556. The secondary drive shaft 1546 is connected to a drive gear 1548 that engages a proximal drive gear 1562 of the helical drive screw 1560. The vertical bevel gear 1552 is pivotally supported in an opening 1543 in the distal end of the proximal spine segment 1542. A distal spine segment 1570 may be used to enclose the secondary drive shaft 1546 and the drive gears 1548, 1562. Collectively, the main drive shaft 1544, the secondary drive shaft 1546, and the articulation assembly (e.g., the bevel gear assembly 1550) are sometimes referred to herein as the "main drive shaft assembly."

Figure 53:
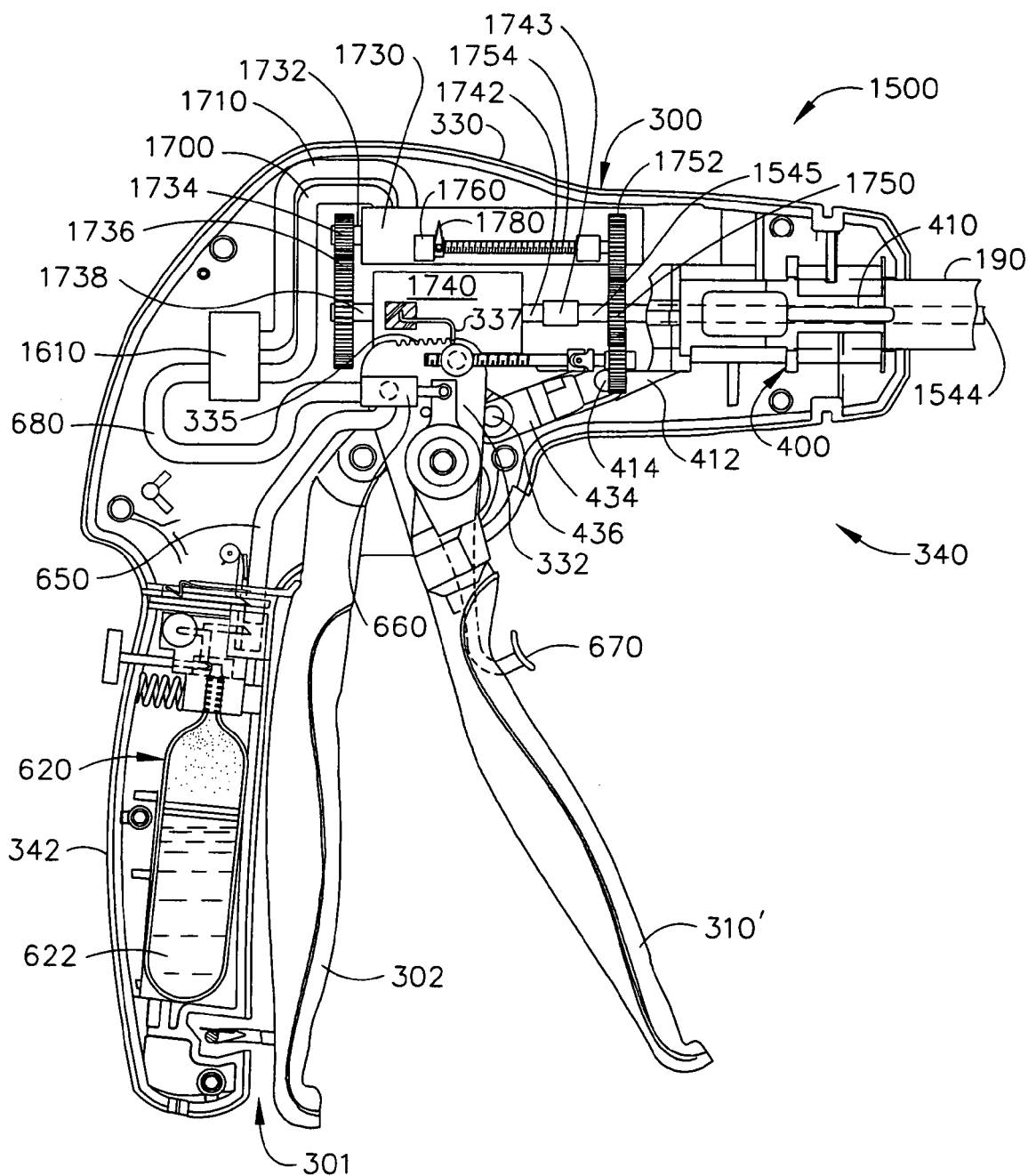
FIG. 53 is a cross-sectional view of a handle assembly that may be employed in connection with the embodiment of FIG. 49.
Figure 53A:
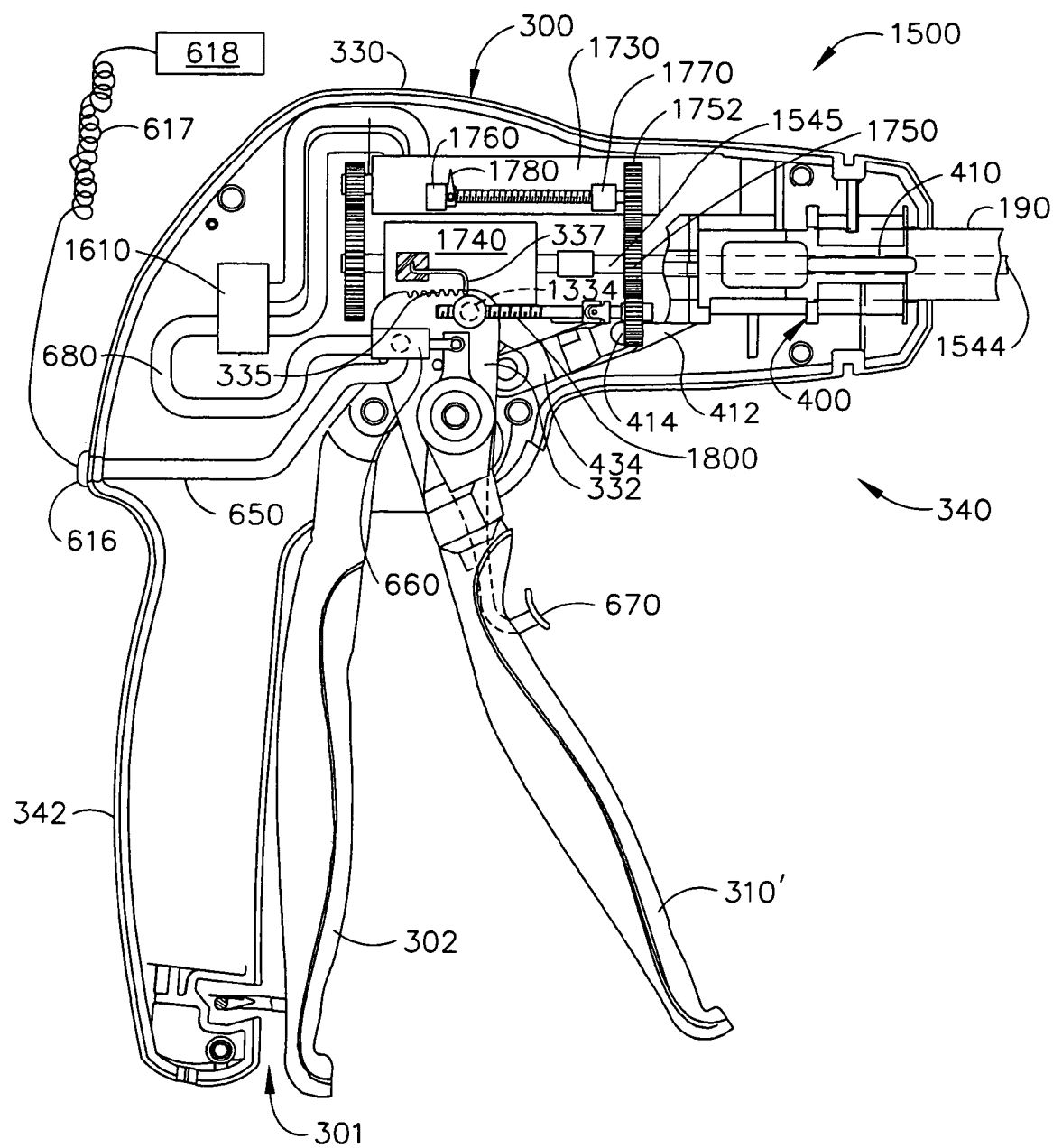
FIG. 53A is a cross-sectional view of another handle assembly that may be employed with the embodiment of FIG. 49 wherein the source of pressurized gas is external to the handle assembly.
Figure 54:
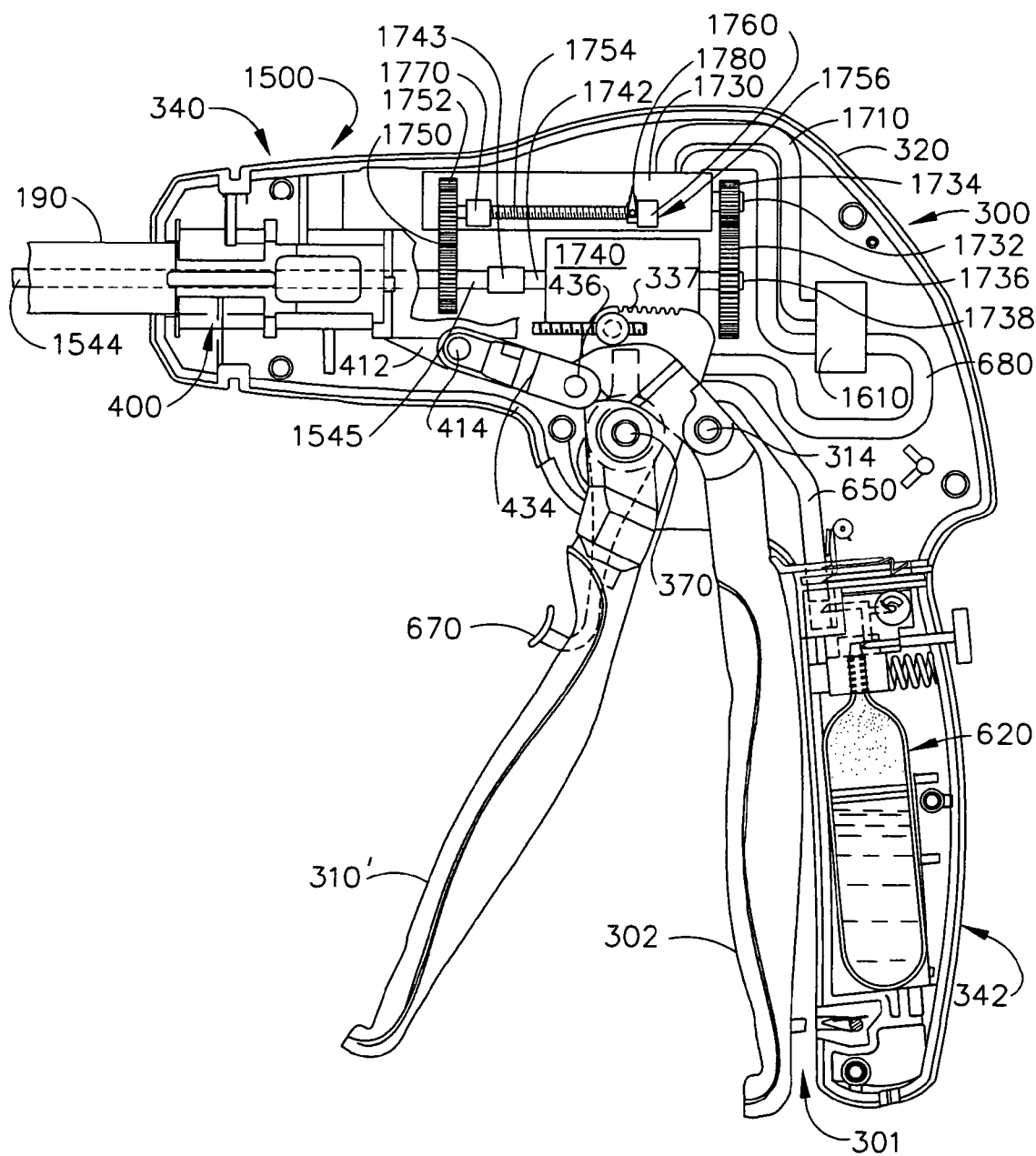
FIG. 54 is another cross-sectional view of the handle assembly of FIG. 53.

As can be seen in FIGS. 53 and 54, various embodiments of the instrument 1500 are powered by a source of pneumatic power in the form of pressurized gas 620. In the embodiments depicted in those FIGS., the source 620 comprises a replaceable/rechargeable canister 622 that is supported within the grip portion 642 of the housing assembly 300. The cylinder 622 may be rechargeable. Those of ordinary skill in the art will appreciate, however, that nonreplaceable/rechargeable sources (cylinders) of pressurized gas could also be effectively employed. Still in other embodiments, the handle assembly 300 may be provided with a port 616 for supplying pressurized gas from an external source 618 of pressurized gas. For example, the instrument 1500 could be coupled to the facility's compressed air line (not shown) through a flexible supply line 617. See FIG. 53A.

The unique and novel aspects of the removable/rechargeable cylinder 622 will be discussed in further detail below. However, for the purpose of explaining the drive system for providing rotary motion to the end effector 1512, it can be seen that pressurized gas flows under pressure from the cylinder 622 or external pressure source 618 through a supply line 650 into a conventional rate valve 660. The rate valve 660 is coupled to a supply linkage 662 that is attached to an activation trigger 670. See FIGS. 53 and 55. In various embodiments, activation trigger 670 is supported adjacent a travel monitoring member or relative position firing trigger 310' that is pivotally coupled to the handle assembly 300 by a pivot pin 370 that extends between the right hand case member 320 and left hand case member 330. The relative position trigger 310' may be fabricated from plastic or other suitable material and has a portion with a substantially U-shaped cross-section to accommodate the activation trigger 670 as shown. The clinician can position his or her hand on the grip portion 352 of the housing assembly 300 such that their lower three fingers are on the relative position trigger 310' and their index finger is on the activation trigger 670. Squeezing the activation trigger 670 inward towards the relative position trigger 310' causes the rate valve 660 to permit gas to pass under pressure therethrough from the source 620 (or 618 in FIG. 53A) into a supply line 680 into the directional control valve 1610.

Figure 56:
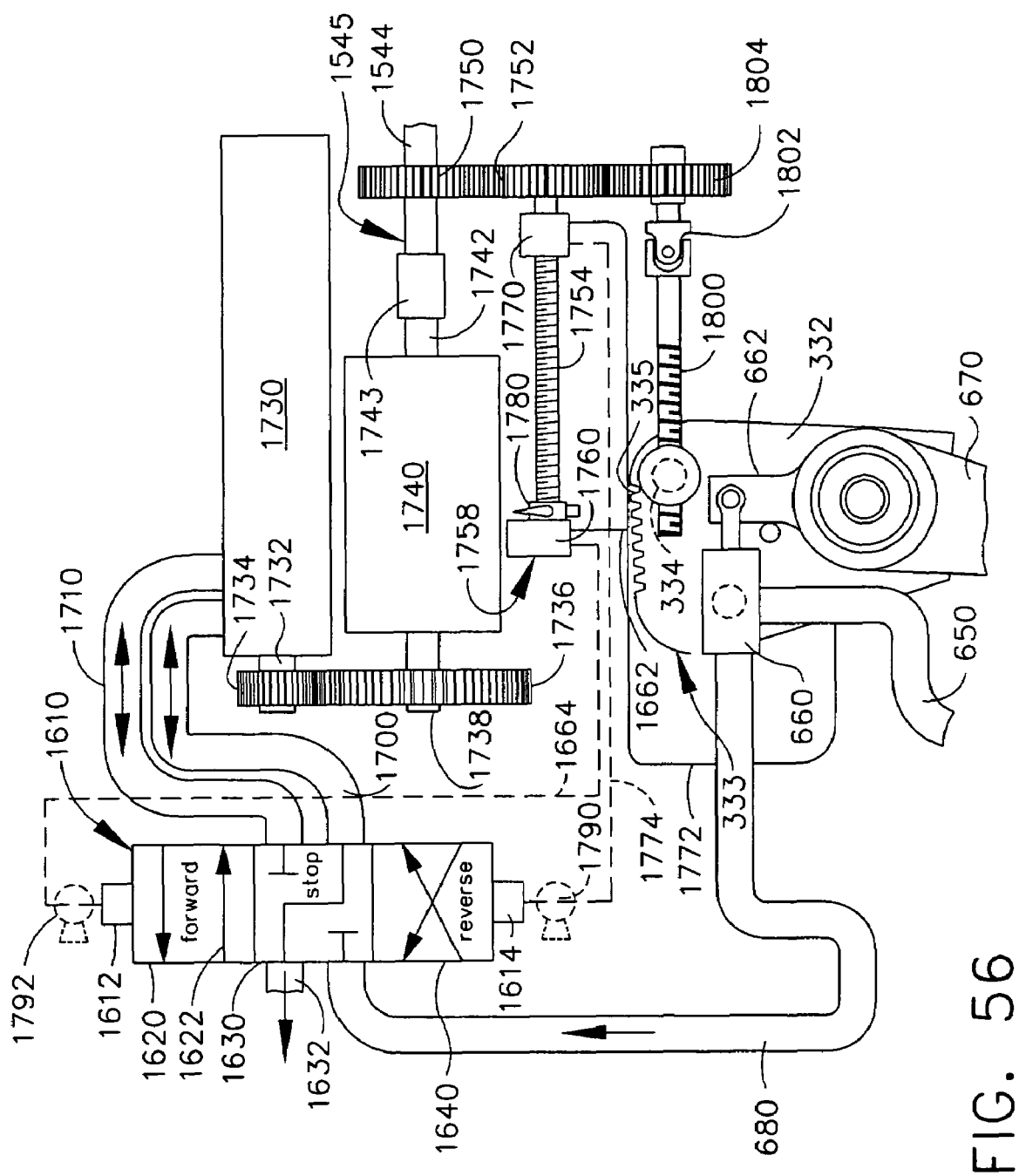
FIG. 56 is a schematic of a control system embodiment of the present invention that may be employed in connection with various embodiments of the present invention.

As can be seen in FIG. 56, the directional control valve 1610 has a forward position section 1620, a stop section 1630, and a reverse section 1640. The control valve sections 1620, 1630, 1640 may be manually shifted by the push buttons 1612 and 1614 that protrude through the handle housing 300. See FIGS. 49 and 56. Two supply/exhaust lines 1700, 1710 extend from the directional control valve 1610 to a conventional pneumatically powered motor 1730. Thus, when the clinician shifts the control valve 1610 to the forward position, the forward passage 1622 permits the pressurized gas to flow from the supply line 680 and into the supply/exhaust line 1700 to cause the pneumatically driven motor 1730 to drive the motor drive shaft 1732 in a first direction that will, as will be discussed in further detail below, result in the transmission of rotary motion to the drive shaft 1544 which will drive the wedge sled assembly 1532 and knife portion 1538 distally through the end effector 1512 in a firing stroke. The gas exiting the pneumatically powered motor 1730 through the supply line 1710 is exhausted through a vent port 1632. When the control valve 1610 is shifted to the reversed position, gas passing through the supply line 680 is permitted to flow through the supply line 1710 into the pneumatically powered motor 1730. Gas exiting the pneumatically powered motor 1730 through the supply/exhaust line 1700 is exhausted through the vent port 1632. When the control valve is in the stopped position, the supply line 1680 and the supply/exhaust line 1710 are closed and supply line 1700 is connected to the vent port 1632. See FIG. 56.

As can further be seen in FIG. 56, the output shaft 1732 of the pneumatically powered motor 1730 may have a first drive gear 1734 thereon that is in meshing engagement with a second drive gear 1736 that is mounted to an input shaft 1738 of a planetary gear assembly 1740. The planetary gear assembly 1740 has an output shaft 1742 that is coupled to the proximal end 1545 of the drive shaft 1544 by a conventional shaft coupling member 1743 to convey rotary motion thereto. Thus, when the control valve 1610 is shifted to the forward position, the output shaft 1732 of the pneumatically powered motor 1730 imparts a rotary motion to the drive shaft 1544 through gears 1734, 1736 and the planetary gear assembly 1740 to cause the wedge sled assembly 1530 and knife portion 1538 to drive through the cartridge 50 severing tissue clamped in the end effector 1512 and driving the staples in the cartridge 50 into forming contact with the anvil 40. When the control valve 1610 is shifted to the reverse position, the output shaft 1732 of the pneumatically powered motor 1730 imparts an opposite rotary motion to the drive shaft 1544 to retract the wedge sled assembly 1530 and knife portion 1538 in a proximal direction back through cartridge 50.

The embodiments depicted in FIGS. 49-56, also have further unique and novel features that enhance the operability of the instrument and provide various forms of feedback to the clinician so that the clinician can monitor the position of the wedge sled assembly 1530 and knife portion 1538 within the cartridge 50 as it is advanced distally therein and also retracted. Turning again to FIG. 56, it can be seen that a feed back gear 1750 is provided on the drive shaft 1544 or on the output shaft 1742 of the planetary gear assembly 1740. The feed back gear 1750 is in meshing contact with a knife position gear 1752 that is mounted on a threaded knife position shaft 1754. The knife position shaft 1754 may be supported by appropriate bearing arrangements (not shown) that facilitate its free rotation therein. A proximal limit switch 1760 is associated with the proximal end 1756 of the shaft 1754 and a distal limit switch 1770 is associated with the distal end 1758 of the shaft 1754. A knife indicator 1780 is threaded onto the knife position shaft 1754 for distal and proximal travel thereon. As the drive shaft 1544 is rotated in the direction which causes the wedge sled assembly 1530 and knife portion 1538 to move distally through the cartridge 50, the knife indicator 1780 also moves proximally towards the distal limit switch 1770. The distal limit switch 1770 is oriented such that when the wedge sled 1530 and knife portion 1538 are at the distal-most position, the knife indicator 1789 actuates the distal limit switch 1770. A window is provided in the left hand case member 330 (or right hand case member 320 depending upon the location of the knife position shaft 1754 in the housing assembly 300) such that the clinician can view the position of the knife indicator 1780 to determine the position of the firing mechanism (wedge assembly 1530 and knife portion 1538) within its firing stroke and also provide the clinician with means for monitoring the position of the wedge assembly 1530 during the retraction stroke.

Also in various embodiments, a distal pilot line 1772 may be provided from the supply line 650 to the distal limit switch 1770. A distal limit switch line 1774 may be provided between the distal limit switch 1770 and the directional control valve 1610. Thus, when the wedge sled assembly 1530 and knife portion 1538 have completed the firing stroke and the knife indicator 1780 activates the distal limit switch 1770, the distal limit switch 1770 permits the gas to flow under pressure from the supply line 650 to the distal limit switch line 1774 and into the directional control valve 1610 which, in various embodiments, causes the directional control valve 1610 to automatically shift to the reverse position and thereby cause the pneumatically powered motor 1730 to reverse and ultimately impart a reversing rotary motion to the drive shaft 1544. As the pneumatically powered motor 1730 reverses the drive shaft 1544, the reverse rotary motion is transmitted to the knife position shaft 1754 to thereby drive the knife position indicator 1780 back toward the proximal limit switch 1760. A proximal pilot line 1662 may also extend between the proximal limit switch 1760 and the supply line 650 such that when the knife position indicator 1780 actuates the proximal limit switch 1760 (signifying that the wedge sled 1530 and knife portion 1538 has moved to its fully retracted position), the proximal limit switch 1660 then permits gas to flow into a proximal limit switch line 1664 and into the directional control valve 1610 to cause the directional control valve 1610 to automatically shift to the stopped position.

In various embodiments, a first air powered whistle 1790 or other suitable sound generating device may communicate with the distal limit switch line 1774 (or distal limit switch 1770) such that when the distal limit switch 1770 is actuated at the end of the firing stroke, air passing through the distal limit switch line 1774 activates the first whistle 1790 to provide the clinician with an audible signal indicating that the wedge sled/knife has reached the end of the firing stroke. Likewise, a second air powered whistle 1792 or other suitable sound generating device may communicate with the proximal limit switch 1760 such that when the proximal limit switch 1760 is actuated at the end of the retraction stroke, air passing through the proximal limit switch line 1764 activates the second whistle 1792 to provide the clinician with another audible signal indicating that the wedge sled/knife has reached the end of the retraction stroke. In other embodiments, for example, battery powered light emitting diodes or other signal devices may communicate with the distal and proximal limit switches 1770, 1760 to provide the user with another indication when the wedge sled/knife has reached the end of the firing stroke and/or the retraction stroke. In alternative embodiments, the whistles 1790, 1792 may be replaced with pressure sensors or gages to indicate when the device has reached the end of the firing stroke and/or the retraction stroke.

Figure 52A:
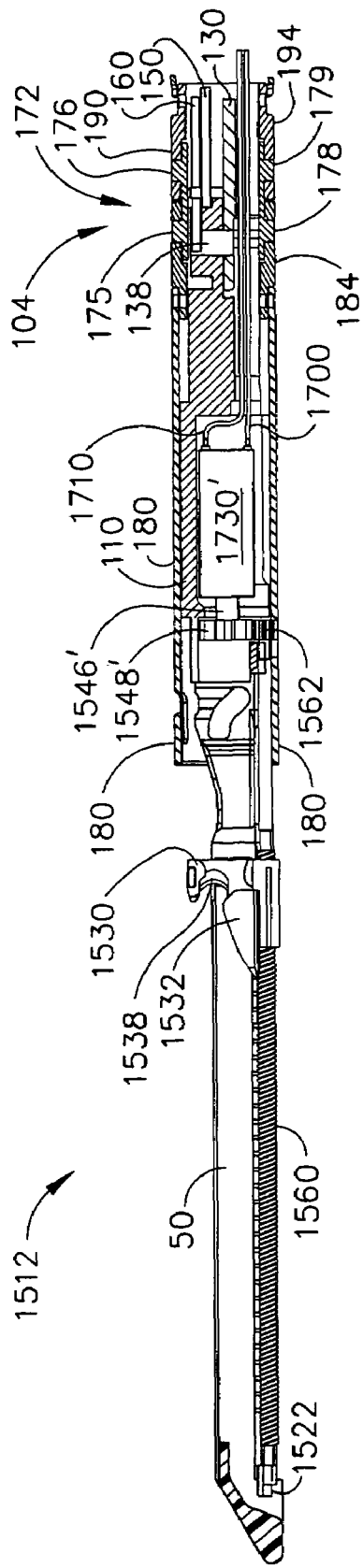
FIG. 52A is a cross-sectional side elevational view of an end effector, spine assembly and closure tube assembly of another non-limiting embodiment of the present invention wherein the pneumatically powered motor is supported distally from the handle assembly.
Figure 52B:
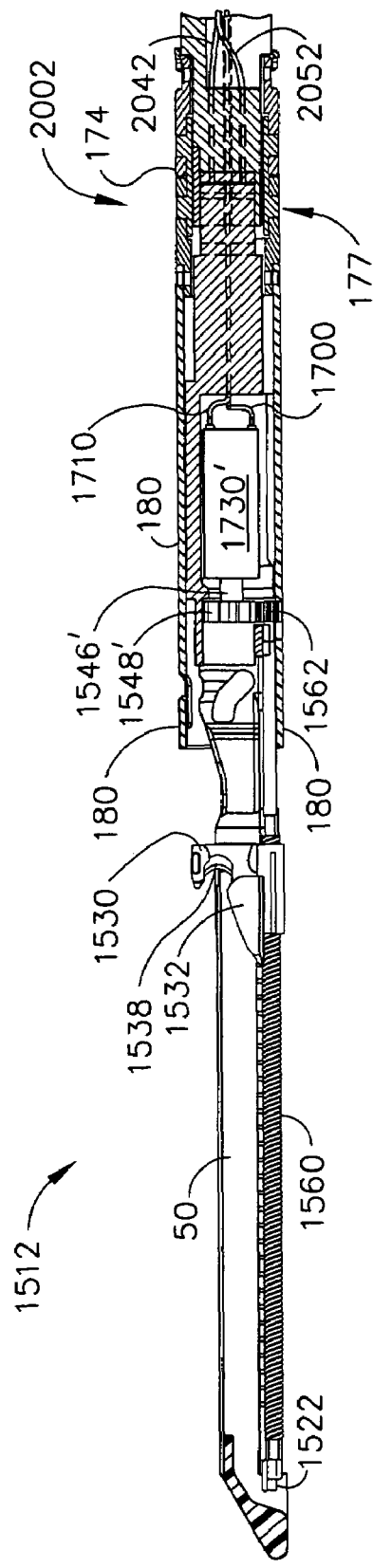
FIG. 52B is a cross-sectional side elevational view of an end effector, spine assembly and closure tube assembly of another non-limiting embodiment of the present invention wherein the pneumatically powered motor is supported distally from the handle assembly.

In the various embodiments depicted in FIGS. 49-56, the pneumatically driven motor is supported within the handle assembly 300. In the embodiments depicted in FIGS. 52A and 52B, the pneumatically powered motor 1730' is located within the distal spine section 110. The motor drive shaft 1546 has a drive gear 1548' thereon that is in meshing engagement with proximal drive gear 1562 of the helical drive screw 1560. FIG. 52A depicts such distally mounted pneumatically powered air motor in connection with an articulation joint 104 as was described above. The embodiment depicted in FIG. 52B employs a pneumatically powered articulation 2002 joint assembly as was described above. Such distally mounted air motor arrangements could also be employed in connection with surgical instruments that employ other articulating joint arrangements or used in connection with instruments wherein the end effector does not articulate relative to the handle assembly or portion of the elongate shaft assembly to which it is attached. Those of ordinary skill in the art will understand that such distally mounted pneumatically powered motor arrangements minimize power losses that may be encountered through elongated drive shaft arrangements for embodiments wherein the motor is supported in the handle assembly and the firing and retraction motions must be transmitted through the articulation joint to the end effector. The embodiments such as those depicted in FIGS. 52A and 52B only require two lines 1710 and 1760 to pass through the articulation joint to power the motor 1730'. Lines 1710 and 1760 may comprise flexible tubing or the like and are less likely to limit the articulation joints when compared to other arrangements that require one or more drive members to pass through the joint.

Also, various embodiments of the present invention may be constructed to provide the user with a tactile form of feedback concerning the relative position of the instrument's firing components. In some embodiments, this is accomplished by linking the travel monitoring member or relative position trigger 310' to the advancement and retraction motions applied to the drive shaft or firing mechanism of the device. More particularly and with reference to FIGS. 53-55, this embodiment may include a feedback linkage assembly 1800 that, in various non-limiting embodiments, may comprise a threaded manual feedback shaft 1801 that is threadably attached to a nut member 334 that is rotatably mounted to an upper attachment plate portion 332 of the relative position trigger 310'. The distal end of the manual feedback shaft 1801 has a universal joint portion 1802 that supports a manual feedback gear 1804 that is in meshing engagement with the knife position gear 1752. When the directional control valve 1610 is in the forward position, the pneumatically powered motor 1730 drives the drive shaft 1544 such that the firing mechanism in the form of a wedge sled 1530 and knife portion 1538 is driven distally through the cylinder (firing stroke). The feed back gear 1750 drives the knife position gear 1752 which, in turn, drives the manual feedback gear 1804. The manual feedback gear 1804 then rotates the manual feedback shaft which, by virtue of its threaded engagement with the nut 334, draws the relative position trigger 310' towards the grip portion 342 of the handle assembly 300 thereby providing the clinician with a "tactile" indication of the advancement of the wedge sled 1530 and knife portion 1538. Those of ordinary skill in the art will understand that if the clinician attempts to pivot the relative position trigger 310' towards the grip portion 342 of the handle assembly 300, the manual feed back shaft 1801 and nut 334 will prevent any travel thereof. However, the relative position trigger 310' will automatically pivot in relation to the advancement and retraction of the wedge sled 1530 and knife portion 1538. Such arrangement provides the clinician with an automatic tactile indication of the advancement and retraction of the wedge sled assembly 1530 and knife portion 1538 (firing mechanism) simply by the grasping the relative position trigger 310' throughout the surgical procedure. Thus, the clinician does not have to look at anything to obtain such feedback. Such arrangement provides the clinician with a one handed non-visual feedback of the progress of the firing mechanism between the unactuated position and the actuated position and also when the firing mechanism is traveling back from the actuated position to the unactuated position.

Various embodiments may be further provided with another tactile feed back arrangement, generally designated as 333. For example, as can be seen in FIGS. 53-56, the upper attachment plate portion 332 of the relative position trigger 310' may be provided with a series of slots 335, detents, grooves, etc. that are designed to interface with a spring arm 337 mounted within the handle assembly 300 as the relative position trigger 310' pivots about pin 370 during the firing and retraction strokes. As the upper attachment plate portion 332 pivots with the relative position trigger 310', the end of the spring arm 337 drops into each successive slot 335 and serves to impart (in series) a force to the upper attachment plate portion 332 which can be felt by the clinician when grasping the relative position trigger 310'. Thus, as the relative position trigger 310' advances, the clinician will be provided with a series of additional tactile feedback motions corresponding to the movement of the firing mechanism to confirm that the relative position trigger 310' (and ultimately the firing mechanism) are either advancing during the firing stroke or retracting during the retraction stroke, which ever the case may be. In addition, as the end of the spring arm 337 drops into each successive slot, it may create an audible sound, click, etc. to provide the clinician with audible feedback concerning the movement of the firing mechanism through the firing stroke and the retraction stroke. Thus, this embodiment provides a series (at least two) audible sounds that relate to the movement of the firing mechanism between unactuated and actuated positions.

Those of ordinary skill in the art will appreciate that the instrument 1500 represents a vast improvement over prior pneumatically powered endocutter arrangements. For example, various embodiments provide a means for the clinician to monitor the position of the firing mechanism (wedge sled/knife) as it is being driven through its firing stroke. In some embodiments, when the wedge sled/knife reaches the end of its firing stroke, it is automatically retracted. Once in the fully retracted position, the control valve may be automatically switched to a stopped position thereby discontinuing the supply of air from the source 618 or 620 to the pneumatically powered motor 1730. If, however, during the activation process, the clinician wishes to stop the advancement of the wedge sled/knife distally in the cylinder, he or she can simply manually switch the control valve 1610 to the reverse position and continue to activate the activation trigger 670 to supply pressurized gas to the pneumatically powered motor 1730 until the wedge sled/knife is moved to the desired retracted position. Furthermore, the unique and novel relative position trigger 310' provides the clinician with manual or tactile feedback that he or she can feel while gripping the relative position trigger 310'. Also, the clinician can be provided with audible signals when the wedge sled/knife has reached the end of the firing stroke and/or has been fully retracted.

The skilled artisan will also appreciate that the unique and novel advantages provided by the travel monitoring device may also be attained when employing the drive members 500, 800 or bellows assembly 900 by connecting each of those drive members to the upper attachment plate portion 332 or other portion of the relative position trigger 310' by a push/pull flexible cable (not shown) or rigid member (for non-articulating embodiments) such that the advancement and retraction of those drive members is directly or indirectly linked to the relative position trigger 310'. This unique and novel arrangement may also be employed with the embodiment depicted in FIGS. 70-83 described below.

As indicated above, the feedback linkage assembly 1800 not only automatically moves the relative position trigger 310' at a rate that corresponds to the rate of movement of the firing mechanism so as to provide the clinician with a means to monitor the progress of the firing mechanism, the feedback linkage assembly 1800 may employ threads or other means that effectively would prevent or greatly limit the clinician from being able to manually pivot the relative position trigger 310'. In such non-limiting embodiments, the only time that the relative position trigger 310' moves is when the feedback linkage assembly moves it. In still other embodiments, the manual movement of the relative position trigger 310' may be prevented by a motor (not shown) or another gas cylinder (not shown) configured to prevent any pivotal travel of the relative position trigger 310' when actuated. For example, the presence of force on the activation trigger 670 activates the release of the gas, but until the firing mechanism begins to move, the relative position trigger 310' would not be allowed to substantially move, and should the firing mechanism cease to move, so would motion of the relative position trigger 310'.

In other various embodiments, however, the feedback linkage assembly 1800 may be so constructed as to provide the clinician with the ability to assist the drive member in the form of a pneumatically powered motor 1740 during the firing stroke so as to add force thereto or to retard advancement of the firing mechanism if the clinician so desires. In these various embodiments, for example, the feedback shaft 1801 may be formed with an acme-type thread or other thread arrangement or configuration that would actually permit the clinician to apply pressure to the relative position trigger 310' and thereby impart a rotational force to the shaft 1801 by virtue of its engagement with the nut 334. By imparting a rotational motion to shaft 1801, the clinician also applies a rotational force to gear 1804 which is in meshing engagement with gear 1750 that is journaled on the drive shaft 1544. Thus, if the firing mechanism encounters resistance, the clinician can apply mechanically generated power to the drive shaft 1544 by squeezing the relative position trigger 310'. If the clinician desires to slow down or retard the movement of the firing mechanism, the clinician can apply force to the relative portion trigger 310' which will in turn resist/slow rotation of the shaft 1801 and the gear 1804 and ultimately the rotation of the drive shaft 1544.

Various embodiments described above have been described in connection with the use of a material storage member in the form of a removable cylinder 622 for supplying gas under pressure to operate the device. In various embodiments, the removable cylinder 622 may initially be filled with gas under pressure and be rechargeable. In other embodiments, the cylinder may not be refillable. For example, the cylinder 622 may comprise a conventional disposable cylinder filled with carbon dioxide. Once the cylinder is emptied, the user removes it from the handle assembly and replaces it with a new filled cylinder. Other types of gases that may be employed, for example, are compressed air, Carbon Dioxide ($CO_2$), Nitrogen, Oxygen, Argon, Helium, Sodium Hydride, Propane, Isobutane, Butane, Chlorofluorocarbons, Dimethylether, Methylethyl ether, Nitrous Oxide, Hydrofluoroalkanes (HFA): either HFA 134a (1,1,1,2,-tetrafluoroethane) or HFA 227 (1,1,1,2,3,3,3,-heptafluoropropane). Such arrangement provides a vast improvement over prior pneumatically powered surgical instrument arrangements. However, the number of times the instrument may be used is dependent upon the volume of gas that can be stored in such cylinders and the need to effectively maintain the sterility of the device.

Other embodiments of the present invention employ a cylinder 622 that stores the material in a non-gaseous, liquid state when at a storage pressure and then at least some of the liquid vaporizes to a gaseous state when placed under a lower pressure upon activation of the device. Examples of such liquids that may be employed in these embodiments comprise Nitrous Oxide, Dimethylethyl ether, methylethyl ether, Sodium Hydride, Propane, Isobutane, Butane, Hydrofluoroalkanes (HFA): either HFA 134a (1,1,1,2,-tetrafluoroethane) or HFA 227 (1,1,1,2,3,3,3-heptafluoropropane), and Carbon Dioxide ($CO_2$) under higher pressures.

Figure 57:
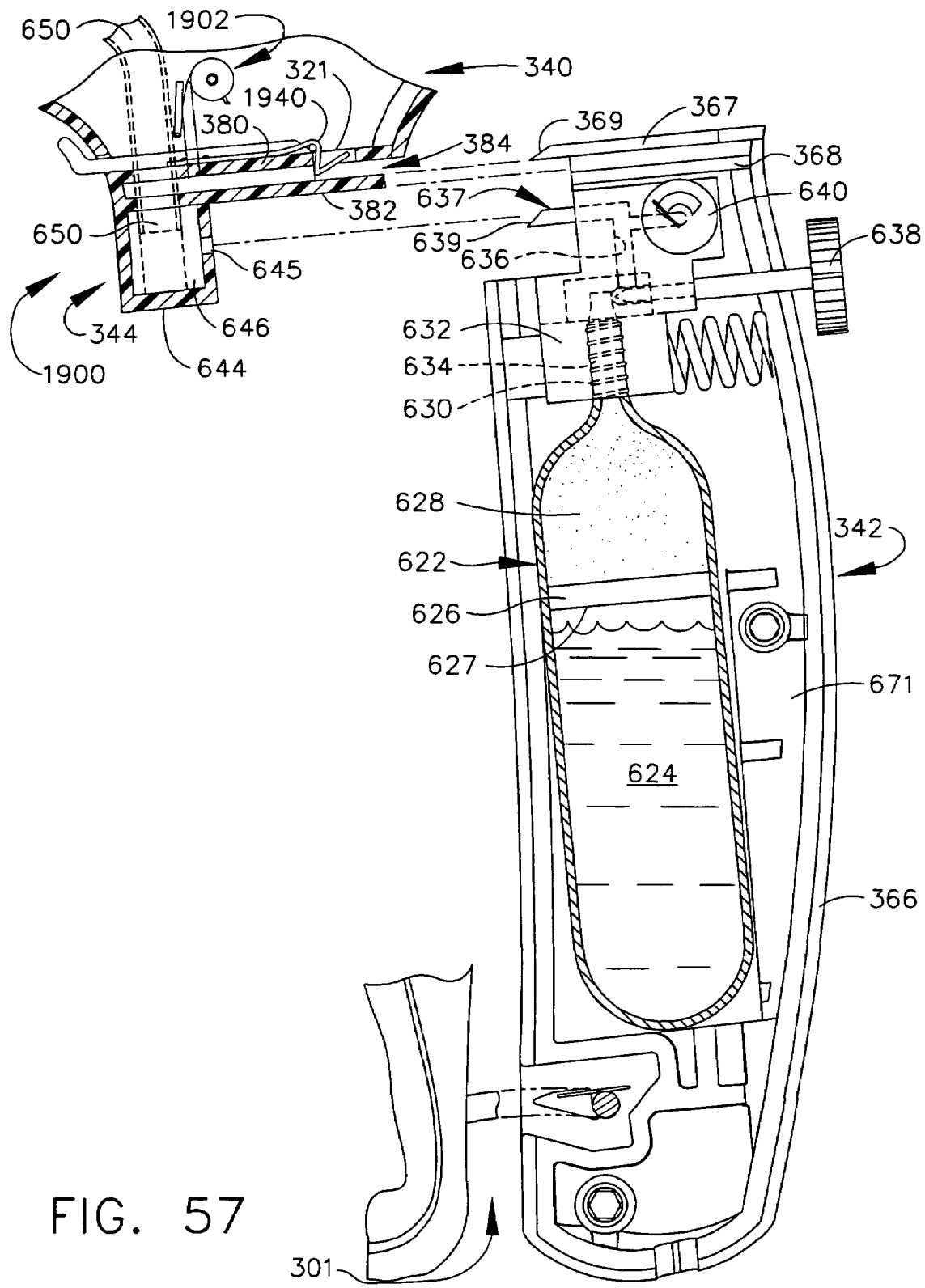
FIG. 57 is a cross-sectional view of a detachable grip portion detached from a primary attachment portion of various handle assembly embodiments of the present invention.

FIG. 57 depicts one non-limiting example of a cylinder 622 that has one of the liquid materials 624 mentioned above therein. The cylinder 622 may be fabricated from steel, aluminum or other material that is compatible with the liquid/vapors stored therein and capable of withstanding the internal pressures generated therein. When employing such surgical instruments of the types described herein, the clinician often turns the handle assembly 300 in a variety of positions—including upside-down to obtain the desired position of the end effector 12. In these embodiments, therefore, to prevent the liquid from undesirably moving out of the cylinder 622 into the control system during such manipulation, a membrane 626 is provided within the cylinder 622. The membrane 626 may be fabricated from material that prevents the passage of the liquid material therethrough but permits the vapor 628 formed from the liquid to pass through the membrane 626. Thus, the clinician can freely manipulate the handle assembly 300 without the danger of the liquid material 624 passing into the directional control valve 1610 and/or pneumatically powered motor 1730. Although the cylinder 622 is illustrated with one piece construction, the cylinder 622 may be fabricated in two or more pieces to facilitate installation of the liquid material 624 and membrane 626 therein. Appropriate seal member(s) may be employed to establish fluid-tight seals between the various portions of the cylinder in such embodiment. In addition, a fill port (not shown) may be provided to fill the cylinder 622.

In the embodiment depicted in FIG. 57, when the clinician shifts the directional control valve 1610 to the forward position and activates the rate valve 660, the pressure within the cylinder 622 is decreased. Such decrease in pressure causes the liquid material 624 to start to vaporize and the vapor 628 passes through the membrane 626 and is used to power the various control systems described above. Thus, by decreasing the pressure in the cylinder 622, the liquid material 624 starts to vaporize and the pressurized vapor 628 is used to power the device.

Other embodiments may use liquid materials that require combustion to convert the liquid material to its gaseous state. Examples of such liquid materials are propane, butane and other petroleum products. A conventional pushbutton igniter or other igniter system could be employed to ignite the liquid material. In such applications, the other components of the device would be manufactured from materials and in such a way to safely disperse any heat/fumes generated thereby. Still other embodiments may employ phase change materials that are designed specifically to convert from solid to fluid, solid to gas or fluid to gas at a low pressure and temperature through the input of heat. Examples of these materials are paraffin and numerous mixtures of sodium hybrids. These phase change materials may have large volumetric changes with the input of heat to the system. Such devices would employ a means such as a burner to provide the requisite heat to the material. Again, the components of these devices that may be exposed to such heat would be designed and constructed from materials to safely dissipate the heat and protect the clinician during use.

The embodiment depicted in FIG. 57 may be used with variety of the different types of cylinders described above and provides various advantages over other embodiments wherein the cylinder is permanently mounted within the handle assembly 300. More specifically and with reference to FIG. 57, the cylinder 622 may be received within a cavity 671 formed in the grip portion 342 of the handle assembly 300. To gain access to the cavity 671, the grip portion 342 may be manufactured in two readily separable pieces or be provided with a removable cover panel (not shown) that snaps or is otherwise removably attached thereto. In various embodiments, the discharge end 630 of the cylinder 622 is threaded into a threaded port 634 in a header block 632. The threaded port 634 communicates with a supply passage 636 that is open and closed by a needle valve 638. In particular, in various embodiments, the needle valve 638 is threaded into the header block 632 such that the supply passage 636 may be opened and closed by rotating the needle valve 638. However other valve or flow control arrangements may be employed.

To provide the clinician with an indication of the cylinder's pressure during use, a conventional pressure gage 640 may be mounted in fluid communication with the supply passage 636. A gage window 642 may be provided in the grip portion 342 to enable the user to view the gage 640 during use. See FIG. 49.

Figure 58:
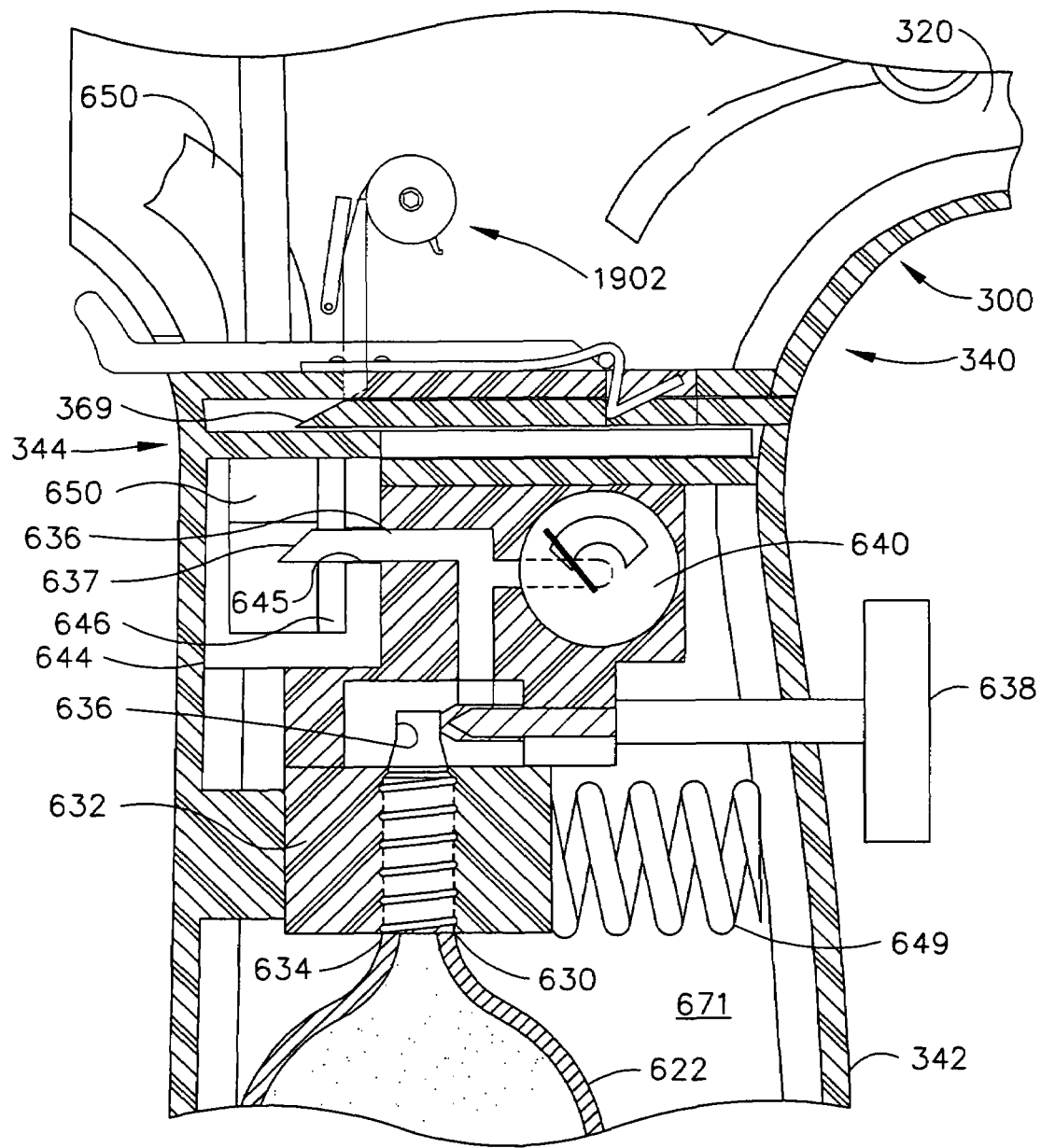
FIG. 58 is a partial cross-sectional view showing the detachable grip portion coupled to the primary attachment portion of a handle assembly of various embodiments of the present invention.

As can be seen in FIGS. 57 and 58, the cylinder 622 may be supported in a detachable grip portion 342 that is removably attachable to a primary attachment portion 344 that protrudes downwardly from the primary handle portion 340. The detachable grip portion 342 may be engaged with the primary attachment portion 344 by any suitable arrangement. For example, according to various embodiments, the engagement of the detachable grip portion 342 with the primary attachment portion 344 may be realized by a straight linear slide arrangement as shown. As shown, for example, in FIGS. 57-59 and 61, the releasable grip portion 342 further comprises first and second upper slide rails 367 and first and second lower slide rails 368. As can also be seen in those Figures, the first upper slide rail 367 defines a ramp 369. The upper slide rails 367 are designed to be received within corresponding areas 384 defined in the primary handle portion 340 by panels 380 and 382.

The surgical instrument may further comprise a lockout system 1900. The lockout system 1900, shown in greater detail, for example, in FIGS. 59 and 64-69, is structured and arranged to block connection of the primary attachment portion 344 to the detachable grip portion 342 after the detachable grip portion 342 is disconnected from the primary attachment portion 344 a predetermined number of times. The predetermined number of times may be any number of times. Such arrangement may be particularly advantageous in ensuring that the sterility of the device is effectively maintained by limiting the number of times that a device may be used. For example, according to various embodiments, the lockout system 1900 may block connection of the primary attachment portion 344 to the detachable grip portion 342 after the detachable grip portion 342 is disconnected from the primary attachment portion 344 two times. Although the lockout system 1900 is shown predominately within the primary housing portion 340, it is understood that according to other embodiments the lockout system 1900 may be predominately within the detachable grip portion 342.

Figure 59:
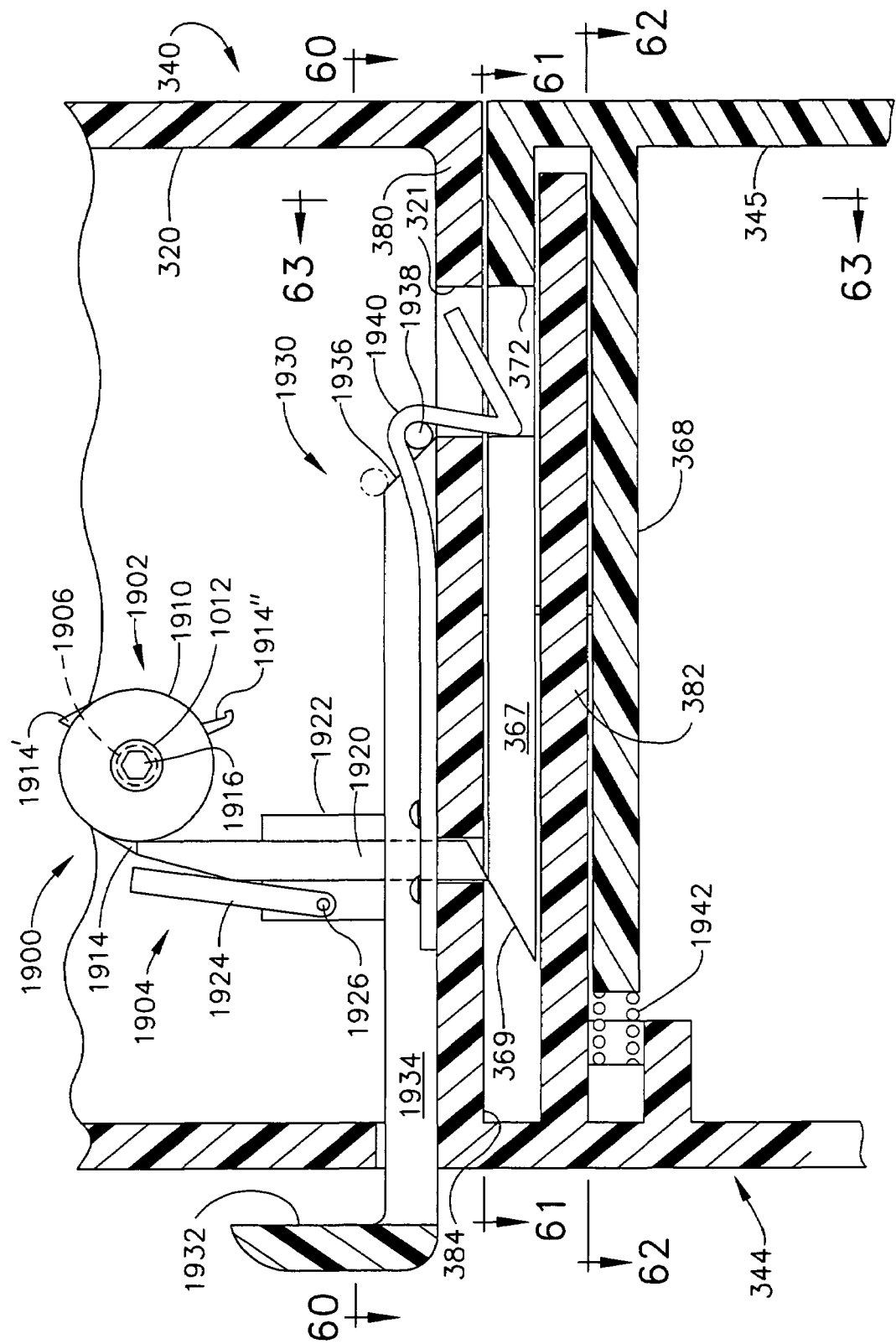
FIG. 59 is a partial cross-sectional view of the detachable grip portion and primary attachment portion of FIG. 58 with the headers and cylinder-related components omitted for clarity.

As shown in FIG. 59, the lockout system 1900 comprises a counter 1902, and a blocking assembly 1904 coupled to the counter 1902. The counter 1902 is structured and arranged to advance when the detachable grip portion 342 is disconnected from the primary attachment portion 344 of the handle assembly 300. As can be seen in FIG. 59, the counter 1902 is connected to a shaft 1906 which is supported by a boss 1908 connected to the right hand case member 320. The counter 1902 comprises an index wheel 1910 coupled to the shaft 1906, and a biasing member 1912 coupled to the index wheel 1910. The biasing member 1912 may comprise, for example, a torsion spring configured to bias the index wheel 1910 in a counterclockwise direction. See FIG. 59.

The index wheel 1910 defines protrusions 1914, 1914', 1914" that cooperate with the blocking assembly 1904 to limit the advancement of the index wheel 1910. One of the protrusions 1914" is structured and arranged to cooperate with the blocking assembly 1904 to block connection of the detachable grip portion 342 to the primary attachment portion 344 after the grip portion 342 is disconnected from the primary attachment portion 344 a predetermined number of times. Although the index wheel 1910 is shown as defining protrusions 1914, 1914', 19141", it is understood that according to other embodiments, the index wheel 1910 may define indents that cooperate with the blocking assembly 1904 to limit the advancement of the index wheel 1910, and one of the indents may cooperate with the blocking assembly 1904 to block connection of the detachable grip portion 342 to the primary attachment portion 344 after the grip portion 342 is disconnected from the primary attachment portion 344 a predetermined number of times.

Figure 60:
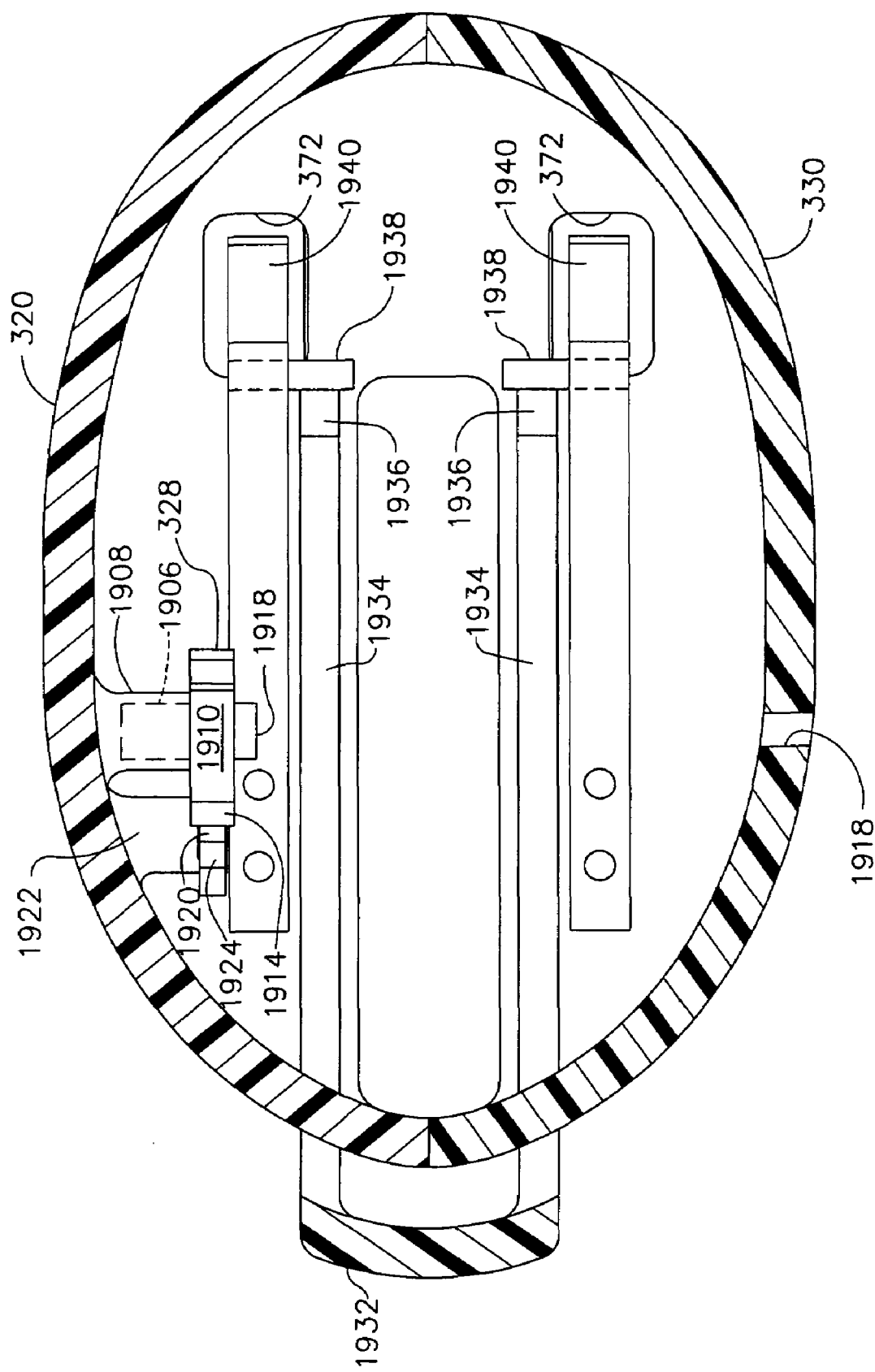
FIG. 60 is a cross-sectional view of the detachable grip portion and primary attachment portion of FIGS. 58 and 59 taken along line 60-60 in FIG. 59.
Figure 61:
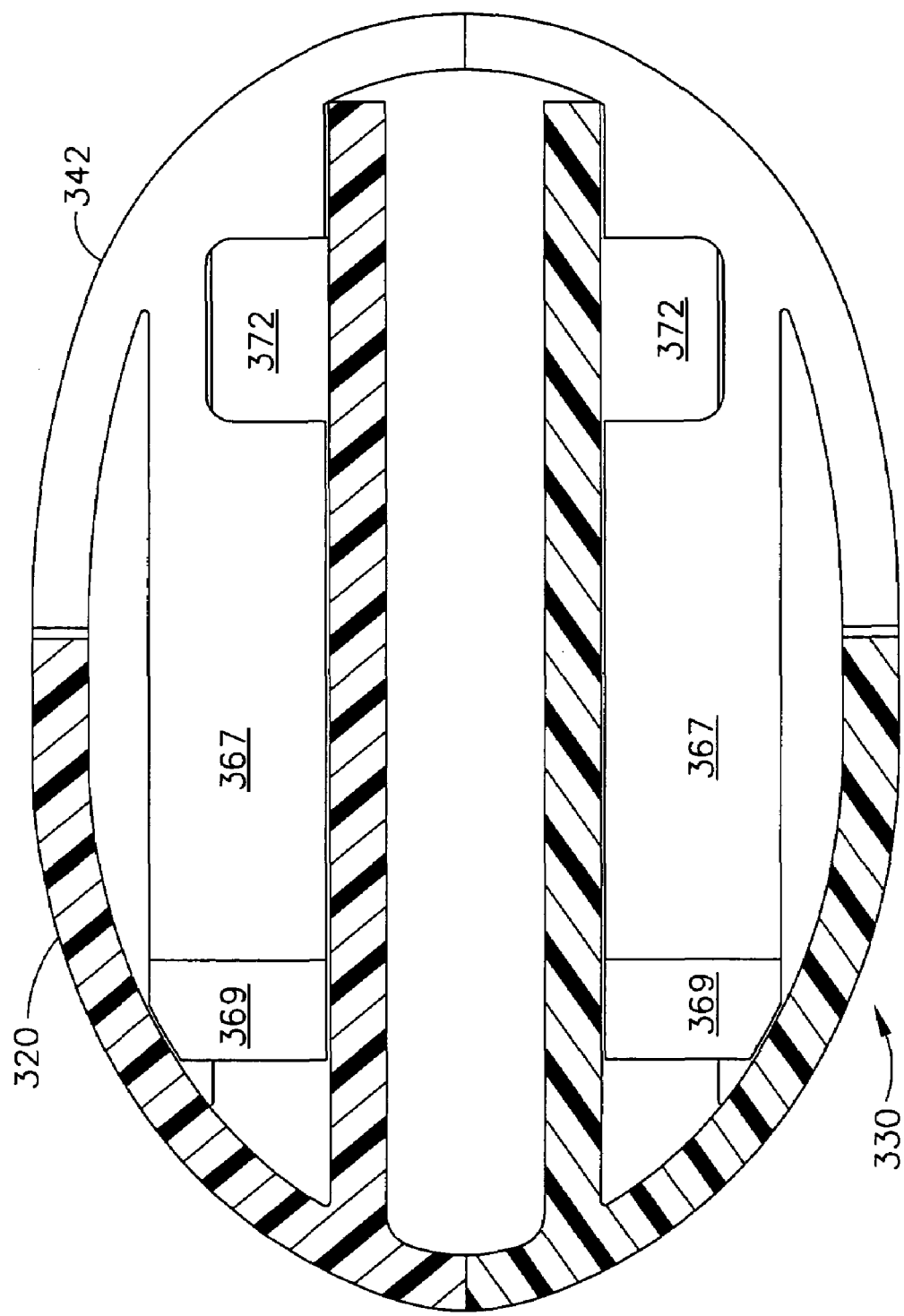
FIG. 61 is a cross-sectional view of the detachable grip portion and primary attachment portion of FIGS. 58, 59, and 60 taken along line 61-61 in FIG. 59.
Figure 62:
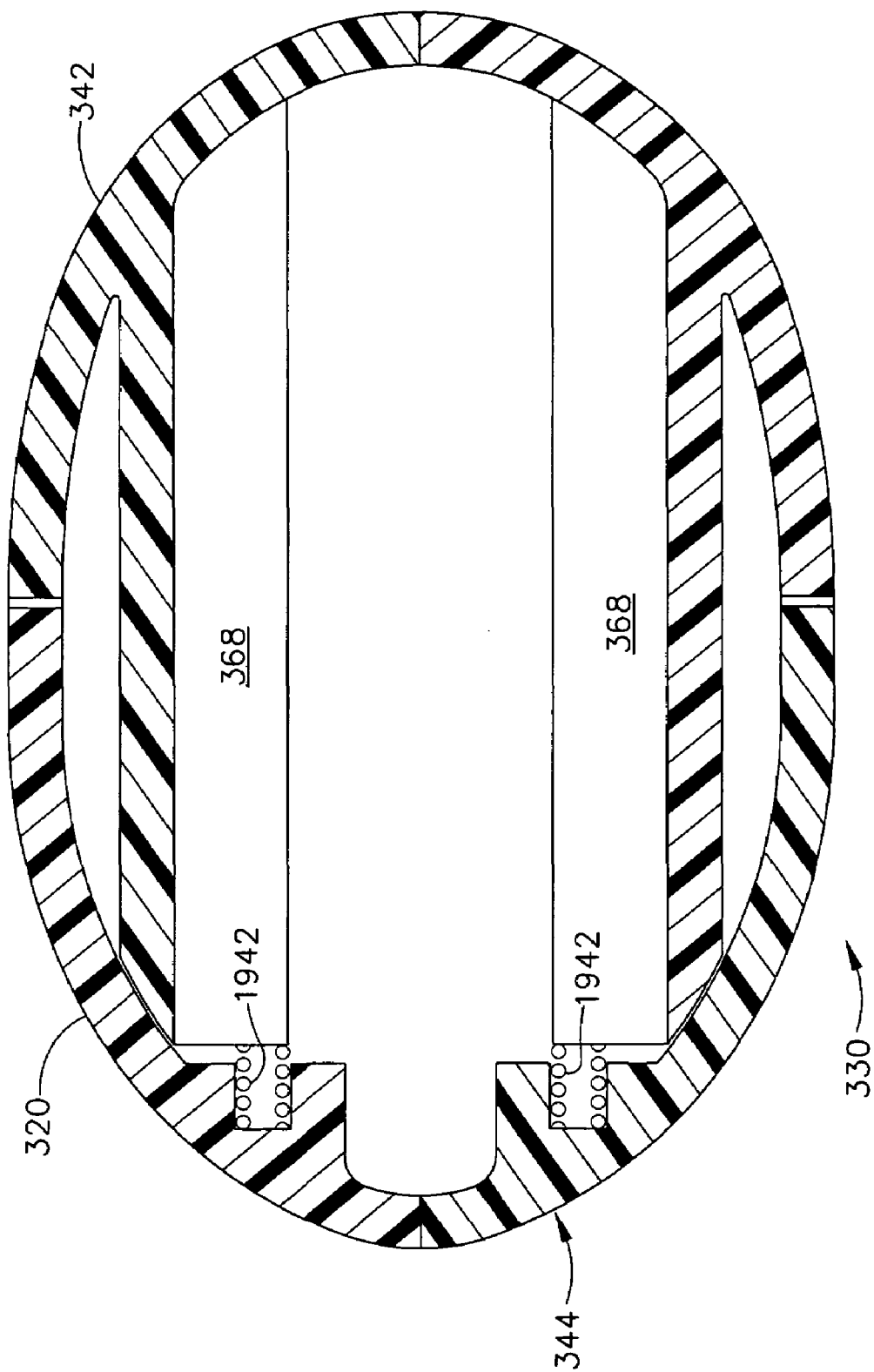
FIG. 62 is a cross-sectional view of the detachable grip portion and primary attachment portion of FIGS. 58-61 taken along line 62-62 in FIG. 59.
Figure 63:
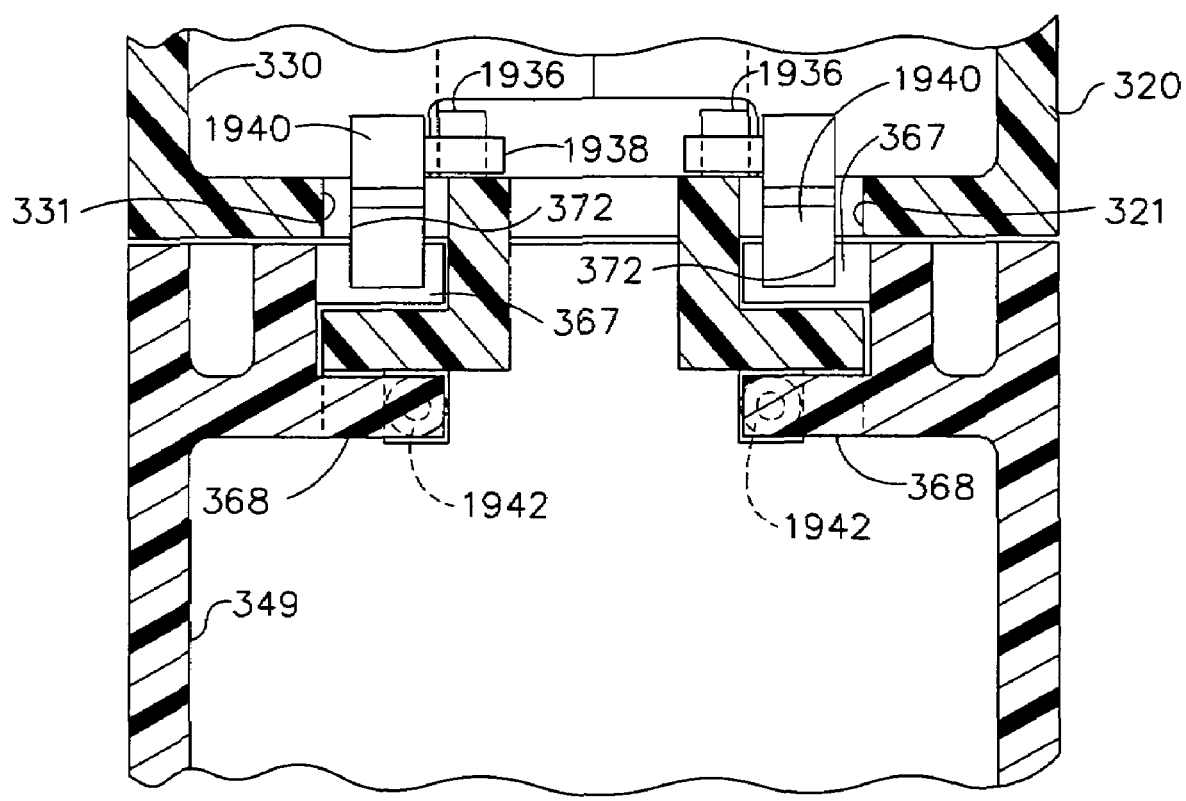
FIG. 63 is another partial cross-sectional view of the detachable grip portion and primary attachment portion of FIGS. 58-62 taken along line 63-63 in FIG. 59.
Figure 70:
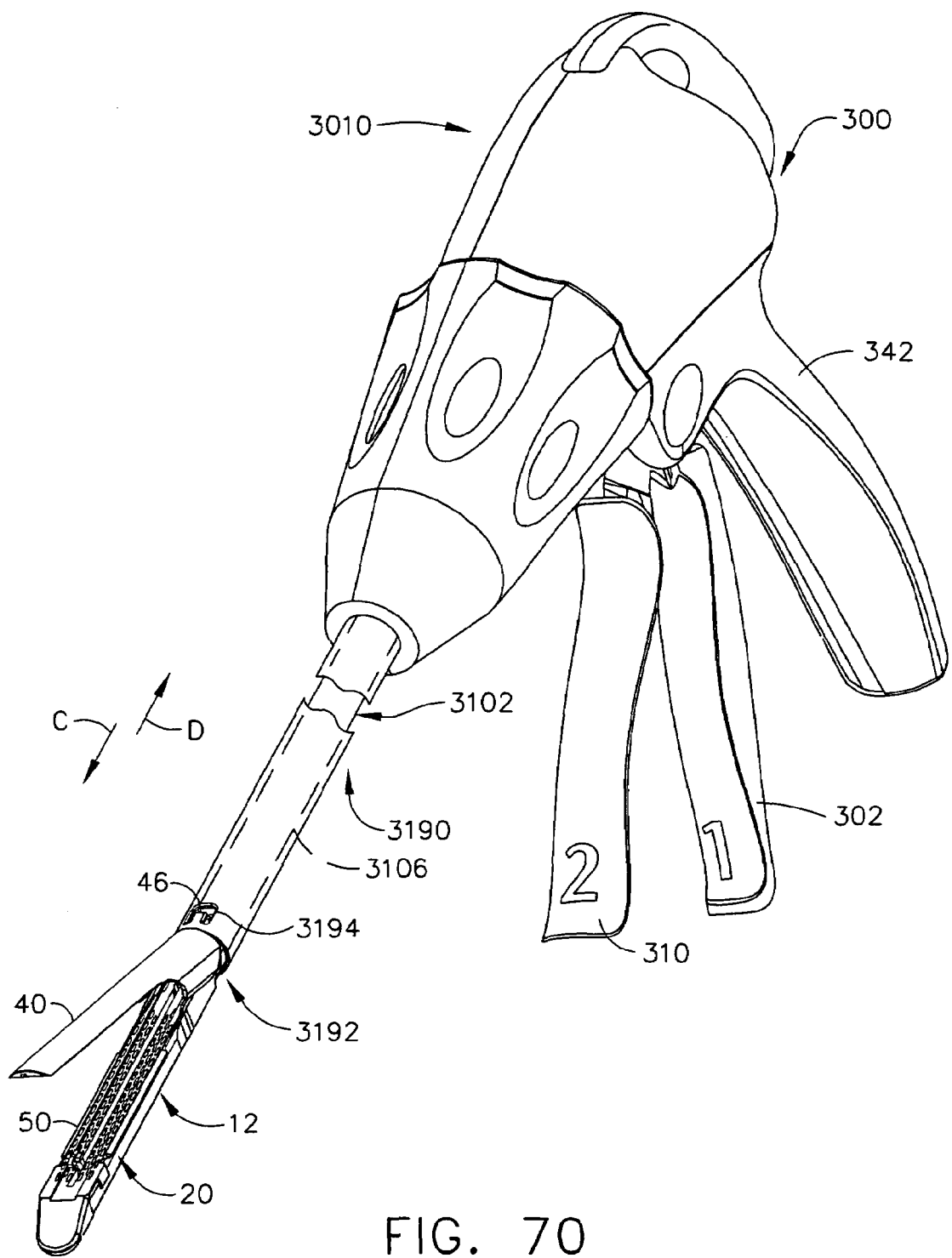
FIG. 70 is a perspective view of another surgical cutting and fastening instrument embodiment of the present invention.

The shaft 1906 is structured and arranged to permit the index wheel 1910 to be reset to a previous position. For example, the shaft 1906 may define a hexagonal shaped opening 1916, and a hexagonal shaped tool may be inserted through an opening 1918 in the left hand case member 330 (shown in FIG. 60) and into the hexagonal shaped opening 1916, then rotated in clockwise direction to reset the index wheel 1910 to a previous position.

As shown in FIG. 59, the blocking assembly 1904 comprises a blocking member 1920, a blocking member guide 1922, a gate member 1924, and a biasing member 1926. The gate member 1924 is in contact with the blocking member 1920, is pivotably connected to the blocking member guide 1922, and cooperates with the protrusions 1914, 1914', 1914" to limit the advancement of the index wheel 1910. The biasing member 1926 is coupled to the gate member 1924. The biasing member 1926 may comprise, for example, a torsion spring configured to bias the gate member 1924 in a clockwise direction. The operation of the lockout system 1900 will be described in more detail hereinbelow with respect to FIGS. 64-69.

As shown, for example, in FIGS. 59-63, the handle assembly 300 further comprises a release system 1930 structured and arranged to initiate disengagement of the detachable grip segment 342 from the primary attachment portion 344. The release system 1930 is within the primary attachment portion 344 and comprises a release button 1932, and first and second release members 1934 connected to or integral with the release button 1932. The first and second release members 1934 each define a release ramp 1936. The release system 1930 further comprises first and second release pins 1938 in contact with the respective release ramps 1936, first and second lock springs 1940 in contact with the first and second release pins 1938, and first and second ejection springs 1942 in contact with the first and second lower slide rails 368. See FIG. 62. As can be seen in FIG. 59, the free end 1941 of springs 1940 extend through a corresponding hole 321 in the right hand case member 320 and a corresponding hole 331 in the heft hand case member 330 into corresponding holes 372 in the upper slide rails 367 to retain the detachable grip portion 342 in engagement with the primary attachment portion 344.

To initiate the disengagement of the detachable grip portion 342 from the grip attachment portion 344, the release button 1932 is advanced, causing the first and second release members 1934 and the respective release ramps 1936 to also advance. As the release ramps 1936 advance, the release ramps 1936 cause the first and second release pins 1938 to change position. The change of the respective positions of the first and second release pins 1938 causes the first and second lock springs 1940 to move upward out of the holes 372 in the upper slide rails 367 a sufficient amount to allow the first and second upper slide rails 367 to slide out of engagement therewith. As the detachable grip portion 342 moves away from the primary grip attachment portion 344, each of the first and second ejection springs 1942 release stored energy, thereby respectively imparting a force against each of the first and second lower slide rails 368. The imparted force assists the disengagement of the detachable grip portion 342 from the primary grip attachment portion 344. It is understood that, according to other embodiments, the release system 1930 may comprise other components and/or configurations suitable for initiating the release of the detachable grip portion 342 from the primary grip attachment portion 344.

Referring to FIGS. 57 and 58, the distal end 637 of the supply passage 636 has a point 639 formed thereon to enable the distal end 637 to puncture through the sterile seal membrane 646 mounted within an enclosed header chamber 644 provided in the primary attachment section 344. In particular, the distal end 637 of the supply passage 636 is inserted through a port 645 in the header chamber 644. The sterile membrane 646 may be fabricated from any suitable pierceable material that can be sterilized and achieve a substantially fluid-tight or airtight seal between the distal end 637 of the supply passage 636 when inserted therethrough yet maintain the sterility of the area within the header chamber 644 when the end 637 of the supply passage 636 is removed therefrom.

As can also be seen in FIGS. 57 and 58, the supply line 650 is fluidically coupled to the header chamber 644 such that pressurized gas entering the header chamber 644 from the supply line 636 flows into the supply line 650. FIG. 57 illustrates the detachable grip portion 342 prior to attachment to the primary attachment portion 644. FIG. 58 illustrates the grip portion 342 attached to the primary attachment portion 344. As can be seen in FIG. 58, the distal end 637 of the supply passage 636 has punctured through the sterile membrane 646. To assist with the insertion of the distal end 637 of the supply passage 636 through the sterile membrane, a compression spring 649 is provided between the wall of the detachable grip portion 342 and the header block 632. Such arrangement provides some "give" to the header block 632 as the distal end 637 of the supply passage 636 is inserted through the membrane 646.

FIGS. 64-69 illustrate the relative positions of the components of the lockout system 1900 at various times during the attachment/disconnect process. FIG. 64 illustrates the relative positions prior to the first full engagement of the grip portion 342 to the primary attachment portion 344. The gate member 1924 is in contact with protrusion 1914 thereby preventing the index wheel 1910 from advancing.

The grip portion 342 is attached to the attachment portion 344 by advancing the slide rails 637 into the corresponding passages 384. The blocking member 1920 protrudes into one of the passages 384 through a hole 381 in the panel 380. See FIG. 59. As the first and second upper slide rails 367 advance, the ramp 369 on one of the first upper slide rails 367 contacts the blocking member 1920 and causes it to move upward toward the index wheel 1910. As the blocking member 1920 advances toward the index wheel 1910, the blocking member 1920 causes the gate member 1924 to advance away from the index wheel 1910. See FIG. 65. As the first upper slide rail 367 and the ramp 369 continue to advance, the blocking member 1920 continues to advance toward the index wheel 1910. When the grip portion 352 is fully engaged with the primary portion 351, the blocking member 1920 is in contact with the protrusion 1914 that was initially in contact with the gate member 1924, thereby preventing the index wheel 1910 from advancing as shown in FIG. 66.

After the disengagement of the grip portion 342 from the primary attachment portion 344 is initiated, the first and second upper slide rails 367 advance in the opposite direction, the ramp 369 defined by the first upper slide rail 367 allows the blocking member 1920 to advance away from the index wheel 1910. As the blocking member 1920 advances away from the index wheel 1910, the blocking member 1920 allows the gate member 1924 to advance toward the index wheel 1910 and past the protrusion 1914 as shown in FIG. 67. As the grip portion 342 is disconnected from the primary attachment portion 344, the blocking member 1920 advances far enough away from the index wheel 1910 to lose contact with the protrusion 1914 and allow index wheel 1910 to rotate until a second protrusion 1914' comes into contact with the gate member 1924 as shown in FIG. 68.

At this point, the counter 1902 has advanced one position, and the grip portion 342 is able to be reattached to the primary attachment portion 344. The attachment/disconnect cycle may be repeated. FIG. 68 illustrates the second reattachment process. When the grip portion 342 is fully engaged with the primary attachment portion 344, the blocking member 1920 is in contact with the protrusion 1914" thereby preventing the index wheel 1910 from advancing as shown in FIG. 69. At the end of the second cycle, when the grip portion 342 is disconnected from the primary attachment portion 344, the gate member 1926 is in contact with a third protrusion 1914" as shown in FIG. 69. The third protrusion 1914" is structured and arranged to prevent the gate member 1926 from being advanced away from the index wheel 1910 by the blocking member 1920, thereby preventing the primary attachment portion 344 from being reattached to the grip portion 342 (or attached to a replacement grip section). Therefore, according to these embodiments, the surgical instrument is effectively a two-use instrument. However, one skilled in the art will appreciate that the number of uses can be increased if the index wheel 1910 defines additional protrusions or indents. Other embodiments of the present invention lack the lockout system 1900, but is configured such that panels 382 or another portion or portions of the handle assembly 300 break off or are otherwise disabled to prevent the reattachment of the grip portion 342 or other grip portion to the handle assembly.

FIGS. 70-83 illustrate another unique and novel pneumatically powered surgical cutting and fastening device 3010 of the present invention that provides the clinician with the ability to monitor the progress of the firing stroke while also providing the ability to manually retract the firing components thereof. This embodiment may be used in connection with the end effector 12 described above or with other end effector arrangements.

The elongate spine assembly 3102 of this embodiment may comprise a proximal spine segment 3104 that is attached to a distal spine segment 3106. In alternative embodiments, the elongate spine assembly 3102 may comprise a single component. The elongate spine assembly 3102 is substantially hollow and is non-movably coupled to the housing assembly 300. As can be seen in FIGS. 79 and 80, the proximal end 3105 of the proximal spine segment may be attached to the housing assembly by a right attachment peg 3110 protruding from the right hand case member 320 and a left attachment peg 3112 protruding from the left hand case member 330. The distal end of the elongate spine member 3102 may be coupled to the elongate channel 20 in the manner described above.

Also in this embodiment, an elongate closure tube 3190 extends from the handle assembly 300 to the end effector 12. The distal end 3192 of the closure tube 3190 has a horseshoe aperture 3194 therethrough and serves to interact with the open/closing tab 46 on the anvil 40 in the manner described above when the closure tube 3190 is moved axially on the spine member 3102. See FIG. 70.

Figure 71:
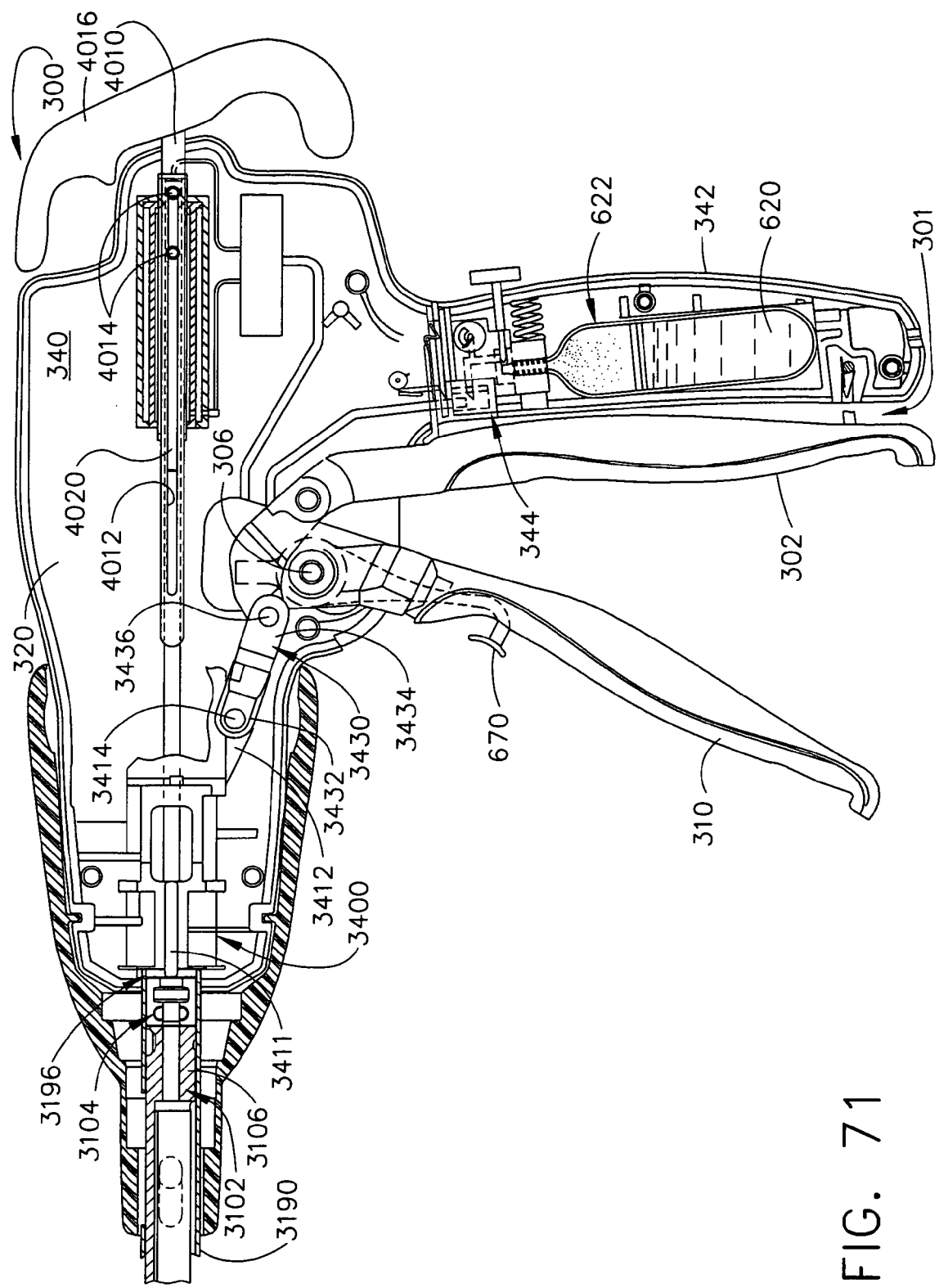
FIG. 71 is a cross-sectional view of a handle assembly embodiment that may be employed in connection with the instrument depicted in FIG. 70.

As can be seen in FIG. 71, a shuttle assembly 3400 that is coupled to the closure trigger 302 by a linkage assembly 430 is supported within the primary housing portion 340. Shuttle assembly 3400 may also be fabricated in two pieces 3402, 3404 (FIG. 73) that are molded or otherwise fabricated from a polymer or other suitable material and are designed to mate together. The pieces 3402, 3404 may be retained together by snap members and/or adhesive and/or bolts, screws, clips, etc. The right hand portion 3402 of the shuttle assembly 3400 has a right retention flange segment 3405 (FIG. 72) that is adapted to cooperate with a left retention flange segment (not shown) on the left hand portion 3404 of the shuttle assembly 3400 to form a retention flange assembly that may extend into the retention groove (not shown) in the proximal end 3196 of the elongate closure tube 3190 in the manner described above. The proximal end 3104 of the elongate spine member 3102 extends into the opening 3403 formed in the distal end of the shuttle assembly 3400 and is non-movably attached to the right hand case member 320 by the right retention peg 3110 that extends through the opening 3406 and a left retention peg 3112 that extends through opening 3408 in the right hand portion 3402 and left hand portion 3404, respectively. In addition, the shuttle assembly 3400 is provided with laterally extending guide rails 3410, 3411. Rail 3410 is configured to be slidably received within a corresponding rail guide in the right hand case member 320 and rail 3411 is configured to be slidably received within a corresponding rail guide in left hand case member 330. Thus, the shuttle assembly 3400 and the closure tube 3190 can move axially relative to the spine assembly 3102 that is attached to the handle assembly 300.

Axial movement of the shuttle assembly 3400 and the elongate closure tube 3190 in the distal direction (arrow "C") is created by moving the closure trigger 302 toward the grip portion 342 of the handle assembly 300 and axial movement of the shuttle assembly 3400 in the proximal direction (arrow "D") is created by moving the closure trigger 302 away from the grip portion 342. In various embodiments, the shuttle assembly 3400 is provided with a connector tab 3412 that facilitates the attachment of the closure linkage assembly 3430 thereto. See FIGS. 71 and 72. The closure linkage assembly 3430 includes a yoke portion 3432 that is pivotally pinned to the connector tab 3412 by a pin 3414. The closure linkage assembly 3430 further has a closure arm 3434 that is pivotally pinned to a yoke assembly 304 formed on the closure trigger 302 by a closure pin 3436 as illustrated in FIG. 71. The closure trigger 302 is pivotally mounted within the handle assembly 300 by a pivot pin 306 that extends between the right hand case member 320 and the left hand case member 330.

When the clinician desires to close the anvil 40 and to clamp tissue within the end effector 12, the clinician draws the closure trigger 302 toward the grip portion 342. As the clinician draws the closure trigger 302 toward the grip portion 342, the closure linkage assembly 3430 moves the shuttle assembly 3400 in the distal "C" direction until the closure linkage assembly 3430 moves into the locked position illustrated in FIG. 71. When in that position, the linkage assembly 3430 will tend to retain the shuttle assembly 3400 in that locked position. As the shuttle assembly 3400 is moved to the locked position, the closure tube 3190 is moved distally on the spine assembly 3102 causing the closure/opening tab 46 on the anvil 40 to be contacted by the proximal end of the horseshoe aperture 3194 in the distal end 3192 of the closure tube segment 3190 to thereby pivot the anvil 40 to the closed (clamped) position. To further retain the shuttle assembly 3400 in the closed position, a locking mechanism 301 may be employed as described above.

Figure 72:
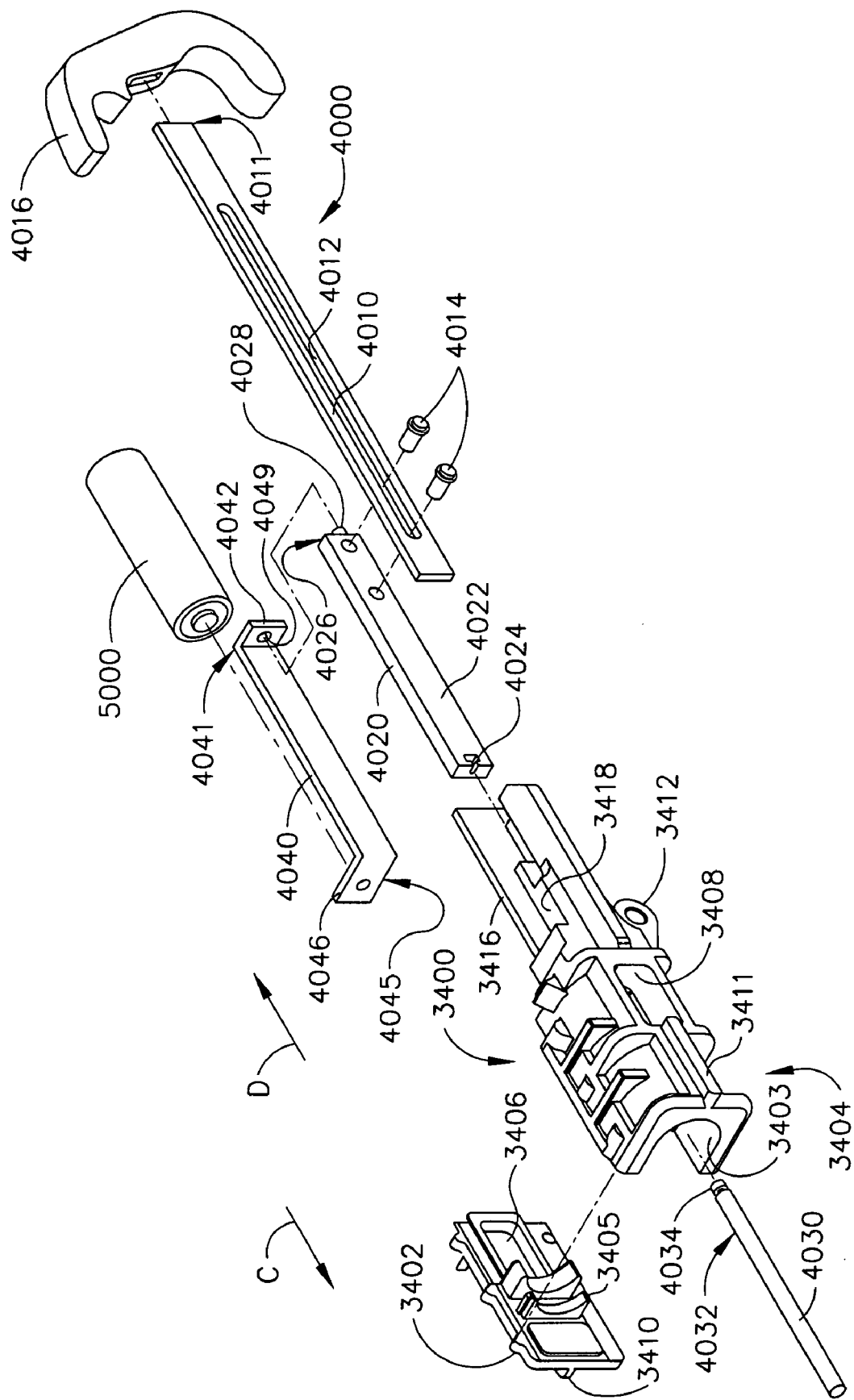
FIG. 72 is an exploded assembly view of a shuttle and retraction rod assembly of various embodiments of the present invention.

As indicated above, these various embodiments of the present invention employ a unique and novel retraction rod assembly 4000 that enables the clinician to monitor the progress of the firing and retraction strokes and also provide the capability to manually retract a firing bar 4030. As can be seen in FIG. 72, the retraction rod assembly 4000 includes a retraction rod 4010 that is slidably pinned to a push bar 4020. In particular, the retraction rod 4010 has an elongate slot 4012 therethrough that is sized to slidably receive two pins 4014 for attaching the retraction rod 4010 to the push bar 4020. A retraction handle grip 4016 may be attached to the proximal end 4011 of the retraction rod 4010.

The push bar 4020 has a distal end 4022 that is designed to interface with the proximal end of an elongated firing bar 4030. As shown in FIG. 72, the proximal end 4032 of the firing bar 4030 has a connector portion 4034 formed thereon that sized to be received in a correspondingly shaped connector aperture 4024 in the distal end 4022 of the push bar 4020. Thus, the push bar 4020 may be used to axially push the firing bar 4030 in the distal direction for a firing stroke or pull the firing bar 4030 in the proximal direction for a retraction stroke. Those of ordinary skill in the art will appreciate that the firing bar 4030 extends through the spine assembly 3102. In alternative embodiments, the firing bar 4030 may have a rectangular, square, etc. cross-sectional shape and be attached to the distal end 31 of the knife assembly 30 as described above or be connected to different types of knife bars and other end effector components that require an axial motion to activate the end effector.

FIGS. 72-77 comprise various views of shuttle assembly 3400. As can be seen in those Figures, the left hand shuttle portion 3404 includes two spaced vertical support walls 3416 and 3418 that define a push bar opening 3420 therebetween. The distal end 4022 of the push bar 4020 extends through the push bar opening 3420 to be coupled to the proximal end 4032 of the firing bar 4030. As can be seen in FIG. 72 the proximal end 4026 of the push bar 4020 is coupled to a "Z"-shaped connector piece 4040. In particular, the proximal end 4026 of the push bar may have a connection peg 4028 protruding therefrom that may be received in an opening 4049 in an attachment tab 4042 on the proximal end 4041 of the Z-shaped connector piece 4040. See FIG. 72. However, the proximal end 4026 of the push bar 4020 may be attached to the attachment tab 4042 by a screw or other suitable fasteners. The distal end 4045 of the Z-shaped connector piece 4040 has a distal attachment tab 4046 thereon that is adapted to be connected to a piston cylinder 5040 protruding from a pneumatically powered cylinder assembly 5000.

As can be seen in FIG. 79, the cylinder assembly 5000 may comprise a first cylinder housing 5010 that has a first closed proximal end 5012 and a first open distal end 5014 that opens into a first axial passage 5016 within the first cylinder housing 5010. The cylinder assembly 5000 also comprises a second cylinder housing 5020 that has a second proximal end 5022 and a second open distal end 5024 that opens into a second axial passage 5026. The second proximal end 5022 has a first piston head 5028 formed thereon that is sized relative to the first axial passage 5016 to create a substantially airtight sliding seal with the first wall 5011 of the first cylinder housing 5010 to define a first cylinder area 5015 between the distal side of the first proximal end 5012 and the proximal side of the first piston head 5028. The first distal end 5014 of the first cylinder housing 5010 further has an inwardly extending first flange 5017 formed thereon for establishing a substantially airtight sliding seal with the outer wall surface of the second cylinder housing 5020 to define a second cylinder area 5018 between the proximal side of the first flange 5017 and the distal side of the first piston head 5028.

A first passage 5027 is provided through the first piston head 5028. As can also be seen in FIG. 79, a piston cylinder 5040 extends through the second open distal end 5024 of the second cylinder housing 5020 and into second axial passage 5026. The piston cylinder 5040 has a proximal end 5042 and a closed distal end 5044. A second piston head 5046 is formed on the proximal end 5042 of the piston cylinder 5040. The second piston head 5046 is sized relative to the second axial passage 5026 to create a substantially airtight sliding seal with a second wall 5021 of the second cylinder housing 5020 to define a third cylinder area 5032. The second distal end 5024 of the second cylinder housing 5020 further has an inwardly extending second flange 5025 formed thereon for establishing a substantially airtight sliding seal with the piston cylinder 5040 to define a fourth cylinder area 5034 between the proximal side of the second flange 5025 and the distal side of the second piston head 5046. An opening 5047 is provided through the second piston head 5046 into a passage 5048 in the piston cylinder 5040.

As can be seen in FIGS. 79 and 80, the cylinder assembly 5000 is mounted within the housing assembly 300. A first supply line or supply conduit 5050 extends from a directional control valve 1610 in the handle assembly 300 to be coupled to the first proximal end 5012 of the first cylinder housing 5010 to supply pressurized gas through a first supply port 5013 or opening in the first proximal end 5012 of the first cylinder housing 5010. In addition, a second supply line or supply conduit 5052 extends from the directional control valve 1610 to the first cylinder housing 5010 adjacent the distal end 5014 thereof to supply pressurized gas into the second cylinder area 5018 through a second port 5029. See FIG. 78.

Figure 78:
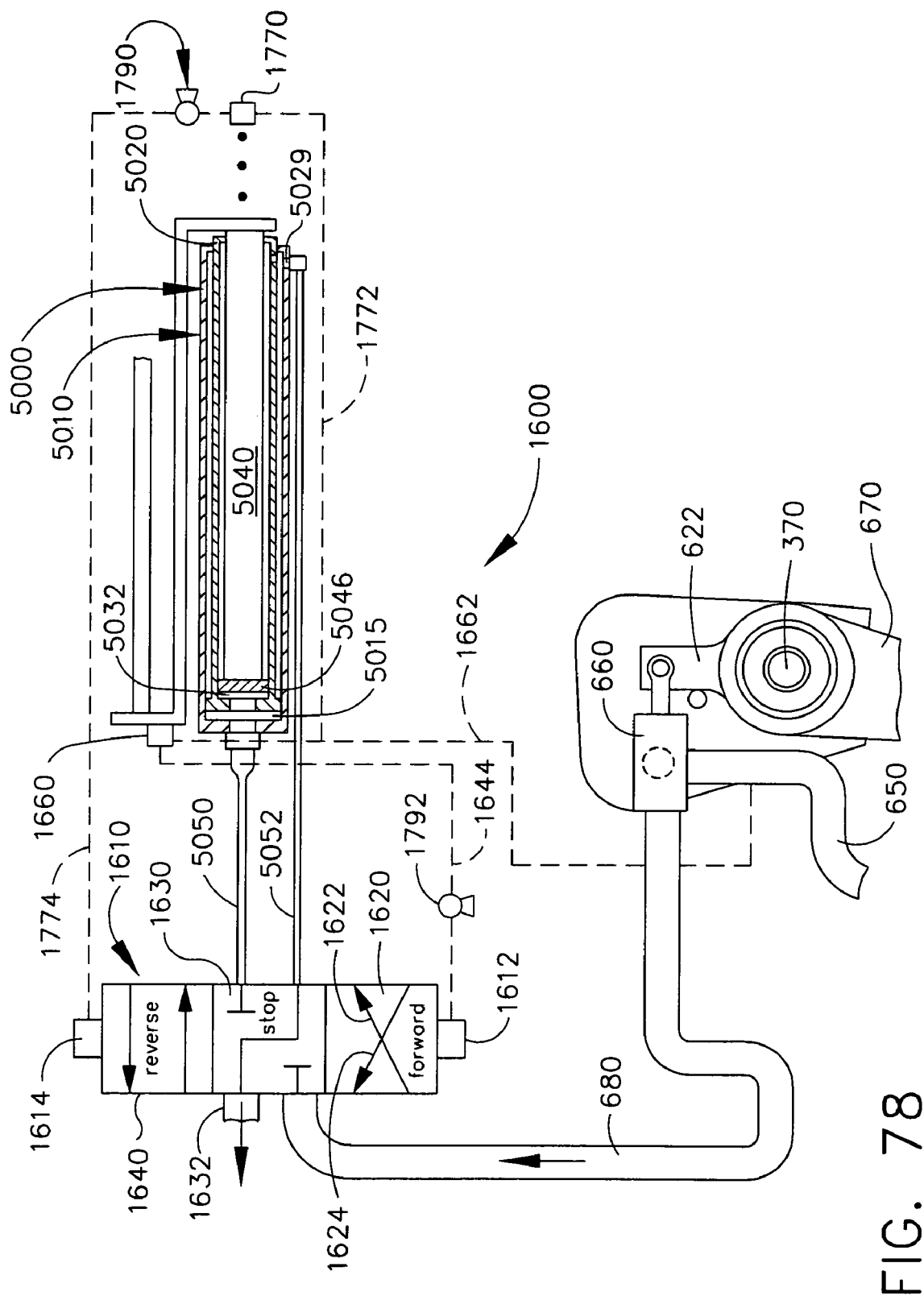
FIG. 78 is a schematic depiction of a control system arrangement that may be used with the embodiments depicted in FIGS. 70-77.
Figure 81:
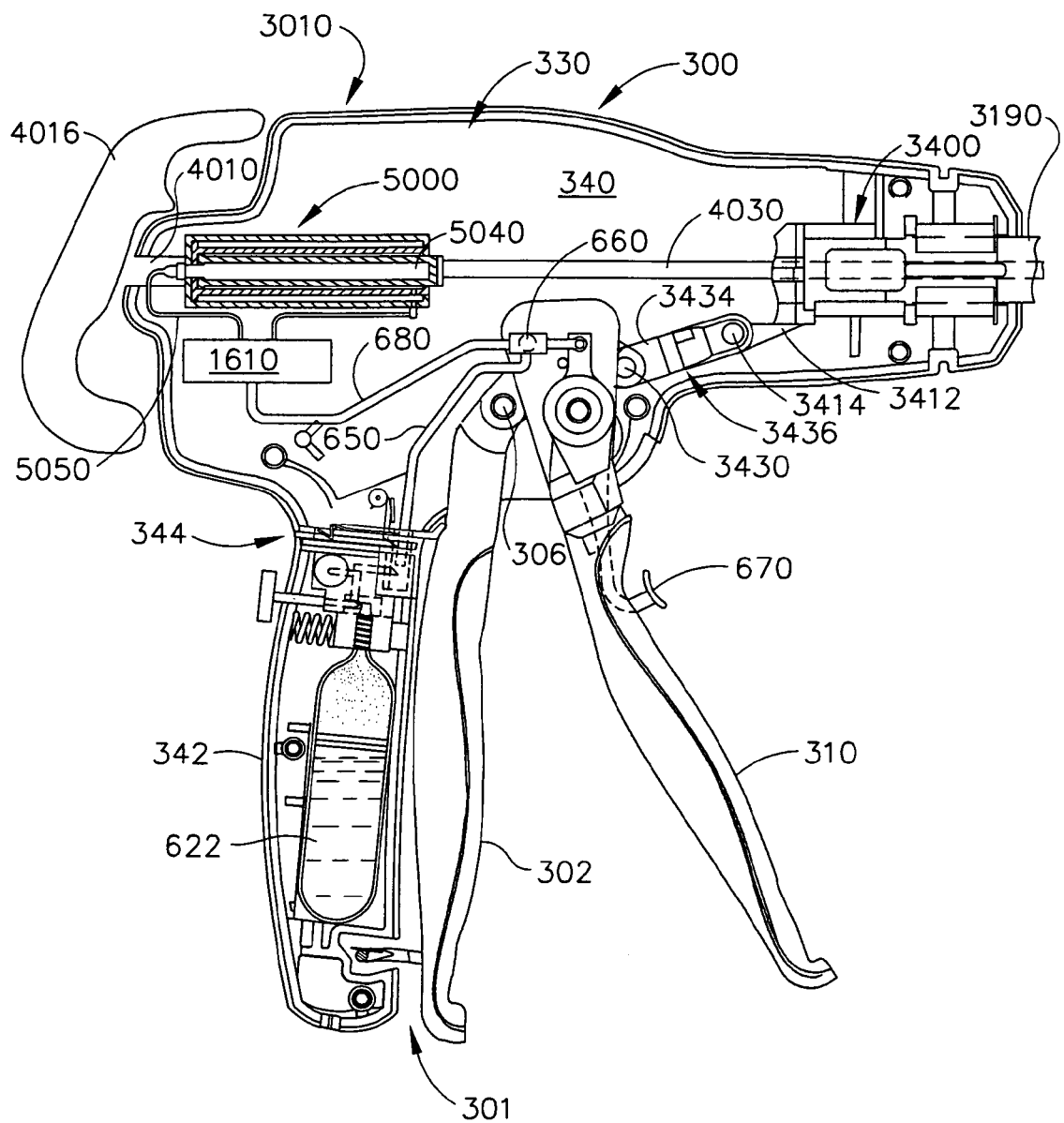
FIG. 81 is a cross-sectional view of a handle assembly of the embodiments depicted in FIGS. 70-80.
Figure 81A:
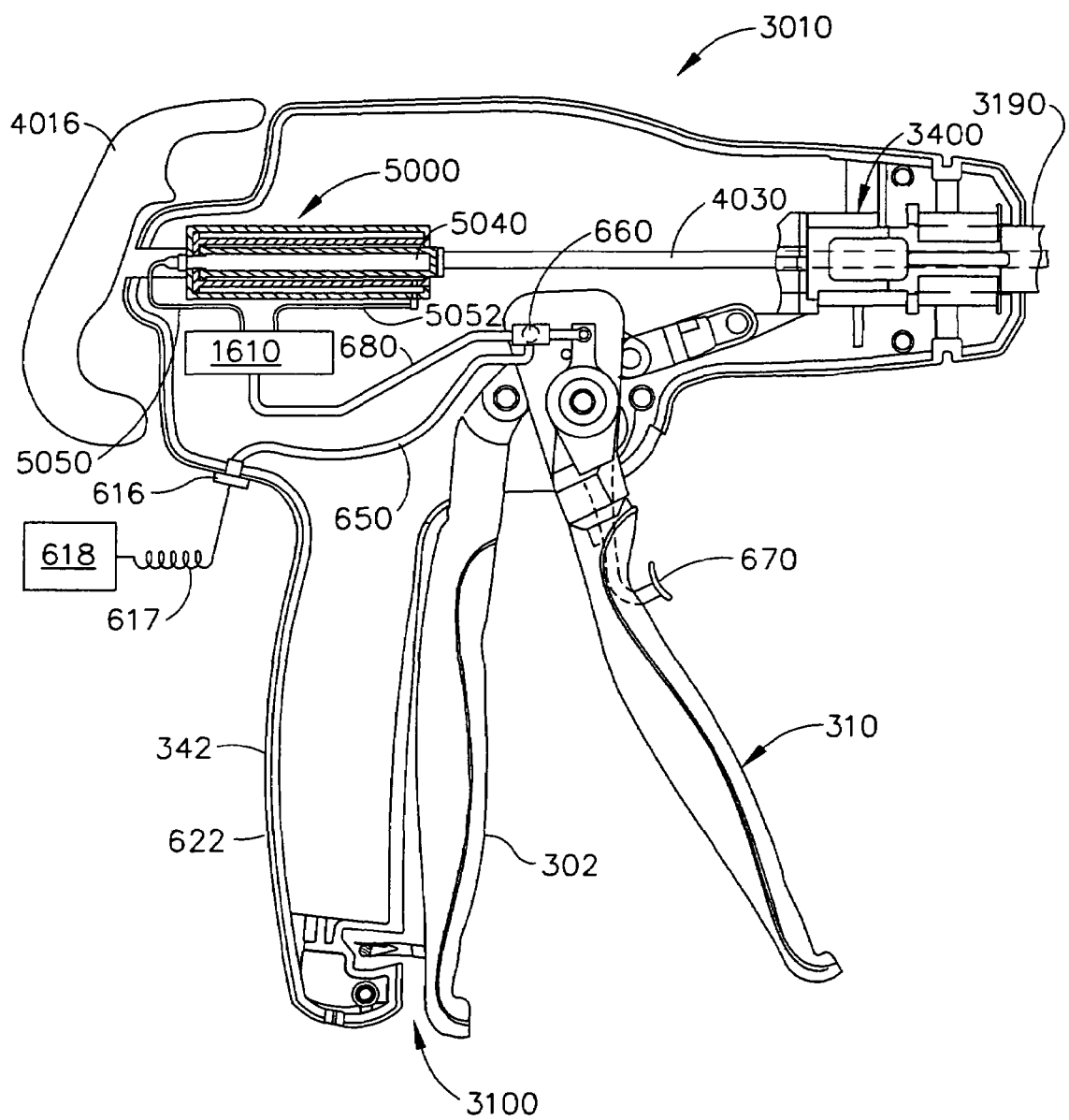
FIG. 81A is a cross-sectional view of a handle assembly embodiment that may be employed with the embodiment depicted in FIGS. 70-80 wherein the source of pressurized gas is external to the handle assembly.
Figure 82:
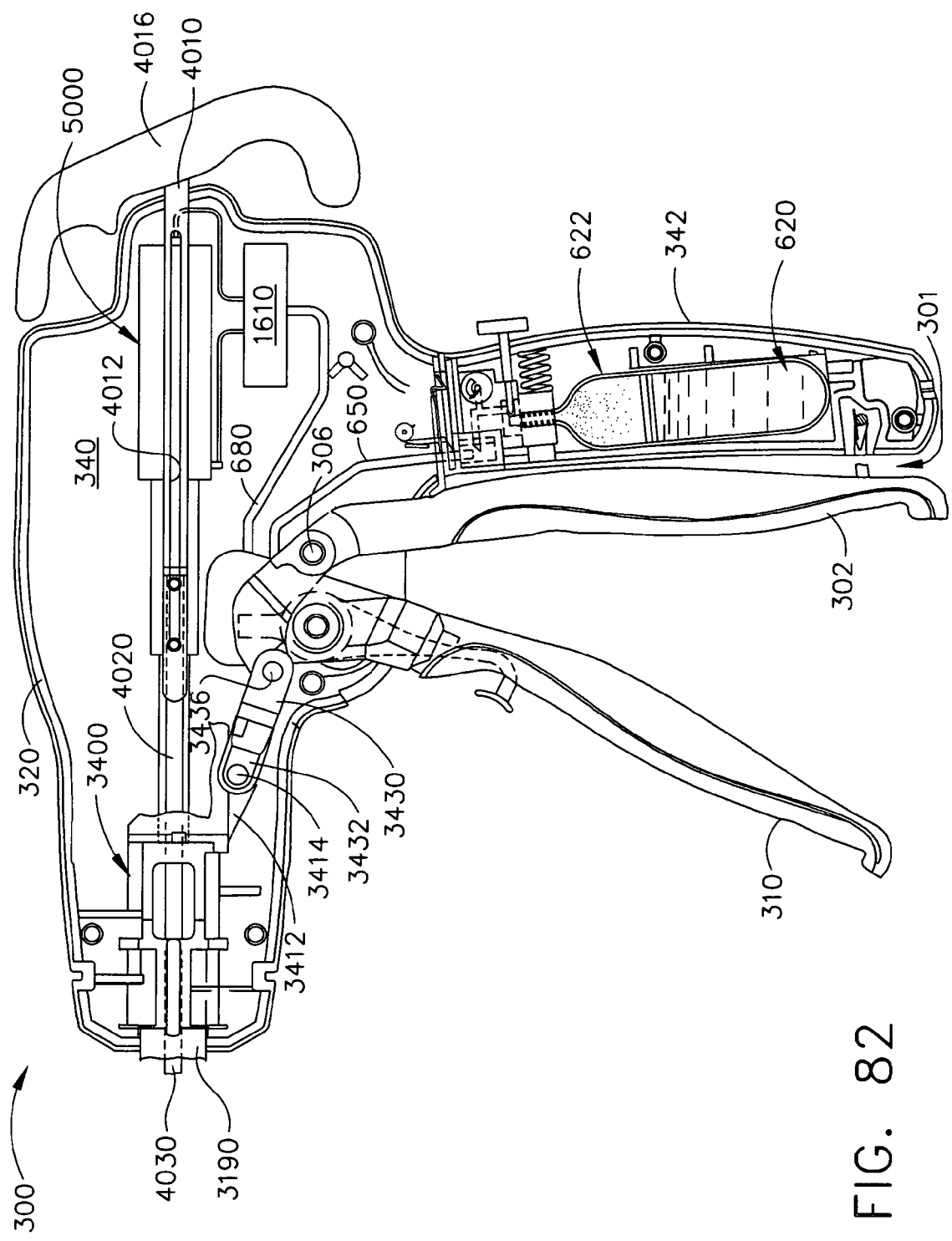
FIG. 82 is another cross-sectional view of the handle assembly of FIG. 81 wherein cylinder assembly is extended.

With reference to FIGS. 78 and 79, the extension and retraction of the firing bar 4030 will now be explained. As can be seen in FIG. 78, the supply lines 5050 and 5052 are coupled to a conventional directional valve 1610 which is part of an actuator system 1600 housed within the handle assembly 300. The directional control valve 1610 has a forward position section 1620, a stop section 1630, and a reverse section 1640. The control valve sections 1620, 1630, 1640 may be manually shifted by the push buttons 1612 and 1614 that protrude through the handle housing 300. In various embodiments, a removable source 620 of pressurized gas is employed. See FIGS. 71 and 81-83. Those of ordinary skill in the art will appreciate, however, that nonreplaceable/rechargeable sources (cylinders) of pressurized gas could also be effectively employed. Still in other embodiments, the handle assembly 300 may be provided with a port 616 for supplying pressurized gas from an external source 618 of pressurized gas. For example, the instrument 3010 could be coupled to the facility's compressed air supply 618 through a flexible supply line 617. See FIG. 81A.

Figure 73:
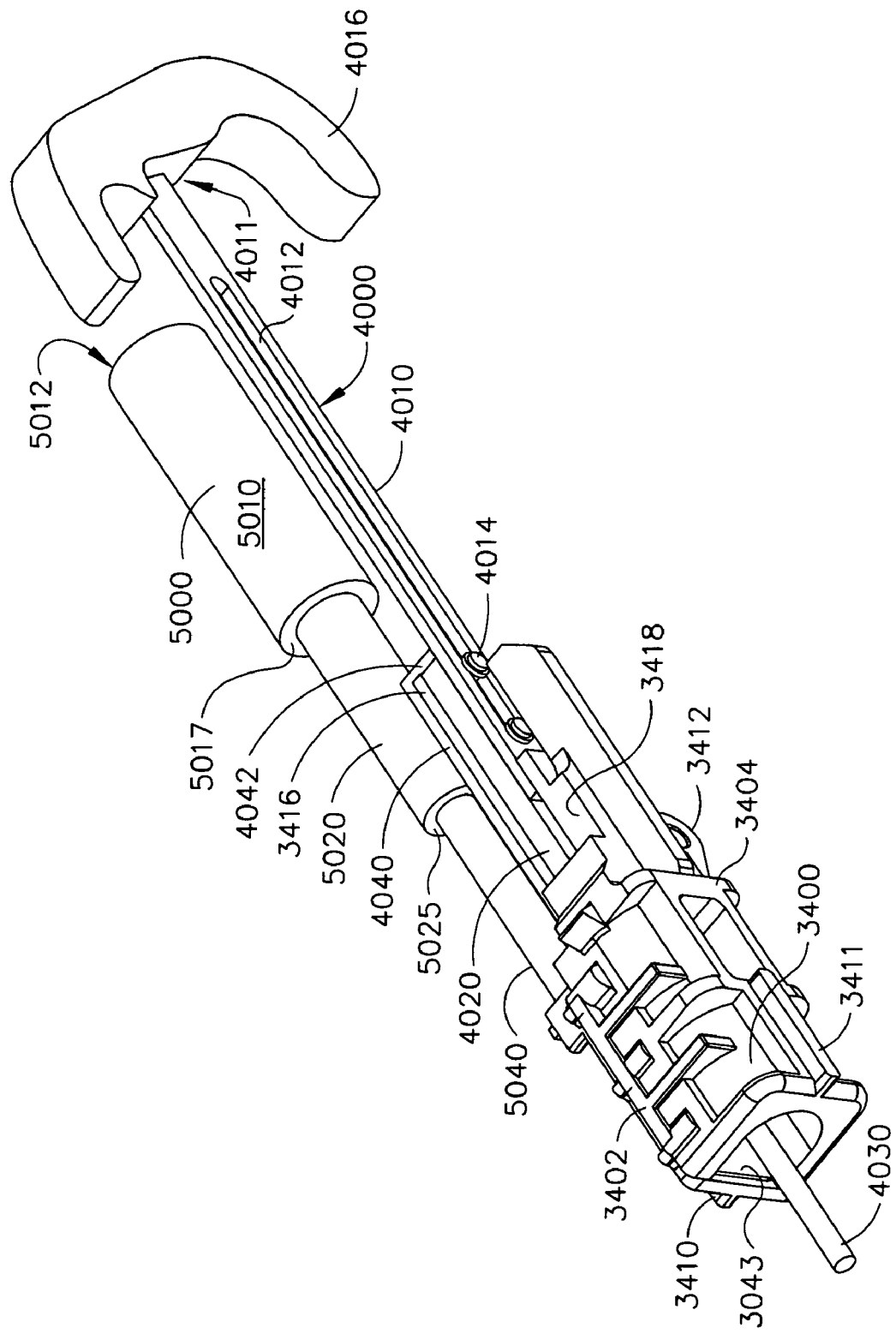
FIG. 73 is an assembled view of the components depicted in FIG. 72 with the cylinder assembly thereof in a fully extended position.
Figure 74:
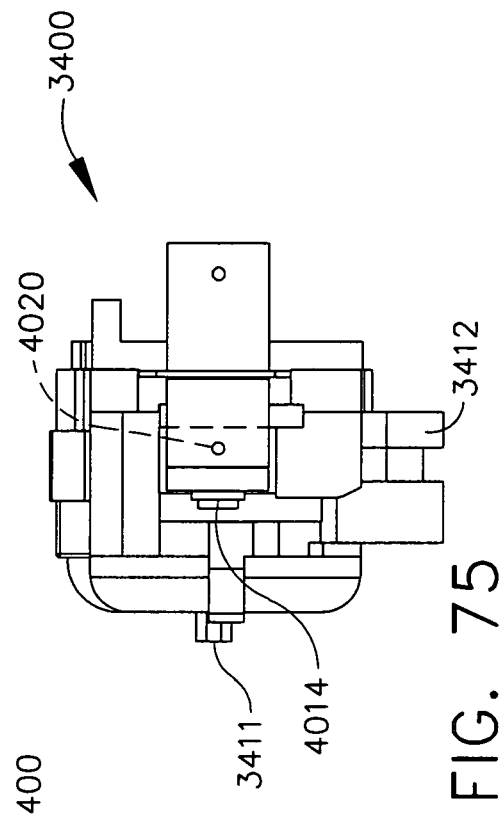
FIG. 74 is a rear elevational view of a shuttle assembly embodiment of the present invention.
Figure 75:
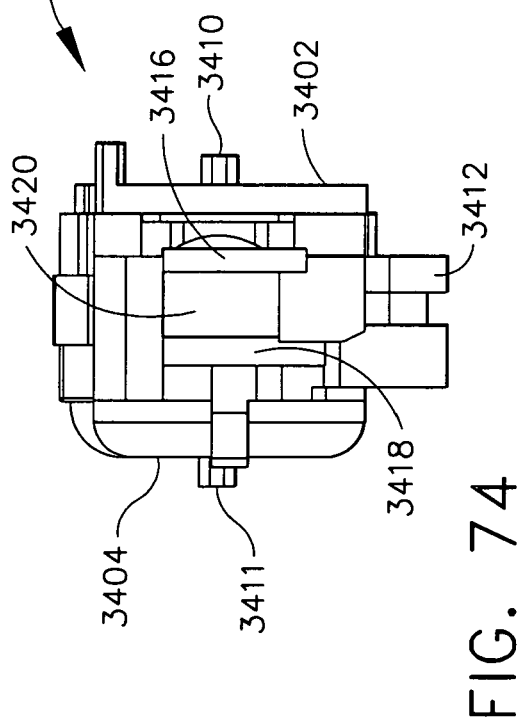
FIG. 75 is another rear elevational view of the shuttle assembly of FIG. 74 with the retraction rod and push bar assembly extending into the push bar opening and with the push bar attached to the connector member.
Figure 76:
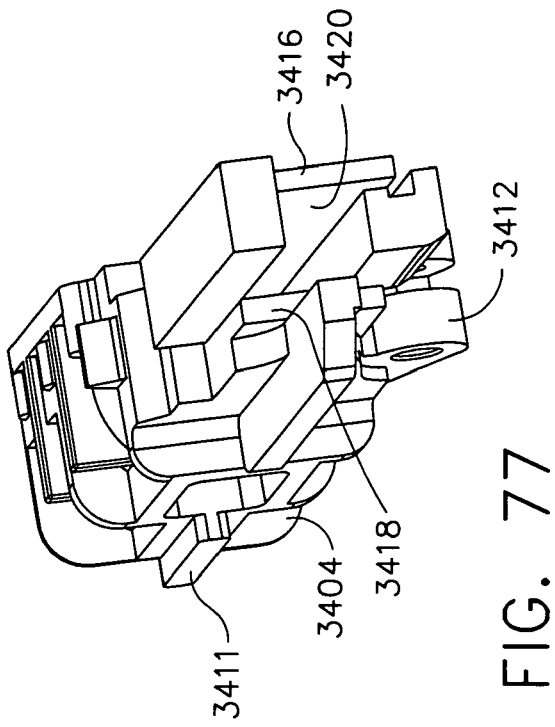
FIG. 76 is a rear elevational perspective view of the left side portion of the shuttle assembly.
Figure 77:
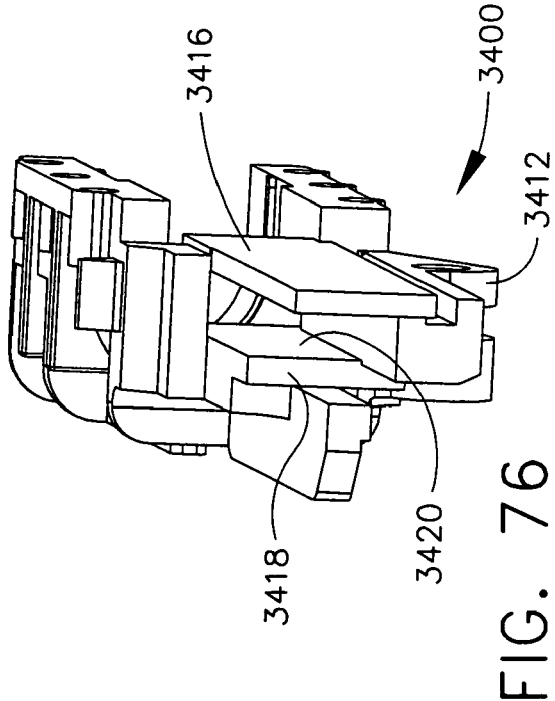
FIG. 77 is another rear elevational perspective view of the left side portion of the shuttle assembly.

Pressurized gas flows from the cylinder 622 (or external pressure source 618) through a supply line 650 into a conventional rate valve 660. As can most particularly be seen in FIG. 78, the rate valve 660 is coupled to a supply linkage 662 that is attached to an activation trigger 670. In various embodiments, activation trigger 670 is supported adjacent the firing trigger 310 that is pivotally coupled to the handle assembly 300 by a pivot pin 370 that extends between the right hand case member 320 and left hand case member 330. Squeezing the activation trigger 670 inward towards the firing trigger 310 causes the rate valve 660 to permit more pressurized gas to pass therethrough into a supply line 680 into the directional valve 1610. Depending upon the position of the directional valve 1610, the pressurized gas will either flow into supply line 5050 or 5052. For example, when the directional valve 1610 is actuated by the clinician to extend the firing bar 30, the control valve 1610 is shifted to the forward position such that forward passage 1622 permits the pressurized gas to flow from the supply line 680 into the supply line 5050. Gas flowing through supply line 5050 enters into the first cylinder area 5015 (FIG. 79) through the first supply port 5013 in the closed end 5012 and through the opening 5027 in the first piston head 5028 and into the third cylinder area 5032. The pressurized gas entering the third cylinder area 5032 also passes through the opening 5047 in the second piston head 5046 into the hollow piston cylinder 5040 and forces the piston cylinder 5040 distally. Gas located in the fourth cylinder area 5034 vents therefrom through exhaust opening 5023 in the second cylinder housing 5020. Similarly, the gas located in the second cylinder area 5018 is permitted to vent therefrom through second opening 5029 into the second supply line 5052. The second supply line 5052 carries the vented gas to passage 1624 in directional valve 1610 (FIG. 78) wherein it is ultimately vented from vent passage 1632. Continued application of pressurized gas to the first cylinder area 5015, the third cylinder area 5032, and passage 5048 in the piston cylinder 5040 causes the piston cylinder 5040 to extend distally as shown in FIGS. 73 and 79. As the piston cylinder 5040 extends distally, the Z-shaped connector also 4040 extends distally by virtue of its attachment to the distal end 5044 of the piston cylinder 5040. The Z-shaped connector 4040 forces the push bar 4020 distally which also forces the firing bar 4030 distally. As the firing bar 4030 moves distally, the distal end portion 31 of the knife assembly 30 attached thereto is advanced through the cartridge 50 to sever the tissue clamped in the end effector 12 and fire the staples. Once the knife assembly 30 has been advanced to its distalmost position in the end effector 12, the clinician discontinues the application of pressurized gas by releasing the activation trigger 4670.

This embodiment may also be provided with a means for indicating when the knife assembly 30 has reached its distal most position in the cartridge 50. In particular, a distal pilot line 1772 may be provided from the supply line 650 to the distal limit switch 1770. A distal limit switch line 1774 is provided between the distal limit switch 1770 and the directional control valve 1610. Thus, when the knife assembly 30 has completed the firing stroke the distal limit switch 1770 is so oriented relative to a portion of the cylinder assembly 5000 such that it is activated by a portion thereof. The distal limit switch 1770 permits the air to flow under pressure from the supply line 650 to the distal limit switch line 1774 and into the directional control valve 1610 which, in various embodiments, causes the directional control valve 1610 to automatically shift to the reverse position which, as will be discussed below causes the firing bar 4030 to be retracted. In various embodiments, a first air powered whistle 1790 or other suitable sound generating device may communicate with the distal limit switch line 1774 (or distal limit switch 1770) such that when the distal limit switch 1770 is actuated at the end of the firing stroke, air passing through the distal limit switch line 1774 activates the first whistle 1790 to provide the clinician with an audible signal indicating that the knife assembly 30 has reached the end of the firing stroke. In alternative embodiments, pressure switches gages, etc. may be used in place of whistle 1790 to provide the clinician with an indication of when the knife assembly 30 has reached the end of the firing stroke.

To pneumatically retract the firing bar 4030, the clinician may push button 1614 to shift the control valve 1610 to the reverse position and begins to squeeze the activation trigger 670 which causes the pressurized gas to flow into the second supply line 5052. Gas flowing through the second supply line 5052 enters the second cylinder area 5018 which causes the second cylinder housing 5020 to retract proximally into the first cylinder housing 5010. Gas in the first cylinder area 5015 is permitted to vent through the first supply opening 5013 into the first supply line 5050. Gas passing through the first supply line 5050 enters the directional valve 1610 wherein it is vented from vent 1632. Once the pressurized gas entering the second cylinder area 5018 has caused the second cylinder housing 5020 to retract into the first cylinder housing 5010, gas passing through the second opening 5029 is now able to pass through the exhaust opening 5023 in the second cylinder housing 5020 and into the fourth cylinder area 5034. As pressurized gas enters the fourth cylinder area 5034, the second piston head 5046 draws the piston cylinder 5040 proximally into the second cylinder housing 5020. Gas in the third cylinder area 5032 passes through the first opening 5027 into the first cylinder area 5015 from which it is vented in the manner described above. As the piston cylinder 5040 is retracted, the Z-shaped connector 4040 moves proximally and pulls with it the push bar 4020 and the firing bar 4030 which is attached thereto.

In various embodiments, a proximal pilot line 1662 also extends between a proximal limit switch 1660 and the supply line 650. See FIG. 78. The proximal limit switch 1660 is so oriented relative to the cylinder assembly 5000 or the connector 4040 such that when the firing bar 4030 has been completely retracted, the proximal limit switch 1760 is actuated and then permits air to flow into a proximal limit switch line 1764 and into the directional control valve 1610 to cause the directional control valve 1610 to automatically shift to the stopped position. In alternative embodiments, a second air powered whistle 1792 or other suitable sound generating device may communicate with the proximal limit switch 1760 such that when the proximal limit switch 1760 is actuated at the end of the retraction stroke, gas passing through the proximal limit switch line 1764 activates the second whistle 1792 to provide the clinician with another audible signal indicating that the firing bar 4030 and knife portion 30 have reached the end of the retraction stroke. In other embodiments, for example, battery powered light emitting diodes or other signal devices may communicate with the distal and proximal limit switches 1770, 1760 to provide the user with another indication when the wedge sled/knife has reaches the end of the firing stroke and/or the retraction stroke. Those of ordinary skill in the art will readily appreciate that, if during the firing stroke, the clinician wishes to stop the firing stroke and retract the firing bar and knife, all he or she has to do is manually switch the control valve 1610 to the reverse position.

In the above-described examples, the clinician did not employ the unique and novel retraction rod assembly 4000 of this embodiment of the present invention. The reaction rod assembly has multiple advantages. First, if during the course of the firing or retraction strokes, pneumatic power is inadvertently lost due, perhaps to an empty supply cylinder 620 or otherwise due to an inadvertent interruption in the supply of pressurized gas, the clinician can manually retract the firing bar (and knife assembly 30) simply by manually shifting the control valve 1610 to the reverse position and grasping the handle grip 4016 attached to the proximal end of the retraction rod and pulling the rod in the proximal direction until the firing bar has been completed retracted. See FIG. 83. By shifting the control valve 1610 to the reversed position enables the gas in the cylinder assembly to be vented as the knife bar is retracted.

Another advantage provided by this embodiment of the present invention is the ability to visually monitor the firing progress of the firing bar and knife portion as they move distally during the firing stroke. This advantage may be attained simply by pulling the retraction rod to its proximal most position shown in FIG. 83 prior to commencing the firing stroke. When in that position, as the cylinder assembly 5000 advances the connector 4040, push bar 4020 and firing bar 4030 distally, the push bar 4020 draws the retraction bar 4010 distally with it by virtue of the pinned connection therewith. In various embodiments, the length of the retraction rod 4010 is provided such that when the firing bar 4030 is fully extended, no portion of the retraction rod 4010 protrudes from the handle assembly 300. Thus, the clinician can determine the progress of the firing bar 4030 and knife assembly 30 by observing the portion of the retraction rod 4010 protruding from the handle assembly 300.

Figure 72A:
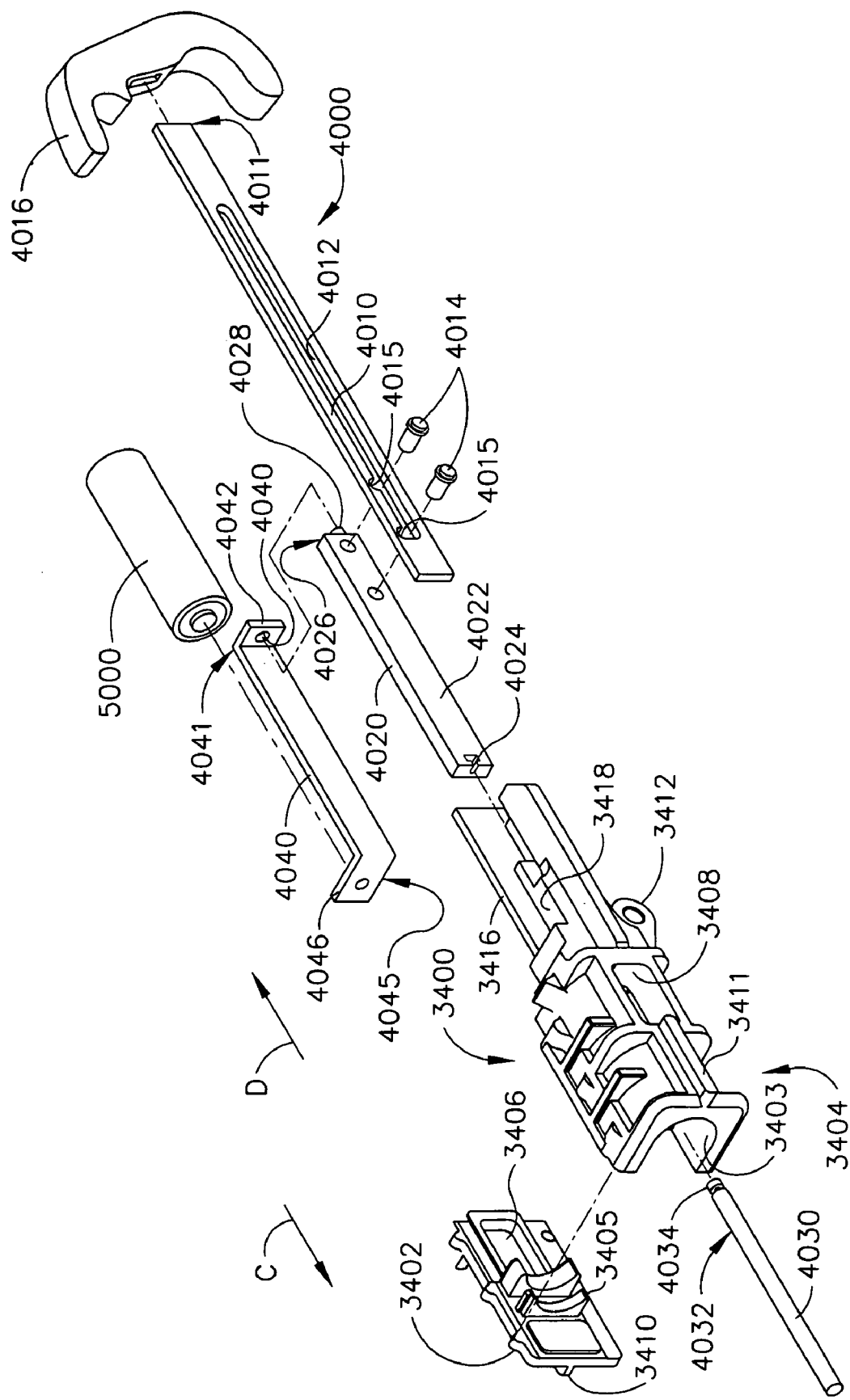
FIG. 72A is an exploded assembly view of a shuttle and retraction rod assembly of other embodiments of the present invention.
Figure 83:
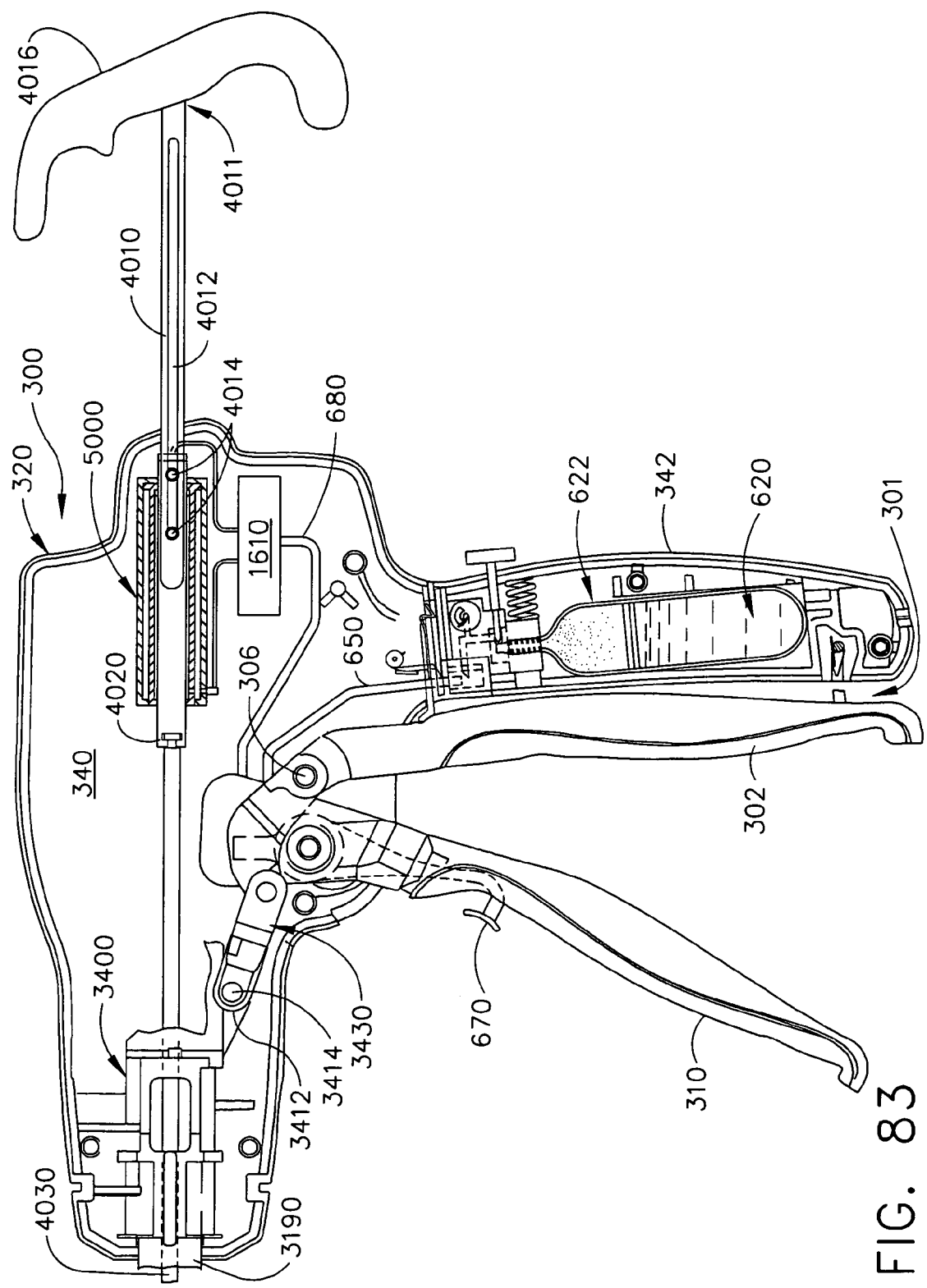
FIG. 83 is another cross-sectional view of the handle assembly of FIG. 81 wherein cylinder assembly is retracted.
Figure 83A:
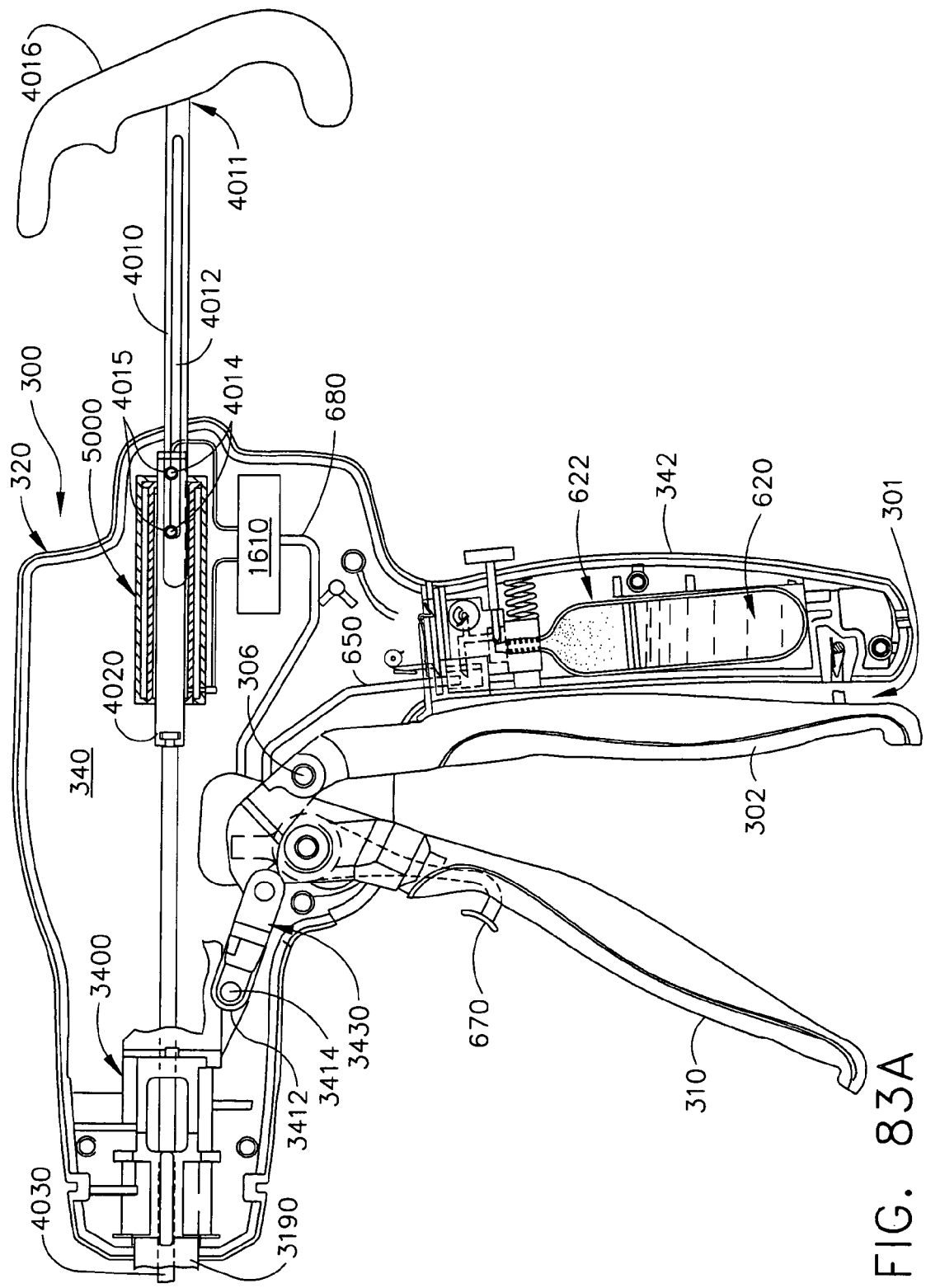
FIG. 83A is a cross-sectional view of a handle assembly of the embodiment depicted in FIG. 72B wherein the cylinder assembly is retracted and the firing rod is in its proximal most position.

In alternative embodiments shown in FIGS. 72A and 83A, the retraction rod 4010 may be provided with at least one and preferably at least two notches 4015 for receiving the pins 4014 therein. Those of ordinary skill in the art will appreciate that such arrangement will provide the clinician with the ability to visually monitor the progress of the firing bar 4030 and knife assembly 30 during the retraction stroke. In particular, as the firing bar 4030 is retracted, the push bar 4020 causes the retraction rod 4010 to advance proximally out of the housing assembly 300 by virtue of the pins 4014 engagement in the notches 4015. Thus, the clinician can judge the distance the firing bar 4030 has progressed during the retraction stroke by observing the distance that the retraction rod 4010 protrudes out of the handle assembly 300. However, when the instrument is not in use, the retraction rod 4010 can be pushed into the handle assembly to the position shown in FIG. 81.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical instrument for use in connection with a pneumatically powered tool having a firing mechanism operably supported therein that is movable between an unactuated position and an actuated position, said surgical instrument comprising:
   a drive system operably communicating with the pneumatically powered tool and being configured to selectively apply at least a drive system generated firing motion to the firing mechanism of the pneumatically powered tool to cause the firing mechanism to move from the unactuated position to the actuated position in response to a flow of gas from a source of gas fluidically coupled to said drive system; and
   a retraction member communicating with said drive system to enable a manually generated retraction motion to be applied thereto to manually move the firing mechanism in a proximal direction from the actuated position to the unactuated position.

2. The surgical instrument of claim 1 wherein said drive system is configured to apply a drive system generated retraction motion to the firing mechanism to cause the firing mechanism to move in a proximal direction from the actuated position to the unactuated position in response to another flow of gas from said source of gas.

3. The surgical instrument of claim 2 further comprising:
   a handle assembly operably supporting at least some of said drive system therein;
   a distal member configured to operably support the pneumatically powered tool; and
   an elongate shaft assembly having a proximal end operably coupled to said handle assembly and a distal end operably coupled to said distal member, said elongate shaft assembly being configured to transmit said drive system generated firing and retraction motions to the pneumatically powered tool.

4. The surgical instrument of claim 3 wherein said drive system comprises:
   a pneumatically powered cylinder assembly operably supported by said handle assembly and coupled to said source of gas, said pneumatically powered cylinder assembly having a piston portion therein that is selectively extendable in said distal direction in response to said flow of gas from said source of gas and being selectively retractable in a proximal direction in response to another flow of gas from said source of gas and wherein said elongate shaft assembly further comprises:
   a firing bar extending through said elongate shaft assembly and operably communicating with said piston portion and said firing mechanism in the pneumatically powered tool such that when said piston portion is extended in the distal direction, the firing bar causes said firing mechanism to move in the distal direction between the unactuated and actuated positions and when said piston portion is retracted in the proximal direction, the firing bar causes said firing mechanism to move in the proximal direction between the actuated position and unactuated position.

5. The surgical instrument of claim 4 wherein said retraction member is linked to said piston portion of said cylinder assembly.

6. The surgical instrument of claim 5 wherein said retraction member is movably linked to said piston portion.

7. The surgical instrument of claim 6 wherein said retraction member is selectively movable to a first position wherein at least a portion of said retraction member protrudes from said handle assembly when said piston portion is in a retracted position such that when said piston portion is extended in said distal direction to cause the firing mechanism to move in the distal direction between the unactuated and actuated positions at a firing rate, said portion of said retraction member protruding from said handle assembly is drawn into said handle assembly at said firing rate.

8. The surgical instrument of claim 7 wherein said retraction member is sized such that the portion of said retraction member protruding from said housing assembly corresponds to a remaining distance that the firing mechanism must travel from the unactuated position to the actuated position.

9. The surgical instrument of claim 6 wherein the retraction member comprises:
   a retraction rod movably coupled to said piston portion; and
   a handle grip attached to said retraction rod.

10. The surgical instrument of claim 1 wherein said retraction member provides a visual indication of progress of the firing mechanism as said firing mechanism moves between the unactuated and actuated positions.

11. A surgical instrument for use in connection with a pneumatically powered tool having a firing mechanism operably supported therein that is movable between an unactuated position and an actuated position, said surgical instrument comprising:
   drive means for selectively applying at least a drive system generated firing motion to the firing mechanism of the pneumatically powered tool to cause the firing mechanism to move from the unactuated position to the actuated position in response to a flow of gas from a source of gas fluidically coupled to said drive means; and
   retraction means communicating with said drive means for selectively applying a manual retraction motion to said drive means to move the firing mechanism in a proximal direction from the actuated position to the unactuated position.

12. The surgical instrument of claim 11 wherein said drive means is further configured to apply a drive system generated retraction motion to the firing mechanism to cause the firing mechanism to move in a proximal direction from the actuated position to the unactuated position in response to another flow of gas from said source of gas.

13. A surgical instrument comprising:
   a handle assembly;
   a closure drive supported by said handle assembly and configured to generate a closing motion and an opening motion;
   a pneumatically powered drive system supported by said handle assembly and being configured to selectively generate a firing motion and a retraction motion;
   an elongate shaft assembly coupled to said handle assembly and communicating with said closure drive to transfer said opening and closing motions and further communicating with said pneumatically powered drive system to transfer said firing and retraction motions;
   an end effector coupled to said elongate shaft assembly, said end effector comprising:
     an elongate channel sized to receive a staple cartridge therein;
     an anvil pivotally coupled to said elongate channel and being pivotally responsive to said open and closing motions from said elongate shaft assembly; and
     a firing mechanism operably supported within one of said elongate channel and the staple cartridge and being movable from an unactuated position to an actuated position in response to an application of said firing motion from said pneumatically powered drive system and being movable from said actuated position to said unactuated position in response to another application of said retraction motion from said pneumatically powered drive system and wherein said surgical instrument further comprises:
   a retraction member communicating with said pneumatically powered drive system to enable a manually generated retraction motion to be applied thereto to manually move the firing mechanism in a proximal direction from the actuated position to the unactuated position.

14. The surgical instrument of claim 13 wherein said retraction member provides a visual indication of progress of the firing mechanism as said firing mechanism moves between the unactuated and actuated positions.

15. The surgical instrument of claim 13 wherein the retraction member comprises:
   a retraction rod movably coupled to said piston portion; and
   a handle grip attached to said retraction rod.

16. The surgical instrument of claim 13 wherein said pneumatically powered drive system comprises a pneumatically powered cylinder assembly operably supported by said handle assembly and coupled to a source of gas, said pneumatically powered cylinder having a piston portion therein that is selectively extendable in said distal direction in response to said flow of gas from said source of gas and a being selectively retractable in a proximal direction in response to another flow of gas from said source of gas and wherein said elongate shaft assembly further comprises:
   a firing bar extending through said elongate shaft assembly and operably communicating with said piston portion and said firing mechanism in the pneumatically powered tool such that when said piston portion is extended in the distal direction, the firing bar causes said firing mechanism to move in the distal direction between the unactuated position to the actuated position and when said piston portion is retracted in the proximal direction, the firing bar causes said firing mechanism to move in the proximal direction between the actuated position and unactuated position.

17. The surgical instrument of claim 16 wherein said retraction member is movably linked to said piston portion of said cylinder assembly such that said retraction member is selectively movable to a first position wherein at least a portion of said retraction member protrudes from said handle assembly when said piston portion is in a retracted position such that when said piston portion is extended in said distal direction to cause the firing mechanism to move in the distal direction between the unactuated and actuated positions at a firing rate, said portion of said retraction member protruding from said handle assembly is drawn into said handle assembly at said firing rate.

18. The surgical instrument of claim 17 wherein said retraction member is sized such that the portion of said retraction member protruding from said housing assembly corresponds to a remaining distance that the firing mechanism must travel from the unactuated position to the actuated position.

19. The surgical instrument of claim 13 wherein said pneumatically powered drive system is fluidically coupled to a source of pneumatic power supported by said handle assembly.

* * * * *